United States Patent
Lo et al.

(10) Patent No.: US 11,591,642 B2
(45) Date of Patent: Feb. 28, 2023

(54) MOLECULAR ANALYSES USING LONG CELL-FREE FRAGMENTS IN PREGNANCY

(71) Applicant: The Chinese University of Hong Kong, Shatin (HK)

(72) Inventors: Yuk-Ming Dennis Lo, Hong Kong (CN); Rossa Wai Kwun Chiu, Hong Kong (CN); Kwan Chee Chan, Hong Kong (CN); Peiyong Jiang, Hong Kong (CN); Suk Hang Cheng, Hong Kong (CN); Cheuk Yin Yu, Hong Kong (CN); Yee Ting Cheung, Hong Kong (CN); Wenlei Peng, Hong Kong (CN)

(73) Assignee: The Chinese University of Hong Kong, Shatin (HK)

( * ) Notice: Subject to any disclaimer, the term of this patent is extended or adjusted under 35 U.S.C. 154(b) by 0 days.

(21) Appl. No.: 17/743,315

(22) Filed: May 12, 2022

(65) Prior Publication Data

US 2022/0275433 A1    Sep. 1, 2022

Related U.S. Application Data

(63) Continuation of application No. 17/196,765, filed on Mar. 9, 2021, now Pat. No. 11,371,084, which is a
(Continued)

(51) Int. Cl.
*C12Q 1/68* (2018.01)
*C12Q 1/6827* (2018.01)
(Continued)

(52) U.S. Cl.
CPC ......... *C12Q 1/6827* (2013.01); *C12Q 1/6806* (2013.01); *C12Q 1/6881* (2013.01);
(Continued)

(58) Field of Classification Search
CPC ....................................................... C12Q 1/68
(Continued)

(56) References Cited

U.S. PATENT DOCUMENTS

| 11,371,084 B2 | 6/2022 | Lo et al. |
| 2007/0111233 A1 | 5/2007 | Bianchi et al. |

(Continued)

FOREIGN PATENT DOCUMENTS

| AU | 2018201992 A1 | 4/2018 |
| CN | 109402247 | 3/2019 |

(Continued)

OTHER PUBLICATIONS

Fan et al, Noninvasive diagnosis of fetal aneuploidy by shotgun sequencing DNA from maternal blood, PNAS, 105 (42) 16266-16271, Oct. 21, 2008.*

(Continued)

*Primary Examiner* — Aaron A Priest
(74) *Attorney, Agent, or Firm* — Kilpatrick Townsend & Stockton LLP

(57) ABSTRACT

Methods and systems described herein involve using long cell-free DNA fragments to analyze a biological sample from a pregnant subject. The status of methylated CpG sites and single nucleotide polymorphisms (SNPs) is often used to analyze DNA fragments of a biological sample. A CpG site and a SNP are typically separated from the nearest CpG site or SNP by hundreds or thousands of base pairs. Finding two or more consecutive CpG sites or SNPs on most cell-free DNA fragments is improbable or impossible. Cell-free DNA fragments longer than 600 bp may include multiple CpG sites and/or SNPs. The presence of multiple CpG sites and/or SNPs on long cell-free DNA fragments may allow for analysis than with short cell-free DNA fragments alone. The long cell-free DNA fragments can be used to
(Continued)

identify a tissue of origin and/or to provide information on a fetus in a pregnant female.

22 Claims, 106 Drawing Sheets

Specification includes a Sequence Listing.

Related U.S. Application Data continuation of application No. 17/168,950, filed on Feb. 5, 2021.

(60) Provisional application No. 63/135,486, filed on Jan. 8, 2021, provisional application No. 62/970,634, filed on Feb. 5, 2020.

(51) Int. Cl.
| | |
|---|---|
| *C12Q 1/6806* | (2018.01) |
| *G16B 30/10* | (2019.01) |
| *G16B 20/20* | (2019.01) |
| *G16B 40/00* | (2019.01) |
| *C12Q 1/6881* | (2018.01) |
| *C12Q 1/6883* | (2018.01) |

(52) U.S. Cl.
CPC .......... *C12Q 1/6883* (2013.01); *G16B 20/20* (2019.02); *G16B 30/10* (2019.02); *G16B 40/00* (2019.02); *C12Q 2600/154* (2013.01)

(58) Field of Classification Search
USPC ........................................................ 435/6.1
See application file for complete search history.

(56) References Cited

U.S. PATENT DOCUMENTS

| | | | |
|---|---|---|---|
| 2013/0096011 A1 | 4/2013 | Rava et al. | |
| 2016/0017419 A1 | 1/2016 | Chiu et al. | |
| 2016/0217251 A1* | 7/2016 | Lo ................ | G16B 20/20 |
| 2017/0029900 A1 | 2/2017 | Lo et al. | |
| 2017/0220735 A1* | 8/2017 | Duenwald .......... | C12Q 1/6869 |
| 2018/0105807 A1* | 4/2018 | Lo ................ | C12Q 1/6883 |
| 2018/0142300 A1 | 5/2018 | Hui et al. | |
| 2018/0298425 A1* | 10/2018 | Thomann .......... | C12N 15/1003 |
| 2019/0130065 A1* | 5/2019 | Lo ................ | C12Q 1/6883 |
| 2019/0341127 A1 | 11/2019 | Lo et al. | |
| 2020/0123532 A1* | 4/2020 | Lo ................ | C12Q 1/6827 |

FOREIGN PATENT DOCUMENTS

| | | | |
|---|---|---|---|
| CN | 109890984 | 6/2019 | |
| WO | WO-2011075774 A1 * | 6/2011 | ........... C12Q 1/6806 |
| WO | 2016038220 | 3/2016 | |
| WO | 2016049877 | 4/2016 | |
| WO | 2018072705 | 4/2018 | |
| WO | 2018090991 A1 | 5/2018 | |

OTHER PUBLICATIONS

Sun et al, An efficient method for noninvasive prenatal diagnosis of fetal trisomy 13, trisomy 18, and trisomy 21, PLoS One. 2019; 14(4): e0215368. Published online Apr. 12, 2019.*
Xu et al, A Method to Quantify Cell-Free Fetal DNA Fraction in Maternal Plasma Using Next Generation Sequencing: Its Application in Non-Invasive Prenatal Chromosomal Aneuploidy Detection, PLoS One. Jan. 14, 2016;11(1):e0146997. doi: 10.1371/journal.pone.0146997. eCollection 2016.*
Wikipedia, Normalization (statistics), avail at https://en.wikipedia.org/wiki/Normalization_(statistics), accessed Jul. 8, 2022.*
Yu et al., Size-based molecular diagnostics using plasma DNA for noninvasive prenatal testing, Proc Natl Acad Sci USA. Jun. 10, 2014;111(23):8583-8. doi: 10.1073/pnas.1406103111. Epub May 19, 2014.*
Shi et al, Size profile of cell-free DNA: A beacon guiding the practice and innovation of clinical testing, Theranostics. Mar. 26, 2020; 10(11):4737-4748. doi: 10.7150/thno.42565. eCollection 2020.*
U.S. Appl. No. 17/196,765, Non-Final Office Action dated Oct. 7, 2021, 21 pages.
Altschul et al., Basic Local Alignment Search Tool, Journal of Molecular Biology, vol. 215, No. 3, Oct. 5, 1990, pp. 403-410.
Amicucci et al., Prenatal Diagnosis of Myotonic Dystrophy Using Fetal DNA Obtained from Maternal Plasma, Clinical Chemistry, vol. 46, No. 2, Feb. 1, 2000, pp. 301-302.
Ashley, Towards Precision Medicine, Nature Reviews Genetics, vol. 17, No. 9, Aug. 16, 2016, pp. 507-522.
AU et al., Improving PacBio Long Read Accuracy by Short Read Alignment, PLoS One. vol. 7, No. 10, Oct. 4, 2012, 8 pages.
Bansal et al., HapCUT: An Efficient and Accurate Algorithm for the Haplotype Assembly Problem, Bioinformatics, vol. 24, No. 16, Aug. 15, 2008, pp. i153-i159.
Beretta et al., HapCHAT: Adaptive Haplotype Assembly for Efficiently Leveraging High Coverage in Long Reads, BMC Bioinformatics, vol. 19, No. 252, Jul. 3, 2018, pp. 1-19.
Chaisson et al., Mapping Single Molecule Sequencing Reads Using Basic Local Alignment With Successive Refinement (BLASR): Application and Theory, BMC Bioinformatics, vol. 13, No. 238, Sep. 19, 2012, 18 pages.
Chan et al., Hypermethylated RASSF1A in Maternal Plasma: A Universal Fetal DNA Marker that Improves the Reliability of Noninvasive Prenatal Diagnosis, Clinical Chemistry, vol. 52, No. 12, Dec. 2006, pp. 2211-2218.
Chan et al., Plasma DNA Profile Associated with DNASE1L3 Gene Mutations: Clinical Observations, Relationships to Nuclease Substrate Preference, and In Vivo Correction, The American Journal of Human Genetics, vol. 107, No. 5, Nov. 5, 2020, pp. 882-894.
Chan et al., Second Generation Noninvasive Fetal Genome Analysis Reveals De Novo Mutations, Single-Base Parental Inheritance, and Preferred DNA Ends, Proceedings of the National Academy of Sciences of the United States of America, vol. 113, No. 50, Dec. 13, 2016, pp. 1-10.
Chan et al., Size Distributions of Maternal and Fetal DNA in Maternal Plasma, Clinical Chemistry, vol. 50, No. 1, Jan. 2004, pp. 88-92.
Cheng et al., Noninvasive Prenatal Testing by Nanopore Sequencing of Maternal Plasma DNA: Feasibility Assessment, Clinical Chemistry, vol. 61, No. 10, 2015, pp. 1305-1306.
Cotton et al., Landscape of DNA Methylation on the X Chromosome Reflects CpG Density, Functional Chromatin State and X-chromosome Inactivation, Human Molecular Genetics, vol. 24, No. 6, Mar. 15, 2015, pp. 1528-1539.
De Maio et al., Comparison of Long-read Sequencing Technologies in the Hybrid Assembly of Complex Bacterial Genomes, Microbial Genomics, vol. 5, No. 9, Sep. 2019, pp. 1-12.
Delaneau et al., A Linear Complexity Phasing Method for Thousands of Genomes, Nature Methods, vol. 9, No. 2, Dec. 4, 2011, pp. 179-181.
Edge et al., HapCUT2: Robust and Accurate Haplotype Assembly for Diverse Sequencing Technologies, Genome Research, vol. 27, No. 5, May 2017, pp. 801-812.
Edge et al., Longshot Enables Accurate Variant Calling in Diploid Genomes From Single-molecule Long Read Sequencing, Nature Communications, vol. 10, No. 4660, Oct. 11, 2019, pp. 1-10.
Eid et al., Real-Time DNA Sequencing from Single Polymerase Molecules, Science, vol. 323, No. 5910, Jan. 2, 2009, pp. 133-138.
Enquobahrie et al., Early Pregnancy Peripheral Blood Gene Expression and Risk of Preterm Delivery: A Nested Case Control Study, BMC Pregnancy and Childbirth, vol. 9, No. 56, Dec. 10, 2009, pp. 1-16.
Fan et al., Analysis of the Size Distributions of Fetal and Maternal Cell-Free DNA by Paired-End Sequencing, Clinical Chemistry, vol. 56, No. 8, Aug. 2010, pp. 1279-1286.
Faxen et al., Altered mRNA Expression Pattern of Placental Epidermal Growth Factor Receptor (EGFR) in Pregnancies Compli-

(56) References Cited

OTHER PUBLICATIONS cated by Preeclampsia and/or Intrauterine Growth Retardation, American Journal of Perinatology, vol. 15, No. 1, Jan. 1, 1998, pp. 9-13.

Flusberg et al., Direct Detection of DNA Methylation During Single-Molecule, Real-Time Sequencing, Nature Methods, vol. 7, No. 6, Jun. 2010, pp. 461-465.

Goodwin et al., Oxford Nanopore Sequencing, Hybrid Error Correction, and De Novo Assembly of a Eukaryotic Genome, Genome Research, vol. 25, No. 11, Nov. 2015, pp. 1750-1756.

Han et al., The Biology of Cell-Free DNA Fragmentation and the Roles of DNASE1, DNASE1L3, and DFFB, The American Journal of Human Genetics; vol. 106, No. 2, Feb. 6, 2020, pp. 202-214.

Head et al., Library Construction For Next-Generation Sequencing: Overviews and Challenges, Biotechniques, vol. 56, No. 2, Feb. 1, 2014, pp. 61-77.

Hong et al., Longitudinal Profiling of Human Blood Transcriptome in Healthy and Lupus Pregnancy, Journal of Experimental Medicine, vol. 216, No. 5, May 6, 2019, pp. 1154-1169.

Hsiao et al., Application of FTA® Sample Collection and DNA Purification System on the Determination of CTG Trinucleotide Repeat Size by PCR-Based Southern Blotting, Journal of Clinical Laboratory Analysis, vol. 13, No. 4, 1999, pp. 188-193.

Hui et al., Universal Haplotype-Based Noninvasive Prenatal Testing for Single Gene Diseases, Clinical Chemistry 2017, vol. 63, No. 2, Feb. 1, 2017, pp. 513-524.

Jahr et al., DNA Fragments in the Blood Plasma of Cancer Patients: Quantitations and Evidence for their Origin from Apoptotic and Necrotic Cells, Cancer Research, vol. 61, No. 4, Feb. 15, 2001, pp. 1659-1665.

Jiang et al., Plasma DNA End-Motif Profiling as a Fragmentomic Marker in Cancer, Pregnancy, and Transplantation, Cancer Discovery, vol. 10, No. 5, May 2020, pp. 664-673.

Kaartokallio et al., Gene expression profiling of pre-eclamptic placentae by RNA sequencing, Scientific Reports, Sep. 21, 2015, 15 pages.

Kelly et al., RNA Sequencing Exposes Adaptive and Immune Responses to Intrauterine Growth Restriction in Fetal Sheep Islets, Endocrinology, vol. 158, No. 4, Apr. 1, 2017, pp. 743-755.

Kielbasa et al., Adaptive Seeds Tame Genomic Sequence Comparison, Genome Research, vol. 21, No. 3, Mar. 2011, pp. 487-493.

Kinde et al., FAST-SeqS: A Simple and Efficient Method for the Detection of Aneuploidy by Massively Parallel Sequencing, PLoS ONE, vol. 7, No. 7, Jul. 18, 2012, 8 pages.

Kovtun et al., Features of Trinucleotide Repeat Instability in Vivo, Cell Research, vol. 18, No. 1, Jan. 1, 2008, pp. 198-213.

Leung et al., Increased Placental Apoptosis in Pregnancies Complicated by Preeclampsia, American Journal of Obstetrics and Gynecology, vol. 184, No. 6, May 2001, pp. 1249-1250.

Leung et al., Maternal Plasma Fetal DNA as a Marker for Preterm Labour, The Lancet, vol. 352, No. 9144, Dec. 12, 1998, pp. 1904-1905.

Levy et al., Trophoblast Apoptosis From Pregnancies Complicated by Fetal Growth Restriction is Associated With Enhanced p53 Expression, American Journal of Obstetrics & Gynecology, vol. 186, No. 5, May 2002, pp. 1056-1061.

Li et al., Cancer Detector: Ultrasensitive and Non-invasive Cancer Detection at the Resolution of Individual Reads Using Cell-free DNA Methylation Sequencing Data, Nucleic Acids Research, vol. 46, No. 15, Sep. 6, 2018, 11 pages.

Li et al., Detection of Paternally Inherited Fetal Point Mutations for 3-Thalassemia Using Size-Fractionated Cell-Free DNA in Maternal Plasma, Journal of the American Medical Association, vol. 293, No. 7, Feb. 16, 2005, 8 pages.

Li et al., Fast and Accurate Long-Read Alignment with Burrows-Wheeler transform, Bioinformatics, vol. 26, No. 5, Mar. 1, 2010, pp. 589-595.

Lim et al., Validation of a Commercially Available Screening Tool for the Rapid Identification of CGG Trinucleotide Repeat Expansions in FMR1, Journal of Molecular Diagnostics, vol. 17, No. 3, May 2015, pp. 302-314.

Liu et al., Detection of DNA Base Modifications by Deep Recurrent Neural Network on Oxford Nanopore Sequencing Data, Nature Communications, vol. 10, No. 2449, Jun. 4, 2019, 11 pages.

Lo et al., Maternal Plasma DNA Sequencing Reveals the Genome-Wide Genetic and Mutational Profile of the Fetus, Science Translational Medicine, vol. 2, No. 61, Supporting Online Material, Decembers, 2010, 73 pages.

Lo et al., Quantitative Abnormalities of Fetal DNA in Maternal Serum in Preeclampsia, Clinical Chemistry, vol. 45, No. 2, Feb. 1, 1999, pp. 184-188.

Lo et al., Quantitative Analysis of Fetal DNA in Maternal Plasma and Serum: Implications for Noninvasive Prenatal Diagnosis, American Journal of Human Genetics, vol. 62, No. 4, Apr. 1998, pp. 768-775.

Loomis et al., Sequencing the Unsequenceable: Expanded CGG-repeat Alleles of the Fragile X Gene, Genome Research, vol. 23, No. 1, Jan. 2013, pp. 121-128.

Lun et al., Noninvasive Prenatal Methylomic Analysis by Genomewide Bisulfite Sequencing of Maternal Plasma DNA, Clinical Chemistry, vol. 59, No. 11, Nov. 2013, pp. 1583-1594.

Lyon et al., A Simple, High-Throughput Assay for Fragile X Expanded Alleles Using Triple Repeat Primed PCR and Capillary Electrophoresis, Journal of Molecular Diagnostics, vol. 12, No. 4, Jul. 2010, pp. 505-511.

Ma et al., Topologic Analysis of Plasma Mitochondrial DNA Reveals the Coexistence of Both Linear and Circular Molecules, Clinical Chemistry, vol. 65, No. 9, Sep. 2019, pp. 1161-1170.

Magi et al., Nanopore Sequencing Data Analysis: State of the Art, Applications and Challenges, Briefings in Bioinformatics, vol. 19, No. 6, Nov. 27, 2018, pp. 1256-1272.

Magor et al., KLF1-Null Neonates Display Hydrops Fetalis and a Deranged Erythroid Transcriptome, Blood, vol. 125, No. 15, Apr. 9, 2015, pp. 2405-2417.

McMurray, Mechanisms of Trinucleotide Repeat Instability During Human Development, Nature Reviews Genetics, vol. 11, No. 11, Nov. 2010, pp. 786-799.

Medina-Bastides et al., Placental Microarray Profiling Reveals Common mRNA and lncRNA Expression Patterns in Preeclampsia and Intrauterine Growth Restriction, International Journal of Molecular Sciences, vol. 21, No. 10, May 20, 2020, pp. 1-21.

Ni et al., Deepsignal: Detecting DNA Methylation State From Nanopore Sequencing Reads Using Deep-Learning, Bioinformatics, vol. 35, No. 22, 2019, pp. 4586-4595.

Orr et al., Trinucleotide Repeat Disorders, Annual Review of Neuroscience, vol. 30, 2007, pp. 575-621.

Patterson et al., WhatsHap: Weighted Haplotype Assembly for Future-Generation Sequencing Reads, Journal of Computational Biology, vol. 22, No. 6, Jun. 2015, 13 pages.

International Application No. PCT/CN2021/075394, International Search Report and Written Opinion dated Apr. 25, 2021, 10 pages.

Schreiber et al., Error Rates for Nanopore Discrimination among Cytosine, Methylcytosine, and Hydroxymethylcytosine along Individual DNA Strands, Proceedings of the National Academy of Sciences, vol. 110, No. 47, Nov. 19, 2013, pp. 18910-18915.

Sedlazeck et al., Accurate Detection of Complex Structural Variations Using Single-molecule Sequencing, Nature Methods, vol. 15, No. 6, Apr. 30, 2018, 22 pages.

Sekizawa et al., Cell-free Fetal DNA in the Plasma of Pregnant Women with Severe Fetal Growth Restriction, American Journal of Obstetrics & Gynecology, vol. 188, No. 2, Feb. 1, 2003, pp. 480-484.

Serpas et al., Dnase1/3 Deletion Causes Aberrations in Length and End-Motif Frequencies in Plasma DNA, Proceedings of the National Academy of Sciences of the United States of America, vol. 116, Issue 2, Jan. 8, 2019, pp. 641-649.

Sharp et al., Placental Apoptosis in Health and Disease, American Journal of Reproductive Immunology, vol. 64, No. 3, Sep. 2010, pp. 159-169.

(56) References Cited

OTHER PUBLICATIONS

Simpson et al., Detecting DNA Cytosine Methylation Using Nanopore Sequencing, Nature Methods, vol. 14, No. 4, Apr. 2017, pp. 407-410.

Slonim et al., Functional Genomic Analysis of Amniotic Fluid Cell-free mRNA Suggests That Oxidative Stress is Significant in Down Syndrome Fetuses, Proceedings of the National Academy of Sciences of the U.S.A., vol. 106, No. 23, Jun. 9, 2009, pp. 9425-9429.

Smid et al., Quantitative Analysis of Fetal DNA in Maternal Plasma in Pathological Conditions Associated with Placental Abnormalities, Annals of the New York Academy of Sciences, vol. 945, Sep. 2001, pp. 132-137.

Smith et al., Increased Placental Apoptosis in Intrauterine Growth Restriction, American Journal of Obstetrics and Gynecology, vol. 177, No. 6, Dec. 1997, pp. 1395-1401.

Stevens et al., A Novel CRISPR/Cas9 Associated Technology for Sequence-specific Nucleic Acid Enrichment, PLOS One, vol. 14, No. 4, Apr. 18, 2019, 12 pages.

Stoiber et al., De novo Identification of DNA Modifications Enabled by Genome-Guided Nanopore Signal Processing, bioRxiv preprint, Available Online at: https://doi.org/10.1101/094672, Apr. 10, 2017, 28 pages.

Sun et al., Orientation-Aware Plasma Cell-Free DNA Fragmentation Analysis in Open Chromatin Regions Informs Tissue of Origin, Genome Research, vol. 29, No. 3, Mar. 2019, pp. 418-427.

Sun et al., Plasma DNA Tissue Mapping by Genome-Wide Methylation Sequencing for Noninvasive Prenatal, Cancer, and Transplantation Assessments, Proceedings of the National Academy of Sciences, vol. 112, No. 40, Sep. 21, 2015, pp. E5503-E5512.

Tan et al., Long Fragments Achieve Lower Base Quality in Illumina Paired-end Sequencing, Scientific Reports, vol. 9, No. 2856, Feb. 27, 2019, 7 pages.

Van Den Oever et al., Noninvasive Prenatal Diagnosis of Huntington Disease: Detection of the Paternally Inherited Expanded CAG Repeat in Maternal Plasma, Prenatal Diagnosis, vol. 35, No. 10, Oct. 2015, pp. 945-949.

Van Dijk et al., HELLP Babies Link a Novel lincRNA to the Trophoblast Cell Cycle, The Journal of Clinical Investigation, vol. 122, No. 11, Nov. 2012, pp. 4003-4011.

Vermeulen et al., Sensitive Monogenic Noninvasive Prenatal Diagnosis by Targeted Haplotyping, The American Journal of Human Genetics, vol. 101, No. 3, Sep. 7, 2017, pp. 326-339.

Watson et al., Cas9-based Enrichment and Single-molecule Sequencing for Precise Characterization of Genomic Duplications, Laboratory Investigation, vol. 100, No. 1, Jul. 4, 2019, pp. 135-146.

Wenger et al., Accurate Circular Consensus Long-read Sequencing Improves Variant Detection and Assembly of a Human Genome, Nature Biotechnology, vol. 37, No. 10, Oct. 2019, pp. 1155-1162.

Yasukochi et al., X Chromosome-wide Analyses of Genomic DNA Methylation States and Gene Expression in Male and Female Neutrophils, Proceedings of the National Academy of Sciences of the U.S.A., vol. 107, No. 8, Feb. 23, 2010, pp. 3704-3709.

Zhang et al., Mass Spectrometry Based Trinucleotide Repeat Sequence Detection Using Target Fragment Assay, Analytical Methods, vol. 8, No. 25, 2016, pp. 5039-5044.

Zheng et al., Nonhematopoietically Derived DNA is Shorter than Hematopoietically Derived DNA in Plasma: A Transplantation Model, Clinical Chemistry, vol. 58, No. 3, Mar. 2012, pp. 549-558.

Examination Report under Section 18(3) dated Aug. 18, 2022 in GB Patent Application No. 2209581.4. 4 pages.

Patent Examination Report No. 1 dated Nov. 15, 2022 in NZ Patent Application No. 790326. 5 pages.

English translation of Office Action dated Dec. 7, 2022 in KR Patent Application No. 10-2022-7027103. 10 pages.

Extended European Search Report dated Jan. 3, 2023 in EP Patent Application No. 21751377.9. 10 pages.

Vong, Joaquim S.L et al.; "Enrichment of fetal and maternal long cell-free DNA fragments from maternal plasma following DNA repair"; Prenatal Diagnosis; Jan. 2019; vol. 39, Issue 2; pp. 88-99.

Examination Report No. 2 dated Jan. 9, 2023 in AU Patent Application No. 2021216616. 4 pages.

* cited by examiner

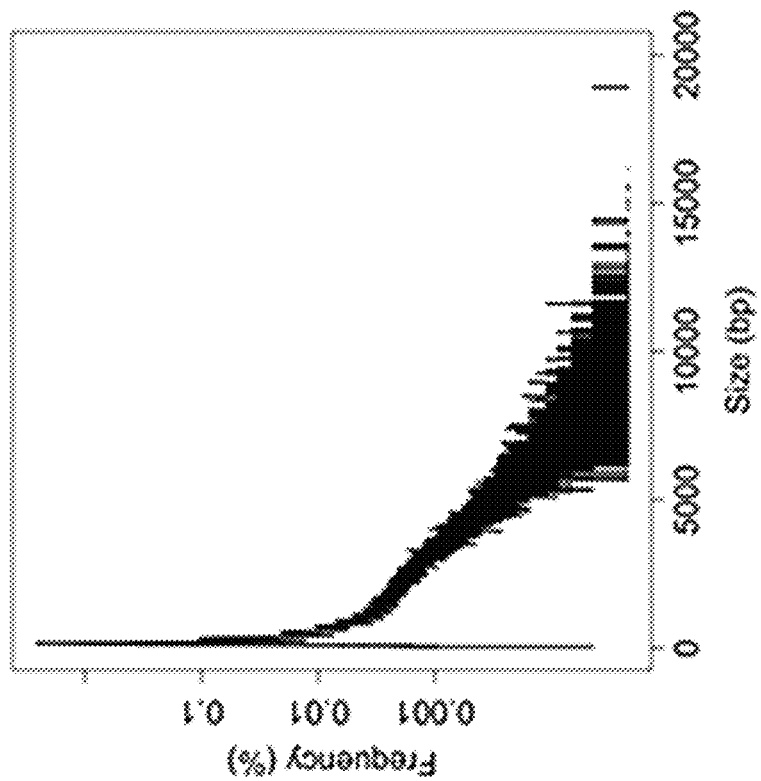
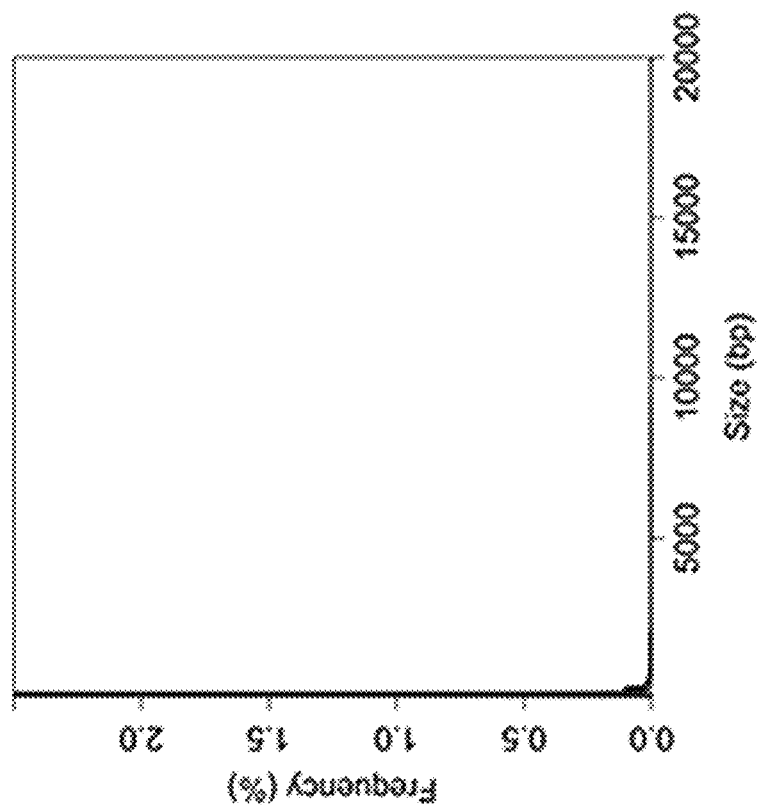
FIG. 1B
FIG. 1A

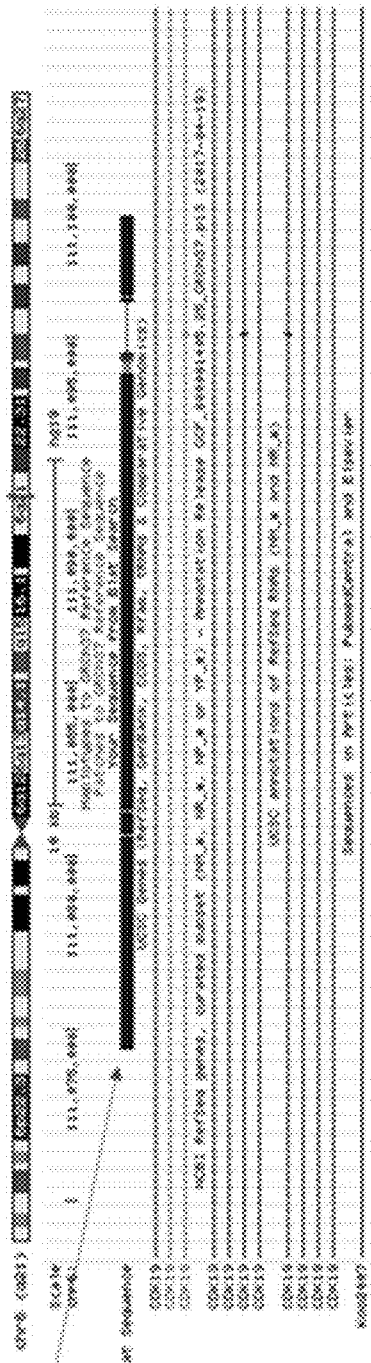

FIG. 12A

| Chr | Well id | The mapping coordinates of | | Length | PacBio SMRT sequence | | | | | | Illumina sequencing of tissue DNA | | |
|---|---|---|---|---|---|---|---|---|---|---|---|---|---|
| | | Start | End | | Fetal-specific alleles | | Sequence information | The number of CpG sites classified as methylated | The number of CpG sites classified as unmethylated | Single-molecule, double-stranded DNA methylation level | Mother genotype | Fetal genotype | Maternal haplotype | Paternal haplotype transmitted to the fetus |
| | | | | | Start | End | | | | | | | | |
| chr6 | 1296448561 | 111074371 | 111098536 | 24165 | 111075831 | 111075832 | A | 81 | 40 | 66.9 | AA | AG | A | G |
| | | | | | 111076442 | 111076443 | G | | | | GG | GT | G | T |
| | | | | | 111076870 | 111076871 | A | | | | AA | AT | A | T |
| | | | | | 111077506 | 111077507 | C | | | | CC | CT | C | T |
| | | | | | 111078649 | 111078650 | T | | | | TT | CT | T | C |
| | | | | | 111079042 | 111079043 | A | | | | AA | GA | A | G |
| | | | | | 111081132 | 111081133 | C | | | | CC | CT | C | T |
| | | | | | 111083336 | 111083337 | G | | | | GG | CG | G | C |
| | | | | | 111084746 | 111084747 | G | | | | GG | TG | G | T |
| | | | | | 111086718 | 111086719 | C | | | | CC | TC | C | T |
| | | | | | 111087391 | 111087392 | A | | | | AA | AT | A | T |
| | | | | | 111088191 | 111088192 | C | | | | CC | CA | C | A |
| | | | | | 111091243 | 111091244 | C | | | | CC | TC | C | T |
| | | | | | 111093070 | 111093071 | T | | | | TT | TC | T | C |
| | | | | | 111093763 | 111093764 | A | | | | AA | GA | A | G |
| | | | | | 111097401 | 111097402 | T | | | | TT | CT | T | C |
| | | | | | 111097556 | 111097557 | C | | | | CC | CG | C | G |
| | | | | | 111098297 | 111098298 | A | | | | AA | CA | A | C |

Sequencing a plurality of cell-free nucleic acid molecules, where over 20% of the plurality of the cell-free nucleic acid molecules sequenced have lengths greater than 200 nt —— 2010

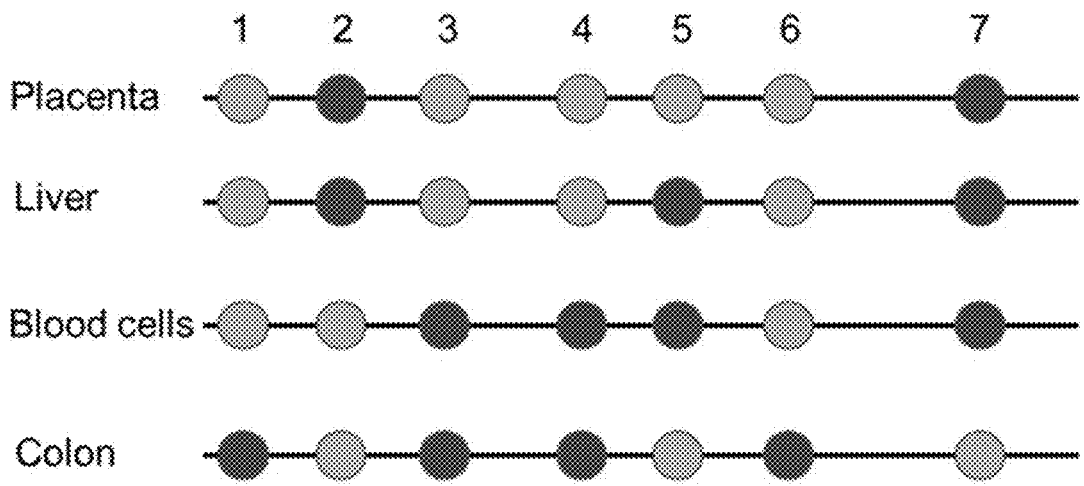
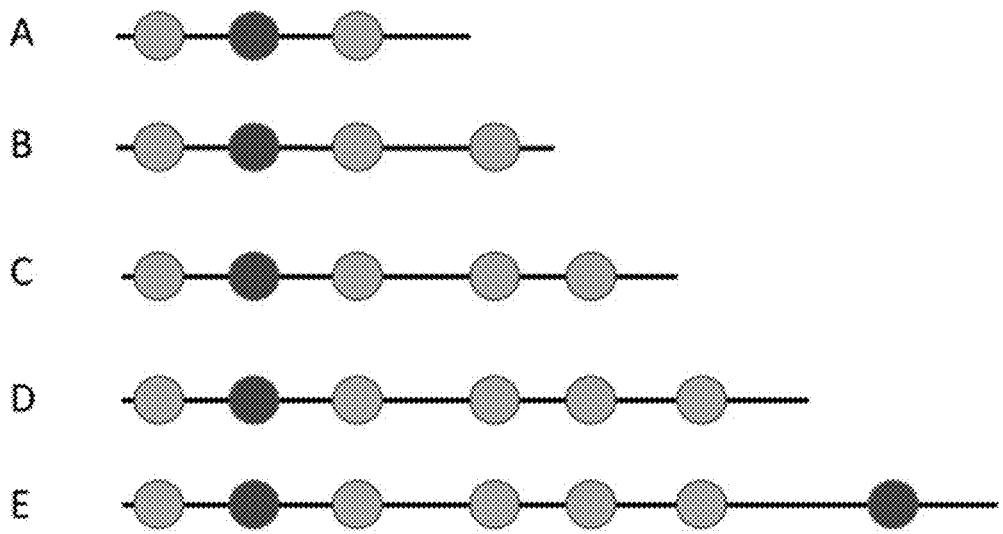
FIG. 22

| Chromosome | Number of marker regions |
|---|---|
| 1 | 22418 |
| 2 | 20311 |
| 3 | 14559 |
| 4 | 15700 |
| 5 | 15363 |
| 6 | 12758 |
| 7 | 15108 |
| 8 | 15172 |
| 9 | 11742 |
| 10 | 13914 |
| 11 | 13545 |
| 12 | 13697 |
| 13 | 10449 |
| 14 | 9523 |
| 15 | 7132 |
| 16 | 13962 |
| 17 | 11177 |
| 18 | 8186 |
| 19 | 15622 |
| 20 | 8264 |
| 21 | 5960 |
| 22 | 7004 |

*FIG. 25*

| Percentage of buffy coat DNA molecules having a mismatch score of greater than 0.3 (%) | | Classification based on the single-molecule methylation pattern | | Percentage of DNA molecules with correct classification (%) |
|---|---|---|---|---|
| | | Placenta-specific | Not specific for placenta | |
| > 60 | Plasma DNA molecules covering a fetal-specific allele | 24 | 17 | 58.5 |
| | Plasma DNA molecules covering a maternal-specific allele | 63 | 597 | 90.5 |
| > 70 | Plasma DNA molecules covering a fetal-specific allele | 23 | 14 | 62.2 |
| | Plasma DNA molecules covering a maternal-specific allele | 53 | 550 | 91.2 |
| > 75 | Plasma DNA molecules covering a fetal-specific allele | 20 | 13 | 60.6 |
| | Plasma DNA molecules covering a maternal-specific allele | 45 | 493 | 91.6 |
| > 80 | Plasma DNA molecules covering a fetal-specific allele | 17 | 11 | 60.7 |
| | Plasma DNA molecules covering a maternal-specific allele | 34 | 433 | 92.7 |
| > 85 | Plasma DNA molecules covering a fetal-specific allele | 14 | 11 | 56.0 |
| | Plasma DNA molecules covering a maternal-specific allele | 21 | 342 | 94.2 |
| > 90 | Plasma DNA molecules covering a fetal-specific allele | 9 | 7 | 56.3 |
| | Plasma DNA molecules covering a maternal-specific allele | 10 | 209 | 95.4 |

*FIG. 26*

```
┌─────────────────────────┐
│   Cell-free DNA in a    │
│    pregnant woman       │
└─────────────────────────┘
            ↓
┌─────────────────────────┐
│  Single molecule real-  │
│    time sequencing      │
└─────────────────────────┘
            ↓
┌─────────────────────────┐
│    Long plasma DNA      │
│       molecules         │
└─────────────────────────┘
            ↓
┌─────────────────────────────────────────┐
│   Methylation haplotype deduction       │
└─────────────────────────────────────────┘
            ↓
┌─────────────────────────────────────────┐
│   The fetal inheritance analysis        │
│ according to the placenta-specific      │
│      methylation haplotype              │
└─────────────────────────────────────────┘
```

FIG. 27 chrX: 143,782,435 - 143,782,707
Methylation profile of placenta tissue (BS-seq) 
Methylation pattern of a plasma DNA 
Methylation profile of buffy coat tissue (BS-seq) 
FIG. 34

| No. of CpG sites | No. of regions | Proportion (%) |
|---|---|---|
| ≥1 CpG sites | 5,333,526 | 86.14 |
| ≥2 CpG sites | 4,534,728 | 73.24 |
| ≥3 CpG sites | 3,604,867 | 58.22 |
| ≥4 CpG sites | 2,782,129 | 44.94 |
| ≥5 CpG sites | 2,141,548 | 34.59 |
| ≥6 CpG sites | 1,668,019 | 26.94 |
| ≥7 CpG sites | 1,317,812 | 21.28 |
| ≥8 CpG sites | 1,052,634 | 17.00 |
| ≥9 CpG sites | 847,632 | 13.69 |
| ≥10 CpG sites | 685,932 | 11.08 |

*FIG. 35*

| No. of CpG sites | No. of regions | Proportion (%) |
|---|---|---|
| ≥1 CpG sites | 2,837,927 | 91.67 |
| ≥2 CpG sites | 2,752,954 | 88.93 |
| ≥3 CpG sites | 2,587,701 | 83.59 |
| ≥4 CpG sites | 2,353,438 | 76.02 |
| ≥5 CpG sites | 2,085,412 | 67.37 |
| ≥6 CpG sites | 1,817,052 | 58.70 |
| ≥7 CpG sites | 1,570,860 | 50.74 |
| ≥8 CpG sites | 1,356,211 | 43.81 |
| ≥9 CpG sites | 1,173,199 | 37.90 |
| ≥10 CpG sites | 1,018,695 | 32.91 |

*FIG. 36*

| No. of CpG sites | No. of regions | Proportion (%) |
|---|---|---|
| ≥1 CpG sites | 953,995 | 92.45 |
| ≥2 CpG sites | 953,934 | 92.45 |
| ≥3 CpG sites | 953,690 | 92.42 |
| ≥4 CpG sites | 953,021 | 92.36 |
| ≥5 CpG sites | 951,431 | 92.20 |
| ≥6 CpG sites | 948,049 | 91.87 |
| ≥7 CpG sites | 941,929 | 91.28 |
| ≥8 CpG sites | 932,143 | 90.33 |
| ≥9 CpG sites | 918,007 | 88.96 |
| ≥10 CpG sites | 898,679 | 87.09 |

*FIG. 37*

| Sample | Hematopoietic cell contribution (%) | Liver contribution (%) | Placental contribution (%) |
|---|---|---|---|
| M13323 | 59.31 | 12.1 | 28.6 |
| M13324 | 53.12 | 14.61 | 32.27 |
| M13315 | 55.15 | 16.16 | 28.69 |
| M13318 | 57.26 | 14.28 | 28.47 |
| M13211 | 55.4 | 15.58 | 29.02 |
| M13230 | 49.41 | 18.51 | 32.09 |
| M13304 | 55.03 | 14.57 | 30.39 |
| M13199 | 55.86 | 13.55 | 30.59 |
| M13198 | 57.72 | 12.46 | 29.82 |

*FIG. 38*

|  | Proportion of DNA molecules > 500 bp (%) | Proportion of DNA molecules > 1 kb (%) |
|---|---|---|
| First trimester maternal plasma | 15.8 | 11.3 |
| Second trimester maternal plasma | 16.1 | 10.6 |
| Third trimester maternal plasma | 32.3 | 21.4 |

*FIG. 42*

| | Proportion of fetal DNA molecules > 500 bp (%) | Proportion of maternal DNA molecules > 500 bp (%) | Proportion of fetal DNA molecules > 1 kb (%) | Proportion of maternal DNA molecules > 1 kb (%) |
|---|---|---|---|---|
| First trimester maternal plasma | 19.8 | 65.6 | 15.2 | 59.0 |
| Second trimester maternal plasma | 23.2 | 62.6 | 16.5 | 53.9 |
| Third trimester maternal plasma | 31.7 | 76.2 | 19.9 | 64.3 |

FIG. 45

| Base end | Expected proportion for an end species | First trimester maternal plasma | | Second trimester maternal plasma | | Third trimester maternal plasma | |
|---|---|---|---|---|---|---|---|
| | | Observed proportion of an end species among fragments ≤ 500 bp | Observed proportion of an end species among fragments > 500 bp | Observed proportion of an end species among fragments ≤ 500bp | Observed proportion of an end species among fragments > 500 bp | Observed proportion of an end species among fragments ≤ 500bp | Observed proportion of an end species among fragments > 500 bp |
| A-end | 29.5 | 19.8 | 29.6 | 19.4 | 26.0 | 19.3 | 26.7 |
| T-end | 29.5 | 22.4 | 13.9 | 23.3 | 16.9 | 24.1 | 16.4 |
| C-end | 20.5 | 30.4 | 25.5 | 30.4 | 27.5 | 31.3 | 27.1 |
| G-end | 20.5 | 27.4 | 31.0 | 26.9 | 29.5 | 25.3 | 29.9 |

FIG. 48

| Base end | Expected end-base proportions | First trimester maternal plasma | | Second trimester maternal plasma | | Third trimester maternal plasma | |
|---|---|---|---|---|---|---|---|
| | | End-base proportions among fragments ≤ 500 bp | End-base proportions among fragments > 500 bp | End-base proportions among fragments ≤ 500bp | End-base proportions among fragments > 500 bp | End-base proportions among fragments ≤ 500bp | End-base proportions among fragments > 500 bp |
| A-end | 29.5 | 18.3 | 30.5 | 19.7 | 25.7 | 18.4 | 22.9 |
| T-end | 29.5 | 24.2 | 14.7 | 23.2 | 16.0 | 23.0 | 17.7 |
| C-end | 20.5 | 31.1 | 24.9 | 29.7 | 28.5 | 31.8 | 29.0 |
| G-end | 20.5 | 26.4 | 29.9 | 27.4 | 29.8 | 26.9 | 30.5 |

FIG. 49

| Base end | Expected end-base proportions | First trimester maternal plasma | | Second trimester maternal plasma | | Third trimester maternal plasma | |
|---|---|---|---|---|---|---|---|
| | | End-base proportions among fragments ≤ 500 bp | End-base proportions among fragments > 500 bp | End-base proportions among fragments ≤ 500 bp | End-base proportions among fragments > 500 bp | End-base proportions among fragments ≤ 500 bp | End-base proportions among fragments > 500 bp |
| A-end | 29.5 | 19.3 | 32.4 | 19.4 | 28.1 | 19.6 | 29.0 |
| T-end | 29.5 | 22.0 | 11.4 | 23.0 | 15.1 | 22.2 | 13.5 |
| C-end | 20.5 | 31.2 | 24.4 | 31.1 | 26.6 | 31.4 | 26.0 |
| G-end | 20.5 | 27.5 | 31.8 | 26.6 | 30.2 | 26.9 | 31.5 |

FIG. 50

| Motif | Rank in short fragments (≤ 500 bp) | Rank in long fragments (> 500 bp) | Frequency in short fragments (%) (A) | Frequency in long fragments (%) (B) | Fold change (A/B) |
|---|---|---|---|---|---|
| CCCA | 1 | 16 | 2.12 | 1.15 | 1.84 |
| CCTG | 2 | 17 | 1.67 | 1.10 | 1.52 |
| CCAG | 3 | 29 | 1.46 | 0.74 | 1.98 |
| CCTC | 4 | 7 | 1.35 | 1.43 | 0.94 |
| CCTT | 5 | 3 | 1.31 | 1.96 | 0.67 |
| CCAA | 6 | 30 | 1.26 | 0.74 | 1.70 |
| AAAA | 7 | 28 | 1.23 | 0.74 | 1.66 |
| CCAC | 8 | 38 | 1.07 | 0.68 | 1.57 |
| CCCT | 9 | 23 | 1.04 | 0.87 | 1.19 |
| GCCT | 10 | 10 | 1.03 | 1.29 | 0.80 |
| CCAT | 11 | 27 | 0.98 | 0.75 | 1.31 |
| GCCA | 12 | 33 | 0.97 | 0.72 | 1.35 |
| CCCC | 13 | 51 | 0.97 | 0.59 | 1.64 |
| GCTG | 14 | 19 | 0.97 | 1.01 | 0.95 |
| GGAG | 15 | 72 | 0.95 | 0.46 | 2.07 |
| GGAA | 16 | 49 | 0.93 | 0.61 | 1.52 |
| CAAA | 17 | 58 | 0.92 | 0.55 | 1.67 |
| GAAA | 18 | 43 | 0.86 | 0.66 | 1.30 |
| TGTG | 19 | 84 | 0.84 | 0.40 | 2.12 |
| GCTT | 20 | 2 | 0.83 | 2.30 | 0.36 |
| TGTT | 21 | 65 | 0.82 | 0.51 | 1.61 |
| GGCT | 22 | 15 | 0.82 | 1.17 | 0.70 |
| CCTA | 23 | 36 | 0.82 | 0.69 | 1.18 |
| GGTG | 24 | 48 | 0.81 | 0.61 | 1.33 |
| CACA | 25 | 40 | 0.81 | 0.67 | 1.20 |

*FIG. 53*

| Motif | Rank in short fragments (≤ 500 bp) | Rank in long fragments (> 500 bp) | Frequency in short fragments (%) (A) | Frequency in long fragments (%) (B) | Fold change (A/B) |
|---|---|---|---|---|---|
| CCCA | 1 | 4 | 2.12 | 1.49 | 1.42 |
| CCTG | 2 | 7 | 1.69 | 1.30 | 1.30 |
| CCAG | 3 | 13 | 1.49 | 1.03 | 1.44 |
| CCTC | 4 | 5 | 1.28 | 1.33 | 0.96 |
| CCTT | 5 | 2 | 1.28 | 1.73 | 0.74 |
| CCAA | 6 | 16 | 1.26 | 0.97 | 1.31 |
| AAAA | 7 | 26 | 1.26 | 0.84 | 1.50 |
| CCAC | 8 | 28 | 1.07 | 0.82 | 1.31 |
| CCCT | 9 | 19 | 1.06 | 0.92 | 1.15 |
| CCAT | 10 | 22 | 1.00 | 0.88 | 1.14 |
| GCCT | 11 | 8 | 0.99 | 1.16 | 0.85 |
| GGAG | 12 | 46 | 0.97 | 0.63 | 1.54 |
| CCCC | 13 | 38 | 0.97 | 0.68 | 1.42 |
| GCCA | 14 | 25 | 0.97 | 0.86 | 1.12 |
| CAAA | 15 | 35 | 0.95 | 0.71 | 1.34 |
| GCTG | 16 | 14 | 0.94 | 1.01 | 0.93 |
| GGAA | 17 | 34 | 0.92 | 0.71 | 1.30 |
| GAAA | 18 | 31 | 0.89 | 0.75 | 1.18 |
| TGTG | 19 | 55 | 0.88 | 0.56 | 1.57 |
| TGTT | 20 | 48 | 0.85 | 0.61 | 1.40 |
| CACA | 21 | 32 | 0.82 | 0.75 | 1.09 |
| CCTA | 22 | 29 | 0.82 | 0.78 | 1.04 |
| GCAG | 23 | 47 | 0.81 | 0.62 | 1.32 |
| TGAG | 24 | 75 | 0.81 | 0.45 | 1.79 |
| GGTG | 25 | 40 | 0.80 | 0.66 | 1.21 |

*FIG. 54*

| Motif | Rank in short fragments (≤ 500 bp) | Rank in long fragments (> 500 bp) | Frequency in short fragments (%) (A) | Frequency in long fragments (%) (B) | Fold change (A/B) |
|---|---|---|---|---|---|
| CCCA | 1 | 6 | 2.21 | 1.40 | 1.58 |
| CCTG | 2 | 7 | 1.80 | 1.28 | 1.40 |
| CCAG | 3 | 17 | 1.53 | 0.98 | 1.57 |
| CCTC | 4 | 4 | 1.39 | 1.40 | 0.99 |
| CCTT | 5 | 3 | 1.28 | 1.68 | 0.77 |
| CCAA | 6 | 22 | 1.26 | 0.89 | 1.42 |
| CCAC | 7 | 26 | 1.13 | 0.80 | 1.41 |
| AAAA | 8 | 29 | 1.12 | 0.76 | 1.47 |
| CCCT | 9 | 25 | 1.06 | 0.84 | 1.26 |
| GCCA | 10 | 24 | 1.05 | 0.87 | 1.21 |
| GCCT | 11 | 8 | 1.04 | 1.23 | 0.85 |
| GGAG | 12 | 46 | 1.02 | 0.63 | 1.63 |
| CCCC | 13 | 44 | 1.00 | 0.64 | 1.57 |
| GCTG | 14 | 14 | 0.98 | 1.03 | 0.95 |
| CCAT | 15 | 27 | 0.97 | 0.78 | 1.24 |
| GGAA | 16 | 35 | 0.95 | 0.72 | 1.32 |
| GGCT | 17 | 12 | 0.87 | 1.09 | 0.80 |
| GGTG | 18 | 38 | 0.87 | 0.70 | 1.24 |
| GGCA | 19 | 33 | 0.86 | 0.72 | 1.19 |
| CAAA | 20 | 42 | 0.86 | 0.64 | 1.33 |
| TGTG | 21 | 62 | 0.85 | 0.51 | 1.67 |
| GAAA | 22 | 34 | 0.83 | 0.72 | 1.15 |
| GCTT | 23 | 2 | 0.82 | 1.88 | 0.44 |
| CACA | 24 | 31 | 0.82 | 0.74 | 1.11 |
| CCTA | 25 | 32 | 0.82 | 0.74 | 1.11 |

*FIG. 55*

| Motif | Rank in long fragments (> 500 bp) | Rank in short fragments (≤ 500 bp) | Frequency in long fragments (%) (A) | Frequency in short fragments (%) (B) | Fold change (A/B) |
|---|---|---|---|---|---|
| ACTT | 1 | 39 | 2.99 | 0.63 | 4.76 |
| GCTT | 2 | 20 | 2.30 | 0.83 | 2.76 |
| CCTT | 3 | 5 | 1.96 | 1.31 | 1.50 |
| GTTT | 4 | 40 | 1.77 | 0.63 | 2.82 |
| ACCT | 5 | 56 | 1.48 | 0.56 | 2.63 |
| ACTG | 6 | 53 | 1.47 | 0.57 | 2.57 |
| CCTC | 7 | 4 | 1.43 | 1.35 | 1.06 |
| ACTC | 8 | 76 | 1.34 | 0.48 | 2.79 |
| GATT | 9 | 83 | 1.29 | 0.46 | 2.81 |
| GCCT | 10 | 10 | 1.29 | 1.03 | 1.26 |
| CTTT | 11 | 31 | 1.24 | 0.69 | 1.79 |
| AGTT | 12 | 102 | 1.21 | 0.41 | 2.99 |
| CATT | 13 | 32 | 1.21 | 0.69 | 1.75 |
| ACAT | 14 | 75 | 1.17 | 0.48 | 2.42 |
| GGCT | 15 | 22 | 1.17 | 0.82 | 1.43 |
| CCCA | 16 | 1 | 1.15 | 2.12 | 0.54 |
| CCTG | 17 | 2 | 1.10 | 1.67 | 0.66 |
| GGTT | 18 | 36 | 1.09 | 0.65 | 1.69 |
| GCTG | 19 | 14 | 1.01 | 0.97 | 1.05 |
| GCTC | 20 | 49 | 0.99 | 0.58 | 1.70 |
| ATTT | 21 | 139 | 0.98 | 0.30 | 3.23 |
| ACCA | 22 | 43 | 0.97 | 0.61 | 1.60 |
| CCCT | 23 | 9 | 0.87 | 1.04 | 0.84 |
| GAAT | 24 | 34 | 0.82 | 0.67 | 1.23 |
| CTTC | 25 | 80 | 0.81 | 0.47 | 1.74 |

*FIG. 56*

| Motif | Rank in long fragments (> 500 bp) | Rank in short fragments (≤ 500 bp) | Frequency in long fragments (%) (A) | Frequency in short fragments (%) (B) | Fold change (A/B) |
|---|---|---|---|---|---|
| ACTT | 1 | 64 | 2.01 | 0.54 | 3.75 |
| CCTT | 2 | 5 | 1.73 | 1.28 | 1.35 |
| GCTT | 3 | 29 | 1.68 | 0.76 | 2.20 |
| CCCA | 4 | 1 | 1.49 | 2.12 | 0.70 |
| CCTC | 5 | 4 | 1.33 | 1.28 | 1.04 |
| GTTT | 6 | 46 | 1.32 | 0.59 | 2.25 |
| CCTG | 7 | 2 | 1.30 | 1.69 | 0.77 |
| GCCT | 8 | 11 | 1.16 | 0.99 | 1.17 |
| ACCT | 9 | 66 | 1.15 | 0.53 | 2.17 |
| ACTG | 10 | 63 | 1.09 | 0.54 | 2.02 |
| CTTT | 11 | 32 | 1.07 | 0.69 | 1.56 |
| CATT | 12 | 31 | 1.05 | 0.69 | 1.52 |
| CCAG | 13 | 3 | 1.03 | 1.49 | 0.69 |
| GCTG | 14 | 16 | 1.01 | 0.94 | 1.07 |
| ACTC | 15 | 94 | 1.00 | 0.43 | 2.32 |
| CCAA | 16 | 6 | 0.97 | 1.26 | 0.77 |
| GGCT | 17 | 26 | 0.96 | 0.79 | 1.21 |
| GATT | 18 | 89 | 0.93 | 0.43 | 2.13 |
| CCCT | 19 | 9 | 0.92 | 1.06 | 0.87 |
| ACAT | 20 | 79 | 0.92 | 0.47 | 1.98 |
| ACCA | 21 | 44 | 0.88 | 0.60 | 1.47 |
| CCAT | 22 | 10 | 0.88 | 1.00 | 0.88 |

*FIG. 57*

| Motif | Rank in long fragments (> 500 bp) | Rank in short fragments (≤ 500 bp) | Frequency in long fragments (%) (A) | Frequency in short fragments (%) (B) | Fold change (A/B) |
|---|---|---|---|---|---|
| ACTT | 1 | 57 | 2.06 | 0.57 | 3.61 |
| GCTT | 2 | 23 | 1.88 | 0.82 | 2.29 |
| CCTT | 3 | 5 | 1.68 | 1.28 | 1.30 |
| CCTC | 4 | 4 | 1.40 | 1.39 | 1.01 |
| GTTT | 5 | 49 | 1.40 | 0.59 | 2.40 |
| CCCA | 6 | 1 | 1.40 | 2.21 | 0.63 |
| CCTG | 7 | 2 | 1.28 | 1.80 | 0.71 |
| GCCT | 8 | 11 | 1.23 | 1.04 | 1.18 |
| ACTG | 9 | 47 | 1.20 | 0.59 | 2.05 |
| ACCT | 10 | 59 | 1.18 | 0.56 | 2.09 |
| ACTC | 11 | 78 | 1.12 | 0.48 | 2.36 |
| GGCT | 12 | 17 | 1.09 | 0.87 | 1.25 |
| CTTT | 13 | 41 | 1.04 | 0.61 | 1.71 |
| GCTG | 14 | 14 | 1.03 | 0.98 | 1.05 |
| CATT | 15 | 34 | 1.00 | 0.64 | 1.57 |
| GATT | 16 | 92 | 0.99 | 0.43 | 2.30 |
| CCAG | 17 | 3 | 0.98 | 1.53 | 0.64 |
| GGTT | 18 | 33 | 0.95 | 0.64 | 1.49 |
| ACAT | 19 | 80 | 0.92 | 0.46 | 1.99 |
| GCTC | 20 | 40 | 0.92 | 0.61 | 1.50 |
| AGTT | 21 | 115 | 0.91 | 0.37 | 2.46 |
| CCAA | 22 | 6 | 0.89 | 1.26 | 0.70 |

*FIG. 58*

| Case number | Gestational age at blood sampling (week) | Fetal sex | Clinical information |
|---|---|---|---|
| M12804 | 34 3/7 | F | Severe PET with pre-existing IgA nephropathy |
| M12873 | 37 | M | Chronic hypertension with superimposed mild PET |
| M12876 | 36 | F | Severe late-onset PET |
| M12903 | 35 5/7 | M | Severe late-onset PET with IUGR |

*FIG. 62*

| Repeat expansion related diseases | Repeat types | No. of repeats in normal subjects | No. of repeats in diseased subjects | Genetic locations related to repeats | Gene names | Patterns of inheritance |
|---|---|---|---|---|---|---|
| Spinocerebellar Ataxia 1 | CAG | 6-39 | 41-83 | CDS | ataxin 1 | autosomal dominant |
| Spinocerebellar Ataxia 2 | CAG | <31 | 33-200 | CDS | ataxin 2 | autosomal dominant |
| Spinocerebellar Ataxia 3 | CAG | <44 | 52-86 | CDS | ataxin 3 | autosomal dominant |
| Spinocerebellar Ataxia 6 | CAG | <18 | 20-33 | CDS | calcium channel, voltage-dependent, P/Q type, alpha 1A subunit | autosomal dominant |
| Spinocerebellar Ataxia 7 | CAG | <28 | >36 | CDS | ataxin 7 | autosomal dominant |
| Spinocerebellar Ataxia 17 | CAG | 25-44 | 47-63 | CDS | TATA box binding protein | autosomal dominant |
| Spinal and Bulbar Muscular Atrophy | CAG | <34 | >38 | CDS | androgen receptor | x-linked recessive |
| Dentatorubral-Pallidoluysian Atrophy, Naito-Oyanagi Disease | CAG | 6-35 | 49-88 | CDS | atrophin 1 | autosomal dominant |
| Huntington Disease | CAG | 9-29 | 36-121 | CDS | huntingtin | autosomal dominant |
| Spinocerebellar Ataxia 8 | CAG | 15-50 | 71-1300 | CDS | Ataxin 8 | autosomal dominant |
| Spastic Paraplegia 4, Autosomal Dominant | CAG | <16 | >60 | CDS | spastin | autosomal dominant |
| Epiphyseal Dysplasia, Multiple, 1 | GAC | 5 | 6-7 | CDS | cartilage oligomeric matrix protein | Autosomal dominant |
| Vacterl Association, X-linked, with or without Hydrocephalus | GCC | 10 | 12 | CDS | Zic family member 3 | x-linked recessive x-linked recessive |
| Neuropathy, Hereditary Sensory and Autonomic, Type VIII | GCC | 12 | 18-19 | CDS | PR/SET domain 12 | autosomal recessive |
| Oculopharyngeal Muscular Dystrophy | GCG | 10 | 12-17 | CDS | poly(A) binding protein, nuclear 1 | autosomal dominant |
| Synpolydactyly 1 | GCG | 15 | 22-29 | CDS | homeobox D13 | autosomal dominant |
| Hand-Foot-Genital Syndrome | GCG | 18 | 24-26 | CDS | homeobox A13 | autosomal dominant |
| Epileptic Encephalopathy, Early Infantile, 1 | GCG | 10-16 | 17-23 | CDS | aristaless related homeobox | x-linked recessive |
| Partington X-Linked Mental Retardation Syndrome | GCG | N/A | 24-bp duplication | CDS | aristaless related homeobox | x-linked recessive |
| Central Hypoventilation Syndrome, Congenital | GCG | 20 | 24-33 | CDS | paired-like homeobox 2b | autosomal dominant |
| Holoprosencephaly 5 | GCG | 15 | 25 | CDS | Zic family member 2 | autosomal dominant |

*FIG. 81*

| Repeat expansion related diseases | Repeat types | No. of repeats in normal subjects | No. of repeats in diseased subjects | Genetic locations related to repeats | Gene names | Patterns of inheritance |
|---|---|---|---|---|---|---|
| Blepharophimosis, Ptosis, and Epicanthus Inversus Syndrome | GCG | 14 | 22-24 | CDS | forkhead box L2 | autosomal dominant |
| Cleidocranial Dysplasia | GCN | 17 | 27 | CDS | runt-related transcription factor 2 | autosomal dominant |
| Mental Retardation, X-linked | GCN | 11 | 15-26 | CDS | SRY-box 3 | x-linked recessive |
| Spinocerebellar Ataxia 12 | CAG | 7-32 | 51-78 | 5' UTR | protein phosphatase 2, regulatory subunit B, beta | autosomal dominant |
| Myoclonic Epilepsy of Unverricht and Lundborg | CCCCGCCCCGCG | 2-3 | 30-75 | 5' UTR | cystatin B | autosomal recessive |
| Mental Retardation, X-Linked, Associated with Fragile Site Fraxe | CGG | 4-39 | >200 | 5' UTR | AF4/FMR2 family member 2 | x-linked recessive |
| Jacobsen Syndrome | CCG | 11 | >100 | 5' UTR | Cbl proto-oncogene | isolated cases |
| Fragile X Tremor/ataxia Syndrome | CGG | <55 | >200 | 5' UTR | fragile X mental retardation 1 | x-linked dominant |
| Fragile X Mental Retardation Syndrome | CGG | 6-52 | 231-2000 | 5' UTR | fragile X mental retardation 1 | X-linked dominant |
| Premature Ovarian Failure 1 | CGG | 7-40 | 55-200 45-54 | 5' UTR | FMR1 fragile X mental retardation 1 | x-linked inheritance |
| Mental retardation, FRA12A type | CGG | 12-26 | >150 | 5' UTR | DIP2 disco-interacting protein 2 homolog B | autosomal dominant |
| Oculopharyngodistal Myopathy | CGG | 13-45 | >51 | 5' UTR | LDL receptor related protein 12 | autosomal dominant |
| Oculopharyngeal Myopathy with Leukoencephalopathy | CGG | 11-16 | >52 | 5' UTR | NOTCH2NLC | autosomal dominant |
| Robin Sequence with Cleft Mandible and Limb Anomalies | CACA/CGCA | 3-12 | 14-16 | 5' UTR | eukaryotic translation initiation factor 4A3 | autosomal recessive |
| Myotonic Dystrophy 1 | CTG | 5-37 | 50-5,000 | 3' UTR | DM1 protein kinase | autosomal dominant |
| Huntington Disease-Like 2 | CTG | 6-28 | >41 | 3' UTR | junctophilin 3 | autosomal dominant |
| Oculopharyngeal Myopathy with Leukoencephalopathy | CGG | <7 | >37 | exon | NUTM2B-AS1 | autosomal dominant |
| Spinocerebellar Ataxia 8 | CTG | 15-34 | 90-250 | exon | ATXN8 opposite strand | autosomal dominant |
| Spinocerebellar Ataxia 10 | ATTCT | 10-29 | 400-4500 | intron 9 | ataxin 10 | autosomal dominant |
| Spinocerebellar Ataxia 37 | ATTTC | <30 | 46-71 | intron 11 | DAB1; reelin adaptor protein | autosomal dominant |
| Myotonic Dystrophy 2 | CCTG | <30 | 75-11,000 | intron 1 | CCHC-type zinc finger nucleic acid binding protein | autosomal dominant |

*FIG. 82*

| Repeat expansion related diseases | Repeat types | No. of repeats in normal subjects | No. of repeats in diseased subjects | Genetic locations related to repeats | Gene names | Patterns of inheritance |
|---|---|---|---|---|---|---|
| Fuchs Endothelial Corneal Dystrophy | CTG | <40 | >50 | intron 3 | transcription factor 4 | autosomal dominant |
| Duchenne Muscular Dystrophy | GAA | 11-33 | 59-82 | intron 62 | dystrophin | x-linked recessive |
| Friedreich Ataxia 1 | GAA | 5-30 | >70 | intron 1 | frataxin | autosomal recessive |
| Spinocerebellar Ataxia 36 | GGCCTG | 3-14 | 650-2500 | intron 4 | NOP56 ribonucleoprotein | autosomal dominant |
| Frontotemporal Degeneration and Amyotrophic Lateral Sclerosis | GGGGCC | 2-19 | 250-1600 | intron 1 | chromosome 9 open reading frame 72 | autosomal dominant |
| Spinocerebellar Ataxia 31 | TGGAA | 26 | 2.5–3.8 kb | intron 1 | brain expressed, associated with NEDD4, 1 | autosomal dominant |
| Familial Adult Myoclonic Epilepsy-1 | TTTCA/TTTTA | 7-20 | 440-3680 | intron | sterile alpha motif domain containing 12 | autosomal dominant |
| Benign Adult Familial Myoclonic Epilepsy 6 | TTTTA/TTTCA | 18 | >22 | intron | Trinucleotide repeat containing 6A | autosomal dominant |
| Benign Adult Familial Myoclonic Epilepsy 7 | TTTTA/TTTCA | 12 | >22 | intron | Rap guanine nucleotide exchange factor 2 | autosomal dominant |

*FIG. 83*

| Repeat types | Repeat unit | Genomic locations | Reference bases | Paternal genotypes (Allele 1 / Allele 2) | Maternal genotypes (Allele 1 / Allele 2) | Fetal genotypes (Allele 1 / Allele 2) | Fetal DNA methylation level linked to paternal alleles (%) | Fetal DNA methylation level linked to maternal alleles (%) |
|---|---|---|---|---|---|---|---|---|
| 1 bp | A | chr1:244287246-244287247 | C | C(A)₂₆/C(A)₂₅ | C/C | C(A)₂₆/C | 51.06 | 45.83 |
| 1 bp | T | chr2:831609-831610 | C | C(T)₂₂/C(T)₂₁ | C/C | C(T)₂₂/C | 52.15 | 52.46 |
| 2 bp | TG | chr1:195547268-195547269 | C | C(TG)₆/C(TG)₇ | C/C(TG)₇ | C(TG)₆/C(TG)₇ | 55.67 | 64.08 |
| 2 bp | TG | chr11:248418036-248418037 | C(TG)₆ | C/C | C(TG)₇/C(TG)₆ | C/C(TG)₆ | 35.57 | 31.91 |
| 2 bp | AC | chr18:64408776-64408777 | A(AC)₇ | A/A | A(AC)₆/A(AC)₅ | A/A(AC)₆ | 43.26 | 44.92 |
| 3 bp | AAT | chr22:24222276-42422277 | A(AAT)₃ | A(AAT)₄/A(AAT)₅ | A/A | A(AAT)₄/A | 79.78 | 82.43 |
| 4 bp | TAAA | chr4:73237157-73237158 | G(TAAA)₅ | G/G | G(TAAA)₄/G(TAAA)₃ | G/G(TAAA)₃ | 62.84 | 95.65 |
| 4 bp | GATA | chr3:192384705-192384706 | T(GATA)₅ | T(GATA)₆/T(GATA)₄ | T/T | T(GATA)₅/T | 50.98 | 62.9 |

*FIG. 84*

| Samples | Groups | No. of sequenced molecules | Mean subread depths (x) | Median fragment sizes (bp) | Proportion of fragments ≥500 bp (%) |
|---|---|---|---|---|---|
| 299 | Without size selection | 2,525,216 | 91 | 176 | 27.3 |
| 300 | Without size selection | 3,057,511 | 67 | 512 | 50.5 |
| B299 | With size selection | 4,103,718 | 18 | 2,463 | 97.6 |
| B300 | With size selection | 1,987,264 | 19 | 2,170 | 97.4 |

FIG. 88

| Sample | Total no. of plasma DNA molecules being analyzed | No. of plasma DNA molecules carrying informative SNPs | Percentage of plasma DNA molecules carrying informative SNPs |
|---|---|---|---|
| Sample 299 (Without size selection) | 1,092,062 | 70,730 | 6.5% |
| Sample B299 (With size selection) | 1,633,040 | 336,539 | 20.6% |

FIG. 91

| Sample | Group | Methylated CpG sites | Unmethylated CpG sites | Methylation level (%) |
|---|---|---|---|---|
| 299 | Without size selection | 600,998 | 268,364 | 69.1 |
| 300 | Without size selection | 934,996 | 413,638 | 69.3 |
| B299 | With size selection (>500 bp) | 1,358,631 | 541,425 | 71.5 |
| B300 | With size selection (>500 bp) | 817,043 | 327,869 | 71.4 |

FIG. 92

| Sample | Group1 | Group2 | Methylated CpG sites | Unmethylated CpG sites | Methylation level (%) |
|---|---|---|---|---|---|
| 299 | Without size selection | Fetal specific plasma DNA molecules | 1,277 | 932 | 57.81 |
| | | Maternal specific plasma DNA molecules | 17,500 | 8,003 | 68.62 |
| B299 | With size selection (>500 bp) | Fetal specific plasma DNA molecules | 2,682 | 1,570 | 63.08 |
| | | Maternal specific plasma DNA molecules | 85,741 | 33,062 | 72.17 |

FIG. 93

| | Without size selection | | | | With size selection | | | |
|---|---|---|---|---|---|---|---|---|
| | M13299 | | M13300 | | B-M13299 | | B-M13300 | |
| Rank | Motif | Frequency (%) | Motif | Frequency (%) | Motif | Frequency (%) | Motif | Frequency (%) |
| 1 | CCCA | 1.76 | ACTT | 1.87 | ACTT | 3.99 | ACTT | 3.37 |
| 2 | CCTG | 1.47 | CCTT | 1.67 | GCTT | 2.73 | GCTT | 2.27 |
| 3 | CCTT | 1.46 | CCCA | 1.66 | CCTT | 2.31 | CCTT | 2.05 |
| 4 | GCTT | 1.41 | GCTT | 1.53 | ACTG | 1.98 | GTTT | 1.80 |
| 5 | CCTC | 1.37 | CCTG | 1.47 | GTTT | 1.88 | ACCT | 1.54 |
| 6 | ACTT | 1.36 | CCTC | 1.27 | ACCT | 1.81 | ACTG | 1.49 |
| 7 | CCAG | 1.19 | GCCT | 1.15 | GGCT | 1.64 | CTTT | 1.42 |
| 8 | GGCT | 1.18 | GTTT | 1.14 | ACAT | 1.59 | ACTC | 1.38 |
| 9 | GCCT | 1.17 | ACCT | 1.14 | CTTT | 1.47 | ATTT | 1.35 |
| 10 | GCTG | 1.05 | CCAG | 1.12 | GATT | 1.46 | ACAT | 1.35 |

*FIG. 94*

| M12970 | | | | |
|---|---|---|---|---|
| Fragment size (bp) | No. of fragments | Frequency (%) | Methylated CpG | Unmethylated CpG | Methylation level (%) |
| ≥500 | 636,828 | 16.63% | 1,247,858 | 698,271 | 64.12% |
| ≥600 | 393,108 | 10.26% | 955,061 | 529,299 | 64.34% |
| ≥1000 | 119,185 | 3.11% | 463,660 | 231,835 | 66.67% |
| ≥2000 | 23,518 | 0.61% | 151,939 | 62,893 | 70.72% |

| M12985 | | | | |
|---|---|---|---|---|
| Fragment size (bp) | No. of fragments | Frequency (%) | Methylated CpG | Unmethylated CpG | Methylation level (%) |
| ≥500 | 201,170 | 7.63% | 644,985 | 346,663 | 65.04% |
| ≥600 | 104,416 | 3.96% | 426,580 | 222,633 | 65.71% |
| ≥1000 | 25,204 | 0.96% | 168,044 | 72,768 | 69.78% |
| ≥2000 | 4,090 | 0.16% | 46,989 | 15,562 | 73.94% |

| M12969 | | | | |
|---|---|---|---|---|
| Fragment size (bp) | No. of fragments | Frequency (%) | Methylated CpG | Unmethylated CpG | Methylation level (%) |
| ≥500 | 590,634 | 12.55% | 1,781,670 | 1,033,066 | 63.30% |
| ≥600 | 350,143 | 7.44% | 1,306,833 | 759,671 | 63.24% |

*FIG. 97*

| Sample | No. of molecules carrying the shared alleles | No. of molecules carrying the fetal-specific alleles | Fetal DNA fraction (%) |
|---|---|---|---|
| M12970 | 84,911 | 17,776 | 34.6% |
| M12985 | 52,059 | 7,385 | 24.9% |
| M12969 | 95,273 | 17,007 | 30.3% |

FIG. 99

| Sample | Fetal-specific DNA | | | Maternal-specific DNA | | |
|---|---|---|---|---|---|---|
| | Methylated CpG | Unmethylated CpG | Methylation level (%) | Methylated CpG | Unmethylated CpG | Methylation level (%) |
| M12970 | 17,340 | 10,434 | 62.43% | 61,268 | 29,770 | 67.30% |
| M12985 | 9,426 | 5,682 | 62.39% | 41,465 | 19,561 | 67.95% |
| M12969 | 26,440 | 16,563 | 61.48% | 94,573 | 45,879 | 67.33% |

| Fragment size (bp) | fetal-specific DNA | | | | | maternal-specific DNA | | | |
|---|---|---|---|---|---|---|---|---|---|
| | No. of fragments | Frequency (%) | Methylated CpG | Unmethylated CpG | Methylation level (%) | No. of fragments | Frequency (%) | Methylated CpG | Unmethylated CpG | Methylation level (%) |
| >=500 | 5328 | 31.2% | 9887 | 5633 | 63.7% | 16464 | 41.2% | 39224 | 19781 | 66.5% |
| >=600 | 3715 | 21.8% | 8366 | 4622 | 64.4% | 11927 | 29.8% | 34222 | 17134 | 66.6% |
| >=1000 | 1596 | 9.3% | 4901 | 2434 | 66.8% | 5693 | 14.2% | 23366 | 10516 | 69.0% |
| >=2000 | 500 | 2.9% | 2003 | 839 | 70.5% | 1793 | 4.5% | 10926 | 4327 | 71.6% |

M12985

| Fragment size (bp) | fetal-specific DNA | | | | | maternal-specific DNA | | | | |
|---|---|---|---|---|---|---|---|---|---|---|
| | No. of fragments | Frequency (%) | Methylated CpG | Unmethylated CpG | Methylation level (%) | No. of fragments | Frequency (%) | Methylated CpG | Unmethylated CpG | Methylation level (%) |
| >=500 | 1261 | 17.6% | 3789 | 2092 | 64.4% | 5132 | 20.4% | 19235 | 9055 | 68.0% |
| >=600 | 749 | 10.4% | 2788 | 1539 | 64.4% | 3157 | 12.5% | 15039 | 6870 | 68.6% |
| >=1000 | 290 | 4.0% | 1502 | 854 | 63.8% | 1193 | 4.7% | 8718 | 3433 | 71.7% |
| >=2000 | 82 | 1.1% | 597 | 433 | 58.0% | 317 | 1.3% | 3448 | 1174 | 74.6% |

M12969

| Fragment size (bp) | fetal-specific DNA | | | | | maternal-specific DNA | | | | |
|---|---|---|---|---|---|---|---|---|---|---|
| | No. of fragments | Frequency (%) | Methylated CpG | Unmethylated CpG | Methylation level (%) | No. of fragments | Frequency (%) | Methylated CpG | Unmethylated CpG | Methylation level (%) |
| >=500 | 4713 | 28.8% | 14412 | 8634 | 62.5% | 14762 | 33.0% | 53302 | 26440 | 66.8% |
| >=600 | 3200 | 19.6% | 11820 | 7188 | 62.2% | 10128 | 22.6% | 44137 | 21631 | 67.1% |
| >=1000 | 1418 | 8.7% | 7283 | 4380 | 62.4% | 4600 | 10.3% | 28579 | 13254 | 68.3% |
| >=2000 | 449 | 2.7% | 3205 | 1594 | 66.8% | 1403 | 3.1% | 13004 | 4950 | 72.4% |

*FIG. 101*

| Sample | Fetal-specific DNA | | | Maternal-specific DNA | | |
|---|---|---|---|---|---|---|
| | Methylated CpG | Unmethylated CpG | Methylation level (%) | Methylated CpG | Unmethylated CpG | Methylation level (%) |
| M12970 | 682 | 522 | 56.64 | 8,634 | 4,001 | 68.33 |
| M12985 | 245 | 177 | 58.06 | 4,175 | 1,680 | 71.31 |
| M12969 | 1,065 | 751 | 58.65 | 13,399 | 6,429 | 67.58 |

FIG. 104

MOLECULAR ANALYSES USING LONG CELL-FREE FRAGMENTS IN PREGNANCY

CROSS-REFERENCES TO RELATED APPLICATIONS

This application is a continuation application of U.S. patent application Ser. No. 17/196,765, filed Mar. 9, 2021, which is a continuation application of U.S. patent application Ser. No. 17/168,950, filed Feb. 5, 2021, which claims the benefit of priority to U.S. Provisional Application No. 63/135,486, filed Jan. 8, 2021, and U.S. Provisional Application No. 62/970,634, filed Feb. 5, 2020, the entire contents of which are incorporated herein for all purposes.

REFERENCE TO A "SEQUENCE LISTING" SUBMITTED AS ASCII TEXT FILES VIA EFS-WEB

The instant application contains a Sequence Listing which has been filed electronically in ASCII format and is hereby incorporated by reference in its entirety. Said ASCII copy, created on May 2, 2022, is named 080015-029730US-1309915_SL.txt and is 120,184 bytes in size.

BACKGROUND

The modal size of circulating cell-free DNA in pregnancy has been reported to be at approximately 166 bp (Lo et al. Sci Transl Med. 2010; 2:61ra91). There are very few published data on fragments larger than 600 bp. One example is the work by Amicucci et al who reported the amplification using PCR of an 8 kb fragment from the basic protein Y2 gene (BPY2) from the Y chromosome from maternal plasma (Amicucci et al. Clin Chem 2000; 40: 301-2). It is not known whether such data can be generalized across the genome. Indeed, there are many challenges for using massively parallel short-read sequencing technologies, e.g. using the Illumina platform, to detect such long DNA fragments, e.g. above 600 bp (Lo et al. Sci Transl Med. 2010; 2:61ra91; Fan et al, Clin Chem. 2010; 56:1278-86). These challenges include: (1) the recommended size range for Illumina sequencing platform typically spans 100-300 bp (De Maio et al. Micob Genom. 2019; 5(9)); (2) DNA amplification would be involved in the sequencing library preparation (via PCR) or sequencing cluster generation via bridge amplification on a flow cell. Such an amplification process may favor amplifying the shorter DNA fragments due partly to the fact that the long DNA templates (e.g. >600 bp) would require a relatively long time to complete the synthesis of the daughter strands compared to the short DNA templates (e.g. <200 bp). Therefore, within a fixed timeframe for these PCR processes prior to or during sequencing on the Illumina platform, those long DNA molecules, whose daughter strands failed to be generated completely during a PCR process, would be not available in the downstream analysis; (3) the long DNA molecule would have higher chance to form secondary structures which would hamper amplification; (4) using Illumina sequencing technology, the long DNA molecules would more likely cause clusters containing more than one clonal DNA molecules, compared to short DNA molecules, as the libraries are denatured, diluted and diffused on the two-dimensional surface followed by bridge amplification (Head et al. Biotechniques. 2014; 56:61-4).

BRIEF SUMMARY

Methods and systems described herein involve using long cell-free DNA fragments to analyze a biological sample. Using these long cell-free DNA fragments allows for analysis not contemplated or not possible with shorter cell-free DNA fragments. The status of methylated CpG sites and single nucleotide polymorphisms (SNPs) is often used to analyze DNA fragments of a biological sample. A CpG site and a SNP are typically separated from the nearest CpG site or SNP by hundreds or thousands of base pairs. The length of most of the cell-free DNA fragments in a biological sample is usually less than 200 bp. As a result, finding two or more consecutive CpG sites or SNPs on most cell-free DNA fragments is improbable or impossible. Cell-free DNA fragments longer than 200 bp, including those longer than 600 bp or 1 kb, may include multiple CpG sites and/or SNPs. The presence of multiple CpG sites and/or SNPs on long cell-free DNA fragments may allow for more efficient and/or accurate analysis than with short cell-free DNA fragments alone. The long cell-free DNA fragments can be used to identify a tissue of origin and/or to provide information on a fetus in a pregnant female. In addition, using long cell-free DNA fragments to accurately analyze samples from pregnant women is surprising as one would expect that such long cell-free DNA fragments are predominantly maternal in origin. One would not expect that long cell-free DNA fragments of fetal origin are present in sufficient amounts to provide information about the fetus.

Long cell-free DNA fragments with a SNP present may be used to determine the haplotype inherited by a fetus. Long cell-free DNA fragments, by having multiple CpG sites, may have a methylation pattern that indicates a tissue of origin. Additionally, trinucleotide repeats and other repeated sequences may be present on long cell-free DNA fragments. These repeats may be used to determine the likelihood of a genetic disorder in fetus or the paternity of a fetus. The amount of long cell-free DNA fragments may be used to determine gestational age. Similarly, the motifs at the end of long cell-free DNA fragments may also be used to determine gestational age. The long-cell free DNA fragments (including, for example, amounts, length distribution, genomic locations, methylation status, etc. of such fragments) may be used to determine a pregnancy-associated disorder.

These and other embodiments of the disclosure are described in detail below. For example, other embodiments are directed to systems, devices, and computer readable media associated with methods described herein.

A better understanding of the nature and advantages of embodiments of the present disclosure may be gained with reference to the following detailed description and the accompanying drawings.

BRIEF DESCRIPTION OF THE DRAWINGS

FIGS. 1A and 1B show the size distribution of cell-free DNA determined according to embodiments of the present invention. (A) 0-20 kb on a linear scale, (B) 0-20 kb on a logarithmic scale.

FIGS. 12A and 12B show an example of a long maternal DNA molecule carrying shared alleles identified in the maternal plasma DNA of a pregnant woman according to embodiments of the present invention. (A) The black bar indicates the long maternal-specific DNA molecule aligned to a region in chromosome 6 of a human reference. (B) The detailed illustration of genetic and epigenetic information determined using PacBio sequencing according to embodiments of the present invention.

Figures 19A, 19B, 19C, 19D, 19E, 19F, 19G:
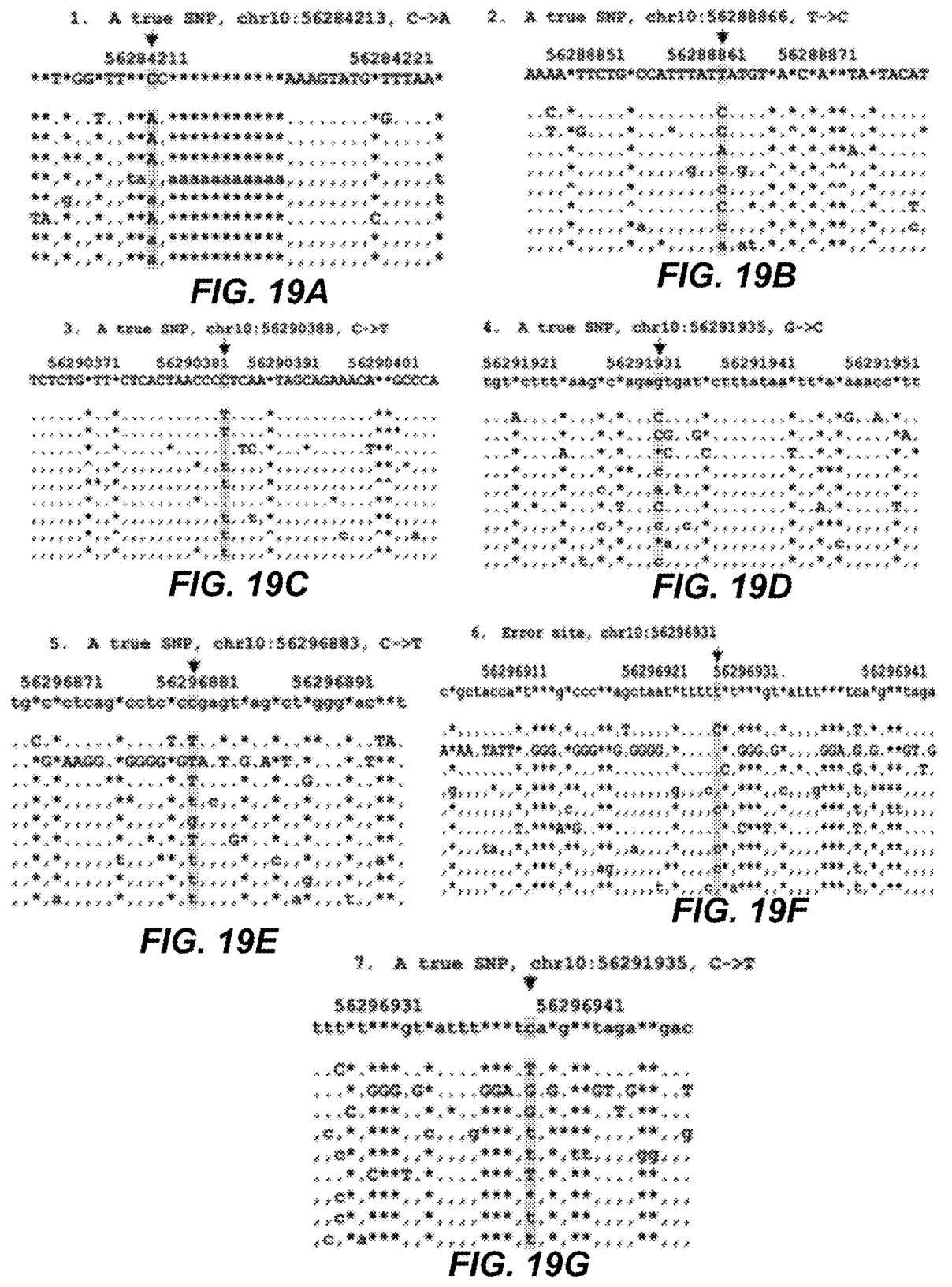

FIGS. 19A-19G show illustrations of error correction of cell-free DNA genotyping using PacBio sequencing according to embodiments of the present invention. A '.' represents a base identical to reference base in the Watson strand. ',' represents a base identical to reference base in the Crick strand. 'Alphabet letter' represents an alternative allele which is different from the reference allele. '*' represents an insertion. '^' represents a deletion. FIGS. 19A-19G disclose SEQ ID NOS 12-79, respectively, in order of appearance by figure.

FIG. 22 shows methylation patterns for determining tissue of origin of a long DNA molecule in plasma according to embodiments of the present invention.

FIG. 25 is a table of the distribution of selected marker regions among different chromosomes according to embodiments of the present invention.

FIG. 26 is a table of the classification of plasma DNA molecules based on their single-molecule methylation patterns using different percentages of buffy coat DNA molecules having a mismatch score of greater than 0.3 as the selection criteria for marker regions according to embodiments of the present invention.

FIG. 27 shows a process flow to use a placenta-specific methylation haplotype to determine the fetal inheritance in a noninvasive manner according to embodiments of the present invention.

FIG. 34 shows a methylation pattern of a plasma DNA compared with methylation profiles of placental and buffy coat DNA according to embodiments of the present invention.

FIG. 35 is a table showing the distribution of CpG sites in a 500-bp region across a human genome according to embodiments of the present invention.

FIG. 36 is a table showing the distribution of CpG sites in a 1-kb region across a human genome according to embodiments of the present invention.

FIG. 37 is a table showing the distribution of CpG sites in a 3-kb region across a human genome according to embodiments of the present invention.

FIG. 38 is a table showing the proportional contributions of DNA molecules from different tissues in maternal plasma using methylation status matching analysis according to embodiments of the present invention.

FIG. 42 is a table showing the proportion of long plasma DNA molecules in different trimesters of pregnancy according to embodiments of the present invention.

FIG. 45 is a table of the proportion of long fetal and maternal plasma DNA molecules in different trimesters of pregnancy according to embodiments of the present invention.

FIG. 48 is a table of the end nucleotide base proportions among short and long cell-free DNA molecules from the first-, second-, and third-trimester maternal plasma according to embodiments of the present invention.

FIG. 49 is a table of the end nucleotide base proportions among short and long cell-free DNA molecules covering a fetal-specific allele from the first-, second-, and third-trimester maternal plasma according to embodiments of the present invention.

FIG. 50 is a table of the end nucleotide base proportions among short and long cell-free DNA molecules covering a maternal-specific allele from the first-, second-, and third-trimester maternal plasma according to embodiments of the present invention.

FIG. 53 is a table of the 25 end motifs with the highest frequencies among short plasma DNA molecules from first-trimester maternal plasma according to embodiments of the present invention.

FIG. 54 is a table of the 25 end motifs with the highest frequencies among short plasma DNA molecules from second-trimester maternal plasma according to embodiments of the present invention.

FIG. 55 is a table of the 25 end motifs with the highest frequencies among short plasma DNA molecules from third-trimester maternal plasma according to embodiments of the present invention.

FIG. 56 is a table of the 25 end motifs with the highest frequencies among long plasma DNA molecules from first-trimester maternal plasma according to embodiments of the present invention.

FIG. 57 is a table of the 25 end motifs with the highest frequencies among long plasma DNA molecules from second-trimester maternal plasma according to embodiments of the present invention.

FIG. 58 is a table of the 25 end motifs with the highest frequencies among long plasma DNA molecules from third-trimester maternal plasma according to embodiments of the present invention.

FIG. 62 is a table showing clinical information of four preeclamptic cases according to embodiments of the present invention.

FIG. 79 discloses "AT(CTG)200AG" as SEQ ID NO: 80 and "GC(CTG)10GA" as SEQ ID NO: 81.

FIG. 80 discloses "GT(CTG)70A" as SEQ ID NO: 82, "AT(CTG)5AG" as SEQ ID NO: 83, and "AT(CTG)6GA" as SEQ ID NO: 84.

FIGS. 81, 82, and 83 are tables showing examples of repeat expansion diseases. FIG. 82 discloses "CCCCGCCCCGCG" as SEQ ID NO: 85.

FIG. 84 is a table showing examples for repeat expansion detection in the fetus and repeat-associated methylation determination according to embodiments of the present invention. FIG. 84 discloses C(A)20 as SEQ ID NO: 86, C(T)22 as SEQ ID NO: 87, C(TG)6 as SEQ ID NO: 88, C(TG)11 as SEQ ID NO: 89, C(TG)5 as SEQ ID NO: 90, G(TAAA)3 as SEQ ID NO: 91, A(AAT)3 as SEQ ID NO: 92, A(AAT)5 as SEQ ID NO: 93, T(GATA)3 as SEQ ID NO: 10, and T(GATA)5 as SEQ ID NO: 11.

FIG. 88 is a table of sequencing information for samples with and without size selection according to embodiments of the present invention.

FIG. 91 is a table of statistics for the number of plasma DNA molecules carrying informative SNPs between samples with and without size selection according to embodiments of the present invention.

FIG. 92 is a table of the methylation level in size-selected and non-size selected plasma DNA samples according to embodiments of the present invention.

FIG. 93 is a table of methylation level in maternal- or fetal-specific cell-free DNA molecules according to embodiments of the present invention.

FIG. 94 is a table of the top 10 end motifs in samples with and without size selection according to embodiments of the present invention.

FIG. 97 is a table of the percentage of the plasma DNA molecules in a particular size range and their corresponding methylation levels according to embodiments of the present invention.

FIG. 99 is a table of the fetal DNA fraction determined using nanopore sequencing according to embodiments of the present invention.

FIG. 100 is a table of the methylation levels between fetal-specific and maternal-specific DNA molecules according to embodiments of the present invention.

FIG. 101 is a table of the percentages of the plasma DNA molecules in a particular size range and their corresponding methylation levels for fetal and maternal DNA molecules according to embodiments of the present invention.

FIG. 104 is a table of the difference in methylation levels between fetal and maternal DNA molecules according to embodiments of the present invention.

TERMS

Figure 2B:
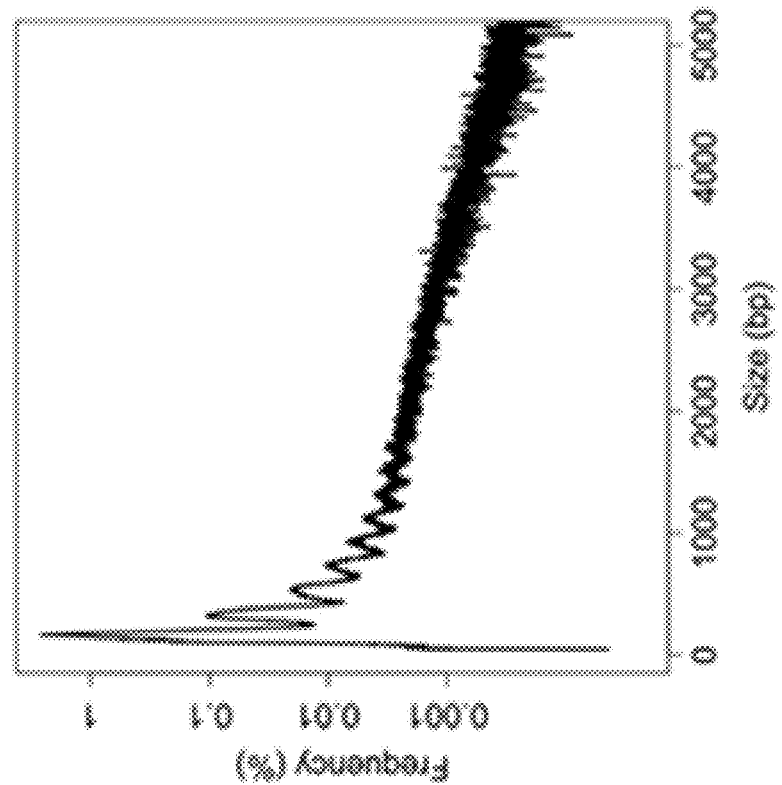
FIGS. 2A and 2B show the size distribution of cell-free DNA determined according to embodiments of the present invention. (A) 0-5 kb on a linear scale for the y-axis. (B) 0-5 kb on a logarithmic scale for the y-axis.

A "tissue" corresponds to a group of cells that group together as a functional unit in a pregnant subject or her fetus. More than one type of cells can be found in a single tissue. Different types of tissue may consist of different types of cells (e.g., hepatocytes, alveolar cells or blood cells), but also may correspond to tissue from different organisms (mother vs. fetus; tissues in a pregnant subject who has received transplantation; tissues of a pregnant organism or its fetus that are infected by a microorganism or a virus). "Reference tissues" can correspond to tissues used to determine tissue-specific methylation levels. Multiple samples of a same tissue type from different pregnant individuals or their fetuses may be used to determine a tissue-specific methylation level for that tissue type.

A "biological sample" refers to any sample that is taken from a pregnant subject (e.g., a human (or other animal), such as a pregnant woman, a person with a disorder, or a pregnant person suspected of having a disorder, a pregnant organ transplant recipient or a pregnant subject suspected of having a disease process involving an organ (e.g., the heart in myocardial infarction, or the brain in stroke, or the hematopoietic system in anemia) and contains one or more nucleic acid molecule(s) of interest. The biological sample can be a bodily fluid, such as blood, plasma, serum, urine, vaginal fluid, vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g. thyroid, breast), intraocular fluids (e.g. the aqueous humor), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells. As part of an analysis of a biological sample, a statistically significant number of cell-free DNA molecules can be analyzed (e.g., to provide an accurate measurement) for a biological sample. In some embodiments, at least 1,000 cell-free DNA molecules are analyzed. In other embodiments, at least 10,000 or 50,000 or 100,000 or 500,000 or 1,000,000 or 5,000,000 cell-free DNA molecules, or more, can be analyzed. At least a same number of sequence reads can be analyzed.

A "sequence read" refers to a string of nucleotides sequenced from any part or all of a nucleic acid molecule. For example, a sequence read may be a short string of nucleotides (e.g., 20-150 nucleotides) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes as may be used in microarrays, or amplification techniques, such as the polymerase chain reaction (PCR) or linear amplification using a single primer or isothermal amplification. As part of an analysis of a biological sample, a statistically significant number of sequence reads can be analyzed, e.g., at least 1,000 sequence reads can be analyzed. As other examples, at least 10,000 or 50,000 or 100,000 or 500,000 or 1,000,000 or 5,000,000 sequence reads, or more, can be analyzed.

A "site" (also called a "genomic site") corresponds to a single site, which may be a single base position or a group of correlated base positions, e.g., a CpG site or larger group of correlated base positions. A "locus" may correspond to a region that includes multiple sites. A locus can include just one site, which would make the locus equivalent to a site in that context.

A "methylation status" refers to the state of methylation at a given site. For example, a site may be either methylated, unmethylated, or in some cases, undetermined.

The "methylation index" for each genomic site (e.g., a CpG site) can refer to the proportion of DNA fragments (e.g., as determined from sequence reads or probes) showing methylation at the site over the total number of reads covering that site. A "read" can correspond to information (e.g., methylation status at a site) obtained from a DNA fragment. A read can be obtained using reagents (e.g.

primers or probes) that preferentially hybridize to DNA fragments of a particular methylation status at one or more sites. Typically, such reagents are applied after treatment with a process that differentially modifies or differentially recognizes DNA molecules depending on their methylation status, e.g. bisulfite conversion, or methylation-sensitive restriction enzyme, or methylation binding proteins, or anti-methylcytosine antibodies, or single molecule sequencing techniques (e.g. single molecule, real-time sequencing and nanopore sequencing (e.g. from Oxford Nanopore Technologies)) that recognize methylcytosines and hydroxymethylcytosines.

The "methylation density" of a region can refer to the number of reads at sites within the region showing methylation divided by the total number of reads covering the sites in the region. The sites may have specific characteristics, e.g., being CpG sites. Thus, the "CpG methylation density" of a region can refer to the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 500 bp, 5 kb, 10 kb, 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" can refer the number of cytosine sites, "C's", that are shown to be methylated (for example unconverted after bisulfite conversion) over the total number of analyzed cytosine residues, i.e. including cytosines outside of the CpG context, in the region. The methylation index, methylation density, count of molecules methylated at one or more sites, and proportion of molecules methylated (e.g., cytosines) at one or more sites are examples of "methylation levels." Apart from bisulfite conversion, other processes known to those skilled in the art can be used to interrogate the methylation status of DNA molecules, including, but not limited to enzymes sensitive to the methylation status (e.g. methylation-sensitive restriction enzymes), methylation binding proteins, single molecule sequencing using a platform sensitive to the methylation status (e.g. nanopore sequencing (Schreiber et al. Proc Natl Acad Sci 2013; 110: 18910-18915) and by single molecule, real-time sequencing (e.g. that from Pacific Biosciences) (Flusberg et al. Nat Methods 2010; 7: 461-465)).

A "methylome" provides a measure of an amount of DNA methylation at a plurality of sites or loci in a genome. The methylome may correspond to all of the genome, a substantial part of the genome, or relatively small portion(s) of the genome.

A "methylation profile" includes information related to DNA or RNA methylation for multiple sites or regions. Information related to DNA methylation can include, but not limited to, a methylation index of a CpG site, a methylation density (MD for short) of CpG sites in a region, a distribution of CpG sites over a contiguous region, a pattern or level of methylation for each individual CpG site within a region that contains more than one CpG site, and non-CpG methylation. In one embodiment, the methylation profile can include the pattern of methylation or non-methylation of more than one type of base (e.g. cytosine or adenine). A methylation profile of a substantial part of the genome can be considered equivalent to the methylome. "DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as $N^6$-methyladenine, has also been reported.

A "methylation pattern" refers to the order of methylated and non-methylated bases. For example, the methylation pattern can be the order of methylated bases on a single DNA strand, a single double-stranded DNA molecule, or another type of nucleic acid molecule. As an example, three consecutive CpG sites may have any of the following methylation patterns: UUU, MMM, UMM, UMU, UUM, MUM, MUU, or MMU, where "U" indicates an unmethylated site and "M" indicates a methylated site. When one extends this concept to base modifications that include, but not restricted to methylation, one would use the term "modification pattern," which refers to the order of modified and non-modified bases. For example, the modification pattern can be the order of modified bases on a single DNA strand, a single double-stranded DNA molecule, or another type of nucleic acid molecule. As an example, three consecutive potentially modifiable sites may have any of the following modification patterns: UUU, MMM, UMM, UMU, UUM, MUM, MUU, or MMU, where "U" indicates an unmodified site and "M" indicates a modified site. One example of base modification that is not based on methylation is oxidation changes, such as in 8-oxo-guanine.

The terms "hypermethylated" and "hypomethylated" may refer to the methylation density of a single DNA molecule as measured by its single molecule methylation level, e.g., the number of methylated bases or nucleotides within the molecule divided by the total number of methylatable bases or nucleotides within that molecule. A hypermethylated molecule is one in which the single molecule methylation level is at or above a threshold, which may be defined from application to application. The threshold may be 5%, 10%, 20%, 30%, 40%, 50%, 60%, 70%, 80%, 90%, or 95%. A hypomethylated molecule is one in which the single molecule methylation level is at or below a threshold, which may be defined from application to application, and which may change from application to application. The threshold may be 5%, 10%, 20%, 30%, 40%, 50%, 60%, 70%, 80%, 90%, or 95%.

The terms "hypermethylated" and "hypomethylated" may also refer to the methylation level of a population of DNA molecules as measured by the multiple molecule methylation levels of these molecules. A hypermethylated population of molecules is one in which the multiple molecule methylation level is at or above a threshold which may be defined from application to application, and which may change from application to application. The threshold may be 5%, 10%, 20%, 30%, 40%, 50%, 60%, 70%, 80%, 90%, or 95%. A hypomethylated population of molecules is one in which the multiple molecule methylation level is at or below a threshold which may be defined from application to application. The threshold may be 5%, 10%, 20%, 30%, 40%, 50%, 60%, 70%, 80%, 90%, and 95%. In one embodiment, the population of molecules may be aligned to one or more selected genomic regions. In one embodiment, the selected genomic region(s) may be related to a disease such as a genetic disorder, an imprinting disorder, a metabolic disorder, or a neurological disorder. The selected genomic region(s) can have a length of 50 nucleotides (nt), 100 nt, 200 nt, 300 nt, 500 nt, 1000 nt, 2 knt, 5 knt, 10 knt, 20 knt, 30 knt, 40 knt, 50 knt, 60 knt, 70 knt, 80 knt, 90 knt, 100 knt, 200 knt, 300 knt, 400 knt, 500 knt, or 1 Mnt.

The term "sequencing depth" refers to the number of times a locus is covered by a sequence read aligned to the locus. The locus could be as small as a nucleotide, or as large as a chromosome arm, or as large as the entire genome. Sequencing depth can be expressed as 50×, 100×, etc., where "×" refers to the number of times a locus is covered with a sequence read. Sequencing depth can also be applied to multiple loci, or the whole genome, in which case × can refer to the mean number of times the loci or the haploid genome, or the whole genome, respectively, is sequenced. Ultra-deep sequencing can refer to at least 100× in sequencing depth.

A "calibration sample" can correspond to a biological sample whose fractional concentration of clinically-relevant DNA (e.g., tissue-specific DNA fraction) is known or determined via a calibration method, e.g., using an allele specific to the tissue, such as in transplantation in a pregnant subject whereby an allele present in the donor's genome but absent in the recipient's genome can be used as a marker for the transplanted organ. As another example, a calibration sample can correspond to a sample from which end motifs can be determined. A calibration sample can be used for both purposes.

A "calibration data point" includes a "calibration value" and a measured or known fractional concentration of the clinically-relevant DNA (e.g., DNA of particular tissue type). The calibration value can be determined from relative frequencies (e.g., an aggregate value) as determined for a calibration sample, for which the fractional concentration of the clinically-relevant DNA is known. The calibration data points may be defined in a variety of ways, e.g., as discrete points or as a calibration function (also called a calibration curve or calibration surface). The calibration function could be derived from additional mathematical transformation of the calibration data points.

A "separation value" corresponds to a difference or a ratio involving two values, e.g., two fractional contributions or two methylation levels. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, e.g., a difference or ratio of the natural logarithms (ln) of the two values. A separation value can include a difference and a ratio.

A "separation value" and an "aggregate value" (e.g., of relative frequencies) are two examples of a parameter (also called a metric) that provides a measure of a sample that varies between different classifications (states), and thus can be used to determine different classifications. An aggregate value can be a separation value, e.g., when a difference is taken between a set of relative frequencies of a sample and a reference set of relative frequencies, as may be done in clustering.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1).

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "size profile" generally relates to the sizes of DNA fragments in a biological sample. A size profile may be a histogram that provides a distribution of an amount of DNA fragments at a variety of sizes. Various statistical parameters (also referred to as size parameters or just parameter) can be used to distinguish one size profile to another. One parameter is the percentage of DNA fragment of a particular size or range of sizes relative to all DNA fragments or relative to DNA fragments of another size or range.

The terms "cutoff" and "threshold" refer to predetermined numbers used in an operation. For example, a cutoff size can refer to a size above which fragments are excluded. A threshold value may be a value above or below which a particular classification applies. Either of these terms can be used in either of these contexts. A cutoff or threshold may be "a reference value" or derived from a reference value that is representative of a particular classification or discriminates between two or more classifications. Such a reference value can be determined in various ways, as will be appreciated by the skilled person. For example, metrics can be determined for two different cohorts of subjects with different known classifications, and a reference value can be selected as representative of one classification (e.g., a mean) or a value that is between two clusters of the metrics (e.g., chosen to obtain a desired sensitivity and specificity). As another example, a reference value can be determined based on statistical analyses or simulations of samples. A particular value for a cutoff, threshold, reference, etc. can be determined based on a desired accuracy (e.g., a sensitivity and specificity).

A "pregnancy-associated disorder" includes any disorder characterized by abnormal relative expression levels of genes in maternal and/or fetal tissue or by abnormal clinical characteristics in the mother and/or fetus. These disorders include, but are not limited to, preeclampsia (Kaartokallio et al. Sci Rep. 2015; 5:14107; Medina-Bastidas et al. Int J Mol Sci. 2020; 21:3597), intrauterine growth restriction (Faxen et al. Am J Perinatol. 1998; 15:9-13; Medina-Bastidas et al. Int J Mol Sci. 2020; 21:3597), invasive placentation, pre-term birth (Enquobahrie et al. BMC Pregnancy Childbirth. 2009; 9:56), hemolytic disease of the newborn, placental insufficiency (Kelly et al. Endocrinology. 2017; 158:743-755), hydrops fetalis (Magor et al. Blood. 2015; 125:2405-17), fetal malformation (Slonim et al. Proc Natl Acad Sci USA. 2009; 106:9425-9), HELLP syndrome (Dijk et al. J Clin Invest. 2012; 122:4003-4011), systemic lupus erythematosus (Hong et al. J Exp Med. 2019; 216:1154-1169), and other immunological diseases of the mother.

The abbreviation "bp" refers to base pairs. In some instances, "bp" may be used to denote a length of a DNA fragment, even though the DNA fragment may be single stranded and does not include a base pair. In the context of single-stranded DNA, "bp" may be interpreted as providing the length in nucleotides.

The abbreviation "nt" refers to nucleotides. In some instances, "nt" may be used to denote a length of a single-stranded DNA in a base unit. Also, "nt" may be used to denote the relative positions such as upstream or downstream of the locus being analyzed. For a double-stranded DNA, "nt" may still refer to the length of a single strand rather than the total number of nucleotides in the two strands, unless context clearly dictates otherwise. In some contexts concerning technological conceptualization, data presentation, processing and analysis, "nt" and "bp" may be used interchangeably.

The term "machine learning models" may include models based on using sample data (e.g., training data) to make predictions on test data, and thus may include supervised learning. Machine learning models often are developed using a computer or a processor. Machine learning models may include statistical models.

The term "data analysis framework" may include algorithms and/or models that can take data as an input and then output a predicted result. Examples of "data analysis frameworks" include statistical models, mathematical models, machine learning models, other artificial intelligence models, and combinations thereof.

The term "real-time sequencing" may refer to a technique that involves data collection or monitoring during progress of a reaction involved in sequencing. For example, real-time sequencing may involve optical monitoring or filming the DNA polymerase incorporating a new base.

The term "subsequence" may refer to a string of bases that is less than the full sequence corresponding to a nucleic acid molecule. For example, a subsequence may include 1, 2, 3, or 4 bases when the full sequence of the nucleic acid molecule includes 5 or more bases. In some embodiments, a subsequence may refer to a string of bases forming a unit where the unit is repeated multiple times in a tandem serial manner. Examples include 3-nt units or subsequences repeated at loci associated with trinucleotide repeat disorders, 1-nt to 6-nt units or subsequences repeated 5 to 50 times as microsatellites, 10-nt to 60-nt units or subsequences repeated 5 to 50 times as minisatellites, or in other genetic elements, such as Alu repeats.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within embodiments of the present disclosure. The upper and lower limits of these smaller ranges may independently be included or excluded in the range, and each range where either, neither, or both limits are included in the smaller ranges is also encompassed within the present disclosure, subject to any specifically excluded limit in the stated range. Where the stated range includes one or both of the limits, ranges excluding either or both of those included limits are also included in the present disclosure.

Standard abbreviations may be used, e.g., bp, base pair(s); kb, kilobase(s); pi, picoliter(s); s or sec, second(s); min, minute(s); h or hr, hour(s); aa, amino acid(s); nt, nucleotide(s); and the like.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the embodiments of the present disclosure, some potential and exemplary methods and materials may now be described.

DETAILED DESCRIPTION

The analysis of cell-free DNA molecules involves predominantly short cell-free DNA fragments, often as a result of limits of analytical techniques. The limited ability to obtain sequence information from long DNA molecules using Illumina sequencing technology was demonstrated in the recent sequencing results of mouse cell-free DNA (Serpas et al., Proc Natl Acad Sci USA. 2019; 116:641-649). Only 0.02% of sequenced DNA molecules were within a range of 600 bp and 2000 bp using Illumina sequencing in wildtype mice. Even using the single-molecule, real-time (SMRT) technology from Pacific Biosciences (i.e., PacBio SMRT sequencing) to sequence the DNA libraries which were originally prepared for Illumina sequencing, there was still only 0.33% of sequenced DNA molecules within a range of 600 bp and 2000 bp. These reported data suggested that the sequencing step would lose 93% of long DNA molecules within a range of 600 bp and 2000 bp present in the original DNA library.

We speculated that the step of DNA library preparation would also lose a considerable proportion of long cell-free DNA molecules because of the limitation of PCR in amplifying long DNA molecules described above. Jahr et al, using gel electrophoresis, reported the presence of large-sized fragments of many kilobases, for example, ~10,000 (Jahr et al. Cancer Res. 2001; 61:1659-65). However, the bands shown in the gel electrophoresis image would not readily provide the sequence information of these molecules in the gel, let alone provide the epigenetic information.

We had previously used the Oxford Nanopore Technologies sequencing platform to study cell-free DNA extracted from maternal plasma (Cheng et al Clin Chem. 2015; 61:1305-6). We observed a very small proportion of long plasma DNA over 1 kb (0.06% to 0.3%). We hypothesized that such a low percentage might be a result of the low sequencing accuracy of this platform.

In this field of cell-free DNA, most of the studies focused on the short DNA molecules (e.g. <600 bp). The properties including genetic and epigenetic information of long cell-free DNA molecules are unexplored. This disclosure provided a systemic way to analyze the long cell-free DNA molecules including decoding their genetic and epigenetic information as well as their clinical utilities in non-invasive prenatal testing, such as, but not limited to, non-invasive detection of single-gene disorders, elucidation of the fetal genome (e.g., noninvasive whole fetal genome sequencing), detection of de novo mutations on a genomewide level, and detection/monitoring of pregnancy-associated disorders such as preeclampsia and preterm labor.

I. Cell-Free DNA Size Analysis

Cell-free DNA samples obtained from pregnant women were sequenced, and a significant portion of the DNA fragments were found to be long. The accurate sequencing of the long cell-free DNA fragments was demonstrated. The size profiles of these long cell-free DNA molecules were analyzed. The amounts of fetal and maternal long cell-free DNA molecules were compared. Long cell-free DNA molecules can be more accurately aligned to a reference genome. The long cell-free DNA molecules can be used for determining haplotype inheritance.

One plasma DNA sample of a pregnant woman at the third trimester was analyzed using PacBio SMRT sequencing. Double-stranded cell-free DNA molecules were ligated with hairpin adaptors and subjected to single-molecule read-time sequencing utilizing zero-mode waveguides and single polymerase molecules (Eid et al. Science. 2009; 323:133-8).

We sequenced 1.1 billion subreads, among which 659.3 million subreads could be aligned to a human reference genome (hg19). The subreads were generated from 4.6 million PacBio Single Molecular Real-Time (SMRT) Sequencing wells which contained at least one subread that could be aligned to a human reference genome. On average, each molecule in a SMRT well was sequenced on average 143 times. In this example, there were 4.5 million circular consensus sequences (CCSs), suggesting 4.5 million cell-free DNA molecules that could be used for downstream analyses. The size of each cell-free DNA was determined from CCSs by counting the number of bases that have been identified.

FIGS. 1A and 1B show the size distribution of cell-free DNA from 0 to 20 kb. The y-axis shows the frequency. The x-axis shows the size in base pairs from 0 to 20 kb on a linear scale (FIG. 1A) or a logarithmic scale (FIG. 1B). Because the sequencing was performed through the full length of the DNA molecules, the size of each DNA molecule could be directly determined by counting the number of nucleotides in a sub-read or CCS. DNA fragment size measurement could be achieved using any sequencing platforms that could read through the full length of DNA fragments and is not limited to the use of single molecule sequencers. For example, Sanger sequencers could read through 800 bp. Short-read sequencing, such as by Illumina platforms, could read through 250 bp. Single molecule sequencers, such as Pacific Biosciences and Oxford Nanopore could read through more than 10,000 bp. The sizes of DNA fragments could also be determined after aligning to the reference genome, e.g. human reference genome. The sizes of DNA fragments could be determined by paired-end sequencing followed by alignment to the reference genome. FIG. 1B shows a long-tailed pattern. Among 4.5 million CCSs, there were 22.5% of cell-free DNA greater than 200 bp, 19.0% of them greater than 300 bp, 11.8% of them greater than 400 bp, 10.6% of them greater than 500 bp, 8.9% of them greater than 600 bp, 6.4% of them greater than 1 kb, 3.5% of them greater than 2 kb, 1.9% of them greater than 3 kb, 0.9% of them greater than 4 kb, and 0.04% of them greater than 10 kb. The longest one observed in the current PacBio SMRT results was 29,804 bp.

One plasma DNA of a pregnant subject was also sequenced on the Illumina sequencing platform using a PCR-based library preparation protocol (Lun et al. Clin Chem. 2013; 59:1583-94). Among 18.2 million paired-end reads, there were 5.3% of cell-free DNA greater than 200 bp, 2.0% of them greater than 300 bp, 0.3% of them greater than 400 bp, 0.2% of them greater than 500 bp, 0.2% of them greater than 600 bp (Table 1). As a comparison, we analyzed the size profiles by aggregating the single molecule real-time sequencing data (i.e., a total of 4.4 million CCSs) from 5 pregnant subjects. We observed more plasma DNA molecules greater than 600 bp (28.56%), in comparison with the counterpart (0.2%) obtained by Illumina sequencing platform. These results suggested that the PacBio SMRT sequencing may enable one to achieve 143 folds more long DNA molecules (longer than 600 bp). We can obtain 4.77% of plasma DNA molecules greater than 3 kb using single molecule real-time sequencing, while there was no readout in the Illumina sequencing platform.

In contrast to the previous report showing a very small proportion of long plasma DNA molecules over 1 kb (0.06% to 0.3%) using the Oxford Nanopore Technologies sequencing platform (Cheng et al Clin Chem. 2015; 61:1305-6), we could obtain 21 times more plasma DNA over 1 kb (6.4%), demonstrating the PacBio SMRT sequencing was much more efficient in obtaining sequence information from the long DNA population.

Compared with paired-end short-read sequencing such as the Illumina sequencing platform, long-read sequencing technologies such as the PacBio SMRT technology have a number of advantages in determining the characteristics (e.g. the length) of a long DNA fragment. For example, a long read would generally allow one to more accurately to align to a human reference genome (e.g. hg19). Long read technologies would also allow one to accurately determine the length of a plasma DNA molecule by directly counting the number of nucleotides sequenced. In contrast, paired-end short reads-based plasma DNA size estimation is an indirect method that use the outermost coordinates of aligned paired-end read to deduce the size of a plasma DNA molecule. For such an indirect approach, errors in alignment would result in an accurate size deduction. In this regard, an increase in the size span between the paired-end reads would increase the chance of error in alignment.

TABLE 1

Comparison of size distribution between PacBio and Illumina sequencing of cell-free DNA.

| Plasma DNA fragment size cutoff (≥X bp) | Percentage of desired fragments obtained by single molecule real-time sequencing (%) | Percentage of desired fragments obtained by Illumina sequencing platform (%) |
|---|---|---|
| 200 | 50.32 | 5.3 |
| 300 | 46.43 | 2 |
| 400 | 35.05 | 0.3 |
| 500 | 32.34 | 0.2 |
| 600 | 28.56 | 0.2 |
| 700 | 26.74 | 0.00 |
| 800 | 24.50 | 0.00 |
| 900 | 23.08 | 0.00 |
| 1000 | 21.37 | 0.00 |
| 1100 | 20.06 | 0.00 |
| 1200 | 18.60 | 0.00 |
| 1300 | 17.36 | 0.00 |
| 1400 | 16.08 | 0.00 |
| 1500 | 14.94 | 0.00 |
| 1600 | 13.84 | 0.00 |
| 1700 | 12.83 | 0.00 |
| 1800 | 11.88 | 0.00 |
| 1900 | 11.00 | 0.00 |
| 2000 | 10.19 | 0.00 |
| 2100 | 9.43 | 0.00 |
| 2200 | 8.75 | 0.00 |
| 2300 | 8.10 | 0.00 |
| 2400 | 7.51 | 0.00 |
| 2500 | 6.96 | 0.00 |
| 2600 | 6.45 | 0.00 |
| 2700 | 5.99 | 0.00 |
| 2800 | 5.55 | 0.00 |

TABLE 1-continued

Comparison of size distribution between PacBio and Illumina sequencing of cell-free DNA.

| Plasma DNA fragment size cutoff (≥X bp) | Percentage of desired fragments obtained by single molecule real-time sequencing (%) | Percentage of desired fragments obtained by Illumina sequencing platform (%) |
| --- | --- | --- |
| 2900 | 5.15 | 0.00 |
| 3000 | 4.77 | 0.00 |

Figure 2A:
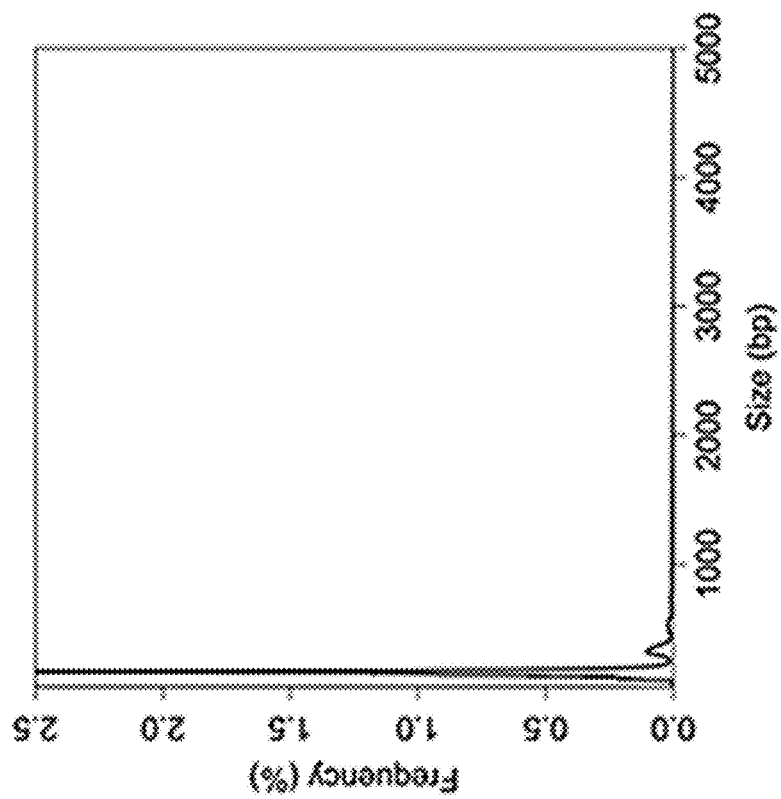

FIGS. 2A and 2B show the size distribution of cell-free DNA from 0 to 5 kb. The y-axis shows the frequency. The x-axis shows the size in base pairs from 0 to 5 kb on a linear scale (FIG. 2A) or a logarithmic scale (FIG. 2B). There were a series of major peaks occurring with periodic patterns. Such periodic patterns even extended to the molecules within a range of 1 kb and 2 kb. The peak with the highest frequency (2.6%) was at 166 bp, which was consistent with the previous finding using Illumina technology (Lo et al. Sci Transl Med. 2010; 2:61ra91). The distance between adjacent major peaks in FIG. 2B was approximately 200 bp, suggesting that the long cell-free DNA generation would also involve the nucleosomal structures.

Figure 3A:
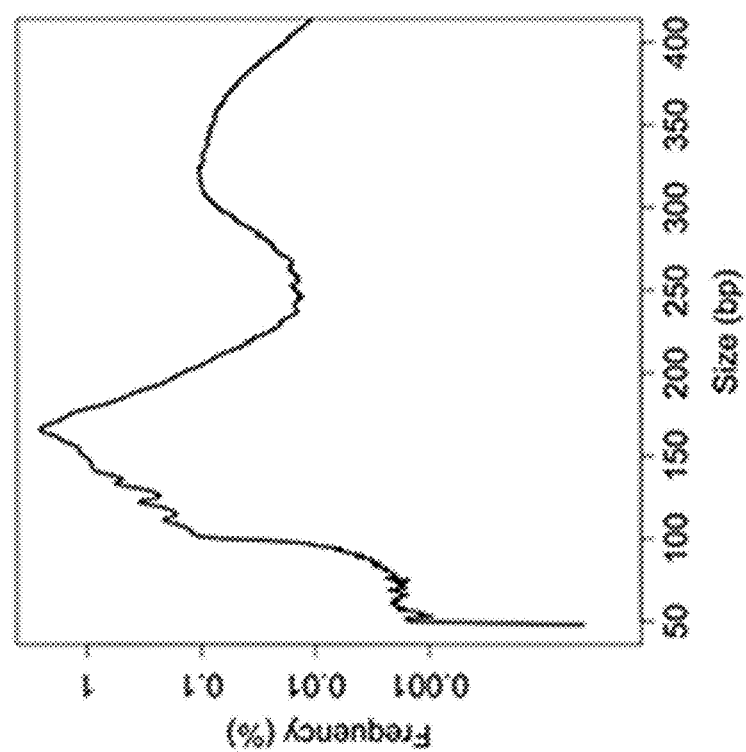
FIGS. 3A and 3B show the size distribution of cell-free DNA determined according to embodiments of the present invention. (A) 0-400 bp on a linear scale for the y-axis. (B) 0-400 bp on a logarithmic scale for the y-axis.
Figure 3B:
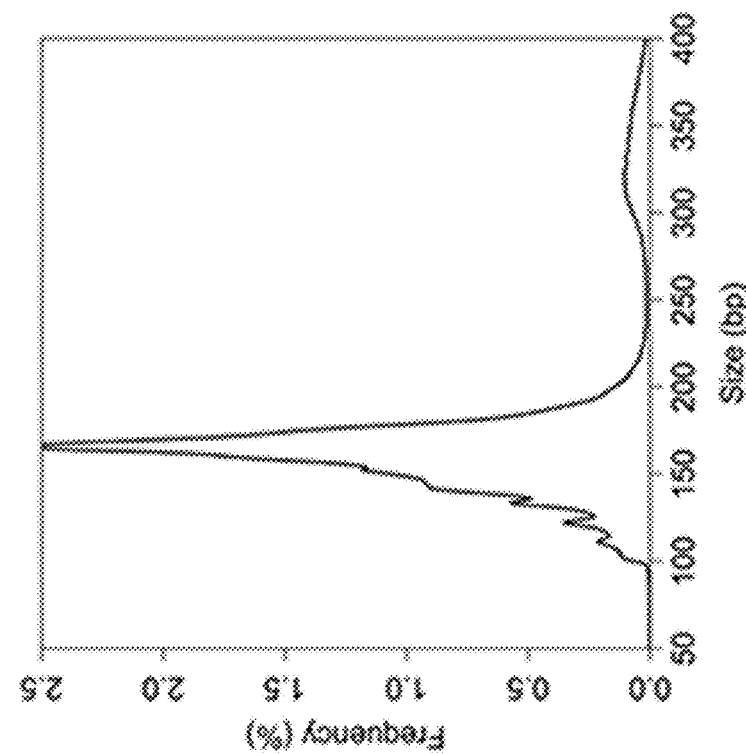

FIGS. 3A and 3B show the size distribution of cell-free DNA from 0 to 400 bp. The y-axis shows the frequency. The x-axis shows the size in base pairs from 0 to 400 bp on a linear scale (FIG. 3A) or a logarithmic scale (FIG. 3B). The characteristic features with a most predominant peak at 166 bp and 10-bp periodicities occurring in the molecules below 166 bp, which was reported previously (Lo et al. Sci Transl Med. 2010; 2:61ra91), was also reproducible using the new method according to this disclosure. These results suggested that the size determination of a molecule by counting the number bases sequenced from a single molecule according to this disclosure was reliable.

A. Size Analysis for Fetal and Maternal DNA

The sizes of maternal and fetal DNA fragments were analyzed and compared. As an example, the buffy coat DNA of one pregnant woman and matched placental DNA were sequenced to obtain 59× and 58× haploid genome coverage, respectively. We identified a total of 822,409 informative single nucleotide polymorphisms (SNPs) for which the mother was homozygous and the fetus was heterozygous. The fetal-specific alleles are defined as those alleles which are present in the fetal genome but absent in the maternal genome. We identified 2,652 fetal-specific fragments and 24,837 shared fragments (i.e., the fragments carrying the shared allele; predominantly of maternal origin) in the maternal plasma (M13160) through PacBio sequencing. The fetal DNA fraction was 21.8%.

Figure 4B:
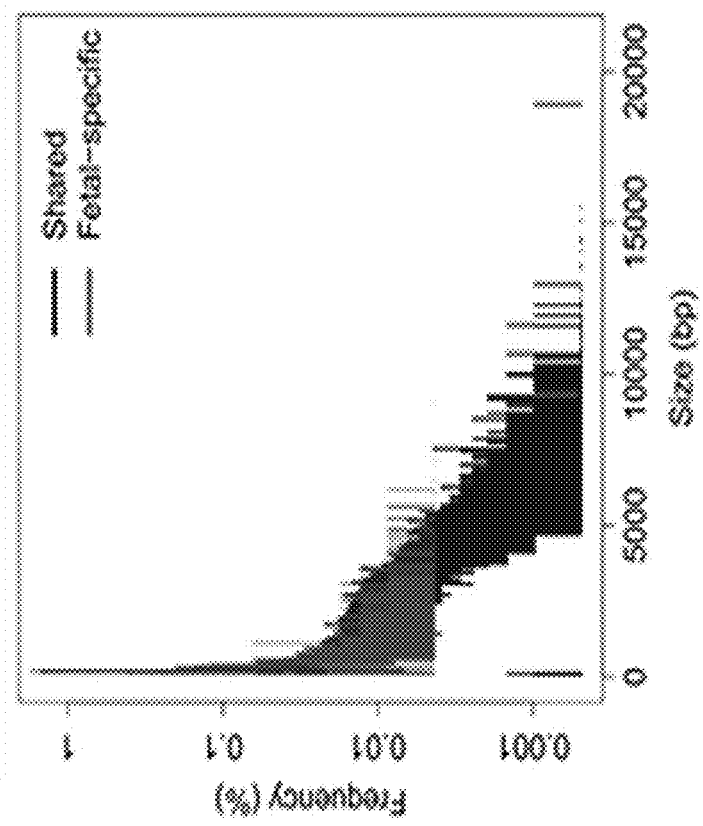
FIGS. 4A and 4B show the size distribution of cell-free DNA between fragments carrying shared alleles (Shared) and fetal-specific alleles (Fetal-specific) determined according to embodiments of the present invention. (A) 0-20 kb bp on a linear scale for the y-axis. (B) 0-20 kb on a logarithmic scale for the y-axis. The blue line indicates the fragments carrying shared alleles (predominant of maternal origin) and the red line indicates the fragments carrying fetal-specific alleles (of placental origin).
Figure 4A:
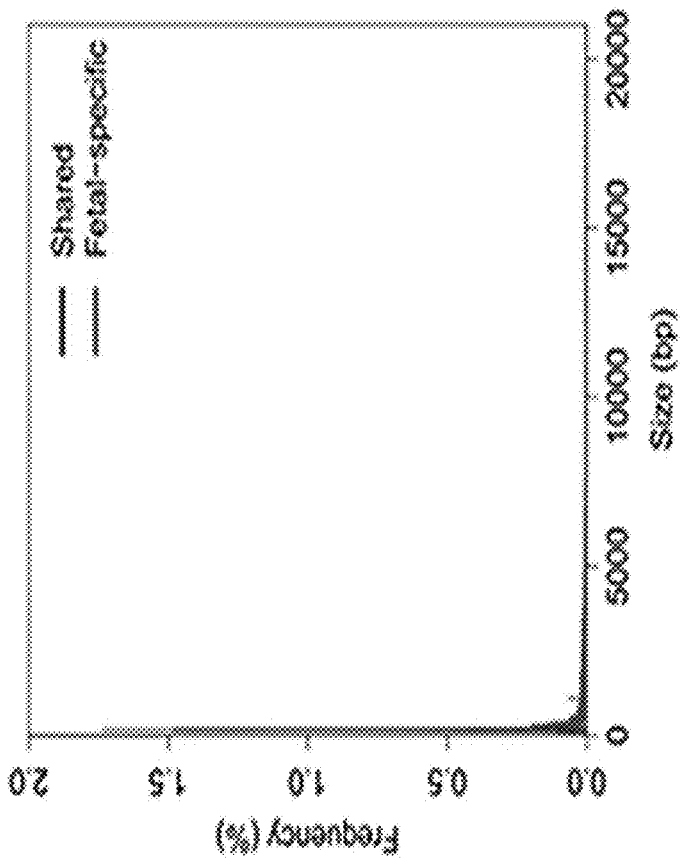

FIGS. 4A and 4B show the size distribution of cell-free DNA between fragments carrying shared alleles (Shared) and fetal-specific alleles (Fetal-specific). The x-axis shows the size in base pairs from 0 to 20 kb on a linear scale (FIG. 4A) or a logarithmic scale (FIG. 4B). Both fragments carrying shared alleles (predominantly of maternal origin) and fetal-specific allele (of placental origin) displayed long-tailed distributions, suggesting the presence of long DNA molecules derived from both fetal and maternal sources. There were 22.6% of plasma DNA molecules whose sizes were greater than 2 kb for the fragments mainly of maternal origin, while there were 8.5% of plasma DNA molecules whose sizes were greater than 2 kb for the fragment of fetal origin. These results suggested that the fetal DNA molecules contained fewer long DNA molecules. The percentage of long DNA present in this SNP-based analysis regarding fetal and maternal origins of plasma DNA was seemingly much higher than that observed in the overall size analysis. Such discrepancy was likely due to the fact that a long DNA molecule has a higher chance of covering one or more SNPs than a short one and thus the long DNA would be favorably selected for SNP-based analysis. The relative proportion of long DNA molecules tagged by SNPs skewed from the corresponding long DNA proportion in the original pool would be governed by the sizes of those molecules. Among those fetal-specific DNA fragments, the longest one was 16,186 bp, while among those fragments carrying shared alleles, the longest one was 24,166 bp.

Figure 5B:
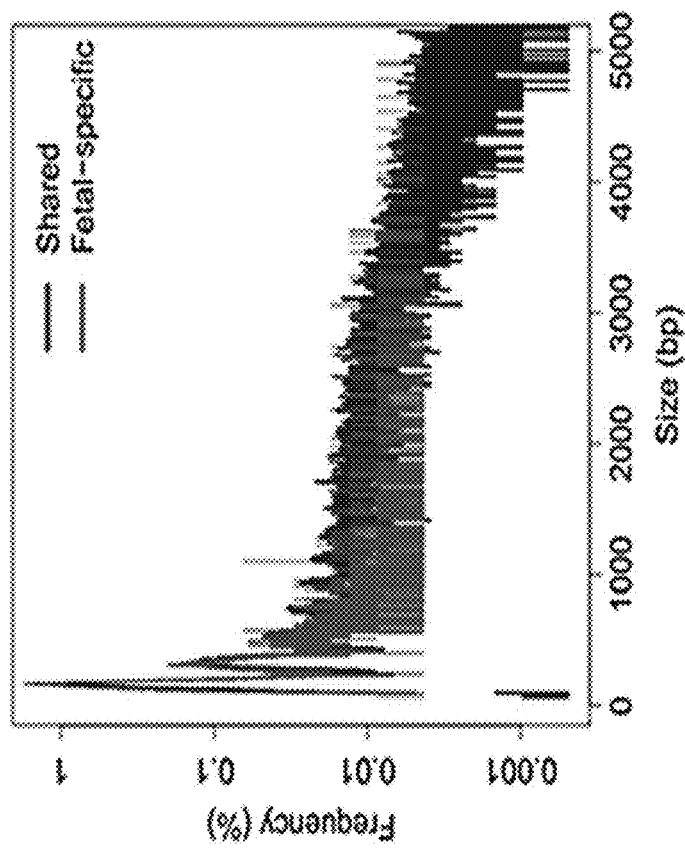
FIGS. 5A and 5B show the size distribution of cell-free DNA between fragments carrying shared alleles (Shared) and fetal-specific alleles (Fetal-specific) determined according to embodiments of the present invention. (A) 0-5 kb bp on a linear scale for the y-axis. (B) 0-5 kb on a logarithmic scale for the y-axis. The blue line indicates the fragments carrying shared alleles (predominant of maternal origin) and the red line indicates the fragments carrying fetal-specific alleles (of placental origin).
Figure 5A:
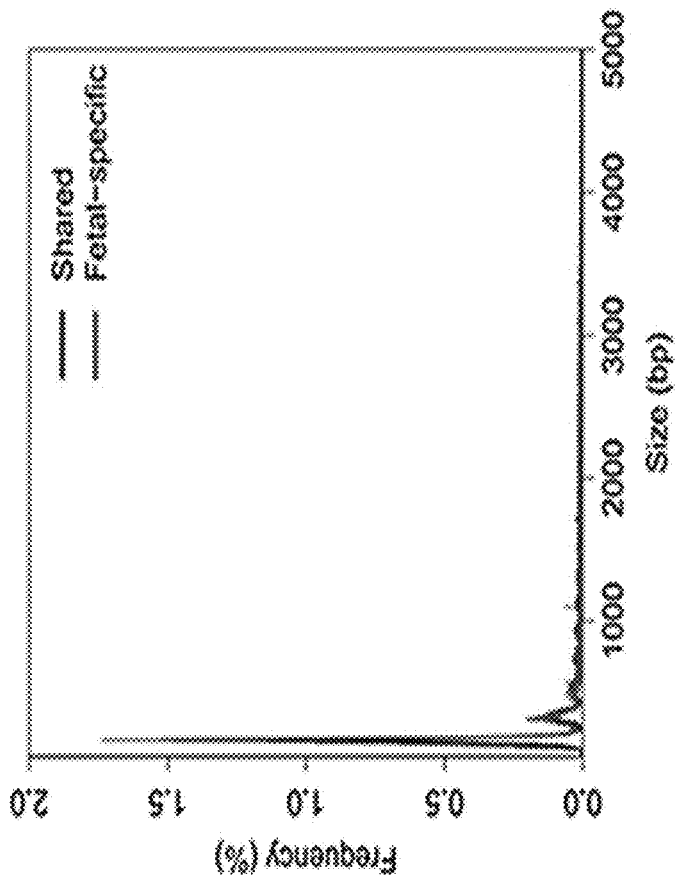

FIGS. 5A and 5B show the size distribution of cell-free DNA between fragments carrying shared alleles (Shared) and fetal-specific alleles (Fetal-specific). The x-axis shows the size in base pairs from 0 to 5 kb on a linear scale (FIG. 5A) or a logarithmic scale (FIG. 5B). There were series of major peaks occurring in a periodic manner for those fragments below 2 kb for both fetal-specific and shared DNA fragments. The major peaks likely aligned with nucleosomal structures.

Figure 6B:
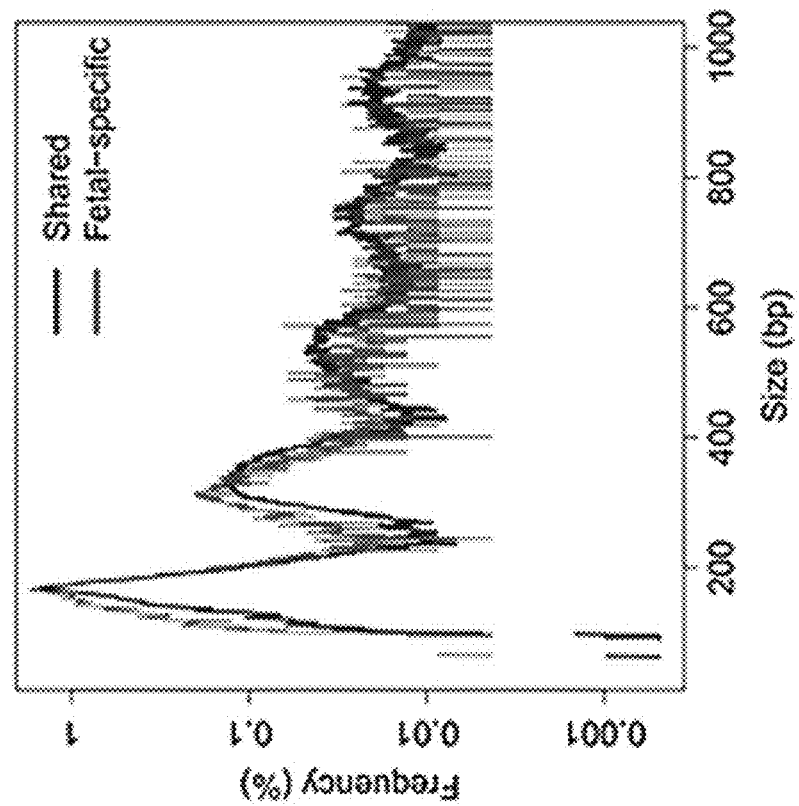
FIGS. 6A and 6B show the size distribution of cell-free DNA between fragments carrying shared alleles (Shared) and fetal-specific alleles (Fetal-specific) determined according to embodiments of the present invention. (A) 0-1 kb on a linear scale for the y-axis. (B) 0-1 kb on a logarithmic scale for the y-axis. The blue line indicates the fragments carrying shared alleles (predominant of maternal origin) and the red line indicates the fragments carrying fetal-specific alleles (of placental origin).
Figure 6A:
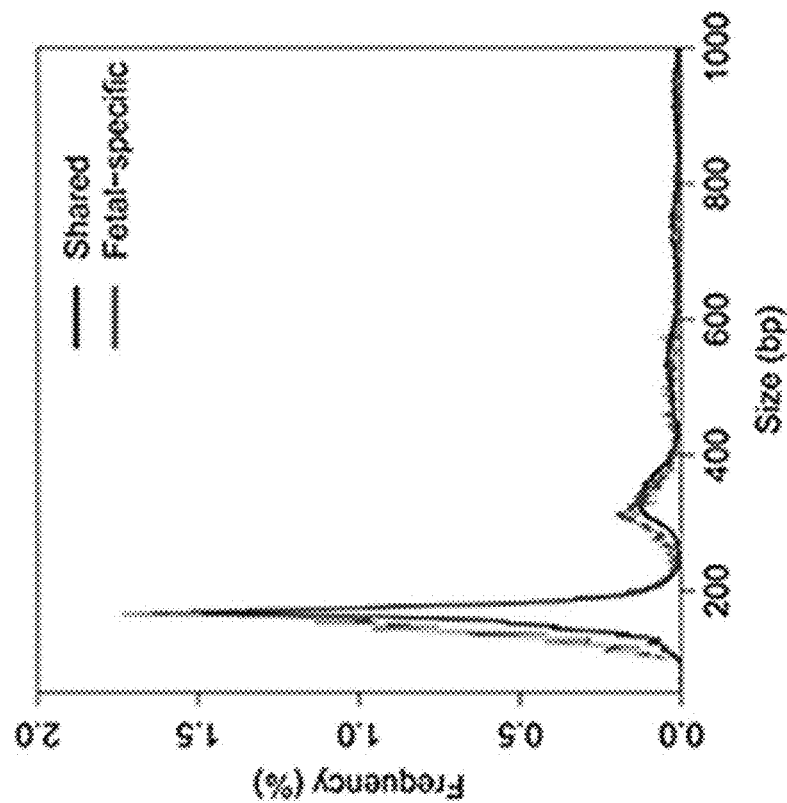

FIGS. 6A and 6B show the size distribution of cell-free DNA between fragments carrying shared alleles (Shared) and fetal-specific alleles (Fetal-specific). The x-axis shows the size in base pairs from 0 to 1 kb on a linear scale (FIG. 6A) or a logarithmic scale (FIG. 6B). There were series of major peaks occurring in a periodic manner for those fragments below 1 kb for both fetal-specific and shared DNA fragments. The major peaks likely aligned with nucleosomal structures. There appeared to be an observable shift of fetal DNA size profile towards the left of the size profile of shared DNA fragments, suggesting that the fetal DNA would comprise more short DNA molecules than maternal DNA.

Figure 7A:
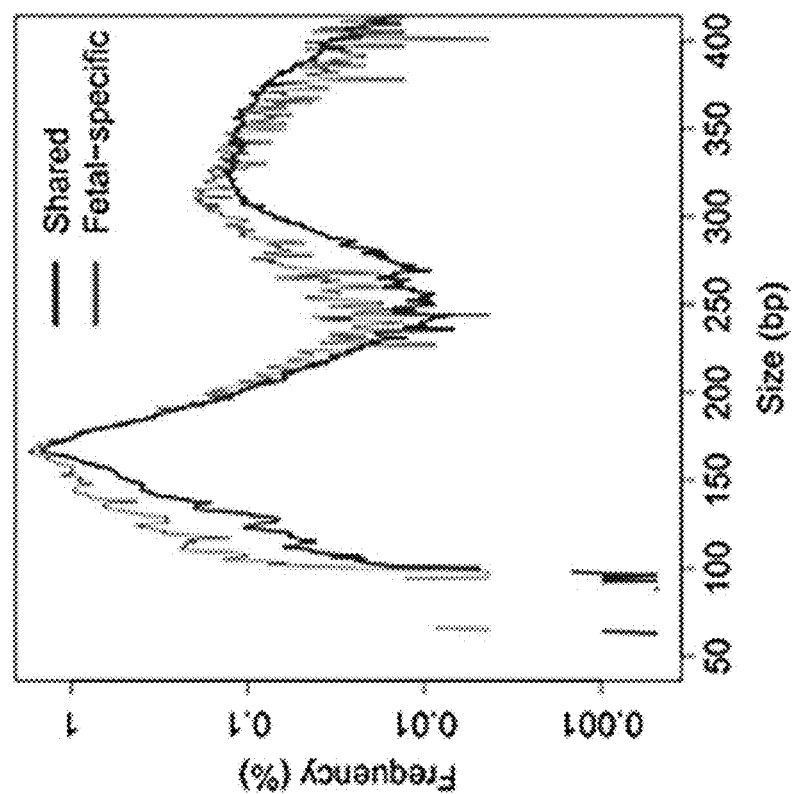
FIGS. 7A and 7B show the size distribution of cell-free DNA between fragments carrying shared alleles (Shared) and fetal-specific alleles (Fetal-specific) determined according to embodiments of the present invention. (A) 0-400 bp on a linear scale for the y-axis. (B) 0-400 bp on a logarithmic scale for the y-axis. The blue line indicates the fragments carrying shared alleles (predominant of maternal origin) and the red line indicates the fragments carrying fetal-specific alleles (of placental origin).
Figure 7B:
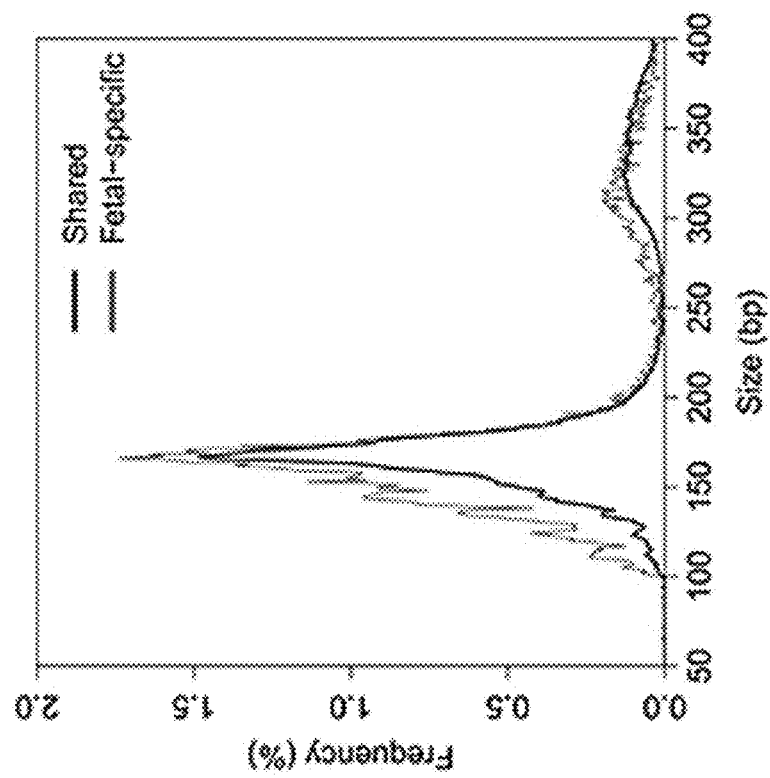

FIGS. 7A and 7B show the size distribution of cell-free DNA between fragments carrying shared alleles (Shared) and fetal-specific alleles (Fetal-specific). The x-axis shows the size in base pairs from 0 to 400 bp on a linear scale (FIG. 7A) or a logarithmic scale (FIG. 7B). The characteristic features with a most predominant peak at 166 bp and 10-bp periodicities occurring in both the fetal and maternal molecules below 166 bp, which was reported previously (Lo et al. Sci Transl Med. 2010; 2:61ra91), was also reproducible using the new method according to this disclosure. These results suggested that the size determination of a molecule by counting the number of bases sequenced from a single molecule according to this disclosure was reliable.

B. Size and Methylation Analysis

The methylation levels of long cell-free maternal and fetal DNA molecules were analyzed. The methylation level of fetal DNA molecules was found to be lower than the methylation level of maternal DNA molecules.

In PacBio SMRT sequencing, a DNA polymerase mediates the incorporation of fluorescently labeled nucleotides into complementary strands. The characteristics of fluorescent pulses produced during DNA synthesis, including inter-pulse duration and the pulse width, would reflect the polymerase kinetics that could be used to determine the nucleotide modifications such as, but not limited to, 5-methylcytosine using the approaches described in our previous disclosure (U.S. application Ser. No. 16/995,607, filed Aug. 17, 2020, entitled "DETERMINATION OF BASE MODI- FICATIONS OF NUCLEIC ACIDS"), the entire contents of which are incorporated herein by reference for all purposes.

In embodiments, we identified 95,210 fragments carrying the maternal-specific alleles and 2,652 fragments carrying fetal-specific alleles, respectively. The maternal-specific alleles are herein defined as those alleles present in the maternal genome but absent in the fetal genome, which could be identified from SNPs where the mother is heterozygous and the fetus is homozygous. We identified a total of 677,375 such informative SNPs in this example. We determined the size for each cell-free DNA molecule. In one embodiment, as the methylation states in a genome are variable for example the methylation levels of CpG islands are generally lower than regions without CpG island, to minimize the variability introduced by genomic context, one could, in silico, select the fragments, which are greater than 1 kb, contain at least 5 CpG sites and correspond to the CpG density less than 5% (i.e. the number of CpG sites in a molecule divided by the total length of that molecule <0.05), were used for downstream analysis.

Figure 8:
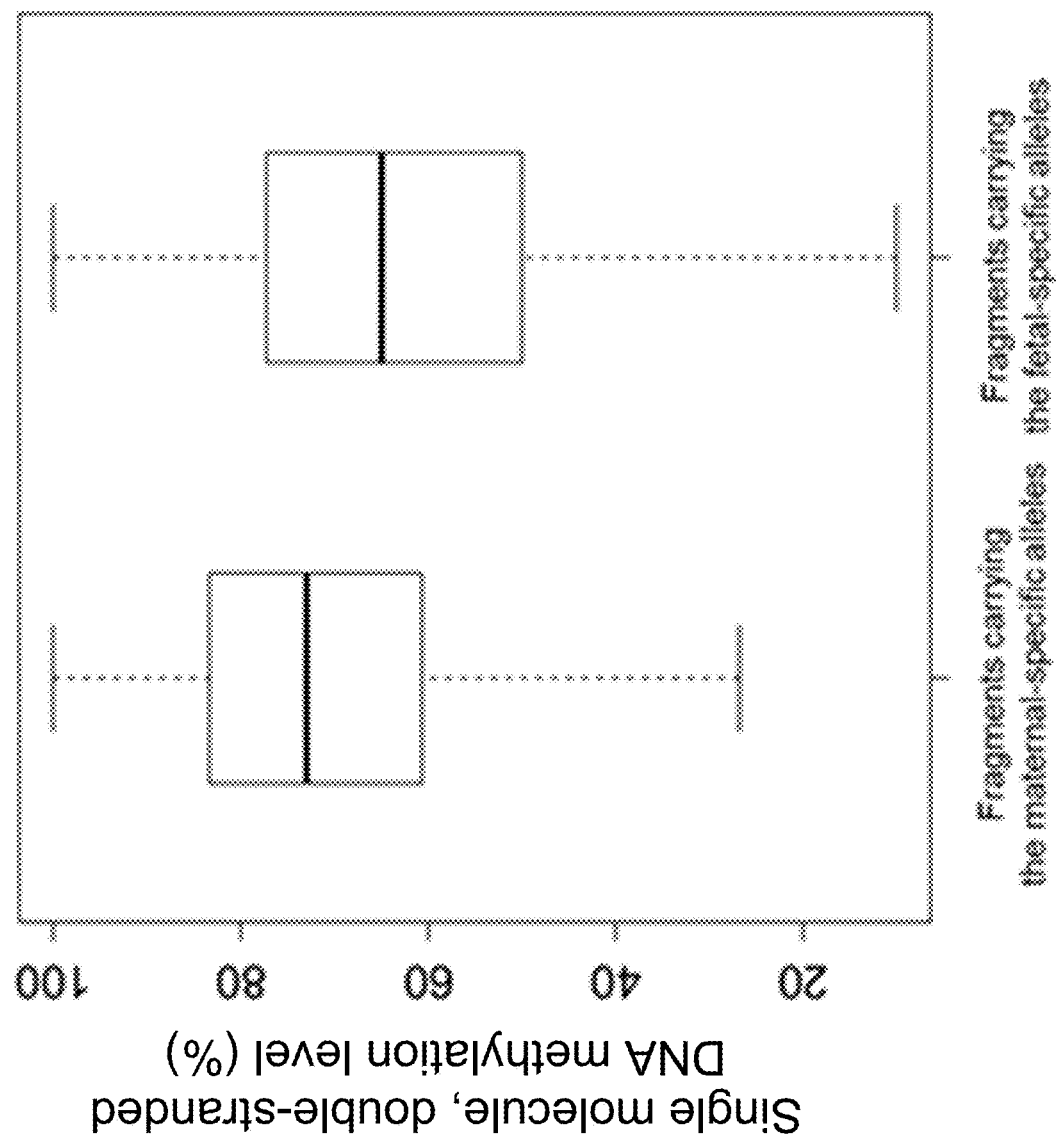
FIG. 8 shows single molecule, double-stranded DNA methylation levels between fragments carrying the maternal-specific alleles and the fetal-specific alleles according to embodiments of the present invention.

FIG. 8 shows single molecule, double-stranded DNA methylation levels between fragments carrying the maternal-specific alleles and the fetal-specific alleles. The y-axis shows the single molecule, double-stranded DNA methylation level in percent. The x-axis shows both fragments carrying maternal-specific alleles and fragments carrying fetal-specific alleles. The single molecule, double-stranded DNA methylation levels of fragments carrying fetal-specific allele (mean: 62.7%; interquartile range, IQR: 50.0%-77.2%) are lower than the counterparts of fragments carrying maternal-specific alleles (mean: 72.7%; IQR: 60.6%-83.3%) ($P<0.0001$).

Figure 9A:
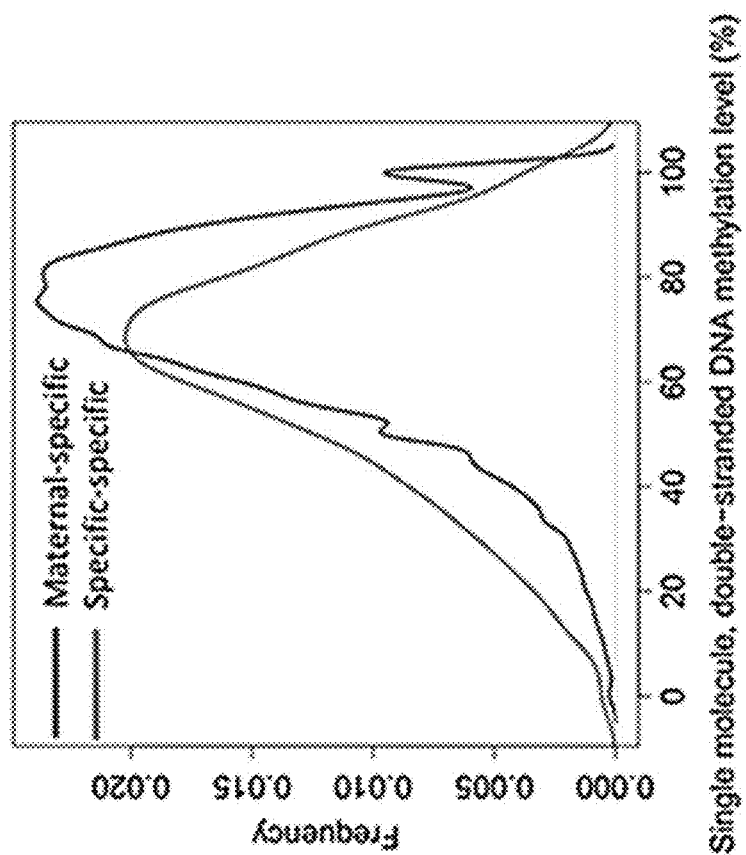
FIGS. 9A and 9B show (A) the fitted distribution of single molecule, double-stranded DNA methylation levels between fragments carrying the maternal-specific alleles and the fetal-specific alleles and (B) receiver operating characteristic (ROC) analysis using single molecule, double-stranded DNA methylation levels according to embodiments of the present invention.

FIG. 9A shows the empirical distribution of single molecule, double-stranded DNA methylation levels of fragments fitted by kernel density estimation implemented in R package (r-project.org/). Frequency is shown on the y-axis. The x-axis shows the single molecule, double-stranded DNA methylation level in percent. The distribution of fetal-specific long DNA fragments is in the left of that of maternal-specific fragments, suggesting the lower single molecule, double-stranded DNA methylation levels present in the fetal DNA molecules.

Figure 9B:
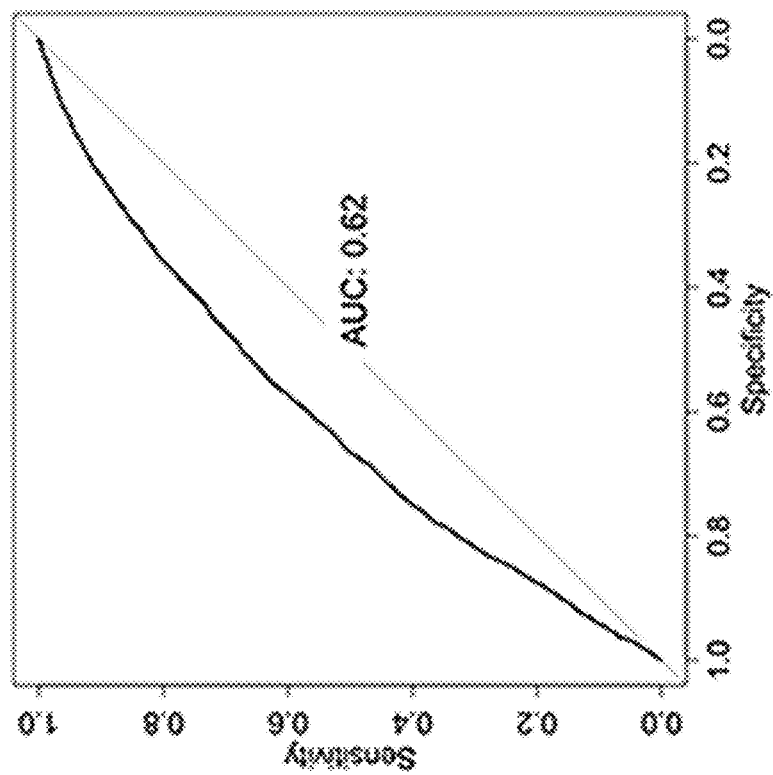

FIG. 9B shows the receiver operating characteristic (ROC) analysis using single molecule, double-stranded DNA methylation levels. The y-axis shows sensitivity. The x-axis shows specificity. Using single molecule, double-stranded DNA methylation levels to perform ROC analysis to investigate the power of distinguishing the fetal DNA fragments from the maternal DNA fragments using single molecule, double-stranded DNA methylation level, the area under ROC curve (AUC) was found to be 0.62, which was greater than the random guessing result of 0.5. In embodiments, one could make use of the spatial patterns of methylation states, such as the sequence of methylation states, relative or absolute distances between modified bases and genomic coordinates, in a single molecule to further improve the determination of fetal/maternal origins for fragments in plasma. In embodiments, one could combine the methylation patterns with other fragmentomic metrics (i.e., parameters concerning the fragmentation of DNA), including but not limited to preferred ends (Chan et al. Proc Natl Acad Sci USA. 2016; 113:E8159-8168), end motifs (Serpas et al. Proc Natl Acad Sci USA. 2019; 116:641-649), sizes (Lo et al. Sci Transl Med. 2010; 2:61ra), orientation-aware (i.e., orientation with regard to specific elements within the genome, e.g. open chromatin regions, fragmentation patterns (Sun et al. Genomes Res. 2019; 29:418-427)), topological forms (e.g. linear versus circular DNA molecules (Ma et al. Clin Chem. 2019; 65:1161-1170)), to improve the classification power of distinguishing the fragments of placental origins (fetal origins).

Figure 10B:
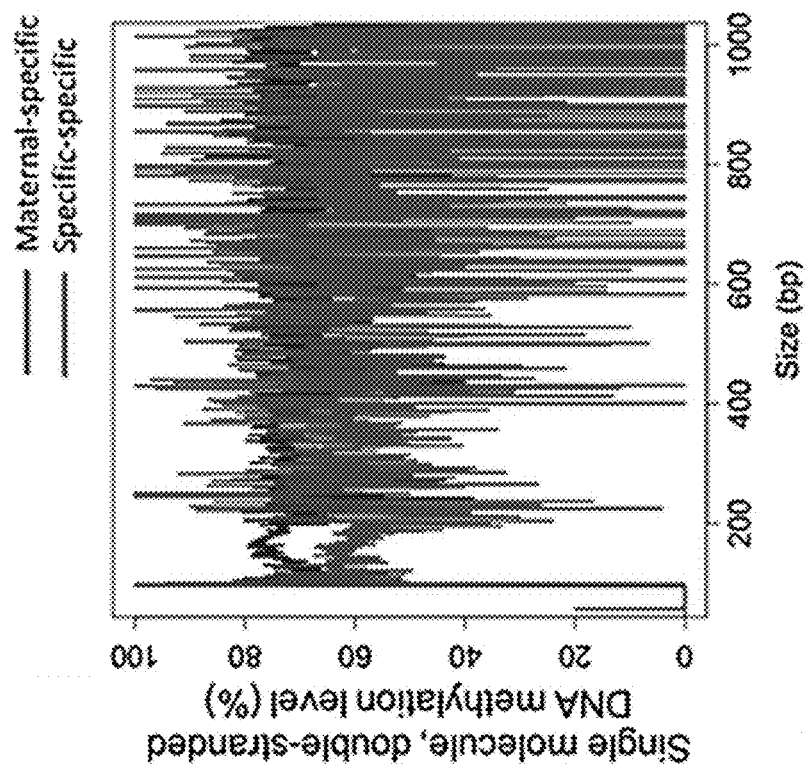
FIGS. 10A and 10B show correlation between the single molecule, double-stranded DNA methylation levels and fragment sizes of plasma DNA according to embodiments of the present invention. (A) a size range of 0-20 kb. (B) a size range of 0-1 kb.
Figure 10A:
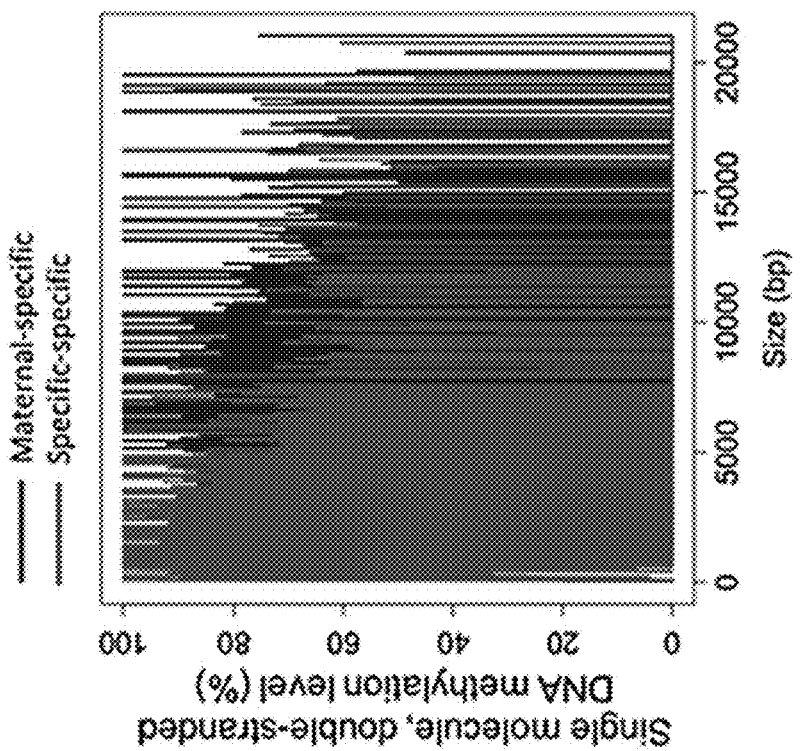

FIGS. 10A and 10B show that the single molecule, double-stranded DNA methylation levels of both the fetal and maternal DNA fragments varied according to fragment sizes. The y-axis shows the single molecule, double-stranded DNA methylation level in percent. The x-axis shows the size from 0 to over 20 kb (FIG. 10A) and from 0 to over 1 kb (FIG. 10B). On the other hand, the single molecule, double-stranded DNA methylation levels of fetal-specific DNA molecules were generally lower than that of maternal-specific DNA molecules in both long (FIG. 10A) and short (FIG. 10B) ranges. This finding was consistent with the current knowledge that the methylation level of the fetal DNA was lower than the maternal DNA in the plasma of a pregnant woman (Lun et al. Clin Chem. 2013; 59:1583-94) for the short DNA molecules.

In embodiments, as the methylation level of fetal DNA molecules is relatively lower than that of maternal DNA molecules, one would select the molecules whose single molecule, double-stranded DNA methylation levels are less than a certain threshold, such as but not limited to, 80%, 70%, 60%, 50%, 40%, 30%, 20%, 10% and 5%, to enrich cell-free DNA molecules of fetal origin in plasma DNA pool. For example, the fetal DNA fraction is 2.6% for the fragments >1 kb. If we select the fragments (>1 kb) with single molecule, double-stranded methylation level <50%, the fetal DNA fraction of those further selected fragments >1 kb will increase to 5.6%, (i.e. a 115.4% increase). In another example, the fetal DNA fraction is 26.2% for the fragments <200 bp. If we select the fragments (<200 bp) with single molecule, double-stranded methylation level <50%, the fetal DNA fraction of those further selected fragments >200 bp will increase to 41.6% (i.e. 58.8%). Thus, the use of thresholding single-molecule, double-stranded DNA methylation levels to enrich the fetal DNA would be more effective for long DNA molecules under certain circumstances.

C. Haplotype and Methylation of Long Cell-Free DNA

In embodiments, one could obtain base compositions, sizes, and base modifications for each single DNA molecules using methods described in this disclosure. SNP and methylation information of long cell-free DNA molecules can be used for haplotyping. The use of long DNA molecules present in cell-free DNA pool revealed in this disclosure would allow for phasing variants in genomes by leveraging the haplotype information present in each consensus sequence, according to but not limited to published methods (Edge et al. Genome Res. 2017; 27:801-812; Wenger et al. Nat Biotechnol. 2019; 37:1155-1162). The implementation of determining haplotypes according to sequence information of cell-free DNA, which is different from previous studies that have to rely on long DNA prepared from the tissue DNA. A haplotype within a genomic region can be sometimes referred to as a haplotype block. A haplotype block could be considered as a set of alleles on a chromosome that have been phased. In some embodiments, a haplotype block would be extended as long as possible according to a set of sequence information which supports two alleles physically linked on a chromosome as well as the allelic overlap information between different sequences.

Figures 11A, 11B:
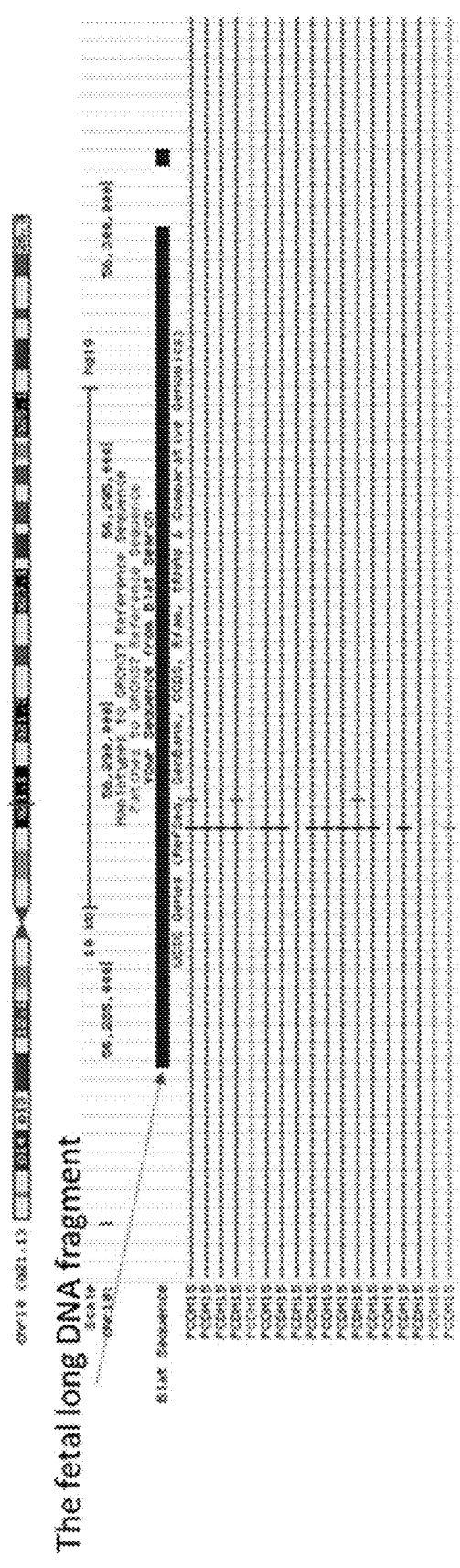
FIGS. 11A and 11B show an example of a long fetal-specific DNA molecule identified in the maternal plasma DNA of a pregnant woman according to embodiments of the present invention. (A) black bar indicates the long fetal-specific DNA molecule aligned to a region in chromosome 10 of a human reference genome. (B) The detailed illustration of genetic and epigenetic determined using PacBio sequencing according to the disclosure. The base highlighted in yellow (marked by an arrow) is likely due to sequence error which could be corrected in some embodiments.

FIGS. 11A and 11B show an example of a long fetal-specific DNA molecule identified in the maternal plasma DNA of a pregnant woman. Among those fetal-specific DNA fragments, we hereby illustrate embodiments of our invention using one molecule that was 16,186 bp, which was aligned to a region in chromosome 10 of the human reference genome (chr10: 56282981-56299166) (FIG. 11A) and carried 7 fetal-specific alleles (FIG. 11B). There were 6 out of 7 fetal-specific alleles that were consistent with the allelic information deduced from the deep sequencing of maternal and fetal genomes (using the Illumina platform) (FIG. 11B). Its methylation level was determined to be 27.1% according to the method described in this disclosure (FIG. 11B), which was much lower than the average level of maternal-specific fragments (72.7%). These results suggested that the single molecule, double-stranded DNA methylation patterns would serve as markers to differentiate cell-free DNA molecules of fetal and maternal origins.

FIGS. 12A and 12B show an example of a long maternal DNA molecule carrying shared alleles identified in the maternal plasma DNA of a pregnant woman. Among those fragments carrying shared alleles, the longest one was 24,166 bp which was aligned to a region in chromosome 6 of a human reference (chr6: 111074371-111098536) (FIG. 12A) and carried 18 shared alleles (FIG. 12B). All those shared alleles were consistent with the allelic information deduced from the deep sequencing of maternal and fetal genomes (using the Illumina platform) (FIG. 12B). Its methylation level was determined to be 66.9% according to the method described in this disclosure (FIG. 12B). The genetic and epigenetic information of cell-free DNA molecules in the order of kilobases long was not able to be readily identified by using short-read sequencing such as bisulfite sequencing (Illumina).

Here we describe a method to determine the relative likelihood of a molecule being derived from the pregnant woman or the fetus. In a pregnant woman, the DNA molecules carrying the fetal genotypes are actually derived from the placenta whereas most of the DNA molecules carrying the maternal genotypes are derived from the maternal blood cells. In this method, we first construct a frequency distribution curve of DNA molecules according to their methylation level for both the placenta and the maternal blood cells. To achieve this, we divided the human genome into different sized bins.

Figure 13:
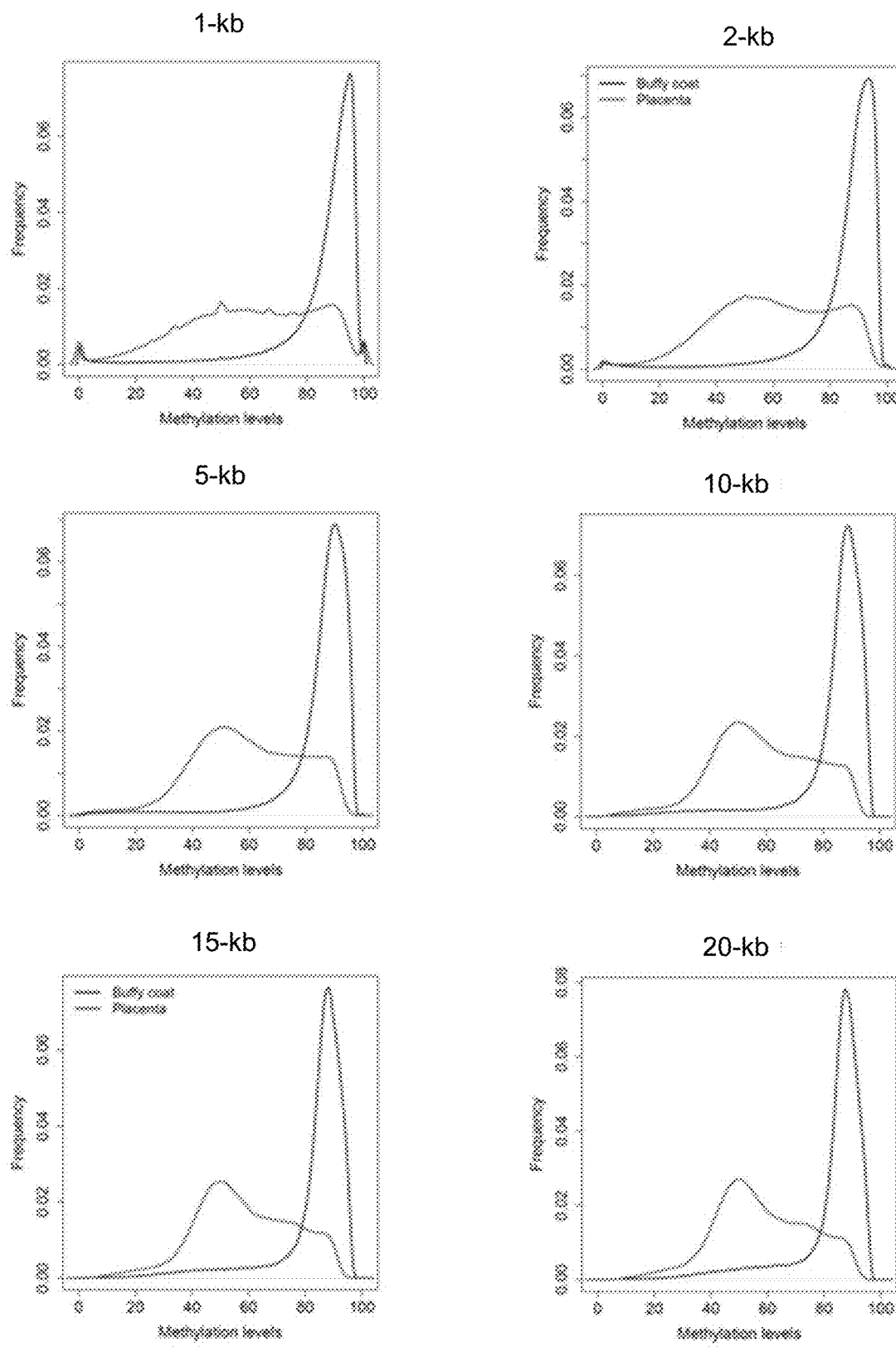
FIG. 13 shows the frequency distribution for DNA from placental (red) and maternal blood cells (blue) according to methylation level at different resolutions from 1 kb to 20 kb according to embodiments of the present invention.

FIG. 13 shows the frequency distribution for DNA from placental (red) and maternal blood cells (blue) according to methylation level at different resolutions from 1 kb to 20 kb. Frequency is shown on the y-axis. Methylation level is shown on the x-axis. Examples of the size of the bins include, but not limited to 1 kb, 2 kb, 5 kb, 10 kb, 15 kb and 20 kb. The methylation level of each bin was determined based on the number of methylated CpG sites divided by the total number of CpG sites. After determining the methylation level of all the bins, a frequency distribution curve can be constructed for each of the placental genome and the maternal blood cells genome, for different bin sizes.

Based on the methylation level of the long DNA molecule, the likelihood of it being derived from the placenta or maternal blood cells can be determined by the relative abundance of the two types of DNA molecules at such a methylation level, as well as the fractional concentration of fetal DNA in the sample.

Let x and y be the frequency of the DNA molecules derived from the placenta and the maternal blood cells, respectively, at a particular methylation level, and f be the fractional concentration of fetal DNA in the sample.

The probability (P) for a DNA molecule being derived from the fetus can be calculated as:

$$P = \frac{x \times f}{(x \times f) + y(1 - f)}$$

From the previous example, a plasma DNA molecule of 16 kb and a methylation level of 27.1% is considered.

Figure 14B:
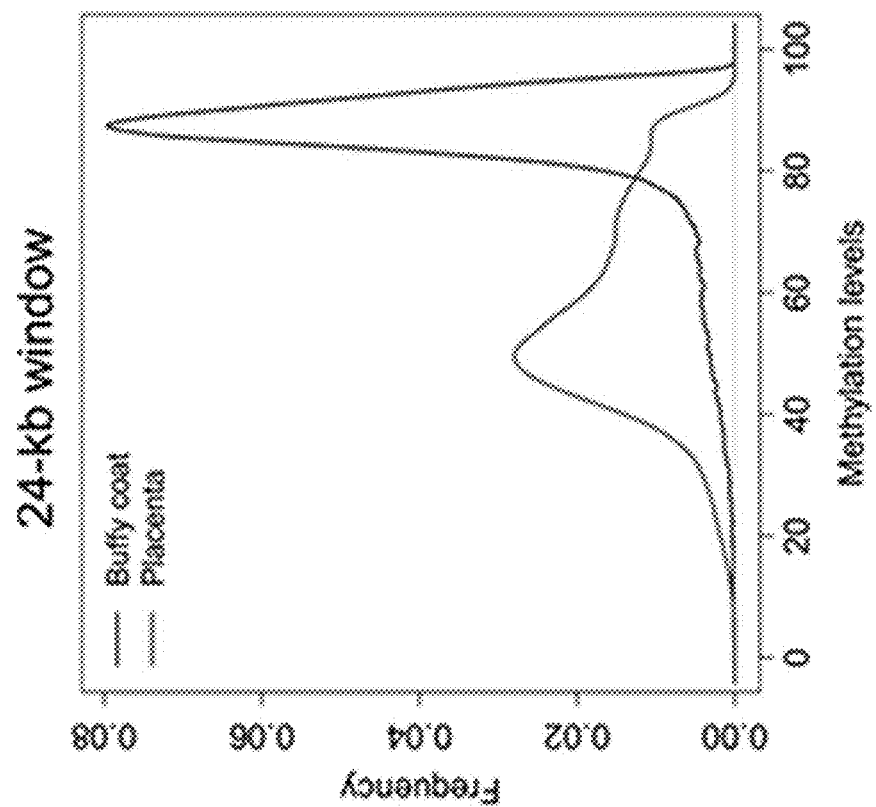
FIGS. 14A and 14B show the frequency distribution for DNA from placental (red) and maternal blood cells (blue) according to methylation levels within 16-kb and 24-kb windows according to embodiments of the present invention.
Figure 14A:
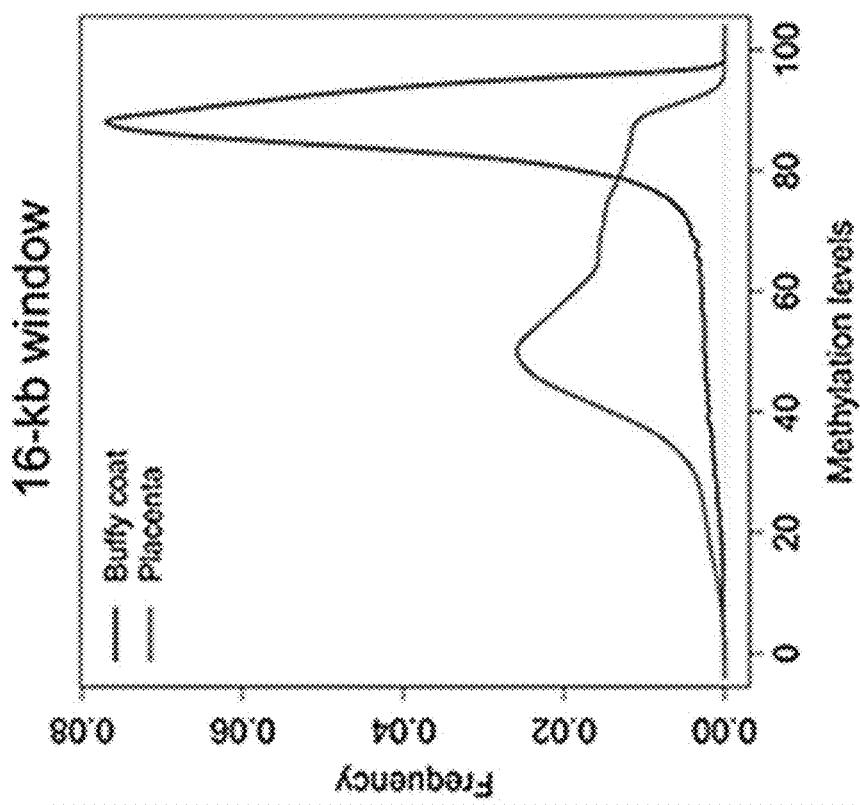

FIGS. 14A and 14B show the frequency distribution for DNA from placental (red) and maternal blood cells (blue) according to methylation levels within 16-kb (FIG. 14A) and 24-kb (FIG. 14B) windows. Frequency is shown on the y-axis. Methylation level is shown on the x-axis. Based on the frequency distribution plot for 16 kb fragments (FIG. 14A), the frequencies for DNA molecules derived from the placenta and maternal blood cells are 0.6% and 0.08%, respectively. As the fetal DNA fraction is 21.8%, the probability of this DNA fragment being derived from the placenta is 64%, suggesting an increased likelihood of a placental origin.

The probability of a DNA molecule being derived from fetal tissues can also be calculated for the plasma DNA molecule of 24 kb and a methylation level of 66.9%. Based on the frequency distribution plot for 24 kb fragments, the frequencies for DNA molecules derived from the placenta and maternal blood cells are 0.05% and 0.16% (FIG. 14B), respectively. The probability of this DNA fragment being derived from the placenta is 0.8%, suggesting it is very unlikely that it is of placental origin. In other words, there is a high likelihood that the molecule is of maternal origin.

This calculation can further take into account the size of the DNA molecules by referring to the size distribution curves for fetal and maternal DNA. Such analysis can be performed, for example, but not limited to using Bayes's theorem, logistic regression, multiple regression and support vector machine, random forest analysis, classification and regression tree (CART), K-nearest neighbors algorithm.

Figures 15A, 15B:
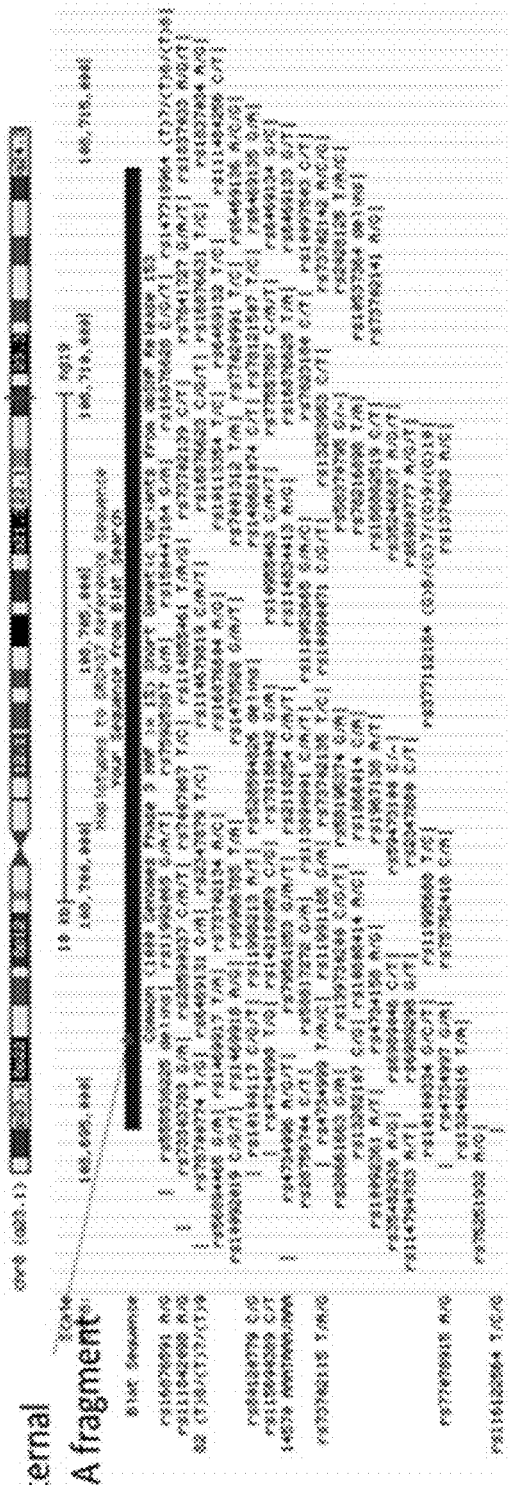
FIGS. 15A and 15B show an example of a long maternal-specific DNA molecule identified in the maternal plasma DNA of a pregnant woman according to embodiments of the present invention. (A) The black bar indicates the long maternal-specific DNA molecule aligned to a region in chromosome 8 of a human reference. (B) The detailed illustration of genetic and epigenetic determined using PacBio sequencing according to embodiments of the present invention.

FIGS. 15A and 15B shows that a long DNA fragment in plasma is 18,896 bp in size which was aligned to a region in chromosome 8 of a human reference (chr8: 108694010-108712904) (FIG. 15A) and carried 7 maternal-specific alleles (FIG. 15B). All those maternal-specific alleles were consistent with the allelic information deduced from the deep sequencing of maternal and fetal genomes (Illumina technology) (FIG. 15B). Its methylation level was determined to be 72.6% according to the method described in this disclosure (FIG. 15B), showing comparable to the pooled methylation level of maternal-specific fragments (72.7%). Thus, such a molecule would be more likely classified as a fragment of maternal origin. The genetic and epigenetic information of cell-free DNA molecules in the order of kilobases long was not able to be readily identified by using short-read sequencing such as bisulfite sequencing (Illumina).

Using the method described above, the probability for this molecule being derived from the placenta can be calculated. Based on the frequency distribution plot for 19 kb fragments, the frequencies for DNA molecules derived from the placenta and maternal blood cells are 0.65% and 0.23%, respectively. The probability of this DNA fragment being derived from the placenta is 43%, suggesting an increased likelihood of it being of maternal origin.

D. Clinical Haplotyping Applications

In embodiments, the ability to analyze both short and long DNA molecule in plasma DNA of a pregnant woman would allow us to carry out relative haplotype dosage (RHDO)

analysis (Lo et al. Sci Transl Med. 2010; 2:61ra91; Hui et al. Clin Chem. 2017; 63:513-524) without the requirement of prior paternal or maternal or fetal genotype information obtained from tissues. This capability would be more cost-effective and clinically applicable than is previously possible.

Figure 16:
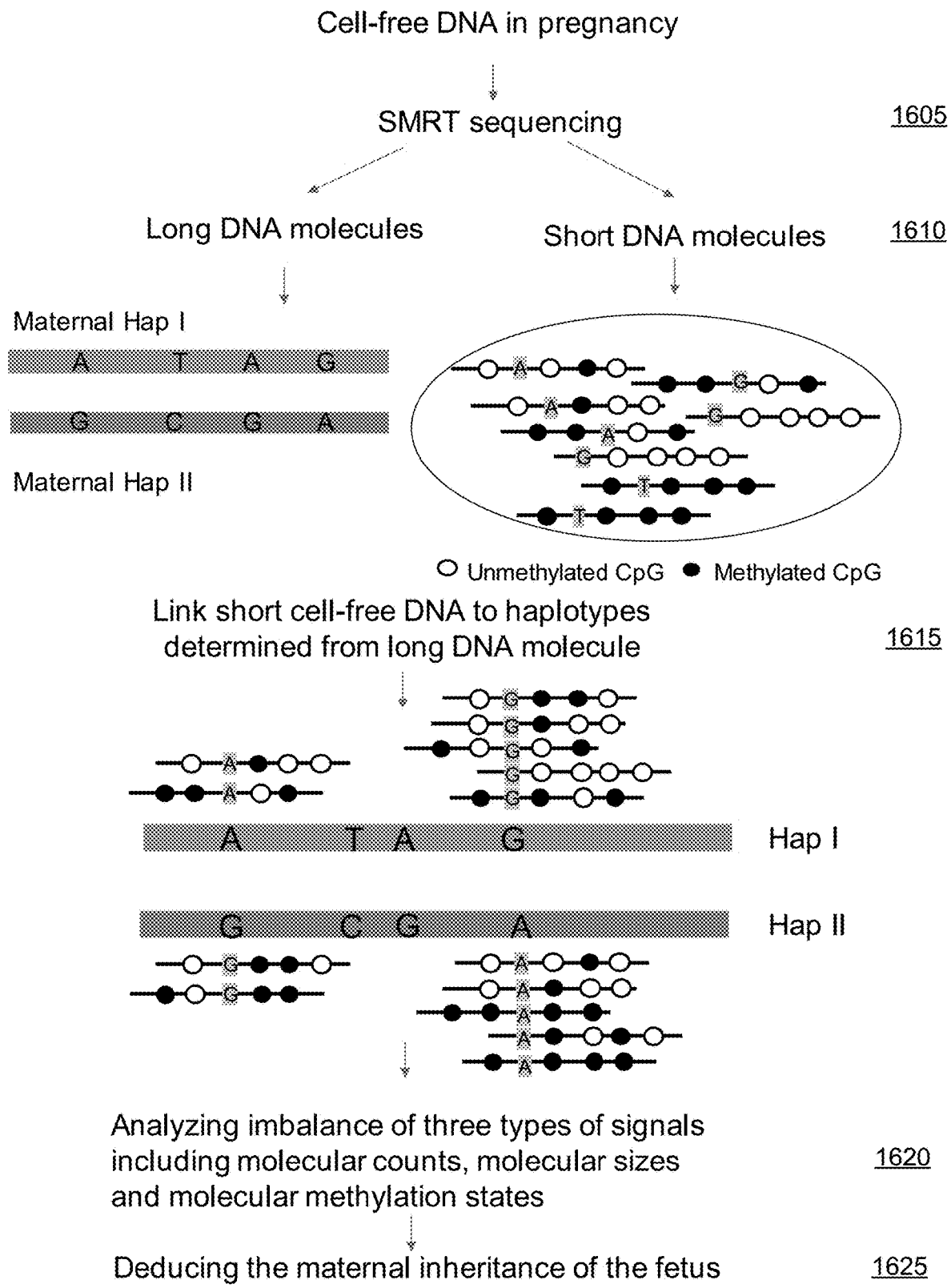
FIG. 16 shows an illustration of deducing the maternal inheritance of the fetus according to embodiments of the present invention.

FIG. 16 illustrates this principle as to how one could use cell-free DNA in pregnancy to carry out RHDO analysis. Cell-free DNA is isolated from a pregnant woman and subjected to SMRT sequencing at stage 1605. The sizes, allelic information and methylation states for each molecule including long and short DNA molecules can be determined according to the methods described in this disclosure. At stage 1610, according to the size information, one could divide the sequenced molecules into two categories, namely long and short DNA molecules. The cutoff used for determining the long and short DNA categories could include, but not limited to, 150 bp, 180 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 950 bp, 1 kb, 1.1 kb, 1.2 kb, 1.3 kb, 1.4 kb, 1.5 kb, 1.6 kb, 1.7 kb, 1.8 kb, 1.9 kb, 2 kb, 2.5 kb, 3 kb, 4 kb, 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 200 kb, 300 kb, 400 kb, 500 kb, or 1 Mb. At stage 1615, in embodiments, the allelic information present in long DNA molecules could be used to construct maternal haplotypes, namely Hap I and Hap II. The short DNA molecules could align to maternal haplotypes according to the allelic information. Hence, the number of cell-free DNA molecules (e.g. short DNA) originating from maternal Hap I and Hap II could be determined.

At stage 1620, an imbalance of haplotypes may be analyzed. The imbalance may be molecular counts, molecular sizes, or molecular methylation states. At stage 1625, the maternal inheritance of the fetus may be deduced. If the dosage of Hap I in maternal plasma DNA is over-represented, the fetus would likely inherit maternal Hap I. Otherwise, the fetus would likely inherit maternal Hap II. Different statistical approaches, including but not limited to, sequential probability ratio test (SPRT), binomial test, Chi-squared test, Student's t-test, nonparametric tests (e.g. Wilcoxon test) and hidden Markov models, would be used for determining which maternal haplotype is overrepresented.

In addition to the counting analysis, in embodiments, the methylation and size of a short DNA molecule are also determined and assigned to the maternal haplotypes. Methylation imbalance between the two haplotypes (i.e. Hap I and Hap II) could be used to determine the fetally inherited maternal haplotype. If the fetus has inherited Hap I, more fragments carrying alleles of Hap I would be present in maternal plasma in comparison with those carrying alleles of Hap II. The hypomethylation of DNA fragments derived from the fetus would lower the methylation level of Hap I compared to that of Hap II. In other words, if the methylation of Hap I showed a lower methylation level than Hap II, the fetus would be more likely to inherit maternal Hap I. Otherwise, the fetus would be more likely to inherit maternal Hap II. In another embodiment, the probability of the individual fragments being derived from the fetus or the mother can be calculated as described above. For all the fragments aligning to the Hap I, an aggregated probability of these fragments being derived from the fetus can be determined based on the Bayes's Theorem. Similarly, the aggregated probability of these fragments being derived from the fetus can be computed for the Hap II. The likelihood of Hap I or Hap II being inherited by the fetus can then be deduced based on the two aggregated probability.

In embodiments, the size lengthening or shortening between the two haplotypes (i.e. Hap I and Hap II) could be used to determine the fetally inherited maternal haplotype. If the fetus has inherited Hap I, more fragments carrying alleles of Hap I would be present in maternal plasma in comparison with those carrying alleles of Hap II. The DNA fragments derived from the fetus would be relatively shorter than those derived from Hap II. In other words, if the molecules originated from Hap I contain more short DNA than Hap II, the fetus would be more likely to inherit maternal Hap I. Otherwise, the fetus would be more likely to inherit maternal Hap II.

In some embodiments, one could perform a combined analysis of count, size and methylation between maternal Hap I and Hap II to deduce the maternal inheritance of the fetus. For example, one could use logistic regression to combine those three metrics including counts, sizes and methylation states.

In clinical practice, haplotype-based analysis concerning counts, sizes, and methylation states would allow for determining whether an unborn fetus has inherited the maternal haplotype associated with genetic disorders, for example, but not limited to, single-gene disorders including fragile X syndrome, muscular dystrophy, Huntington disease or beta-thalassemia. Detection of disorders involving repeats of DNA sequences in long cell-free reads are described separately in this disclosure.

E. Targeted Sequencing of Long Cell-Free DNA Molecules

The methods described in the current disclosure can also be applied to analyze one or more selected long DNA fragments. In embodiments, one or more long DNA fragments of interest can first be enriched by a hybridization method which allow hybridization of DNA molecules from the region(s) of interest to synthetic oligonucleotides with complementary sequences. To decode size, genetic, and epigenetic information all in one using the methods described in the current disclosure, the target DNA molecules are preferred to not be amplified by PCR before subjected to sequencing because the base-modification information in the original DNA molecule would not be transferred to the PCR products.

Several methods have been developed to enrich for these target regions without performing PCR amplification. In another embodiment, the one or more target long DNA molecules can be enriched through the use of clustered regularly interspaced short palindromic repeats (CRISPR)-CRISPR-associated protein 9 (Cas9) system (Stevens et al. PLOS One 2019; 14(4):e0215441; Watson et al. Lab Invest 2020; 100:135-146). Even though such CRISPR-Cas9 mediated cuts would alter the size of the original long DNA molecules, their genetic and epigenetic information is still preserved and able to be obtained using the methods described in this disclosure, including but not limited to base content, haplotype (i.e. phase) information, de novo mutations, base modifications (e.g. 4mC (N4-methylcytosine), 5hmC (5-hydroxymethylcytosine), 5fC (5-formylcytosine), 5caC (5-carboxylcytosine), 1mA (N1-methyladenine), 3mA (N3-methyladenine), 7mA (N7-methyladenine), 3mC (N3-methylcytosine), 2mG (N2-methylguanine), 6mG (O6-methylguanine), 7mG (N7-methylguanine), 3mT (N3-methylthymine), 4mT (O4-methylthymine) and 8oxoG (8-oxoguanine). In embodiments, the ends of DNA molecules in a DNA sample are first dephosphorylated so rendering them not susceptible to the ligation to sequencing adaptors directly. Then the long DNA molecules of interest is directed by the Cas9 protein with guide RNAs (crRNA) to create double-stranded cuts. The long DNA molecules of interested franked by double-stranded cuts on both sides would then be ligated to the sequencing adaptors specified by the sequencing platform of choice. In another embodiment, the DNA can be treated with exonuclease so that the DNA molecules not bounded by Cas9 proteins would be degraded (Stevens et al. PLOS One 2019; 14(4):e0215441). As these methods do not involve PCR amplification, the original DNA molecules with base-modification can be sequenced and the base modification would be determined.

In embodiments, these methods can be used to target a large number of long DNA molecules sharing homologous sequences by designing the guide RNAs with reference to a reference genome such as a human reference genome (hg19), for example the long interspersed nuclear element (LINE) repeats. In one example, such an analysis can be used for the analysis of circulating cell-free DNA in maternal plasma for the detection of fetal aneuploidies (Kinde et al. PLOS One 2012; 7(7):e41162. In embodiments, the deactivated or 'dead' Cas9 (dCas9) and its associated single guide RNA (sgRNA) can be used for enriching targeted long DNA without cutting the double-stranded DNA molecules. For example, the 3' end of sgRNA could be designed to bear an extra universal short sequence. One could use biotinylated single-stranded oligonucleotides complementary to that universal short sequence to capture those target long DNA molecules bound by dCas9. In another embodiment, one could use biotinylated dCas9 protein or sgRNA, or both, to facilitate the enrichment.

In embodiments, one may perform size selection to enrich the long DNA fragments without restricting to one or more particular genomic regions of interest, using approaches including but not limited to chemical, physical, enzymatic, gel-based, and magnetic bead-based methods, or methods that combine more than such approaches. In other embodiments, immunoprecipitation may be used to enrich for DNA fragments of certain methylation profile, such as mediated by the use of anti-methylcytosine antibodies and methyl-binding proteins. The methylation profile of the bound or captured DNA could be determined using non-methylation aware sequencing.

Figure 17:
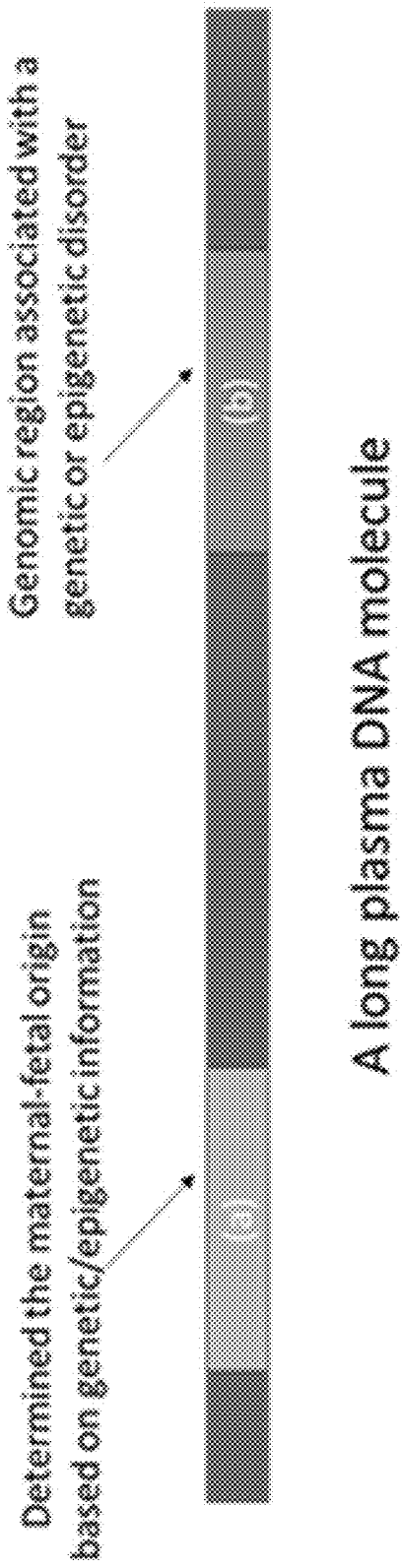
FIG. 17 illustrates the determination of the genetic/epigenetic disorders in a plasma DNA molecule with the information of maternal and fetal origins according to embodiments of the present invention.

F. General Concepts for Fetal Inheritance Analysis Based on Long Plasma DNA Molecules FIG. 17 illustrates the determination of the genetic/epigenetic disorders in a plasma DNA molecule with the information of maternal and fetal origins. A long plasma DNA molecule could be determined to be of fetal or maternal origin in a pregnant woman according to the genetic and/or epigenetic profile of CpG sites in whole or part of the molecule [i.e., region (a)]. The genetic information can be, but not limited to, sequence information, single nucleotide polymorphisms, insertions, deletions, tandem repeats, satellite DNA, microsatellite, minisatellite, inversions, etc. Epigenetic information can be the methylation status of one or more CpG sites as well as their relative orders in a plasma DNA molecule. In other embodiment, the epigenetic information can be modification of any of A, C, G, or T. A long plasma DNA with tissue origin information could be used for noninvasive prenatal testing by determining the presence of genetic and/or epigenetic disorders in such a long plasma DNA molecule [i.e., region (b)].

Figure 18:
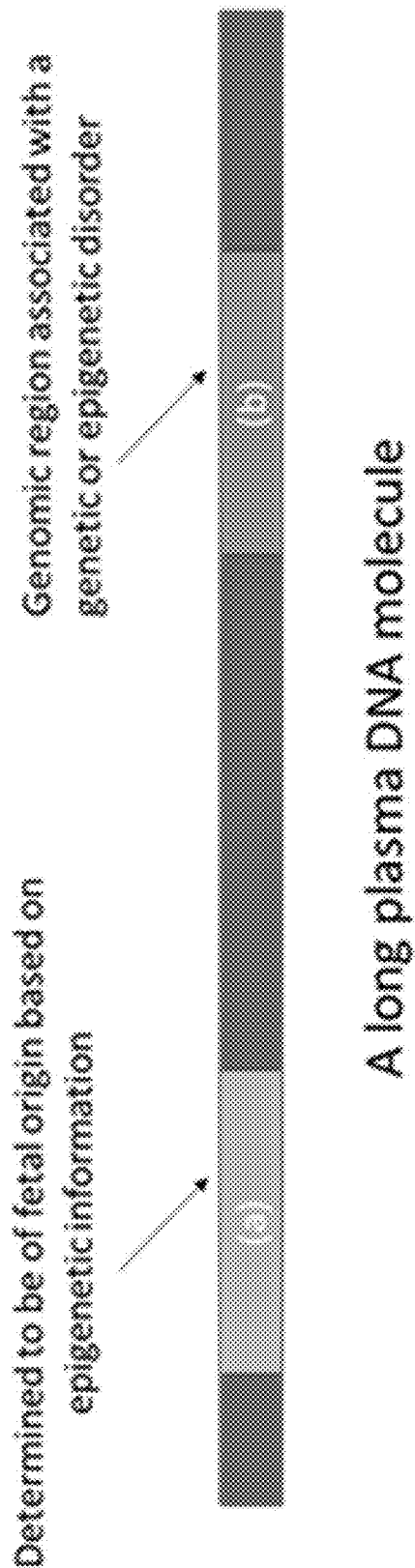
FIG. 18 illustrates the identification of fetal aberrant fragments according to embodiments of the present invention.

FIG. 18 illustrates the identification of fetal aberrant fragments. As an example, a long DNA fragment was identified to be of fetal origin based on methylation patterns of the region (a) according to this disclosure. One could determine the likelihood of a fetus affected by a genetic or epigenetic disorder based on such a molecule of fetal origin. The genetic disorders may involve single nucleotide variants, insertions, deletions, tandem repeats, satellite DNA, microsatellite, minisatellite, inversions, etc. Examples of genetic disorders, include, but not limited to: beta-thalassemia, alpha-thalassemia, sickle cell anemia, cystic fibrosis, sex-linked genetic disorders (e.g., hemophilia, Duchenne muscular dystrophy), spinal muscular atrophy, congenital adrenal hyperplasia, etc. Epigenetic disorders my aberrant levels of DNA methylation, e.g., methylation gains (i.e., hypermethylation) or losses (hypomethylation). Examples of epigenetic disorders included, but not limited to, fragile X syndrome, Angelman's syndrome, Prader-Willi syndrome, Facioscapulohumeral muscular dystrophy (FSHD), Immunodeficiency, centromeric instability and facial anomalies (ICF) syndrome, etc. The genetic or epigenetic disorder may be found to be present in region (b).

G. Improving the Sequencing Accuracy

Sequencing accuracy may improve with sequence reads of long cell-free DNA fragments. In FIG. 11B, among 7 alleles in a long fetal-specific DNA molecule, there was 1 allele that appeared to not be consistent between the PacBio and Illumina sequencing.

FIGS. 19A-19G show illustrations of error correction of cell-free DNA genotyping using PacBio sequencing. We visualized the subread alignment results for those 7 sites of FIG. 11B. The $1^{st}$ row indicates genomic coordinates; the $2^{nd}$ row is a reference sequence. The $3^{rd}$ and after rows indicate the aligned subreads. For example, in FIG. 19A, there are 8 subreads crossing that region. '.' represents identical to reference base in the Watson strand. ',' represents identical to reference base in the Crick strand. 'Alphabet letter' represents an alternative allele. '*' represents an indel. One could see that the inconsistent site shown in FIG. 19F, the major base was called as 'T' in the consensus sequence. However, among 9 subreads in that site (FIG. 19F), only 5 out 9 subreads (i.e. major allele fraction (MAF) of 56%) were determined to be 'T', while the others were determined to be 'C'. The major allele fraction of this site (FIG. 19F) was lower than that of other sites (FIGS. 19A-E and FIG. 19G) (range of MAF: 67-89%). Therefore, if one sets stringent criteria for determining the base compositions for each site in a consensus sequence, for example, using MAF at least 60%, this error site will be ruled out for downstream interpretation. On the other hand, such an erroneous site happed to fall within in a homopolymer (i.e. a series of the consecutive identical base, 'TTTTTTT'). In embodiments, one could set a criterion by which the variants within a homopolymer were flagged as QC failure and temporarily not used for downstream analysis. In embodiments, one could apply different mapping qualities and base qualities to correct or filter low-quality base or subreads to improve base composition analysis.

With further improvements in the sequencing accuracy of nanopore sequencing, embodiments of the present invention can also be used with such an improved sequencing platform and thereby result in improved accuracy.

H. Example Methods

Long cell-free DNA fragments may be sequenced from biological samples obtained from pregnant women with cell-free DNA fragments. These long cell-free DNA fragments may be used to determine the inheritance of a haplotype by a fetus.

1. Sequencing Long Cell-Free DNA Fragments

Figure 20:
FIG. 20 shows a method of analyzing a biological sample obtained from a female pregnant with a fetus according to embodiments of the present invention.

FIG. 20 shows a method 2000 of analyzing a biological sample of a pregnant organism. The biological sample may include a plurality of cell-free nucleic acid molecules. The biological sample may be any biological sample described herein. Over 20% of the cell-free nucleic acid molecules in the biological sample have sizes greater than 200 nt (nucleotides).

At block 2010, a plurality of plurality of cell-free nucleic acid molecules are sequenced. Sequencing may be by a single molecule, real-time technique. In some embodiments, sequencing may be by using a nanopore.

Over 20% of the plurality of the cell-free nucleic acid molecules sequenced may have lengths greater than 200 nt. In some embodiments, 15-20%, 20-25%, 25-30%, 30-35%, or more than 35% of the plurality of the cell-free nucleic acid molecules sequenced may have lengths greater than 200 nt.

In some embodiments, over 11% of the plurality of the cell-free nucleic acid molecules sequenced may have lengths greater than 400 nt. In embodiments, 5-10%, 10-15%, 15-20%, 20-25%, or more than 25% of the plurality of the cell-free nucleic acid molecules sequenced may have lengths greater than 400 nt.

In some embodiments, over 10% of the plurality of the cell-free nucleic acid molecules sequenced may have lengths greater than 500 nt. In embodiments, 5-10%, 10-15%, 15-20%, 20-25%, or more than 25% of the plurality of the cell-free nucleic acid molecules sequenced may have lengths greater than 500 nt.

In embodiments, over 8% of the plurality of the cell-free nucleic acid molecules sequenced may have lengths greater than 600 nt. In embodiments, 5-10%, 10-15%, 15-20%, 20-25%, or more than 25% of the plurality of the cell-free nucleic acid molecules sequenced may have lengths greater than 600 nt.

In some embodiments, over 6% of the plurality of the cell-free nucleic acid molecules sequenced may have lengths greater than 1 knt. In embodiments, 3-5%, 5-10%, 10-15%, 15-20%, 20-25%, or more than 25% of the plurality of the cell-free nucleic acid molecules sequenced may have lengths greater than 1 knt.

In embodiments, over 3% of the plurality of the cell-free nucleic acid molecules sequenced may have lengths greater than 2 knt. In embodiments, 1-5%, 5-10%, 10-15%, 15-20%, 20-25%, or more than 25% of the plurality of the cell-free nucleic acid molecules sequenced may have lengths greater than 2 knt.

In embodiments, over 1% of the plurality of the cell-free nucleic acid molecules sequenced may have lengths greater than 3 knt. In embodiments, 1-5%, 5-10%, 10-15%, 15-20%, 20-25%, or more than 25% of the plurality of the cell-free nucleic acid molecules sequenced may have lengths greater than 3 knt.

In some embodiments, at least 0.9% of the plurality of the cell-free nucleic acid molecules sequenced may have lengths greater than 4 knt. In embodiments, 0.5-1%, 1-5%, 5-10%, 10-15%, 15-20%, or more than 20% of the plurality of the cell-free nucleic acid molecules sequenced may have lengths greater than 4 knt.

In some embodiments, at least 0.04% of the plurality of the cell-free nucleic acid molecules sequenced may have lengths greater than 10 knt. In embodiments, 0.01 to 0.1%, 0.1% to 0.5%, 0.5-1%, 1-5%, 5-10%, 10-15%, or more than 15% of the plurality of the cell-free nucleic acid molecules sequenced may have lengths greater than 4 knt.

The plurality of cell-free nucleic acid molecules may include at least 10, 50, 100, 150, or 200 cell-free nucleic acid molecules. The plurality of cell-free nucleic acid molecules may be from a plurality of different genomic regions. For example, a plurality of chromosomal arms or chromosomes may be covered by the cell-free nucleic acid molecules. At least two of the plurality of cell-free nucleic acid molecules may correspond to non-overlapping regions.

The method of sequencing long cell-free DNA fragments may be used by any method described herein. The reads from the sequencing may be used to determine a fetal aneuploidy, an aberration (e.g., copy number aberration), a genetic mutation or variation, or an inheritance of a parental haplotype. The amount of sequence reads may be representative of the amount of cell-free DNA fragments.

2. Haplotype Inheritance

Figure 21:
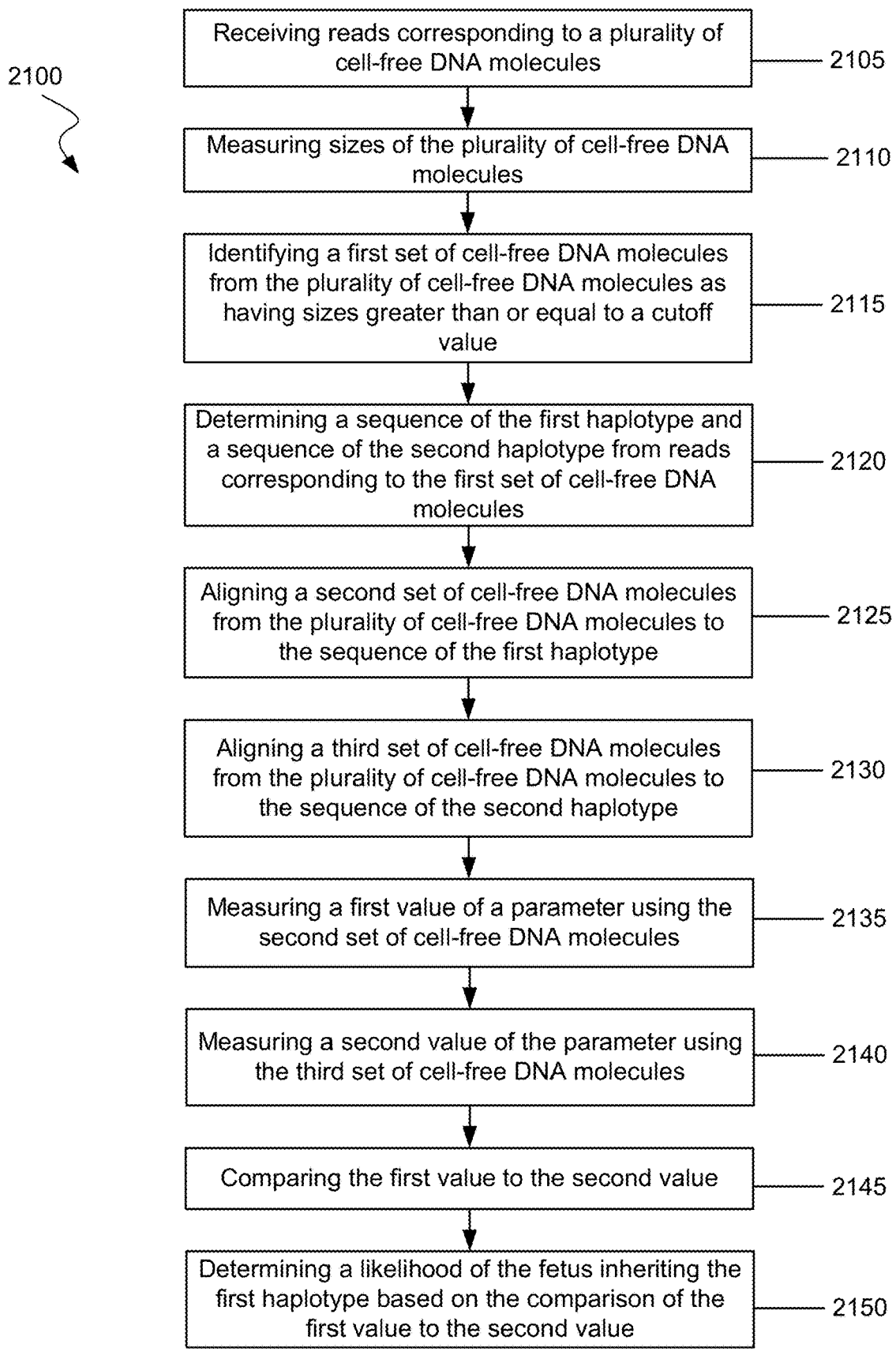
FIG. 21 shows a method of analyzing a biological sample obtained from a female pregnant with a fetus in order to determine inheritance of a haplotype according to embodiments of the present invention.

FIG. 21 shows a method 2100 of analyzing a biological sample obtained from a female pregnant with a fetus. The female may have a first haplotype and a second haplotype in a first chromosomal region. The biological sample may include a plurality of cell-free DNA molecules from the fetus and the female. The biological sample may be any biological sample described herein.

At block 2105, reads corresponding to the plurality of cell-free DNA molecules may be received. The reads may be sequence reads. In some embodiments, the method may include performing the sequencing.

At block 2110, sizes of the plurality of cell-free DNA molecules may be measured. Sizes may be measured by aligning one or more sequence reads corresponding to the ends of a DNA molecule to a reference genome. Sizes may be measured by full length sequencing a DNA molecule and then counting the number of nucleotides in the full length sequence. The genomic coordinates at the outermost nucleotides may be used to determine the length of the DNA molecule.

At block 2115, a first set of cell-free DNA molecules from the plurality of cell-free DNA molecules as having sizes greater than or equal to a cutoff value may be identified. The cutoff value may be any cutoff associated with long DNA. For example, the cutoff may include 150 bp, 180 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 950 bp, 1 kb, 1.5 kb, 2 kb, 2.5 kb, 3 kb, 4 kb, 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 200 kb, 300 kb, 400 kb, 500 kb, or 1 Mb.

At block 2120, a sequence of the first haplotype and a sequence of the second haplotype from reads corresponding to the first set of cell-free DNA molecules may be determined. Determining the sequence of the first haplotype and the sequence of the second haplotype may include aligning reads corresponding to the first set of cell-free DNA molecules to a reference genome.

In some embodiments, determining the sequence of the first haplotype and the sequence of the second haplotype may not include a reference genome. Determining the sequence may include aligning a first subset of the reads to a second subset of the reads to identify a different allele at a locus in the reads. The method may include determining that the first subset of the reads have a first allele at the locus. The method may also include determining that the second subset of the reads have a second allele at the locus. The method may further include determining that the first subset of the reads corresponds to the first haplotype. In addition, the method may include determining that the second subset of the reads corresponds to the second haplotype. The alignment may be similar to the alignment described with FIG. 16.

At block 2125, a second set of cell-free DNA molecules from the plurality of cell-free DNA molecules may be aligned to the sequence of the first haplotype. The second set of cell-free DNA molecules may have sizes less than the cutoff value. The second set of cell-free DNA molecules may be short DNA molecules of the first haplotype.

At block 2130, a third set of cell-free DNA molecules from the plurality of cell-free DNA molecules may be aligned to the sequence of the second haplotype. The third set of cell-free DNA molecules may have sizes less than the cutoff value. The third set of cell-free DNA molecules may be short DNA molecules of the second haplotype.

At block 2135, a first value of a parameter may be measured using the second set of cell-free DNA molecules. The parameter may be a count of cell-free DNA molecules, a size profile of cell-free DNA molecules, or a methylation level of cell-free DNA molecules. The values may be raw values or statistical values (e.g., mean, median, mode, percentile, minimum, maximum). In some embodiments, the values may be normalized to a value of a parameter for a reference sample, another region, both haplotypes, or for other size ranges.

At block 2140, a second value of the parameter may be measured using the third set of cell-free DNA molecules. The parameter is the same parameter as for the second set of cell-free DNA molecules.

At block 2145, the first value may be compared to the second value. The comparison may use a separation value. A separation value may be calculated using the first value and the second value. The separation value may be compared to a cutoff value. The separation value may be any separation value described herein. The cutoff value may be determined from reference samples from pregnant females with euploid fetuses. In other embodiments, the cutoff value may be determined from reference samples from pregnant females with aneuploid fetuses. In some embodiments, the cutoff value may be determined assuming an aneuploid fetus. For example, data from reference samples from pregnant females with euploid fetuses may be adjusted to account for an increase or decrease in a copy number of a chromosomal region for an aneuploidy. The cutoff value may be determined from adjusting the data.

At 2150, a likelihood of the fetus inheriting the first haplotype may be determined based on the comparison of the first value to the second value. The likelihood may be determined based on the comparison of the separation value to the cutoff value. When the parameter is the size profile of cell-free DNA molecules, the method may include determining that the fetus has a higher likelihood of inheriting the first haplotype than the second haplotype when the first value is less than the second value, indicating that the second set of cell-free DNA molecules is characterized by a smaller size profile than the third set of cell-free DNA molecules. When the parameter is the methylation level of cell-free DNA molecules, the method may include determining that the fetus has a higher likelihood of inheriting the first haplotype than the second haplotype when the first value is less than the second value.

In some embodiments, methods may include identifying a number of repeats of a subsequence in a read of the reads corresponding to the first set of cell-free DNA molecules. Determining the sequence of the first haplotype may include determining the sequence includes the number of repeats of the subsequence. The first haplotype may include a repeat-associated disease, which may be any described herein. A likelihood of the fetus inheriting the repeat-associated disease may be determined. The likelihood of the fetus inheriting the repeat-associated disease may be equal to or similar to the likelihood of the fetus inheriting the first haplotype. Identifying repeats of sequences is described later in this disclosure, including with FIG. 16.

II. Analyzing for Tissue of Origin Using Methylation

A long cell-free DNA molecules may have several methylation sites. As discussed in this disclosure, the level of methylation of a long cell-free DNA molecule in a pregnant woman may be used in determining a tissue of origin. In addition, the methylation pattern present on a long cell-free DNA molecule may be used to determine a tissue of origin.

Cells from placental tissues possess unique methylomic patterns compared with white blood cells and cells from tissues such as, but not limited to, the liver, lungs, esophagus, heart, pancreas, colon, small intestines, adipose tissues, adrenal glands, brain, etc. (Sun et al., Proc Natl Acad Sci USA. 2015; 112:E5503-12). Methylation profiles of circulating fetal DNA in the blood of a pregnant mother may resemble that of the placenta, thus providing possibilities to explore a means to develop noninvasive fetus-specific biomarkers that are not dependent on fetal sex or genotype. However, bisulfite sequencing (e.g. using Illumina sequencing platforms) of maternal plasma DNA of pregnant women may lack the ability to differentiate the molecules of fetal origin from those of maternal origin because of a number of limitations: (1) plasma DNA may be degraded during bisulfite treatment, and typically a long DNA molecule would be broken into shorter molecules; (2) DNA molecules greater than 500 bp may not be effectively sequenced with Illumina sequencing platforms for downstream analysis (Tan et al, Sci Rep. 2019; 9:2856).

For the analysis regarding tissues of origin based on methylation, one may focus on a few differentially methylated regions (DMRs) and use the aggregated methylation signal from multiple molecules associated with DMRs (Sun et al, Proc Natl Acad Sci USA. 2015; 112:E5503-12), instead of single-molecule methylation patterns. A number of studies attempted to use methylation-sensitive restriction enzymes-based (Chan et al, Clin Chem. 2006; 52:2211-8) or methylation-specific PCR based approaches (Lo et al, Am J Hum Genet. 1998; 62:768-75) to assess the contribution from the placenta to the plasma DNA pool. However, those studies were only suited for analyzing one or a few markers and may be challenging to be used for analyzing molecules on a genomewide scale. However, those reads were deduced from amplified signals (i.e., PCR-based amplification during DNA library preparation and bridge amplification during sequencing cluster generation in a flow cell). Such amplification steps may potentially create bias preferring the short DNA molecules, leading to the loss of information related to the long DNA molecules. Besides, Li et al. only analyzed those reads related to the DMRs that were mined beforehand (Li et al., Nuclei Acids Res. 2018; 46:e89).

In this disclosure, we describe new approaches to differentiate fetal and maternal DNA molecules in the plasma of pregnant women based on the methylation pattern of a single DNA molecule without bisulfite treatment and DNA amplification. In embodiments, one or more long plasma DNA molecules would be used for analysis (e.g. using bioinformatics and/or experimental assays for size selection). A long DNA molecule may be defined as a DNA molecule with a size of at least, but not limited to, 100 bp, 200 bp, 300 bp, 400 bp, 500 bp, 600 bp, 700 bp, 800 bp, 900 bp, 1 kb, 2 kb, 3 kb, 4 kb, 5 kb, 10 kb, 20 kb, 30 kb, 40 kb, 50 kb, 100 kb, 200 kb, etc. There is a paucity of data regarding the presence and methylation status of longer cell-free DNA molecules in maternal plasma. For example, it is not known if the methylation status of such longer cell-free DNA molecules would reflect that of the cellular DNA of the tissue of origin, e.g., as such long fragments have more sites whose methylation status might change after fragmentation in the body; such a change might occur while fragments are circulating in plasma. For example, a study has shown that methylation status of circulating DNA correlates with the size of DNA fragments (Lun et al. Clin Chem. 2013; 59:1583-94). The feasibility for inferring tissue of origin from such longer cell-free DNA molecules is therefore not known. Thus, the approaches taken to identify tissue-associated methylation signatures and the methodologies taken to determine and interpret the presence of such tissue-specific longer cell-free DNA molecules are substantially different from those applied to short cell-free DNA analysis.

According to embodiments of this disclosure, one could identify the short and long DNA molecules and determine their biological characteristics including but not limited to methylation patterns, fragment ends, sizes, and base compositions. A short DNA molecule could be defined as a DNA molecule with a size of less than, but not limited to, 50 bp, 60 bp, 70 bp, 80 bp, 90 bp, 100 bp, 200 bp, 300 bp, etc. A short DNA molecule may be a DNA molecule that is not in a range that is considered long. We describe a new approach to deduce the tissues of origin for circulating DNA molecules in the plasma of pregnant women. This new approach makes use of the methylation patterns on one or more long DNA molecule in plasma. The longer a DNA molecule is, the larger is the number of CpG sites that it would likely contain. The presence of multiple CpG sites on a plasma DNA molecule would provide tissue of origin information, even though the methylation status of any single CpG site may not informative for determining the tissues of origin. Such methylation patterns in a long DNA molecule may include the methylation status for each CpG site, orders of methylation status, and distances between any two CpG sites. The methylation status between two CpG sites may depend on a distance between two CpG sites. When CpG sites within a certain distance (e.g., CpG island) in a molecule exhibit a tissue-specific pattern, a statistical model may assign more weight to those signals during tissue-of-origin analysis.

FIG. 22 schematically illustrates this principle. FIG. 22 shows methylation patterns for DNA molecules. Seven CpG sites are shown for different tissues (placenta, liver, blood cells, colon) and six plasma DNA fragments A-E. Methylated CpG sites are shown in red, and unmethylated CpG sites are shown in green. As an example, let's consider 7 CpG sites with various methylation status across the placenta, liver, blood cells, and colon tissues. Let's consider the scenario that no single CpG site exhibits a methylation state specific to the placenta in comparison with other tissues. Thus, the tissue of origin for those plasma DNA molecules A, B, C, D and E with variable sizes could not be determined only based on a methylation state at a single CpG site. For the plasma DNA molecules A and B, as the sizes of those two molecules are relatively short, only containing 3 and 4 CpG sites, respectively. In embodiments, methylation pattern in a DNA molecule containing more than one CpG site may be defined as a methylation haplotype. As shown in FIG. 22, the plasma DNA molecules A and B could be contributed by either the placenta or the liver on the basis of their methylation haplotypes, as the placenta and liver shared the same methylation haplotype in those genomic positions corresponding to the molecules A (positions 1, 2, and 3) and B (positions 1, 2, 3, and 4). However, when one can obtain long DNA molecules in plasma such as molecules C, D, and E, those molecules C, D, and E can be unambiguously determined to be derived from the placenta on the basis of methylation haplotype.

The reference pattern for a tissue may be based on the methylation pattern from a reference tissue. In some embodiments, the methylation pattern may be based on several reads and/or samples. A methylation level for each CpG site (also called a methylation index, MI, and described below) may be used to determine whether a site is methylated.

A. Statistical Models for Methylation Patterns

In embodiments, the likelihood of a plasma DNA molecule being derived from the placenta may be determined by comparing the methylation haplotype of a single DNA molecule with the methylation patterns in a number of reference tissues. Long plasma DNA molecules may be favored for such analysis. A long DNA molecule may be defined as a DNA molecule with a size of at least, but not limited to, 100 bp, 200 bp, 300 bp, 400 bp, 500 bp, 600 bp, 700 bp, 800 bp, 900 bp, 1 kb, 2 kb, 3 kb, 4 kb, 5 kb, 10 kb, 20 kb, 30 kb, 40 kb, 50 kb, 100 kb, 200 kb, etc. The reference tissues may include, but not limited to, placenta, liver, lungs, esophagus, heart, pancreas, colon, small intestines, adipose tissues, adrenal glands, brain, neutrophils, lymphocytes, basophils, eosinophils, etc. In embodiments, one may determine the likelihood of a plasma DNA molecule being derived from the placenta, by synergistically analyzing the methylation haplotype of a plasma DNA determined by single-molecule real-time sequencing and the methylome data based on whole-genome bisulfite sequencing of reference tissues. As an example, the placenta and buffy coat samples were sequenced to a mean of 94-fold and 75-fold genomic coverage of a haploid genome, respectively, using whole-genome bisulfite sequencing. The methylation level of each CpG site (also called methylation index, MI) was calculated based on the number of sequenced cytosines (i.e. methylated, denoted by C) and the number of sequenced thymines (i.e. unmethylated, denoted by T) using the following formula:

$$MI = \frac{C}{C+T} \times 100\%.$$

CpG sites were stratified into three categories on the basis of MI values deduced from the placenta DNA:
1. Category A CpG sites whose MI values were ≥70.
2. Category B CpG sites whose MI values were between 30 and 70.
3. Category C CpG sites whose MI values were ≤30.

Similarly, MI values at CpG sites deduced from the buffy coat DNA were used to classify CpG sites into three categories:
1. Category A CpG sites whose MI values were ≥70.
2. Category B CpG sites whose MI values were between 30 and 70.
3. Category C CpG sites whose MI values were ≤30.

The categories used MI cutoffs of 30 and 70. Cutoffs may include other numbers, including 10, 20, 40, 50, 60, 80, or 90. In some embodiments, these categories may be used to determine a reference methylation pattern for a reference tissue (e.g., for use as described with FIG. 22). Category A sites may be considered methylated. Category C sites may be considered unmethylated. Category B sites may be considered non-informative and not included in the reference pattern.

For a plasma DNA molecule harboring n CpG sites, the methylation status for each CpG site was determined by approaches described in our previous disclosure (U.S. application Ser. No. 16/995,607). In some embodiments, methylation status may be determined by bisulfate sequencing or with nanopore sequencing. To determine the likelihood of a plasma DNA molecule being derived from the placenta or the maternal background, the methylation patterns of that molecule were analyzed in conjugation with the prior methylation information in the placenta and the maternal buffy coat DNA. In embodiments, we made use of the principle that if a CpG site determined to be methylated (M) in a plasma DNA fragment coincided with a higher methylation index in the placenta, such an observation would indicate that this molecule was more likely to be derived from the placenta. If a CpG site determined to be methylated (M) in a plasma DNA molecule coincided with a lower methylation index in the placenta, such an observation would indicate that this molecule was less likely to be derived from the placenta; if a CpG site determined to be unmethylated (U) in a plasma DNA coincided with a lower methylation index in the placenta. Such an observation would indicate that this molecule was more likely to be derived from the placenta. If a CpG site determined to be unmethylated (U) in a plasma DNA coincided with a higher methylation index in the placenta, such an observation would indicate that this molecule was less likely to be derived from the placenta.

We implemented the following scoring scheme. The initial score (S) reflecting the likelihood of fetal origin for a plasma DNA fragment was set to 0. When comparing the methylation status of a plasma DNA molecule with the prior methylation information of the placenta DNA, a. if a CpG site on the plasma DNA molecule was determined to be 'M' and its counterpart in the placenta belonged to Category A, a score of 1 would be added to S (i.e. increasing the score unit by 1).
b. if a CpG site on the plasma DNA molecule was determined to be 'U' and its counterpart in the placenta belonged to Category A, a score of 1 would be deducted from S (i.e. decreasing the score unit by 1).
c. if a CpG site on the plasma DNA molecule was determined to be 'M' and its counterpart in the placenta belonged to Category B, a score of 0.5 would be added to S.
d. if a CpG site on the plasma DNA molecule was determined to be 'U' and its counterpart in the placenta belonged to Category B, a score of 0.5 would be added to S.
e. if a CpG site on the plasma DNA molecule was determined to be 'M' and its counterpart in the placenta belonged to Category C, a score of 1 would be deducted from S.
f. if a CpG site on the plasma DNA molecule was determined to be 'U' and its counterpart in the placenta belonged to Category C, a score of 1 would be added to S.

We call the above processes 'methylation status matching'.

After all CpG sites in a plasma DNA molecule had been processed, the final aggregated score, S(placenta), was obtained for that plasma DNA molecule. In embodiments, the number of CpG sites was required to be at least 30 and the length of the plasma DNA molecule was required to be at least 3 kb. Other numbers of CpG sites and lengths may be used, including, but not limited to, any described herein.

When comparing the methylation status of a plasma DNA molecule with the methylation level of the buffy coat DNA at the corresponding sites, a similar scoring scheme would be applied. After all CpG sites in a plasma DNA molecule had been processed, the final aggregated score, S(buffy coat), was obtained for that plasma DNA molecule.

If S(placenta)>S(buffy coat), the plasma DNA molecule was determined to be of fetal origin; otherwise, the plasma DNA molecule was determined to be of maternal origin.

There were 17 and 405 fetal-specific and maternal-specific DNA molecules that were used for evaluating the performance of deducing the fetal-maternal origin for a plasma DNA molecule. The fetal-specific molecules were plasma DNA molecules carrying fetal-specific SNP alleles whereas the maternal-specific DNA molecules were those carrying maternal-specific SNP alleles.

Figure 23:
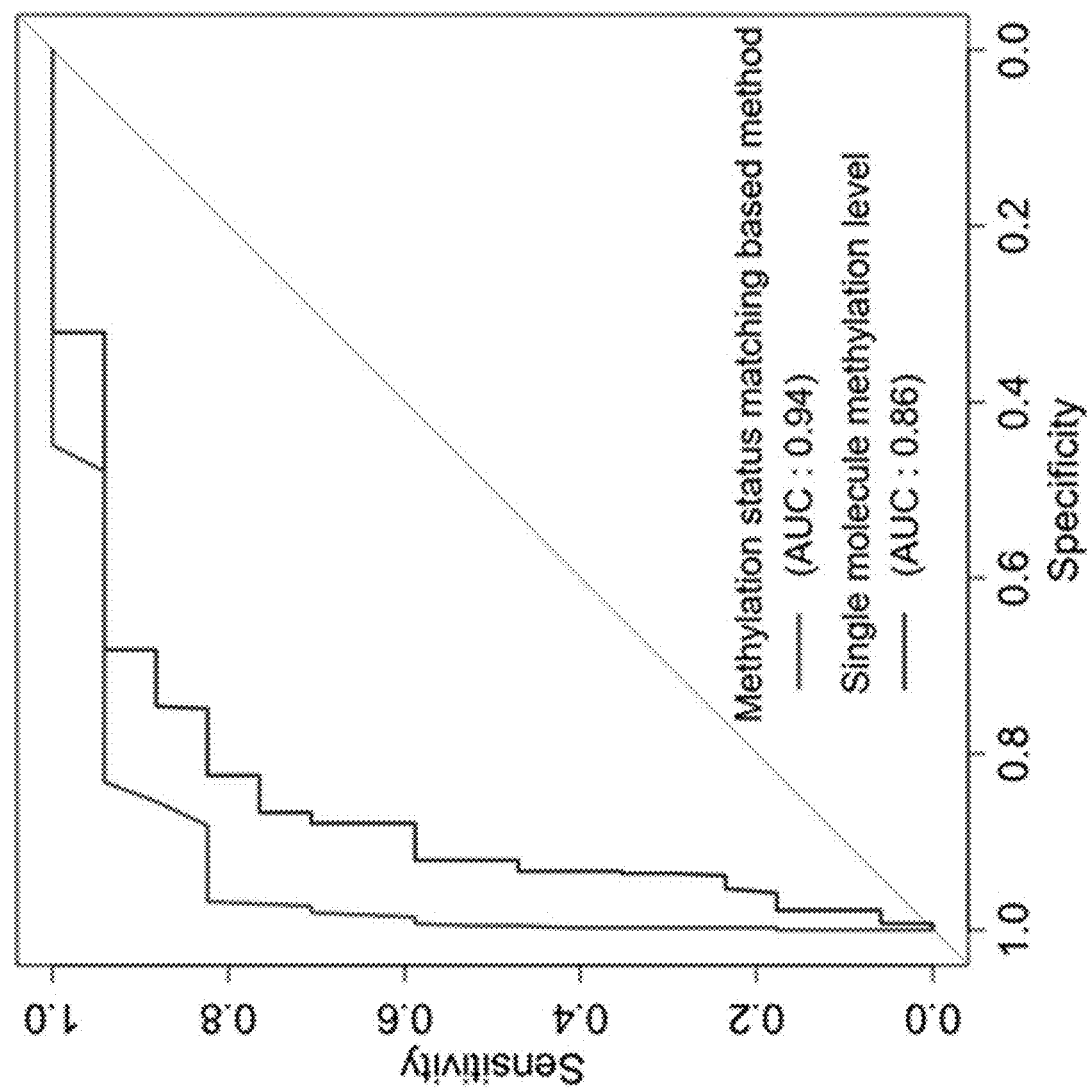
FIG. 23 shows a receiver operating characteristic (ROC) curve for the determination of fetal and maternal origins according to embodiments of the present invention.

FIG. 23 shows a receiver operating characteristic curve (ROC) for the determination of fetal and maternal origins. The y-axis shows sensitivity, and the x-axis shows specificity. The red line represents the performance of differentiating molecules of fetal origin and maternal origin using methylation status matching based method present in this disclosure. The blue line represents the performance of differentiating molecules of fetal origin and maternal origin using single molecule methylation level (i.e., the proportion of CpG sites determined to be methylated in a DNA molecule). FIG. 23 shows that the area under the receiver operating characteristic curve (AUC) for the methylation status matching process (0.94) was significantly higher than that based on single molecule methylation level (0.86) (P value<0.0001; DeLong test). It suggested that the analysis of methylation patterns of a long DNA molecule would be useful for the determination of the fetal/maternal origin.

In embodiments, the magnitude of the difference (ΔS) between S(placenta) and S(buffy coat) may be taken into account when determining whether a plasma DNA was of fetal origin or maternal origin. The absolute value of ΔS may be required to exceed a certain threshold, for example, but not limited to, 5, 10, 20, 30, 40, 50, etc. As an illustration, when we used 10 as a threshold of ΔS, the positive prediction value (PPV) in detecting fetal DNA molecules was improved to 91.67% from 14.95%.

In embodiments, the methylation status of a CpG site would be affected by the methylation status of its neighboring CpG sites. The closer the nucleotide distance between any two CpG sites on a DNA molecule, the more likely the two CpG sites would share the same methylation status. This phenomenon has been referred to as co-methylation. A number of tissue-specific CpG island methylation have been reported; hence, in some statistical models for tissue-of-origin analysis, more weights would be assigned to dense clusters of CpG sites (e.g. CpG islands) sharing the same methylation status. For the scenarios 'a' and 'f', if the current CpG site under interrogation was located within a genomic distance of no more than 100 bp relative to the previous CpG site and the results of the methylation status matching process were identical for these two consecutive CpG sites, an extra 1 point would be added to the score S for the current CpG site. For the scenarios 'b' and 'e', if the current CpG site under interrogation was located within a genomic distance of no more than 100 bp relative to the previous CpG site and the results of the methylation status matching process were identical for these two consecutive CpG sites, an extra 1 point would be deducted from the score S for the current CpG site. However, if the current CpG site under interrogation was located within a genomic distance of no more than 100 bp relative to the previous CpG site but the results of the methylation status matching process for these two consecutive CpG sites were not consistent, the aforementioned default scoring scheme would be used. On the other hand, if the current CpG site under interrogation was located within a genomic distance of greater than 100 bp relative to the previous CpG site, the aforementioned scoring scheme with default parameters would be used. Points other than 1 and distances other than 100 bp may be used, including any described herein.

In other embodiments, CpG sites were stratified into more than three categories on the basis of MI values deduced from the placenta and buffy coat DNA. The prior methylation information of reference tissues could be deduced from single molecule real-time sequencing (i.e. nanopore sequencing and/or PacBio SMRT sequencing). The length of a plasma DNA molecule could be required to be at least, but not limited to, 100 bp, 200 bp, 300 bp, 400 bp, 500 bp, 600 bp, 700 bp, 800 bp, 900 bp, 1 kb, 2 kb, 3 kb, 4 kb, 5 kb, 10 kb, 20 kb, 30 kb, 40 kb, 50 kb, 100 kb, 200 kb, etc. The number of CpG sites could be required to be at least, but not limited to, 3, 4, 5, 6, 7, 8, 9, 10, 20, 30, 40, 50, 60, 70, 80, 90, 100, etc.

In embodiments, one may use a probabilistic model to characterize the methylation patterns of a plasma DNA molecule. The methylation status of k CpG sites (k≥1) on a plasma DNA molecule was denoted as $M=(m_1, m_2, \ldots, m_k)$, where $m_i$ was 0 (for unmethylated status) or 1 (for methylated status) at the CpG site i on a plasma DNA molecule. In embodiments, the probability of M related to a plasma DNA molecule derived from the placenta could depend on the reference methylation patterns in the placenta tissues. The reference methylation patterns in the placenta tissues for those corresponding CpG sites at 1, 2, ..., k would follow beta distributions. The beta distribution is parameterized by two positive parameters $\alpha$ and $\beta$, denoted by Beta($\alpha$, $\beta$). The values derived from beta distribution would range from 0 to 1. Based on high-depth bisulfate sequencing data for a tissue of interest, the parameters $\alpha$ and $\beta$ were determined by the numbers of sequenced cytosines (methylated) and thymines (unmethylated) at each CpG site for that particular tissue, respectively. For the placenta, such a beta distribution was denoted as Beta($\alpha^P$, $\beta^P$). The probability of a plasma DNA molecule derived from the placenta, P(M|Placenta), would be modeled by:

$$P(M \mid \text{Placenta}) = \prod_{i=1}^{i=p} P(m_i \mid \text{Beta } (\alpha_i^p, \beta_i^p))$$

Where 'i' denoted the $i^{th}$ CpG site; Beta($\alpha_i^p$, $\beta_i^p$) indicated the beta distribution related to the methylation patterns at the $i^{th}$ CpG site in the placenta; P was the joint probability of an observed plasma DNA molecule with given methylation patterns across k CpG sites.

The probability of a plasma DNA molecule derived from the buffy coat (i.e. white blood cells), P(M|Buffy coat), would be modeled by:

$$P(M \mid \text{Buffy coat}) = \prod_{i=1}^{i=p} P(m_i \mid (\alpha_i^b, \beta_i^b))$$

Where 'i' denoted the $i^{th}$ CpG site; Beta($\alpha_i^b$, $\beta_i^b$) indicated the beta distribution related to the methylation patterns at the $i^{th}$ CpG site in the buffy coat DNA. P was the joint probability of an observed plasma DNA molecule with given methylation patterns across k CpG sites.

Beta($\alpha_i^p$, $\beta_i^p$) and Beta($\alpha_i^p$, $\beta_i^p$) could be determined from the whole-genome bisulfate sequencing results of the placenta and buffy coat DNA, respectively.

For a plasma DNA molecule, if one observed P(M|Placenta)>P(M|buffy coat), such a plasma DNA molecule would be likely derived from the placenta; otherwise, it would be likely derived from the buffy coat. Using this model, we achieved an AUC of 0.79.

B. Machine Learning Models

In yet other embodiments, one could use a machine learning algorithm to determine the fetal/maternal origin of a particular plasma DNA molecule. To test the feasibility of using the machine learning based approach for classifying the fetal and maternal DNA molecules in pregnant women, we developed a graphical presentation of methylation patterns for a plasma DNA molecule.

Figure 24:
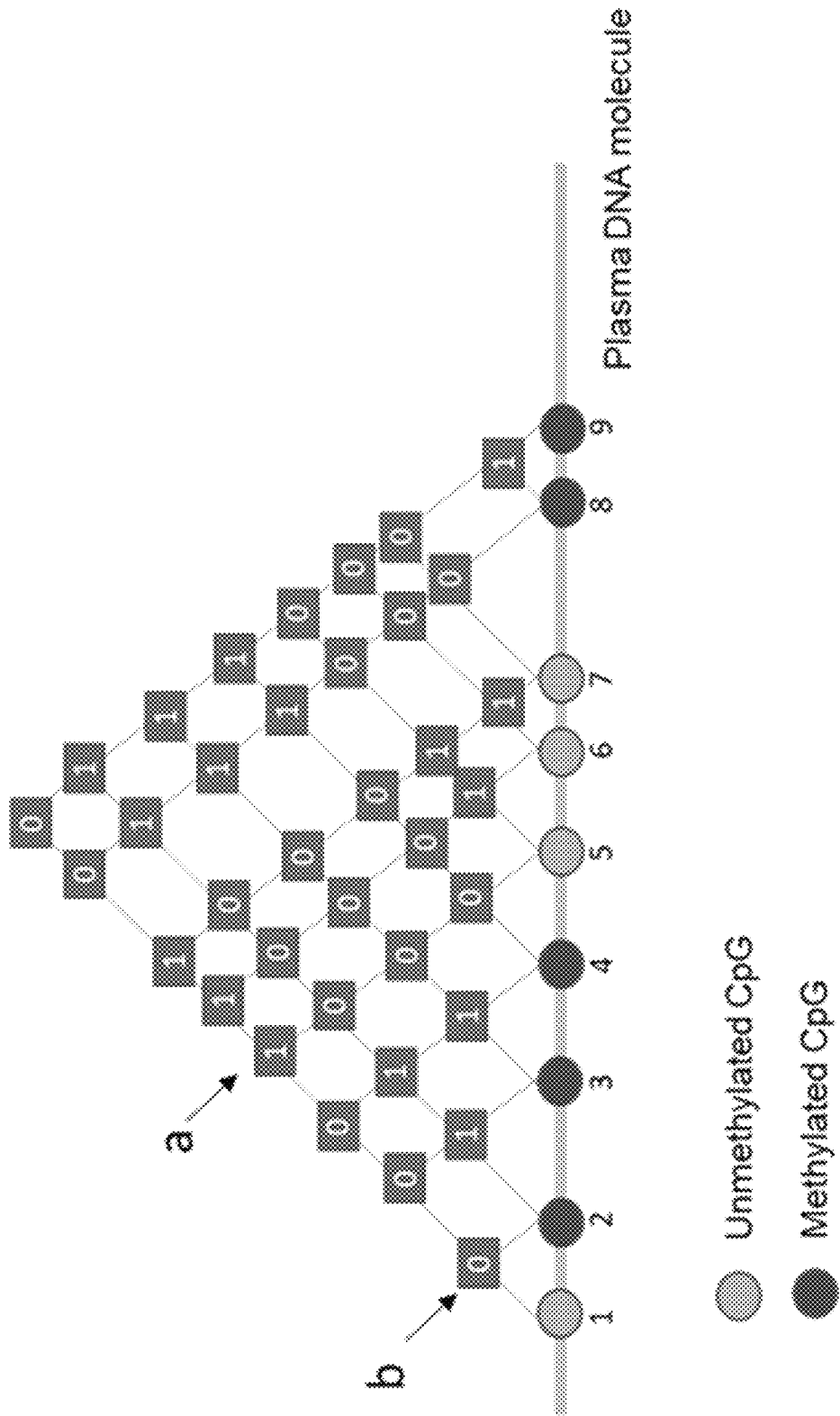
FIG. 24 shows pairwise methylation patterns according to embodiments of the present invention.

FIG. 24 shows a definition for pairwise methylation patterns. Nine CpG sites are shown on a plasma DNA molecule. Methylated CpG sites are shown in red, and unmethylated CpG sites are shown in green. When two CpG sites in a pair shared the same methylation status (e.g. the $1^{st}$ CpG and $5^{th}$ CpG), the pair would be coded as 1, as shown in a position indicated by arrow 'a'. When two CpG sites in a pair had different methylation status (e.g. the $1^{st}$ CpG and $2^{nd}$ CpG), the pair would be coded as 0, as shown in a position indicated by arrow 'b'. The same coding rules applied to all pairs of any 2 CpG sites on a DNA molecule.

We used a plasma DNA molecule containing 9 CpG sites as an example. The methylation pattern for this plasma DNA molecule was determined by approaches described in our previous disclosure (U.S. application Ser. No. 16/995,607), i.e., U-M-M-M-U-U-U-M-M (U and M represented unmethylated CpG and methylated CpG, respectively). The pairwise comparison of methylation status between any two CpG sites may be useful for a machine learning or deep learning based analysis. The same rules were applied to a total of 36 pairs in this example. If there were a total of n CpG sites on a plasma DNA molecule, there would be n*(n−1)/2 pairs of comparison. Different number of CpG sites may be used, including 5, 6, 7, 8, 10, 11, 12, 13, etc. If a molecule includes greater than the number of sites used in the machine learning model, a sliding window can be used to divide the sites into the appropriate number of sites.

We obtained one or more molecules from the placenta and buffy coat DNA samples, respectively. The methylation patterns for those DNA molecules were determined by the Pacific Bioscience (PacBio) Single-Molecule Real-Time (SMRT) sequencing according to approaches described in our previous disclosure (U.S. application Ser. No. 16/995, 607). Those methylation patterns were translated into pairwise methylation patterns.

The pairwise methylation patterns associated with the placenta DNA and those associated with the buffy coat DNA were used for training a convolutional neural network (CNN) for differentiating molecules potentially of fetal origin and maternal origin. Each target output (i.e., analogous to a dependent variable value) for a DNA fragment from the placenta was assigned as '1', while each target output for a DNA fragment from the buffy coat was assigned as '0'. The pairwise methylation patterns were used for training to determine the parameters (often called weights) for the CNN model. The optimal parameters of the CNN for differentiating the fetal-maternal origin of a DNA fragment were obtained when the overall prediction error between the output scores calculated by a sigmoid function and desired target outputs (binary values: 0 or 1) reached a minimum by iteratively adjusting the model parameters. The overall prediction error was measured by a sigmoid cross-entropy loss function in deep learning algorithms (https://keras.io/). The model parameters learned from the training datasets were used for analyzing a DNA molecule (such as a plasma DNA molecule) to output a probabilistic score which would indicate the likelihood of the DNA molecule being derived from the placenta or buffy coat. If the probabilistic score of a plasma DNA fragment exceeded a certain threshold, such a plasma DNA molecule was deemed to be of fetal origin. Otherwise, it would be deemed to be of maternal origin. The threshold would include, but not limited to, 0.1, 0.2, 0.3, 0.4, 0.5, 0.6, 0.7, 0.8, 0.9, 0.95, 0.99, etc. In one example, using this CNN model, we achieved an AUC of 0.63 for determining whether a plasma DNA molecule was of the fetal origin or maternal origin, indicating that it is possible to deduce the tissues of origin of DNA molecules from maternal plasma using deep learning algorithms. By obtaining more single molecule real-time sequencing results, the performance of the deep learning algorithm would be further improved.

In some other embodiments, the statistical models could include, but are not limited to, linear regression, logistic regression, deep recurrent neural network (e.g., long short-term memory, LSTM), Bayes's classifier, hidden Markov model (HMM), linear discriminant analysis (LDA), k-means clustering, density-based spatial clustering of applications with noise (DBSCAN), random forest algorithm, and support vector machine (SVM), etc. Different statistical distributions would be involved, including but not limited to, binomial distribution, Bernoulli distribution, gamma distribution, normal distribution, Poisson distribution, etc.

C. Methylation Haplotypes Specific to the Placenta

The methylation status of each CpG site on a single DNA molecule can be determined using the approaches described in our previous disclosure (U.S. application Ser. No. 16/995,607) or any technique described herein. Besides the single-molecule, double-stranded DNA methylation level, one could determine the single-molecule methylation pattern of each DNA molecule, which may be the sequence of methylation status of adjacent CpG sites along a single DNA molecule.

Different DNA methylation signatures can be found in different tissue and cell types. In embodiments, one could deduce the tissue of origin of individual plasma DNA molecules based on their single-molecule methylation patterns.

Genomic DNA from ten buffy coat samples and six placental tissue samples was sequenced using SMRT sequencing (PacBio). By pooling the mapped high-quality circular consensus sequencing (CCS) reads from each sample type together, we were able to achieve 58.7-fold and 28.7-fold coverages for buffy coat DNA and placenta DNA, respectively.

By using a sliding window approach, the genome was divided into approximately 28.2 million overlapping windows of 5 CpG sites. In other embodiments, different window sizes, such as, but not limited to 2, 3, 4, 5, 6, 7, and 8 CpG sites, could be used. One could also use a non-overlapping window approach. Each window was considered a potential marker region. For each potential marker region, we identified the predominant single-molecule methylation pattern among all sequenced placenta DNA molecules that cover all the 5 CpG sites within that marker region. Comparisons would be made between the CpG sites of a plasma DNA molecule and the corresponding CpG sites of the individual DNA molecules of the reference tissues. We then calculated a mismatch score for each buffy coat DNA molecule covering all the CpG sites within the same marker region by comparing its single-molecule methylation pattern with the predominant single-molecule methylation pattern in the placenta.

$$\text{Mismatch score} = \frac{\text{Number of mismatched } CpG \text{ sites}}{\text{Total number of } CpG \text{ sites}},$$

where the number of mismatched CpG sites refers to the number of CpG sites showing a different methylation status in the buffy coat DNA molecule compared to the predominant single-molecule methylation pattern in the placenta.

A higher mismatch score indicates that the methylation pattern of the buffy coat DNA molecule is more different from the predominant single-molecule methylation pattern in the placenta. From the 28.2 million potential marker regions, we selected those which showed a substantial difference in the single-molecule methylation pattern between the pools of DNA molecules from the placenta and the buffy coat using the following criteria: a) more than 50% of placenta DNA molecules had the predominant single-molecule methylation pattern; and b) more than 80% of buffy coat DNA molecules had a mismatch score of greater than 0.3. Based on these criteria, we selected 281,566 marker regions for downstream analysis.

FIG. 25 is a table of the distribution of selected marker regions among different chromosomes. The first column shows the chromosome number. The second column shows the number of marker regions in the chromosome.

We hereby illustrate our concept of tissue-of-origin classification for individual plasma DNA molecules based on single-molecule methylation patterns using plasma DNA molecules sequenced with SMRT sequencing which covered either a fetal-specific allele or a maternal-specific allele as described previously in this disclosure. Any plasma DNA molecule covering a selected marker region with a methylation pattern identical to the predominant single-molecule methylation pattern in the placenta would be classified as a placenta-specific (i.e., fetal-specific) DNA molecule. On the contrary, if the single-molecule methylation pattern of a plasma DNA molecule is not identical to the predominant single-molecule methylation pattern in the placenta, we would classify this molecule as not specific for the placenta. The correct classification in this analysis was defined in a way that a fetal-specific DNA molecule was identified to be fetal-derived (i.e., specific to the placenta) and a maternal DNA molecule was identified to be non-fetal-derived (i.e., non-specific to the placenta) according to whether placenta-specific methylation haplotypes were present in that molecule. Prior methylation-based methods for the tissue-of-origin analysis typically involved deconvoluting the percentage or proportional contributions of a range of tissue contributors of cell-free DNA within the biological sample. An advantage of the present method over the prior methods is that evidence for the cell-free DNA contribution of a tissue into the biological sample, e.g., placenta-derived DNA in maternal plasma, could be determined without regard to the presence or absence of contributions from the other tissues. Furthermore, the placental origin of any one cell-free DNA molecule could be determined with the present method without regard to the fractional contribution of cell-free DNA molecules from that tissue.

Among the 28 DNA molecules covering a fetal-specific allele, 17 (61%) were classified as placenta-specific, and 11 (39%) were classified as not specific for the placenta. On the other hand, among the 467 DNA molecules covering a maternal-specific allele, 433 (93%) were classified as not specific for the placenta, and 34 (7%) were classified as placenta-specific.

In embodiments, one could use different percentages of buffy coat DNA molecules having a mismatch score of greater than 0.3 as the threshold, including, but not limited to greater than 60%, 70%, 75%, 80%, 85%, and 90%, etc. By adjusting the criteria used in marker region selection, one could improve the overall classification accuracy for placental- or non-placental origins of plasma DNA in pregnant subjects. This is particularly important in the setting of noninvasive prenatal testing when one attempts to determine whether a disease-causing mutation or a copy number aberration is present in the fetus.

FIG. 26 is a table of the classification of plasma DNA molecules based on their single-molecule methylation patterns using different percentages of buffy coat DNA molecules having a mismatch score of greater than 0.3 as the selection criteria for marker regions. The first column shows the percentage of buffy coat DNA molecules having a mismatch score of greater than 0.3%. The second column divides the DNA molecules into those that cover a fetal-specific allele and those that cover a maternal-specific allele. The third and fourth columns show the classification of the DNA molecules as placenta-specific or not specific for the placenta based on a single-molecule methylation pattern. The fifth column shows the percentage of DNA molecules that were classified the same as the specific allele in the second column.

FIG. 27 shows a process flow to use a placenta-specific methylation haplotype to determine the fetal inheritance in a noninvasive manner. As shown in FIG. 27, cell-free DNA from the plasma a pregnant woman was extracted for single molecule real-time sequencing. The long plasma DNA molecules were identified according to the embodiments in this disclosure. The methylation status at each CpG site for each long plasma DNA molecule was determined according to the embodiments in this disclosure. The methylation haplotype of each long plasma DNA molecule was determined according to the embodiments in this disclosure. If a long plasma DNA molecule was identified as carrying a placenta-specific methylation haplotype, the genetic and epigenetic information related to that molecule would be considered as being inherited by the fetus. In embodiments, if one or more long plasma DNA molecules containing a disease-causing mutation, which is the same as the disease-causing mutation carried by a pregnant woman, was determined to be of fetal origin based on the methylation haplotype information according to the embodiments in this disclosure, it would suggest that the fetus had inherited the mutation from the mother.

Embodiments could be applied to genetic diseases including but not limited to beta-thalassemia, sickle cell anemia, alpha-thalassemia, cystic fibrosis, hemophilia A, hemophilia B, congenital adrenal hyperplasia, Duchenne muscular dystrophy, Becker muscular dystrophy, achondroplasia, thanatophoric dysplasia, von Willebrand disease, Noonan syndrome, hereditary hearing loss and deafness, various inborn errors of metabolism (e.g., citrullinemia type I, propionic acidemia, glycogen storage disease type Ia (von Gierke disease), glycogen storage disease type Ib/c (von Gierke disease), glycogen storage disease type II (Pompe disease), mucopolysacchariodosis (MPS) type I (Hurler/Hurler-Scheie/Scheie), MPS type II (Hunter syndrome), MPS, type IIIA (Sanfilippo syndrome A), MPS type IIIB (Sanfilippo syndrome B), MPS type IIIC (Sanfilippo syndrome C), MPS Type IIID (Sanfilippo syndrome D), MPS type IVA (Morquio syndrome A), MPS type IVB (Morquio syndrome B), MPS type VI (Maroteaux-Lamy syndrome), MPS type VII (Sly syndrome), mucolipidosis II (I-cell disease), metachromatic leukodystrophy, GM1 gangliosidosis, OTC deficiency (X-linked ornithine transcarbamylase deficiency), adrenoleukodystrophy (X-linked ALD), Krabbe disease (globoid cell leukodystrophy)), etc.

In other embodiments, a genetic disease in the fetus might be associated with a de novo DNA methylation in the fetal genome which was absent in the parental genomes. An example would be the hypermethylation of the FMRP translational regulator 1 (FMR1) gene in a fetus with fragile X syndrome. Fragile X syndrome is caused by an expansion of the CGG trinucleotide repeat in the 5' untranslated region of the FMR1 gene. A normal allele would contain approximately 5 to 44 copies of the CGG repeat. A premutation allele would contain 55 to 200 copies of the CGG repeat (SEQ ID NO: 1). A full mutation allele would contain more than 200 copies of the CGG repeat.

Figure 28:
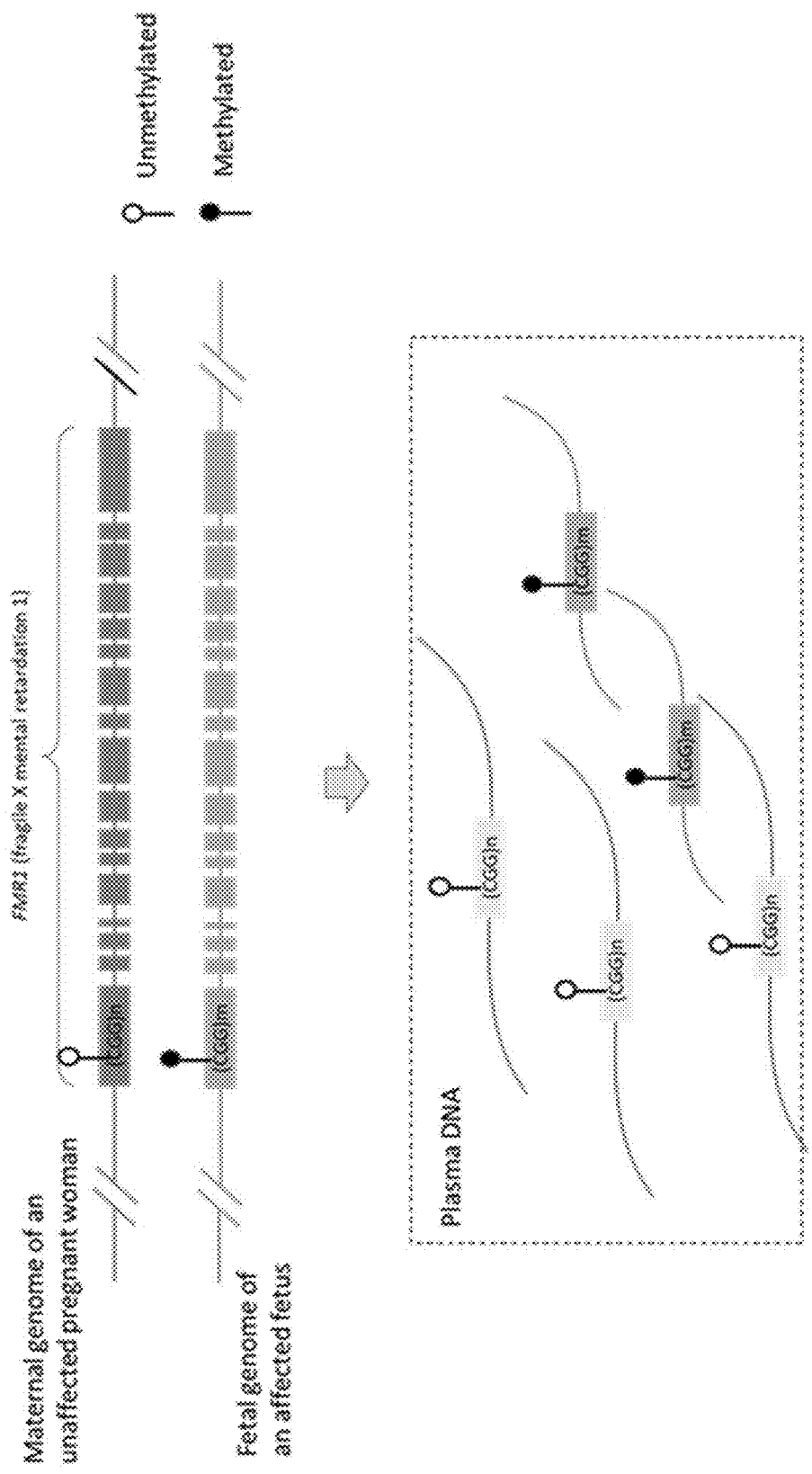
FIG. 28 illustrates the principle of noninvasive prenatal detection of fragile X syndrome using long cell-free DNA in maternal plasma according to embodiments of the present invention.

FIG. 28 illustrates the principle of noninvasive prenatal detection of fragile X syndrome in a male fetus of an unaffected pregnant woman carrying either a normal or a premutation allele. In FIG. 28, 'n' represents the number of copies of CGG in a maternal genome; 'm' represents the number of copies of CGG in a fetal genome. The genome of the unaffected pregnant woman would harbor FMR1 genes which have CGG repeats of not more than 200 copies (i.e., n≤200) (SEQ ID NO: 2) and are unmethylated. In contrast, the genome of the male fetus affected by fragile X syndrome would harbor a FMR1 gene which has more than 200 copies of the CGG repeats (m>200) and is methylated. By performing single molecule sequencing of the maternal plasma DNA, one could identify a number of long DNA molecules from a genomic region of interest (e.g. the FMR1 gene) whose number of repeats and methylation status could be determined simultaneously. If one identified one or more DNA molecules covering the FMR1 gene, containing more than 200 copies of the CGG repeats and are methylated, in the plasma of an unaffected woman, it would indicate that the fetus would likely have fragile X syndrome. In yet another embodiment, one could further ascertain the fetal origin of such plasma DNA molecules using placenta-specific methylation haplotypes according to the embodiments in this disclosure. If one identified one or more molecules containing one or more regions within a molecule which carried placenta-specific methylation haplotypes, and such molecules covered the FMR1 gene, contained more than 200 copies of the CGG repeats and were methylated, one could more confidently conclude that the fetus has fragile X syndrome. On the contrary, if one identified one or more molecules that harbored placenta-specific methylation haplotypes, and such molecules covered the FMR1 gene, contained less than 200 copies of the CGG repeat and were not methylated, it would indicate that the fetus would be likely unaffected. With fragile X syndrome, the full mutation (>200 repeats) actually causes the entire gene to be methylated and to switch off the gene function. Thus, for fragile X in particular, the detection of a long allele that is methylated (rather than showing placental methylation profile) would be highly suggestive of the fetus having the disease.

Detecting genetic disorders may be performed with or without knowing the prior status of the mother. Women with the pre-mutation may not have any symptoms but some might have mild symptoms and often only known in hindsight. If we do not know the maternal mutational status, one approach is to detect a long allele in plasma from a woman who does not appear to have the disease or to analyze the maternal buffy coat and determine that it does not show such a long allele. As another approach, we could combine the repeat length with the methylation status of the cfDNA molecule. If the methylation status is suggestive of a fetal pattern (methylation haplotype) and shows a long allele, then the fetus is likely to be affected. This approach is applicable to many trinucleotide disorders, e.g., Huntington's disease.

D. Noninvasive Construction of Fetal Genome with Long Plasma DNA Molecules

Methylation patterns may be used to determine the inheritance of haplotypes. The determination of haplotype inheritance using a qualitative approach with methylation patterns may be more efficient than a quantitative method characterizing amounts of certain fragments. Methylation patterns may be used to determine maternal and paternal inheritance of haplotypes.

1. Maternal Inheritance of the Fetus

Lo et al. demonstrated the feasibility to construct a genome-wide genetic map and determine the mutational status of the fetus from the maternal plasma DNA sequences, with the use of the information of the parental haplotypes (Lo et al. Sci Transl Med. 2010; 2:61ra91). This technology has been called relative haplotype dosage (RHDO) analysis, and is one approach to solve the maternal inheritance of the fetus. The principle was based on the fact that the maternal haplotype inherited by the fetus would be relatively overrepresented in the plasma DNA of a pregnant woman, when compared with the other maternal haplotype that is not transmitted into the fetus. Thus, RHDO is a quantitative analytic method.

The embodiments present in this disclosure makes use of methylation patterns in a long plasma DNA molecule for determining the tissues of origin of that plasma DNA molecule. In one embodiment, the disclosure herein would allow the qualitative analysis of the maternal inheritance of the fetus.

Figure 29:
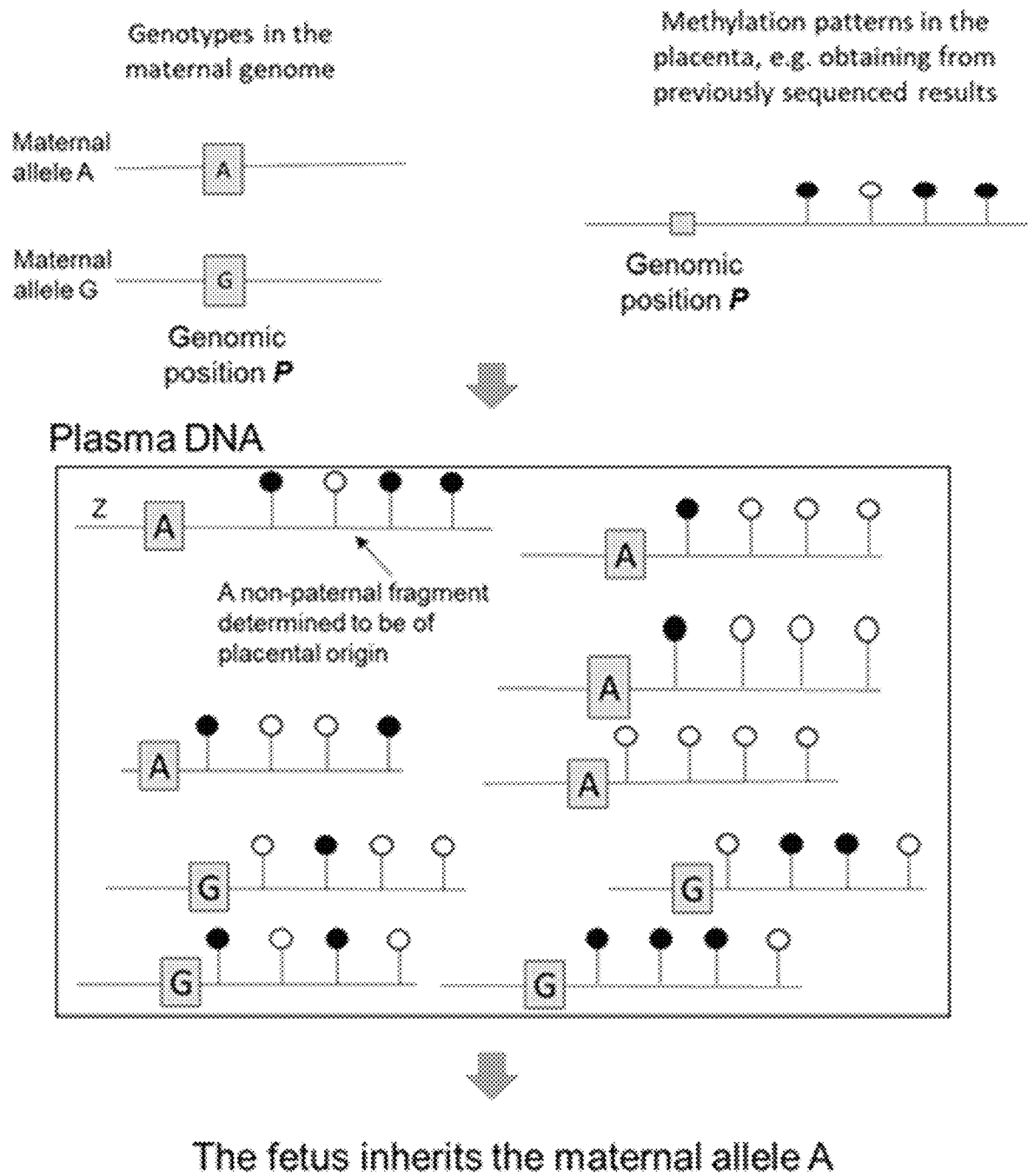
FIG. 29 illustrates the maternal inheritance of the fetus based on methylation patterns according to embodiments of the present invention.

FIG. 29 shows an example of determining the maternal inheritance of a fetus. A genomic position P was heterozygous in the maternal genome (A/G). A filled in circle indicates a methylated site, and an open circle indicates an unmethylated site. The methylation pattern in the placenta was "-M-U-M-M-", where "M" represents a methylated cytosine and "U" represents an unmethylated cytosine at a CpG site. In one embodiment, the methylation pattern in the placenta and relevant reference tissues can be obtained from data previously generated from sequencing (e.g., single molecule real-time sequencing and/or bisulfite sequencing). In plasma DNA, one non-paternal plasma DNA (denoted by Z) carrying an allele of A at that particular genomic locus was found to display the methylation pattern ("-M-U-M-M-") compatible with the methylation pattern in the placenta as opposed to the methylation patterns of other tissues. No molecule carrying an allele of G displaying the methylation pattern compatible with methylation patterns in the placenta was found. Therefore, based on the allele A and the presence of the "-M-U-M-M-" methylation pattern, the fetus may be determined to inherit the maternal allele A.

Figure 30:
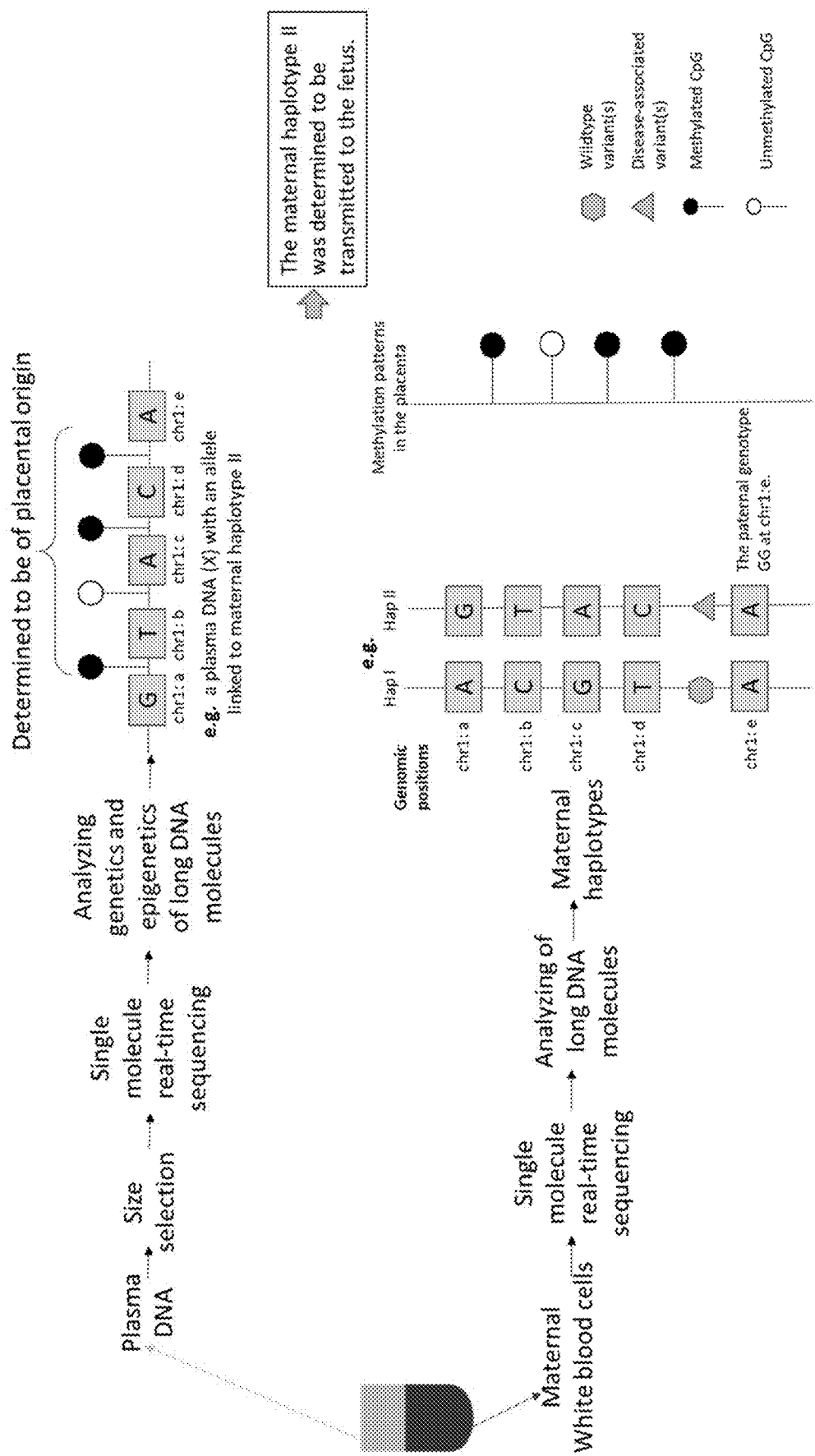
FIG. 30 illustrates the qualitative analysis for the maternal inheritance of the fetus using genetic and epigenetic information of plasma DNA molecules according to embodiments of the present invention.

FIG. 30 shows the qualitative analysis for the maternal inheritance of the fetus using genetic and epigenetic information of plasma DNA molecules. As shown in the top branch of FIG. 30, plasma DNA was extracted, followed by size selection for long DNA according to embodiments in this disclosure. The size-selected plasma DNA molecules were subjected to single molecule real-time sequencing (e.g., using a system manufactured by Pacific Biosciences). The genetic and epigenetic information were determined according to the embodiments in this disclosure. For illustrative purposes, a molecule (X) was aligned to the human chromosome 1, containing an allele of G at the chromosomal position a (chr1:a) and an allele of A at the chromosomal position e (chr1:e). Molecule X has an allele of C at the chromosomal position d.

The CpG methylation status of this molecule X was determined to be "-M-U-M-M-", where "M" represented a methylated cytosine and "U" represented an unmethylated cytosine at a CpG site. A filled in circle indicates a methylated site, and an open circle indicates an unmethylated site. As a result of analysis of a reference sample, placental DNA is known to have a methylation pattern of "-M-U-M-M-" in the region between positions a and e. On the basis of the methylation pattern of molecule X matching the methylation pattern of placental DNA, molecule X was determined to be of placental origin according to the embodiments in this disclosure.

As shown in the lower branch of FIG. 30, the DNA from maternal white blood cells were subjected to single molecule real-time sequencing. The epigenetic and genetic information of maternal white blood cells was obtained according to embodiments in this disclosure. The genetic alleles were phased into two haplotypes, namely, maternal haplotype I (Hap I) and maternal haplotype II (Hap II), using the methods including but not limited to WhatsHap (Patterson et al. J Comput Biol. 2015; 22:498-509), HapCUT (Bansal et al. Bioinformatics. 2008; 24:i1153-9), HapCHAT (Beretta et al. BMC bioinformatics. 2018; 19:252), etc. Here, we obtained two haplotypes, namely, "-A-C-G-T-" (Hap I) and "-G-T-A-C-" (Hap II) in the maternal genomes. Hap I was associated with the wildtype variant(s) whereas Hap II was linked to the disease-associated variant(s). The disease-associated variant(s) could include but is not limited to single nucleotide variants, insertions, deletions, translocations, inversions, repeat expansions, and/or other genetic structural variations.

For the genomic position e, the maternal genotype was determined to be AA and the paternal genotype was determined to be GG. Because of the methylation pattern, plasma DNA molecule X was determined to be of placental origin. Because of the presence of the maternal-specific allele A but the absence of the paternal-specific allele G, molecule X was thus deduced to be inherited from one of the maternal haplotypes.

To further determine which maternal haplotype was transmitted to the fetus, we compared the allelic information at genomic positions other than the position chr1:e of this placental-derived molecule X with the maternal haplotypes. As an example, molecule X has allele G at position a and allele C at position d. The presence of either of these alleles in molecule X indicates that molecule X should be assigned to the maternal Hap II, which includes the same alleles.

Therefore, one could conclude that the maternal haplotype II linked to the disease-associated variant(s) was transmitted to the fetus. The unborn fetus was determined to be at risk of being affected by the disease.

The methylation pattern based qualitative analysis for the maternal inheritance of the fetus may require fewer plasma DNA molecules to make the conclusion as to which maternal haplotype was inherited by the fetus, compared with RHDO that was an approach based on quantitative analysis. We performed computer simulation analyses to assess the detection rate for the maternal inheritance of the fetus in a genomewide manner with different numbers of plasma DNA molecules used for the analysis.

For RHDO simulation analysis, N plasma DNA molecules were collectively aligned to M heterozygous SNPs in a haplotype block of the maternal genome. The fetal DNA fraction was f. The paternal genotypes for those corresponding SNPs were homozygous and identical to the maternal Hap I which was transmitted to the fetus. Among N plasma DNA molecules, the mean of plasma DNA molecules aligned to the maternal Hap I, was N×(0.5+f/2), whereas the mean of plasma DNA molecules aligned to the maternal Hap II would be N×(0.5−f/2). We assumed that the plasma DNA molecules sampled from haplotypes followed the binomial distributions.

The number of plasma DNA molecules was assigned to Hap I (i.e. X), following the below distribution:

$$X \sim \mathrm{Bin}(N, 0.5+f/2) \quad (1),$$

where "Bin" denoted the binomial distribution.

The number of plasma DNA molecules was assigned to Hap II (i.e. Y), following the below distribution:

$$Y \sim \mathrm{Bin}(N, 0.5-f/2) \quad (2).$$

Thus, the plasma DNA molecules assigned to the maternal Hap I would be relatively overrepresented in the maternal plasma, compared with the maternal Hap II. To determine whether the overrepresentation was statistically significant, we compared the difference in plasma DNA counts between two maternal haplotypes with the null hypothesis in which two haplotypes (denoted by X' and Y') were equally represented in the plasma.

$$X' \sim \mathrm{Bin}(N, 0.5) \quad (3),$$

$$Y' \sim \mathrm{Bin}(N, 0.5) \quad (4).$$

We further defined the relative dosage difference between two haplotypes as below:

$$D = (X-Y)/N \quad (5),$$

$$D' = (X'-Y')/N \quad (6).$$

In one example, a statistic D, reflecting the relative haplotype dosage, were compared with the mean of D' (M), normalized by the standard deviation of D' (SD) as below (i.e. z-score):

$$z\text{-score} = (D-M)/SD \quad (7).$$

A z-score of >3 indicated that the Hap I was transmitted to the fetus.

For RHDO analysis, based on formulas (1) to (7), we simulated 30,000 haplotype blocks across a whole genome in which Hap I was transmitted to the fetus. The mean length of the haplotype blocks was 100 kb. Each haplotype block contained a mean of 100 SNPs among which 10 SNPs would be informative in contributing to the haplotype imbalance. In one example, the fetal DNA fraction was 10% and a median of fragment sizes was 150 bp. We calculated the percentage of the haplotype blocks with a z-score of >3, herein referred to as the detection rate, by varying the number of plasma DNA molecules used for RHDO analysis ranging from 1 million to 300 million. The number of plasma DNA molecules herein was adjusted by the probability of plasma DNA covering an informative SNP site according to the Poisson distribution.

For computer simulation related to methylation pattern based qualitative analysis for the maternal inheritance of the fetus, we made the assumptions as below for illustrative purposes:

1) There were N plasma DNA molecules covering a haplotype block in the maternal genome used for analysis.
2) The probability of a plasma DNA fragment used for tissue-of-origin analysis with at least 3 kb in length was denoted by a.
3) The probability of a plasma DNA molecule carrying more than 10 CpG sites was denoted by b.
4) The fetal DNA fraction of those fragments >3 kb was denoted by f.

One could achieve an accurate deduction of the tissues of origin for those plasma DNA molecules greater than 3 kb with at least 10 CpG sites as illustrated in one embodiment of this disclosure. The number of plasma DNA molecules fulfilling the above criteria (Z) was assumed to follow a Poisson distribution, with a mean value of λ (i.e., N×a×b×f).

$$Z \sim \mathrm{Poisson}(\lambda) \quad (8).$$

In one example, on the basis of formula (8), we simulated 30,000 haplotype blocks in which Hap I was transmitted to the fetus. The mean length of each haplotype block was 100 kb. Each haplotype block contained a mean of 100 SNPs among which 20 heterozygous SNPs would be phased into two maternal haplotypes. The fetal DNA fraction was 1%. There was 40% of plasma DNA molecules with sizes of >3 kb after size selection. There was 87.1% of plasma DNA molecules with sizes of >3 kb harboring at least 10 CpG sites. The percentage of haplotype blocks with a Z value ≥1 indicated the detection rate. We repeated multiple runs of computer simulation by varying the number of plasma DNA molecules (N) used for tissue-of-origin analysis by methylation patterns, ranging from 1 million to 300 million. The number of plasma DNA molecules herein was further adjusted by the probability of plasma DNA covering a heterozygous SNP according to the Poisson distribution.

Figure 31:
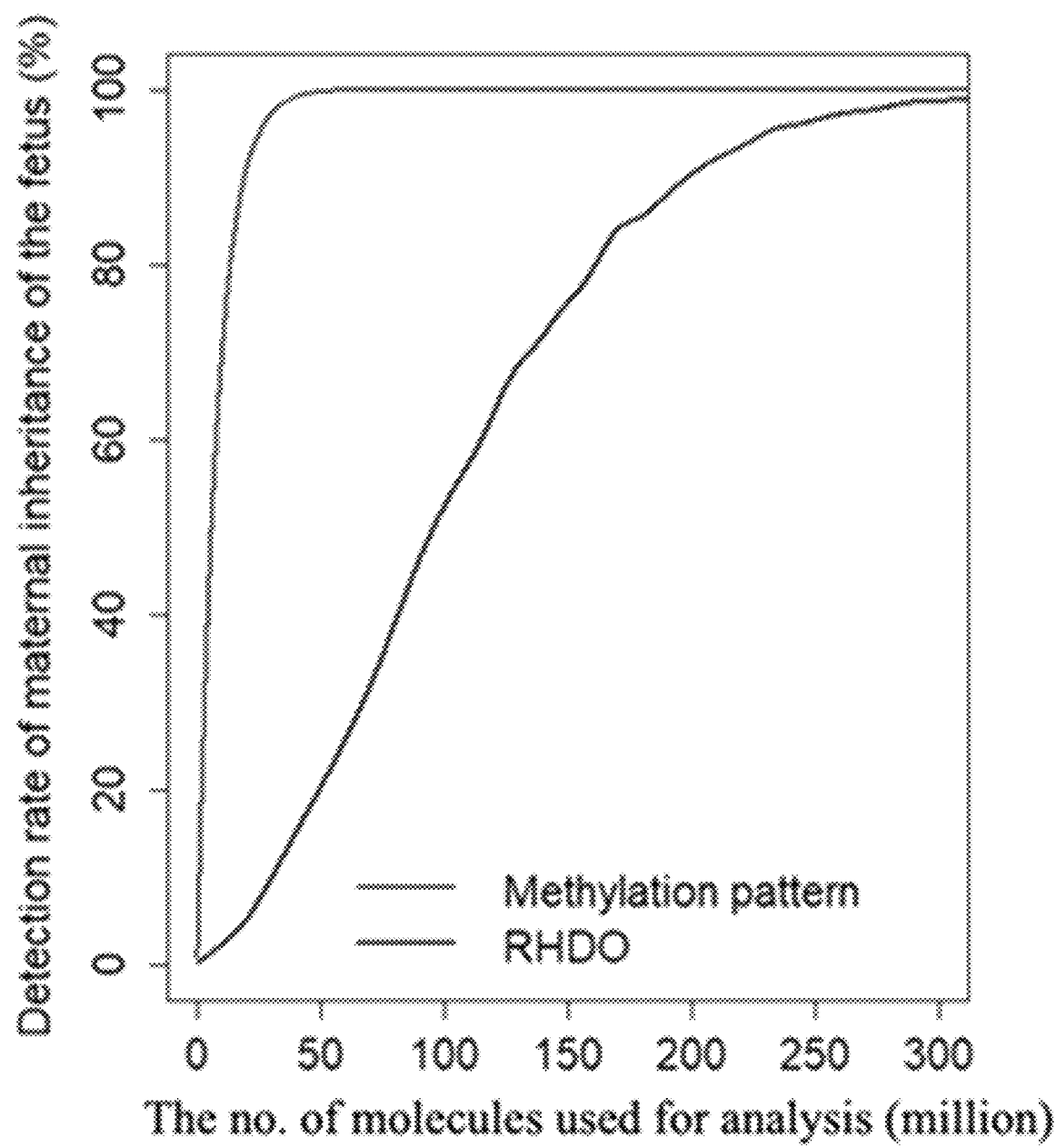
FIG. 31 illustrates the detection rate of the qualitative analysis for the maternal inheritance of the fetus in a genomewide manner using genetic and epigenetic information of plasma DNA molecules compared to relative haplotype dosage (RHDO) analysis according to embodiments of the present invention.

FIG. 31 shows the detection rate of the qualitative analysis for the maternal inheritance of the fetus in a genomewide manner using genetic and epigenetic information of plasma DNA molecules compared to relative haplotype dosage (RHDO) analysis. The number of molecules used for analysis is shown on the x-axis. The detection rate of the maternal inheritance of the fetus as a percent is shown on the y-axis. The detection rates for the maternal inheritance of the fetus were higher using the approach based on methylation patterns, compared with RHDO. For example, using 100 million fragments, the detection rate based on methylation patterns was 100%, whereas the detection rate based on RHDO was only 55%. These results suggested that deduction of the maternal inheritance of the fetus using methylation patterns-based method would be superior to that based on RHDO.

2. Paternal Inheritance of the Fetus

The ability to obtain long plasma DNA molecules for analysis may be useful for improving the detection rate of paternal-specific variants in plasma DNA of a pregnant woman, as the use of long DNA molecules would increase the overall genomic coverage compared with the use of an equal number of short DNA molecules. We further performed a computer simulation based on the following assumptions:

1) The fetal DNA fraction was f depending on the plasma DNA length L. It was rewritten as $f_L$ where the subscript L indicated that the plasma DNA molecules with a length of L bp were used for analysis.
2) The number of paternal-specific variants that needed to be identified in maternal plasma DNA was V.
3) The number of plasma DNA molecules used for analysis was N.
4) The number of plasma DNA molecules originating from a particular genomic locus or region followed a Poisson distribution.

In one example, the fetal DNA fractions of those plasma DNA molecules with a size of 150 bp, 1 kb and 3 kb were 10% ($f_{150bp}$=0.1), 2% ($f_{1kb}$=0.02) and 1% ($f_{3kb}$=0.01), respectively. The number of paternal-specific variants was 250,000 (V=250,000) in a genome. The number of plasma DNA molecules used for analysis (N) ranged from 50 million to 500 million.

Figure 32:
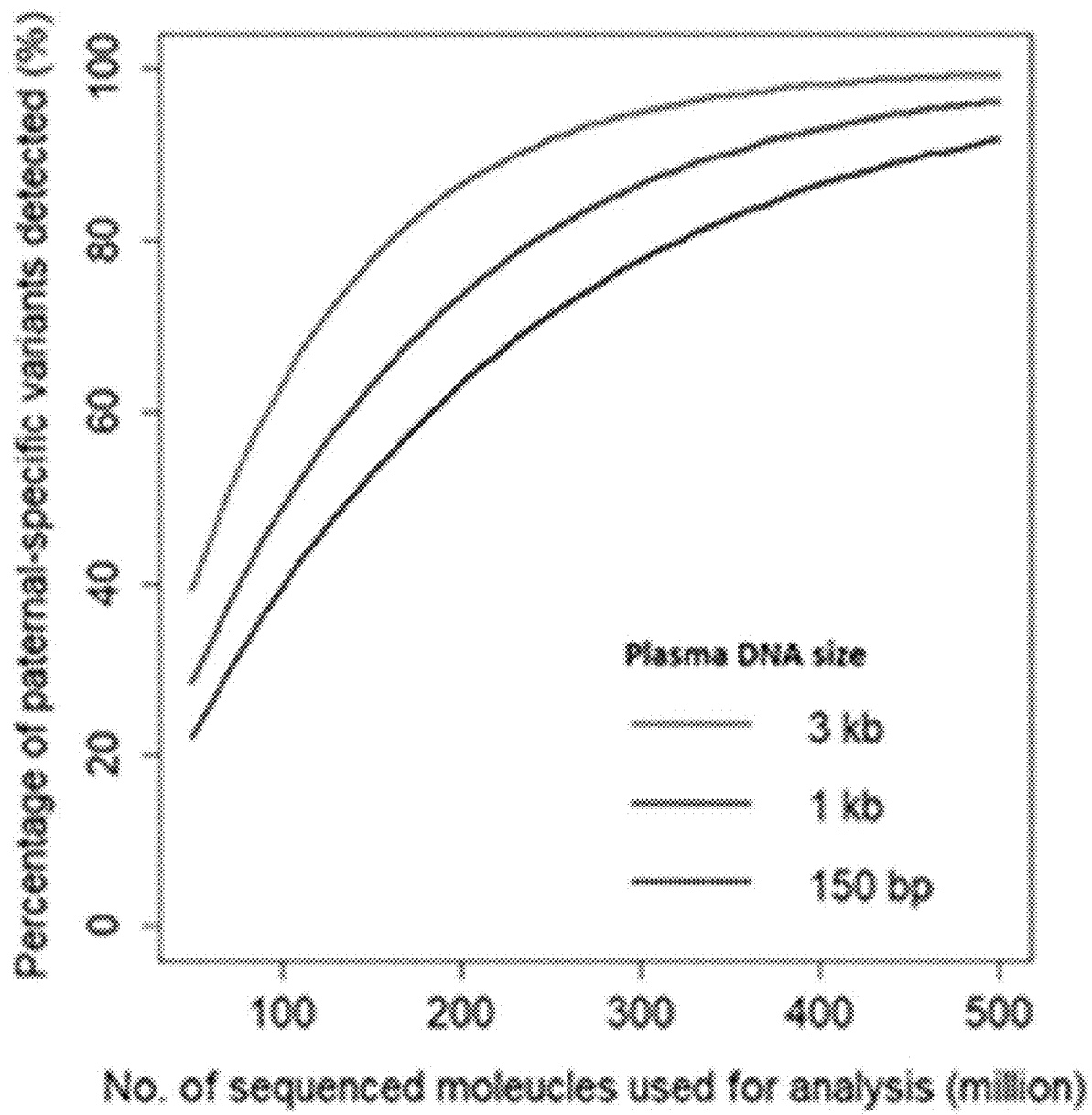
FIG. 32 shows the relationship between the detection rate of paternal-specific variants in a genomewide manner and the number of sequenced plasma DNA molecules with different sizes used for analysis according to embodiments of the present invention.

FIG. 32 shows the relationship between the detection rate of paternal-specific variants in a genomewide manner and the number of sequenced plasma DNA molecules with different sizes used for analysis. The number of sequenced molecules used for analysis in millions are shown on the x-axis. The percentage of paternal-specific variants detected is shown on the y-axis. The different curves show the different size DNA fragments used for analysis, with 3 kb on the top, 1 kb in the middle, and 150 bp on the bottom. The longer the plasma DNA molecules used for analysis, the higher the detection rate of paternal-specific variants could be achieved. For example, using 400 million plasma DNA molecules, the detection rates were 86%, 93%, and 98% when focusing on molecules with sizes of 150 bp, 1 kb, and 3 kb, respectively.

In other embodiments, other distributions could be used, including but not limited to Bernoulli distribution, beta-normal distribution, normal distribution, Conway-Maxwell-Poisson distribution, geometric distribution, etc. In some embodiments, Gibbs sampling and Bayes's theorem would be used for the maternal and paternal inheritance analysis.

3. Fragile X Inheritance Analysis

In embodiments, the methylation pattern-based determination of the maternal inheritance of the fetus may facilitate the noninvasive detection of fragile X syndrome using single molecule real-time sequencing of maternal plasma DNA. Fragile X syndrome is a genetic disorder, typically caused by an expansion of CGG trinucleotide repeats within the FMR1 (fragile X mental retardation 1) gene on the X chromosome. Fragile X syndrome and other disorders caused by expansion of repeats are described elsewhere in this application. Methods for detecting fragile X syndrome in a fetus may also be applied to any other expansion of repeats disclosed herein.

A female subject with a premutation, which is defined as having 55 to 200 copies of the CGG repeats (SEQ ID NO: 1) in the FMR1 gene, is at risk of having a child with fragile X syndrome. The likelihood of being pregnant with a fetus with fragile X syndrome depends on the number of CGG repeats present in the FMR1 gene. The larger the number of repeats in the mother, the higher the risk for an expansion from a premutation to a full mutation when transmitting to the fetus. A maternal plasma sample was collected at a gestational age of 12 weeks from a woman, who was previously confirmed to carry a fragile X premutation allele of 115±2 CGG repeats (SEQ ID NO: 3), and had a son who was diagnosed to have fragile X syndrome (the proband). The maternal plasma was then subjected to single molecule real-time sequencing. In one example, using single molecule real-time sequencing, we obtained 3.3 million circular consensus sequences (CCSs) aligned to a human reference genome, with a median subread depth of 75 folds per CCS (interquartile range: 14-237 folds). The genetic and epigenetic information for each sequenced plasma DNA may be determined according to embodiments of this disclosure. To obtain the two maternal haplotypes of chromosome X, we used the Infinium Omni2.5Exome-8 Beadchip on the iScan System (Illumina) which was a microarray technology, to genotype 2,000 SNPs on the chromosome X for both DNA extracted from the maternal buffy coat and the buccal swab of the proband. The two maternal haplotypes, namely Hap I and Hap II, can be deduced based on genotypic information of the maternal and proband genomes.

Figure 33:
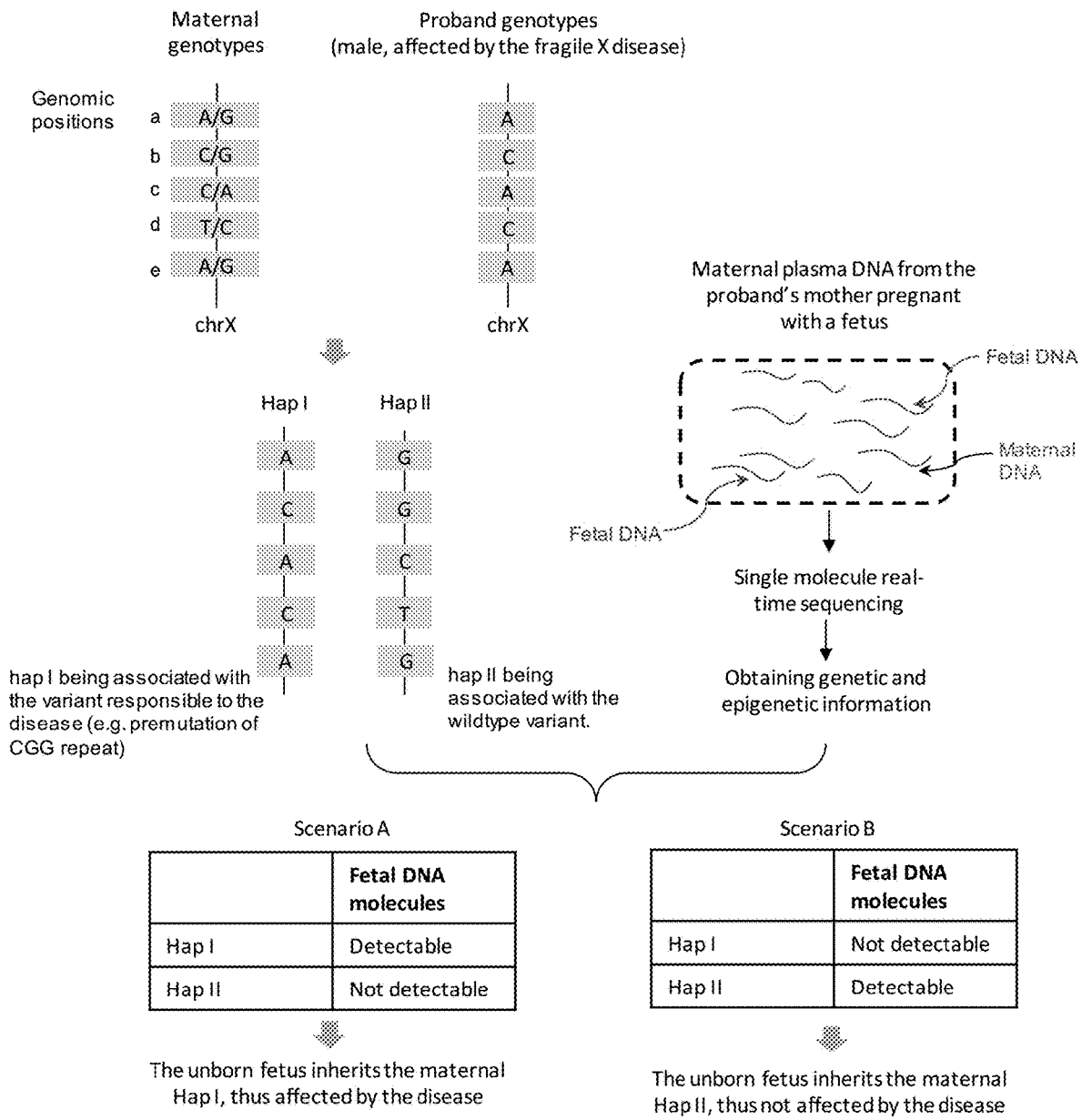
FIG. 33 shows a workflow for the noninvasive detection of fragile X syndrome according to embodiments of the present invention.

FIG. 33 shows a workflow for the noninvasive detection of fragile X syndrome. Across the heterozygous SNP sites of the maternal buffy coat DNA, the alleles identical to the proband's genotypes were used to define the haplotype linked to the premutation allele (i.e., Hap I) which was a potential precursor of a full mutation in subsequent generations. On the other hand, the alleles different from the proband's genotypes were used to define the haplotype linked to the corresponding wildtype allele (Hap II). The maternal plasma DNA from the proband's mother pregnant with a fetus was subjected to single molecule real-time sequencing. The sequencing reads were assigned to the maternal Hap I and Hap II, depending on whether the obtained genetic information was identical to the alleles of Hap I or Hap II across those genomic loci under investigation. The methylation patterns of plasma DNA molecules were used to determine the tissues of origin (i.e., DNA molecules identified as of placental origin based on the methylation pattern analysis would be determined to be originating from the fetus) of those plasma DNA molecules containing a certain number of CpG sites, according to the embodiments in this disclosure.

In Scenario A, if the fetal (i.e., placental) DNA molecules were detectable from those plasma DNA molecules assigned to the maternal Hap I but not detectable in those plasma DNA molecules assigned to the maternal Hap II, then the Hap I would be determined to be transmitted to the unborn fetus. The fetus would be determined to be at a high risk of being affected by the fragile X syndrome. The placental origin of the plasma DNA molecules would be based on the methylation status of the molecule as discussed below.

In Scenario B, if the fetal DNA molecules were detectable from those plasma DNA molecules assigned to the maternal Hap II but not detectable in those plasma DNA molecules assigned to the maternal Hap I, then the Hap II would be determined to be transmitted to the unborn fetus. The fetus would be determined to be unaffected by the fragile X syndrome.

In embodiments, the definitions of "detectable" and "not detectable" for fetal DNA molecules may be dependent on the cutoffs of the percentage of plasma DNA molecules identified to be of fetal (i.e., placental) origin. The cutoffs for "detectable" may include, but are not limited to, above 1%, 2%, 3%, 4%, 5%, 10%, 15%, 20%, 30%, 40%, 50%, etc. The cutoffs for "not detectable" may include, but are not limited to, below 1%, 2%, 3%, 4%, 5%, 10%, 15%, 20%, 30%, 40%, 50%, etc. In some embodiments, the difference in the percentage of plasma DNA molecules determined to be of fetal origin between Hap I and Hap II may be required to be greater than but not limited to 1%, 2%, 3%, 4%, 5%, 10%, 15%, 20%, 30%, 40%, 50%, etc. In some other embodiments, the haplotype information could be obtained from long-read sequencing technologies (e.g., PacBio or nanopore sequencing) (Edge et al. Nat Commun. 2019; 10:4660), synthetic long reads (e.g. using the platform from 10× Genomics) (Hui et al. Clin Chem. 2017; 63:513-14), targeted locus amplification (TLA)-based phasing (Vermeulen et al. Am J Hum Genet. 2017; 101: 326-39), and statistical phasing (e.g. Shape-IT) (Delaneau et al. Nat Method. 2011; 9:179-81).

In embodiments, one may determine the maternal and fetal origins of those plasma DNA molecules that are at least 200 bp and contained at least 5 CpG sites (or any other cutoffs for long DNA molecules), according to the methylation status matching approach disclosed in this application. We identified one plasma DNA molecule, located at the genomic position chrX:143,782,245-143,782,786 (3.2 Mb away from the FMR1 gene), with an allele (position: chrX: 143782434; SNP accession number: rs6626483; the allele genotype: C) identical to the corresponding allele on the maternal Hap II but different from that of maternal Hap I.

FIG. 34 shows a methylation pattern of a plasma DNA compared with methylation profiles of placental and buffy coat DNA. The plasma DNA molecule contained 5 CpG sites. The methylation pattern was determined to be "M-U-U-U-U". This methylation pattern obtained from single molecule real-time sequencing was compared to the reference methylation profiles of placental tissues and buffy coat DNA samples obtained from bisulfite sequencing, according to the methylation status matching approach described in this disclosure. The score for this molecule originating from the placenta [i.e., S(placenta)] was 2, which was greater than that from the buffy coat [i.e., S(buffy coat)] at −3. Therefore, such a plasma DNA molecule (chrX:143,782,245-143,782, 786) was determined to be of fetal origin. However, we did not observe any plasma DNA molecules carrying the alleles from the maternal Hap I to be of fetal origin. Therefore, we concluded that the fetus inherited the maternal Hap II and was not affected by fragile X syndrome.

We envisioned that the performance of the approach described herein might not be significantly affected by X-chromosome inactivation because of the following factors:
1) X-inactivation is not complete in humans. As many as ⅓ of the genes on the X-chromosome showed variable escape from X-inactivation (Cotton et al. Hum Mol Genet. 2015; 25:1528-1539). The CpG sites outside CpG islands (i.e., the majority of CpG sites) were methylated in a similar degree in both genders, suggesting that the methylation status for most of CpG sites in the X chromosome may not be affected by the X inactivation (Yasukochi et al. Proc Natl Acad Sci USA. 2010; 107:3704-9).
2) We used the methylation profile of sex-matched placental tissues with respect to the unborn fetus. This strategy would be useful for detecting the maternal inheritance of the fetus using plasma DNA methylation patterns for a woman pregnant with a male fetus, as the placenta tissues involving a male fetus that were not supposed to be affected by X inactivation would harbor unique methylation patterns different from the other maternal tissues that more or less involved X inactivation for certain regions.

We further sequenced DNA extracted from the maternal buffy coat sample using single molecule real-time sequencing. We obtained 2.3 million CCSs, with a median subread depth of 5 folds per CCS. The results confirmed that the maternal Hap I carried the premutation allele with 124 CGG repeats (SEQ ID NO: 4), and the maternal Hap II carried the wildtype allele with 43 CGG repeats (SEQ ID NO: 5). Besides, we further sequenced the DNA extracted from chorionic villous sampling of the unborn fetus with single molecule real-time sequencing. We obtained 1.1 million CCSs, with a median subread depth of 4 folds per CCS. The result confirmed that the unborn fetus carried a wildtype allele.

E. Distribution of CpG Sites in a Human Genome

Longer DNA fragments result in a greater probability of the fragment having multiple CpG sites. These multiple CpG sites may be used for methylation pattern or other analysis.

FIG. 35 shows the distribution of CpG sites in a 500-bp region across a human genome. The first column shows the number of CpG sites. The second column shows the number of 500-bp regions with the number of CpG sites. The third column shows the proportion of all regions represented by regions having the specific number of CpG sites. For example, 86.14% of 500-bp regions would harbor at least 1 CpG site. In addition, 11.08% of 500-bp regions would harbor at least 10 CpG sites.

FIG. 36 shows the distribution of CpG sites in a 1-kb region across a human genome. The first column shows the number of CpG sites. The second column shows the number of 1-kb regions with the number of CpG sites. The third column shows the proportion of all regions represented by regions having the specific number of CpG sites. For example, 91.67% of 500-bp regions would harbor at least 1 CpG site. Also, 32.91% of 500-bp regions would harbor at least 10 CpG sites.

FIG. 37 shows the distribution of CpG sites in a 3-kb region across a human genome. The first column shows the number of CpG sites. The second column shows the number of 3-kb regions with the number of CpG sites. The third column shows the proportion of all regions represented by regions having the specific number of CpG sites. For example, 92.45% of 3-kb regions would harbor at least 1 CpG site. In addition, 87.09% of 3-kb regions would harbor at least 10 CpG sites.

In some embodiments, different numbers of CpG sites and different size cutoffs would be used for maximizing the sensitivity and specificity of placental-specific marker identification and tissue-of-origin analysis. In general, CpG sites appear more frequently than SNPs. A given size of DNA fragment is likely to have more CpG sites than SNPs. The tables shown above may show lower proportions for regions that have the same number of SNPs as CpG sites as there are fewer SNPs than CpG sites in the same size region. As a result, using CpG sites allow for more fragments to be used and provide better statistics than using only SNPs.

F. Examples of Tissue-of-Origin Analysis

In embodiments, one may extend the tissue-of-origin analysis in maternal plasma to more than two organs/tissues, including T cells, B cells, neutrophils, liver and placenta. We sequenced 9 maternal DNA samples using single molecule real-time sequencing. We deduced the placental contribution to maternal plasma DNA using plasma DNA methylation patterns according to the methylation status matching approach described in this disclosure. For this methylation status matching analysis, in one embodiment, the methylation pattern of each of the DNA molecules that were at least 500 bp long and contained at least 5 CpG sites in a maternal plasma DNA sample was compared with reference tissue methylation profiles obtained from bisulfite sequencing. Five tissues were used as reference tissues, including neutrophils, T cells, B cells, liver, and placenta. A plasma DNA molecule would be assigned to the tissue that corresponded to the maximum methylation status matching score for that plasma DNA molecule. The percentage of plasma DNA molecules assigned to a tissue relative to other tissues would be deemed the proportional contribution of that tissue to maternal plasma DNA of that sample. In embodiments, the sum of proportional contribution of neutrophils, T cells and B cells in maternal plasma provided a proxy for the proportional contribution of hematopoietic cells.

FIG. 38 shows the proportional contributions of DNA molecules from different tissues in maternal plasma using methylation status matching analysis. The first column shows the sample identification. The second column shows the hematopoietic cell contribution as a percent. The third column shows the liver contribution as a percent. The fourth column shows the placental contribution as a percent. FIG. 38 shows that the major contributor of maternal plasma DNA was hematopoietic cells (median: 55.9%), which was consistent with previous reports (Sun et al. Proc Natl Acad Sci USA. 2015; 112:E5503-12; Zheng et al. Clin Chem. 2012; 58:549-58).

Figure 39B:
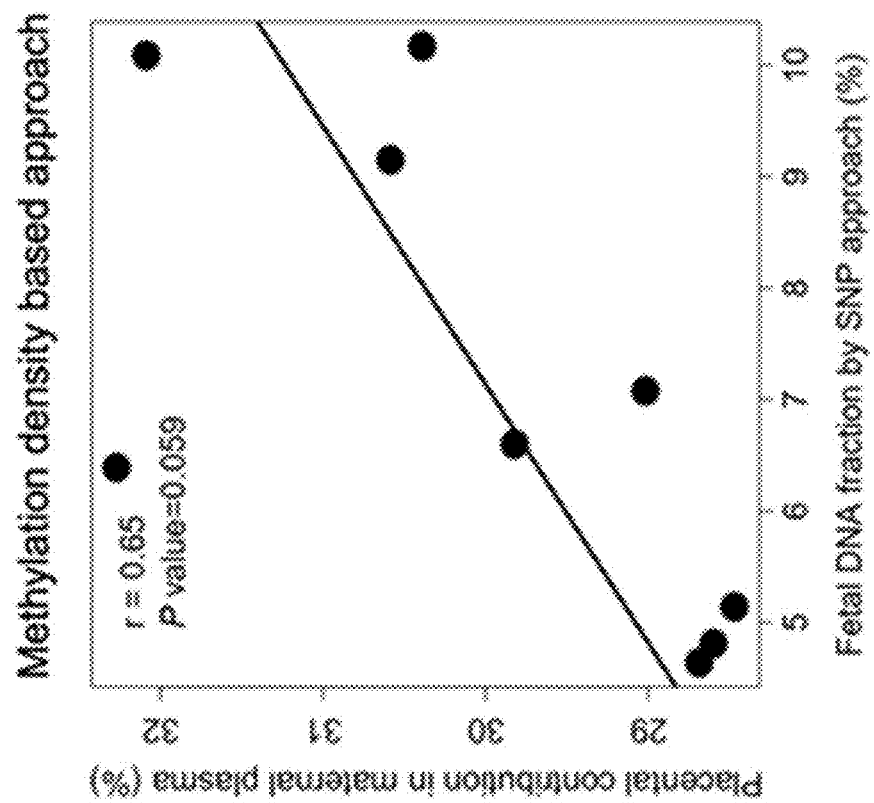
FIGS. 39A and 39B show the relationship between placental contribution and fetal DNA fraction deduced by SNP approach according to embodiments of the present invention.
Figure 39A:
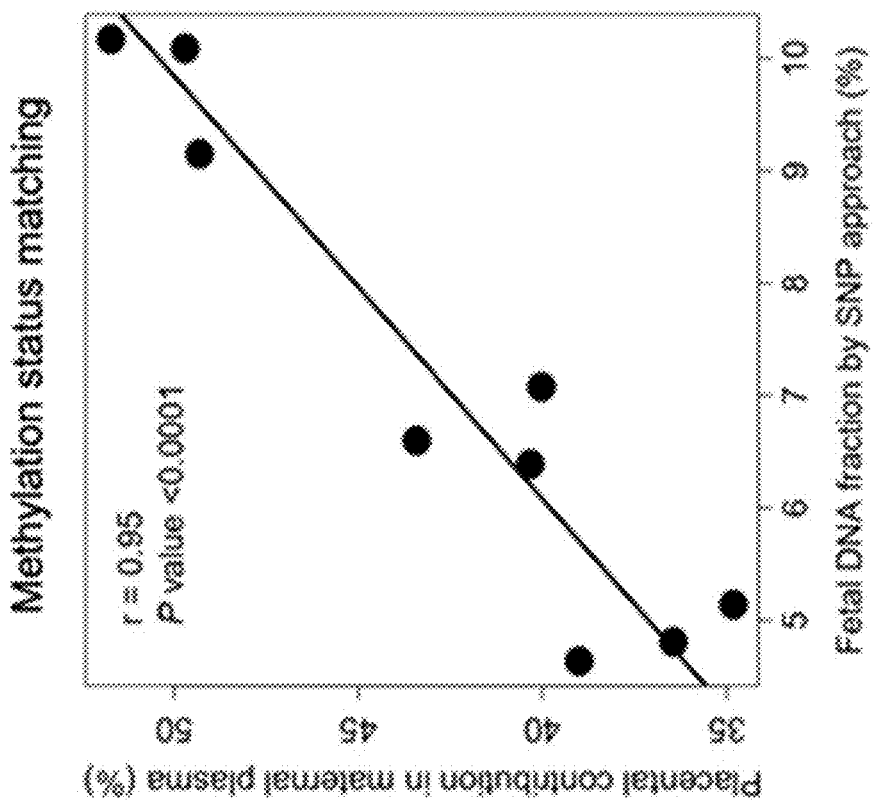

FIGS. 39A and 39B show the relationship between placental contribution and fetal DNA fraction deduced by SNP approach. The x-axis shows the fetal fraction determined by the SNP approach. The y-axis shows the determined placental contribution in the maternal plasma as a percent by using methylation status matching analysis. FIG. 39A shows a good correlation between the placental contribution determined by the methylation status matching analysis and the fetal DNA fraction deduced by SNP (Pearson's r=0.95; P value <0.0001). We further performed the tissue deconvolution analysis of maternal plasma DNA by comparing plasma DNA methylation density determined by single molecule real-time sequencing with various reference tissue methylation profiles obtained from bisulfite sequencing, according to quadratic programming (Sun et al. Proc Natl Acad Sci USA. 2015; 112:E5503-12). FIG. 39B shows that using the methylation density-based approach, the correlation between the placental contribution (Sun et al. Proc Natl Acad Sci USA. 2015; 112:E5503-12) and the fetal DNA fraction was reduced compared with using the methylation status matching analysis (Pearson's r=0.65; P value=0.059).

These data suggested that it was feasible to deduce the proportions of DNA molecules contributed by different tissues in a maternal plasma DNA sample. In another embodiment, this method can also be used to measure DNA molecules from different cell types or tissues in a sample obtained following invasive solid tissue biopsy, or from a solid tissue obtained following surgery. In some embodiments, the use of the methylation pattern on a single DNA molecule level to deduce the proportional contributions of different tissues to maternal plasma DNA would be superior to the approaches based on aggregated methylation densities from all the sequenced plasma DNA molecules across the genome.

G. Example Methods

Figure 40:
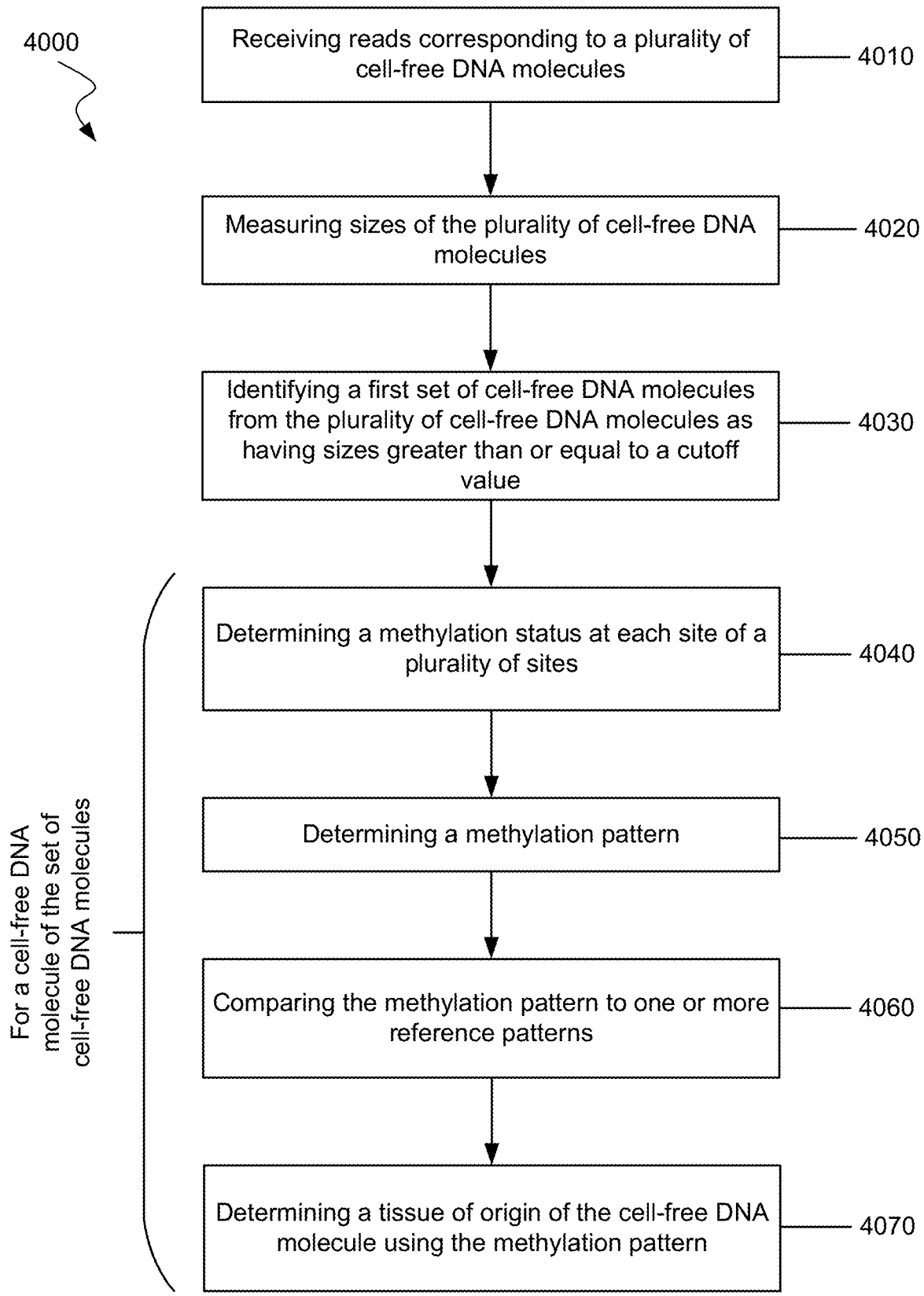
FIG. 40 shows a method of analyzing a biological sample obtained from a female pregnant with a fetus in order to determine the tissue of origin using methylation pattern analysis according to embodiments of the present invention.

FIG. 40 shows a method 4000 of analyzing a biological sample obtained from a female pregnant with a fetus. The biological sample may include a plurality of cell-free DNA molecules from the fetus and the female.

At block 4010, sequence reads corresponding to the plurality of cell-free DNA molecules may be received. In some embodiments, method 4000 may include performing the sequencing of the cell-free DNA molecules.

At block 4020, sizes of the plurality of cell-free DNA molecules may be measured. The measurement may include aligning the sequence reads to a reference genome. In some embodiments, the measurement may include full length sequencing and counting the number of nucleotides in the full length sequence. In some embodiments, measurement may include physically separating the plurality of cell-free DNA molecules from the biological sample from other cell-free DNA molecules in the biological sample, where the other cell-free DNA molecules have sizes less than the cutoff value. The physical separation may include any technique described herein, including using beads.

At block 4030, a set of cell-free DNA molecules from the plurality of cell-free DNA molecules as having sizes greater than or equal to a cutoff value may be identified. The cutoff value may be greater than or equal to 200 nt. The cutoff value may be at least 500 nt, including 600 nt, 700 nt, 800 nt, 900 nt, 1 knt, 1.1 knt, 1.2 knt, 1.3 knt, 1.4 knt, 1.5 knt, 1.6 knt, 1.7 knt, 1.8 knt, 1.9 knt, or 2 knt. The cutoff value may be any cutoff value described herein for long cell-free DNA molecules. Sizes may be a number of CpG sites rather than the length of the molecule. For example, the cutoff value may be 3, 4, 5, 6, 7, 8, 9, 10, 11, 12, 13, 14, 15 or more CpG sites.

At block 4040, for a cell-free DNA molecule of the set of cell-free DNA molecules, a methylation status at each site of a plurality of sites may be determined. The plurality of sites may include at least 5, 6, 7, 8, 9, 10, 11, 12, 13, 14, 15 or more CpG sites. At least one of the plurality of sites may be methylated. Two sites of the plurality of sites may be separated by at least 160 nt, 170 nt, 180 nt, 190 nt, 200 nt, 250 nt, or 500 nt. The method may include sequencing the plurality of cell-free DNA molecules to obtain the sequence reads, and determining a methylation status of the site by measuring a characteristic corresponding to a nucleotide of the site and nucleotides neighboring the site. For example, the methylation may be determined as in U.S. application Ser. No. 16/995,607.

At block 4050, a methylation pattern may be determined. The methylation pattern may indicate a methylation status at each site of the plurality of sites.

At block 4060, the methylation pattern may be compared to one or more reference patterns. Each of the one or more reference patterns may be determined for a particular tissue type. In some embodiments, the comparison may include determining the number of sites that matches the reference pattern.

The reference pattern of the one or more reference patterns may be determined by measuring a methylation density at each reference site of a plurality of reference sites using DNA molecules from a reference tissue. The methylation density at each reference site of the plurality of reference sites may be compared to one or more threshold methylation densities. Each reference site of the plurality of reference sites may be identified as methylated, unmethylated, or non-informative based on comparing the methylation density to the one or more threshold methylation densities, where the plurality of sites is the plurality of reference sites that are identified as methylated or unmethylated. Non-informative sites may include those with methylation densities between two threshold methylation densities. For example, the methylation index of non-informative sites may be between 30 and 70 or any other range, as described herein.

At step 4070, a tissue of origin of the cell-free DNA molecule may be determined using the methylation pattern. The tissue of origin may be the placenta. The tissue of origin may be fetal or maternal. The method may include determining the tissue of origin to be the reference tissue when the methylation pattern matches the reference pattern, similar to the description with FIG. 22. Match may refer to an exact match. In some embodiments, determining the tissue of origin to be the reference tissue may be when the methylation pattern matches a certain percentage of the sites of the reference pattern. For example, the methylation pattern may match at least 60%, 70%, 80%, 85%, 90%, 95%, 97% or more of the sites of the reference pattern.

The method may include determining the tissue of origin by determining a similarity score by comparing the methylation pattern with a first reference methylation pattern from a first reference tissue of a plurality of reference tissues. The similarity score may be calculated with the methylation status matching process or the beta distribution probabilistic model described herein. The similarity score may be compared with a threshold value. The tissue of origin may be determined to be the first reference tissue when the similarity score exceeds the threshold value. The similarity score may be a first similarity score. The method may further include calculating the threshold value by determining a second similarity score by comparing the methylation pattern with a second reference methylation pattern from a second reference tissue of the plurality of reference tissues. The first reference tissue and the second reference tissue may be different tissues. The threshold value may be the second similarity score. The first reference tissue may have the highest similarity score compared to all other reference tissues.

The first reference methylation pattern may include a first subset of sites having at least a first probability of being methylated for the first reference tissue. For example, the first subset of sites may be sites considered to be methylated or usually methylated. The first reference methylation pattern may include a second subset of sites having at most a second probability of being methylated for the first reference tissue. For example, the second subset of sites may be sites considered to be unmethylated or usually unmethylated. Determining the similarity score may include increasing the similarity score when a site of the plurality of sites is methylated and the site of the plurality of sites is in the first subset of sites, and decreasing the similarity score when a site of the plurality of sites is methylated and the site of the plurality of sites is in the second subset of sites. The similarity score may be determined similar to the methylation status matching approach described herein.

The first reference methylation pattern comprises the plurality of sites, with each site of the plurality of sites characterized by a probability of being methylated and a probability of being unmethylated for the first reference tissue. The similarity score may be determined by for each site of the plurality of sites, determining the probability in the reference tissue corresponding to the methylation status of the site in the cell-free DNA molecule. The similarity score may be determined by calculating a product of the plurality of probabilities. The product may be the similarity score. The probability may be determined by a beta distribution, similar to the approach described herein.

Method 4000 may further include determining the tissue of origin for each cell-free DNA molecule of the set of cell-free DNA molecules. This determination may include determining the methylation status at each site of a plurality of respective sites, wherein the plurality of respective sites corresponds to the cell-free DNA molecule. The determination of tissue of origin may further include determining the methylation pattern. In addition, the determination of the tissue of origin may also include comparing the methylation pattern to at least one reference pattern of the one or more reference patterns. In some embodiments, the comparison of the methylation pattern may be similar to FIG. 22 and the accompanying description. In FIG. 22, placenta, liver, blood cells, and colon are examples of reference tissues having the illustrated reference patterns. FIG. 38 shows hematopoietic cells as another example of a reference tissue.

In some embodiments, an amount of cell-free DNA molecules corresponding to each tissue of origin may be determined. Each tissue of origin may include each reference tissue of a plurality of reference tissues. The fractional contribution of the tissue of origin may be determined using the amount of cell-free DNA molecules corresponding to each tissue of origin. For example, the tissue of origin may be the placenta. The other tissues of origin may include hematopoietic cells and the liver. For example, the fractional contribution of the placenta may be determined from the amount of cell-free DNA molecules divided by the total cell-free DNA molecules corresponding to the all tissues of origin. In some embodiments, the fraction calculated from the amount of cell-free DNA molecules divided by the total cell-free DNA molecules may be related to a fractional contribution through a function or a set of calibration data points. The function and the set of calibration data points may both be determined from a plurality of calibration samples with known fractional contributions of the tissue of origin. Each calibration data point may specify a fractional contribution corresponding to a calibration value of the fraction. The function may represent a linear or non-linear fit of the calibration data points and may relate fractional contribution to the fraction of the tissue of origin or other parameter involving the tissue of origin. Embodiments of determining the fractional contribution may be similar to what has been described with FIGS. 39A and 39B.

A machine learning model may be used to determine the tissue of origin. The model may be trained by receiving a plurality of training methylation patterns, each training methylation pattern having a methylation status at one or more sites of the plurality of sites, each training methylation pattern determined from a DNA molecule from a known tissue. Each molecule from the known tissue may be cellular DNA. The training may include storing a plurality of training samples, each training sample including one of the plurality of training methylation patterns and a label indicating the known tissue corresponding to the training methylation pattern. The training may include optimizing, using the plurality of training samples, parameters of the model based on outputs of the model matching or not matching corresponding labels when the plurality of training methylation patterns is input to the model. The parameters may include a first parameter indicating whether one site of the plurality of sites has the same methylation status as another site of the plurality of sites. For example, the model may be similar to the pairwise comparison of FIG. 24. The parameters may include a second parameter indicating a distance between sites of the plurality of sites. In some embodiments, the machine learning model may not require alignment of a methylation site to a reference genome. An output of the model may specify a tissue corresponding to an input methylation pattern.

The machine learning model may be convolution neural networks (CNN) or any model described herein. The model may include, but is not limited to, linear regression, logistic regression, deep recurrent neural network (e.g., long short-term memory, LSTM), Bayes's classifier, hidden Markov model (HMM), linear discriminant analysis (LDA), k-means clustering, density-based spatial clustering of applications with noise (DBSCAN), random forest algorithm, and support vector machine (SVM).

The paternity may be determined by method 4000. The tissue of origin may be fetal. The method may further include aligning a sequence read of the sequence reads to a first region of a reference genome, the first region comprising a plurality of sites corresponding to alleles, the plurality of sites including a threshold number of sites, determining a first haplotype using the respective allele present at each site of the plurality of sites, comparing the first haplotype to a second haplotype corresponding to a male subject, and determining a classification of a likelihood that the male subject being the father of the fetus using the comparison. The male subject may be considered to be likely the father if the haplotypes match or not likely to be the father if the haplotypes do not match. In some embodiments the first haplotype may be compared to both haplotypes of the male subject.

In embodiments, paternity may be tested when the tissue of origin is fetal by aligning a sequence read of the sequence reads to a first region of a reference genome. The first region may include a first plurality of sites corresponding to alleles. The plurality of sites may include a threshold number of sites. The threshold number of sites may be 3, 4, 5, 6, 7, 8, 9, 10, 11, 12, 13, 14, 15 or more sites. The allele at each site of the plurality of sites may be compared to an allele at the corresponding site in the genome of a male subject. A classification of a likelihood that the male subject being the father of the fetus may be determined using the comparison. The male subject may be considered to be likely the father if a certain number or percentage of alleles match and not likely to be the father if less than that number or percentage match. The cutoff percentage may be 100%, 90%, 80%, or 70%.

In some embodiments, a haplotype may be determined. The methods may include for each cell-free DNA molecule of the set of cell-free DNA molecules, aligning the sequence read corresponding to the cell-free DNA molecule to a reference genome. The sequence read may be identified as corresponding to a haplotype present in the female. The haplotype present in the female may be known from genotyping the female. In some embodiments, the haplotype of the female may be known by analyzing concentrations of DNA fragments of the haplotype in a biological sample from the female. The tissue of origin may be determined as fetal using the methylation pattern. The haplotype may be determined to be a maternally inherited fetal haplotype.

The inheritance of a haplotype may be determined using methylation of reference tissues rather than using known methylation profiles such as that associated with imprinting loci. The matching or the similarity score of a methylation pattern to a reference pattern may exclude knowledge of whether a given allele or site is methylated based on the parent from which it was inherited.

The haplotype may be identified as carrying a disease-causing genetic mutation or variation. Identifying the haplotype as carrying the disease-causing genetic mutation may include identifying the genetic mutation or variation in a first sequence read. A genetic variation may include a single nucleotide difference, a deletion, or an insertion. A first methylation level in a second sequence read corresponding to a first genomic location within a first distance of the first sequence read may be measured. A second methylation level in a third sequence read corresponding to a second genomic location within a second distance of the first sequence read may also be measured. The first distance may be 100 nt, 200 nt, 300 nt, 400 nt, 500 nt, 600 nt, 700 nt, 800 nt, 900 nt, 1 knt, 2 knt, 5 knt, or 10 knt. The second sequence read and the third sequence read may be on the same chromosome arm as the first sequence read. The first methylation level and the second methylation level may be associated with the genetic mutation or variation. The first methylation level and the second methylation level may be greater than one or two threshold levels associated with the genetic mutation or variation. The threshold levels may be determined using subjects known to have or to not have the genetic mutation or variation. The method may include classifying that the fetus is likely to have the disease caused by the genetic mutation or variation.

Fetal-specific methylation patterns may be determined. The method may include for each cell-free DNA molecule of the set of cell-free DNA molecules, aligning the sequence read corresponding to the cell-free DNA molecule to a reference genome. The method may include identifying the sequence read as corresponding to a region. The region may be determined by receiving a plurality of fetal sequence reads corresponding to a plurality of fetal DNA molecules from fetal tissue. The method may include receiving a plurality of maternal sequence reads corresponding to a plurality of maternal DNA molecules. The method may include determining a fetal methylation status at each methylation site of a plurality of methylation sites within the region for each fetal sequence read of the plurality of fetal sequence reads. The method may include determining a maternal methylation status at each methylation site of the plurality of methylation sites for each maternal sequence read of the plurality of maternal sequence reads.

The method for determining fetal-specific methylation patterns may include determining value of a parameter characterizing an amount of sites where the fetal methylation status differs from the maternal methylation status. The method may include comparing the value of the parameter to a threshold value. The parameter may be a proportion of sites that differ between the fetal DNA molecules and the maternal DNA molecules. The proportion may be a mismatch score described herein. The threshold value may indicate a minimum level of a mismatch score and may be 0.3, 0.4, 0.5, 0.6, 0.7, 0.8, 0.9 or more. In some embodiments, the threshold value may represent an average mismatch score for maternal or fetal DNA molecules. The method may include determining the value of the parameter exceeds the threshold value. In some embodiments, a certain percentage of maternal or fetal DNA molecules may be required to have the value of the parameter exceed the threshold value. For example, the percentage may be 50%, 60%, 70%, 80%, 90% or more. In some embodiments, a certain percentage of the fetal DNA molecules corresponding to the region may be required to have the fetal-specific methylation pattern. For example, the percentage may be 40%, 50%, 60%, 70%, 80% or more. This method may be similar to methods described with FIG. 25.

The method may include enriching the biological sample for cell-free DNA molecules from the tissue of origin. Enriching the biological sample may include selecting and amplifying the set of cell-free DNA molecules. Enrichment may include size-based selection, as described herein. In some embodiments, enrichment may include methylation pattern-based selection. For example, methyl-CpG binding domain (MBD)-based capture and sequencing may be used. Cell-free DNA may be incubated with tagged MBD proteins that can bind methylated cytosines. The protein-DNA complex may then be precipitated with antibody-conjugated magnetic beads. The DNA molecules with more methylated CpG sites may be preferentially enriched for the downstream analysis.

III. Variation of Long Cell-Free DNA Fragments with Gestational Age

The amount of long cell-free DNA fragments may vary with gestational age. Long cell-free DNA fragments may be used to determine a gestational age. In addition, long cell-free DNA fragments may be more abundant in certain end motifs compared to shorter cell-free DNA fragments, and the relative amount of certain end motifs may vary with gestational age. The amount of end motifs may also be used to determine a gestational age. A deviation of a gestational age determined using long cell-free DNA fragments and a gestational age determined through other clinical techniques may indicate a pregnancy-associated disorder. In some embodiments, long cell-free DNA fragments may be used to determine the likelihood of a pregnancy-associated disorder without necessarily determining a gestational age.

A. Size Analysis for Fetal and Maternal DNA

Plasma DNA of two pregnant women at the first trimester (gestational age: 13 weeks), two at the second trimester (gestational age: 21-22 weeks) and five at the third trimester (gestational age: 38 weeks) was sequenced using single-molecule real-time (SMRT) sequencing (PacBio). A median of 176 million (range: 49-685 million) subreads was obtained for each case, among which 128 million (range: 35-507 million) subreads could be aligned to the human reference genome (hg19). Each molecule in a SMRT well was sequenced 107 times on average. A median of 965,308 (range: 251,686-2,871,525) high-quality circular consensus sequencing (CCS) reads, which was defined as CCS reads with at least 3 subreads, could be used for downstream analyses.

All sequenced molecules from samples obtained from each trimester of pregnancy were pooled together for the size analyses. There were a total of 1.94 million, 5.09 million, and 4.45 million cell-free DNA molecules for the first-, second-, and third-trimester maternal plasma samples, respectively.

Figure 41B:
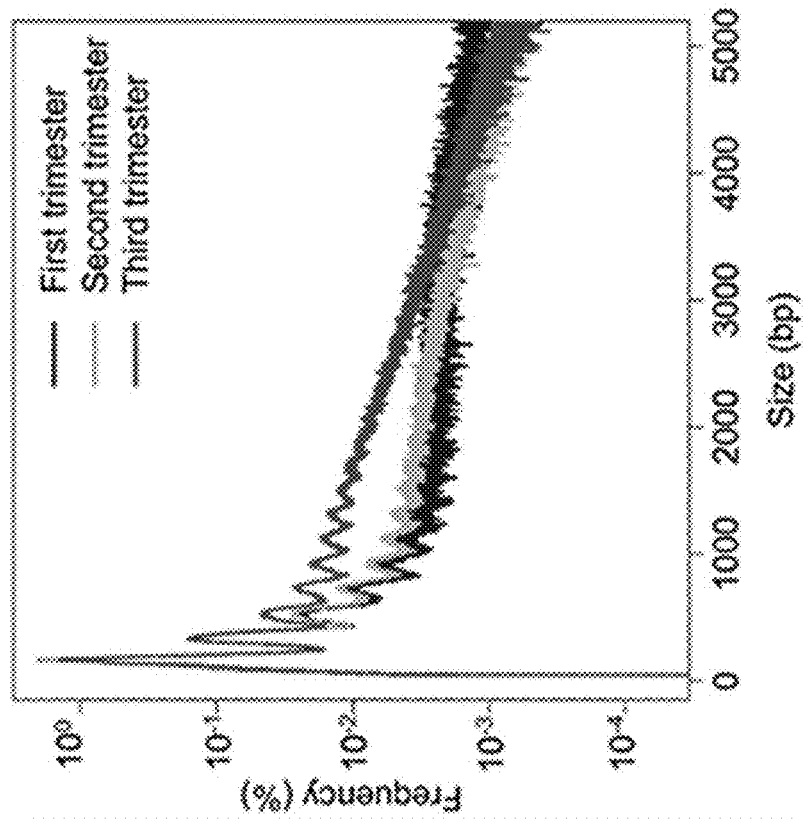
FIGS. 41A and 41B show the size distributions of cell-free DNA molecules from first-, second- and third-trimester maternal plasma samples according to embodiments of the present invention.
Figure 41A:
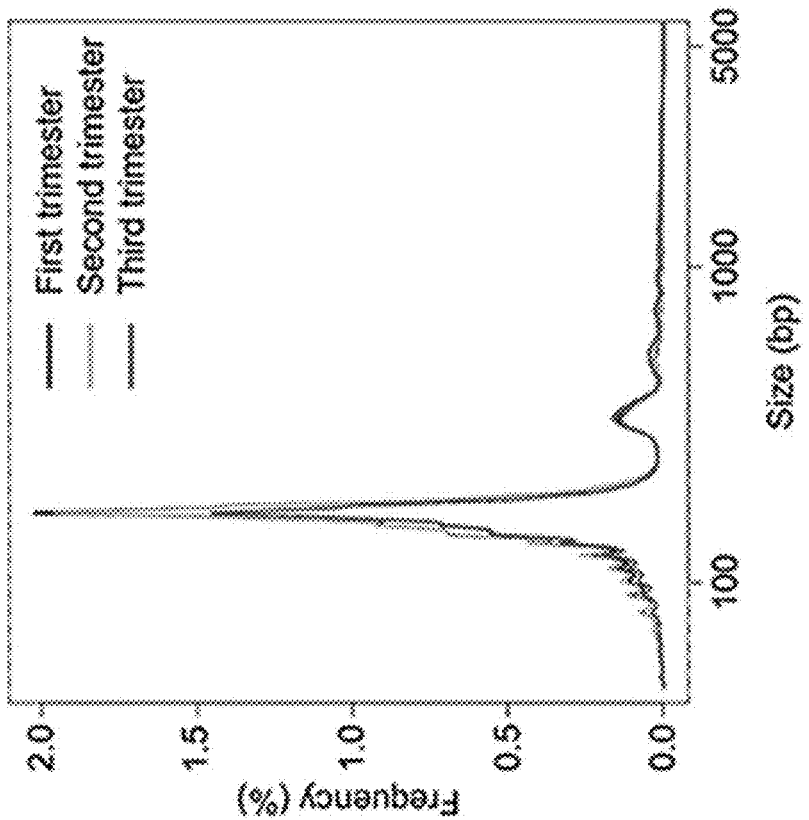

FIGS. 41A and 41B show the size distributions of cell-free DNA molecules from first-, second- and third-trimester maternal plasma samples within a size range of 0 to 5 kb. The x-axis shows the size. The y-axis shows the frequency. The size distribution is plotted in the range for FIG. 41A, from 0 to 5 kb on a linear scale the y-axis and for FIG. 41B, from 0 to 5 kb on a logarithmic scale for the y-axis. Plasma DNA from all three trimesters of pregnancy demonstrated the expected major peak at 166 bp as shown in FIG. 41A and a series of major peaks occurring in periodic patterns which extended to molecules within a range of 1 kb and 2 kb as shown in FIG. 41B.

FIG. 42 is a table showing the proportion of long plasma DNA molecules in different trimesters of pregnancy. The first column shows the gestational age associated with the plasma sample. The second column shows the proportion of DNA molecules longer than 500 bp. The third column shows the proportion of DNA molecules longer than 1 kb. Compared to the first and the second trimesters, the third trimester had an increase in the frequency of plasma DNA molecules of 500 bp or above. The proportions of long plasma DNA molecules over 500 bp were 15.8%, 16.1%, and 32.3% for the first, second, and third trimesters, respectively. The proportions of long plasma DNA molecules over 1 kb were 11.3%, 10.6%, and 21.4% for the first, second, and third trimesters, respectively. While the first- and second-trimester maternal plasma showed a similar proportion of long cell-free DNA molecules, the third-trimester maternal plasma had approximately twice the proportion of long DNA molecules.

For all the maternal plasma DNA samples analyzed for this disclosure, DNA extracted from their paired maternal buffy coat and fetal samples was genotyped with the Infinium Omni2.5Exome-8 Beadchip on the iScan System (Illumina) which is a genotyping method based on array hydridization. Fetal samples were obtained by chorionic villus sampling, amniocentesis, or sampling of the placenta, depending on whether a case was from the first, second, or third trimester, respectively. A median of 203,647 informative single nucleotide polymorphisms (SNPs) for which the mother was homozygous and the fetus was heterozygous was identified for each case. We identified a total of 1,362, 2,984, and 6,082 DNA molecules covering fetal-specific alleles for the first, second, and third trimester, respectively, when sequenced DNA molecules for all cases from each trimester were pooled together. On the other hand, a median of 210,820 informative SNPs for which the mother was heterozygous and the fetus was homozygous was identified for each case. We identified a total of 30,574, 65,258, and 78,346 DNA molecules covering maternal-specific alleles for the first, second, and third trimester, respectively. The median fetal DNA fraction, which was determined from the sequencing data of DNA molecules ≤600 bp, among all maternal plasma samples was 15.6% (range, 7.6-26.7%).

Figure 43B:
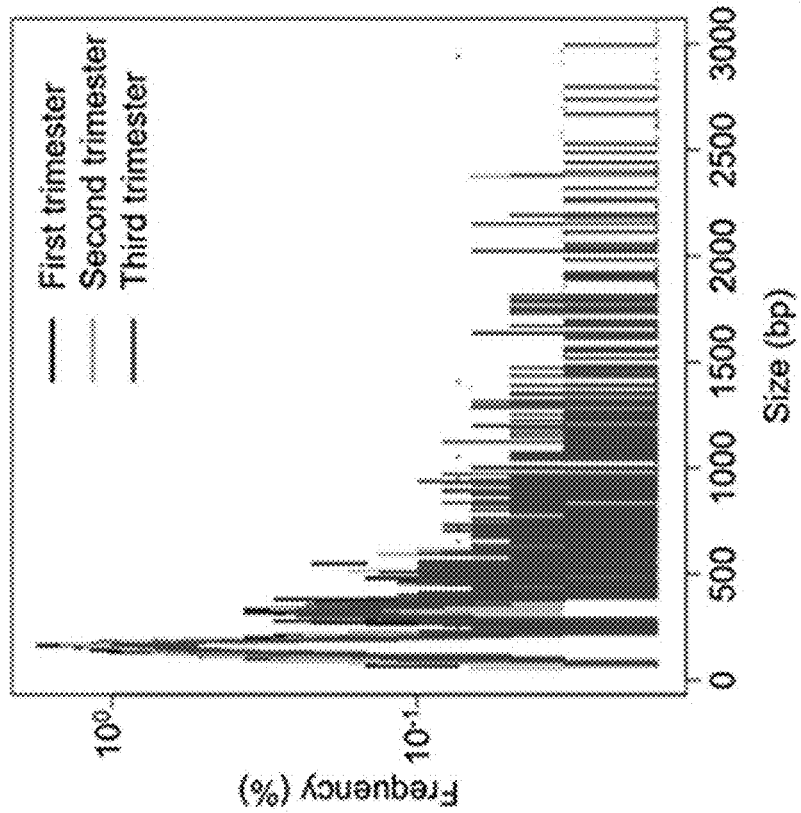
FIGS. 43A and 43B show size distributions of DNA molecules covering fetal-specific alleles from first-, second- and third-trimester maternal plasma according to embodiments of the present invention.
Figure 43A:
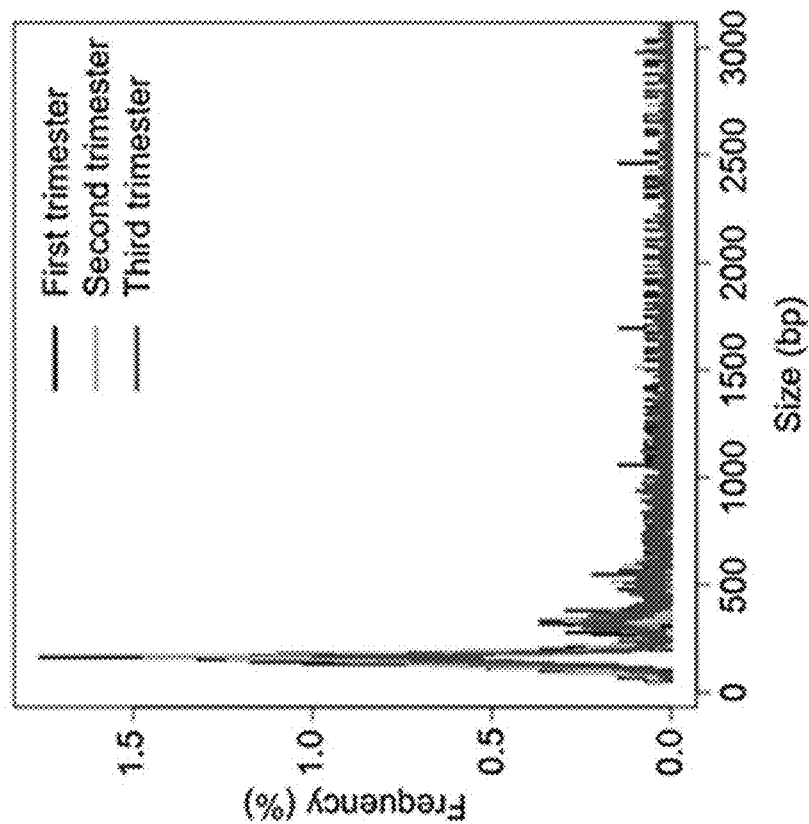

FIGS. 43A and 43B show size distributions DNA molecules covering fetal-specific alleles from first-, second- and third-trimester maternal plasma. The x-axis shows the size. The y-axis shows the frequency. The size distribution is plotted in the range for FIG. 43A, from 0 to 3 kb on a linear scale for the y-axis and for FIG. 43B, from 0 to 3 kb on a logarithmic scale for the y-axis.

Figure 44B:
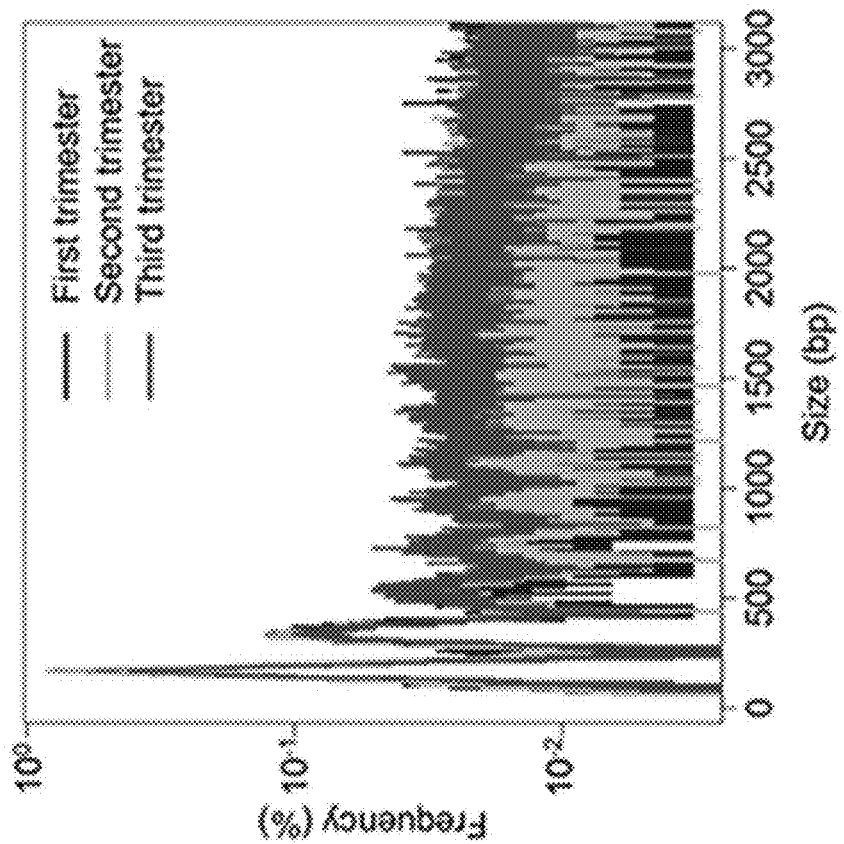
FIGS. 44A and 44B show size distributions of DNA molecules covering maternal-specific alleles from first-, second- and third-trimester maternal plasma according to embodiments of the present invention.
Figure 44A:
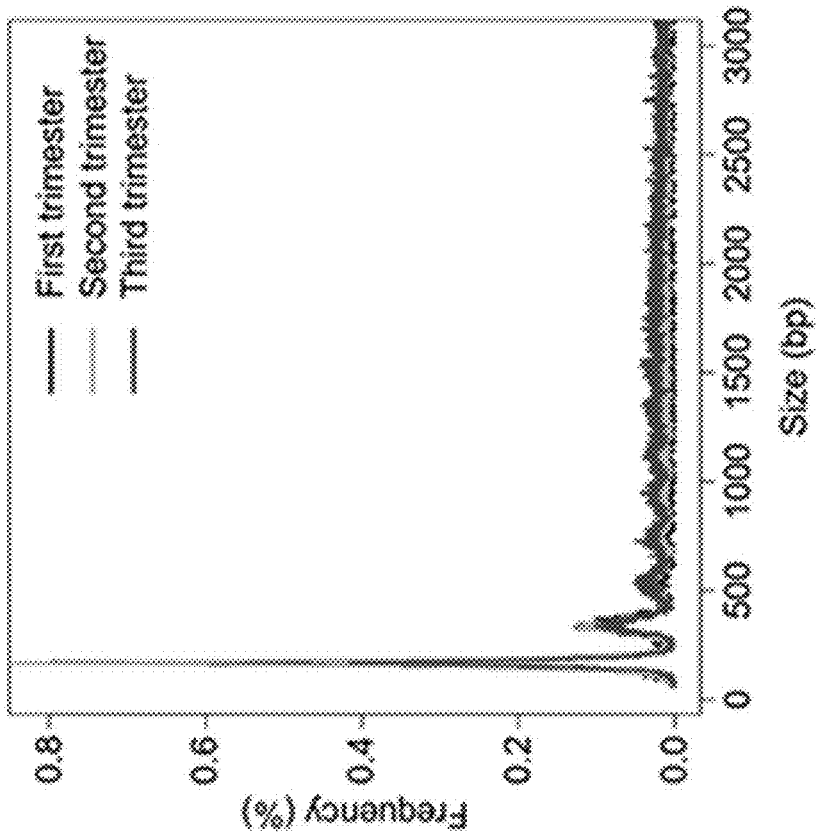

FIGS. 44A and 44B show size distributions of DNA molecules covering maternal-specific alleles from first-, second- and third-trimester maternal plasma. The x-axis shows the size. The y-axis shows the frequency. The size distribution is plotted in the range for FIG. 44A, from 0 to 3 kb on a linear scale for the y-axis and for FIG. 44B, from 0 to 3 kb on a logarithmic scale for the y-axis.

As shown in FIGS. 43A to 44B, plasma DNA molecules covering fetal- and maternal-specific alleles from all three trimesters of pregnancy displayed long-tailed distributions, suggesting the presence of long DNA molecules derived from both fetal and maternal sources in all three trimesters.

FIG. 45 is a table of the proportion of long fetal and maternal plasma DNA molecules in different trimesters of pregnancy. The first column shows the gestational age associated with the plasma sample. The second column shows the proportion of fetal DNA molecules longer than 500 bp. The third column shows the proportion of maternal DNA molecules longer than 500 bp. The fourth column shows the proportion of fetal DNA molecules longer than 1 kb. The fifth column shows the proportion of maternal DNA molecules longer than 1 kb. Among the pool of DNA molecules in the maternal plasma, those covering a fetal-specific allele (of placental origin) had a smaller proportion of long DNA molecules compared to those covering a maternal-specific allele. The proportions of long plasma DNA molecules covering a fetal-specific allele with a size over 500 bp were 19.8%, 23.2%, and 31.7% for the first, second, and third trimesters, respectively. The proportions of long plasma DNA molecules covering a fetal-specific allele with a size over 1 kb were 15.2%, 16.5%, and 19.9% for the first, second, and third trimesters, respectively.

Despite the fact that there was a smaller proportion of long plasma DNA molecules present in the first- and second-trimester maternal plasma compared to the third trimester, and the fetal DNA molecules contained less long DNA molecules in all three trimesters, the method described in our previous and this disclosure allowed us to analyze a substantial proportion of long plasma DNA molecules which was not possible previously with short-read sequencing technologies. In addition, one could use different size selection strategies including but not limited to electrophoretic-, chromatographic- and bead-based methods to enrich for long DNA fragments in plasma samples.

Figure 46A:
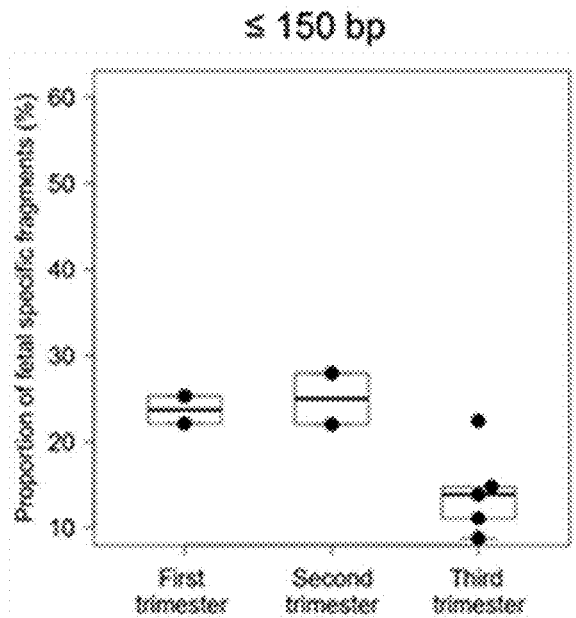
FIGS. 46A, 46B, and 46C show plots of the proportions of fetal-specific plasma DNA fragments of a particular size range across different trimesters according to embodiments of the present invention.
Figure 46B:
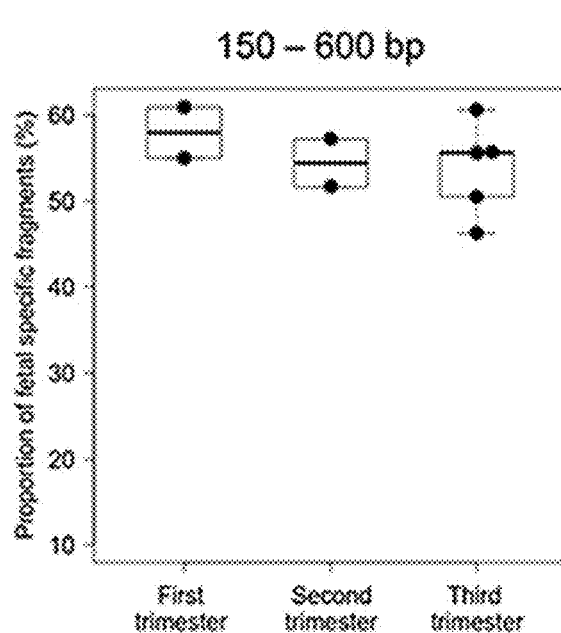
Figure 46C:
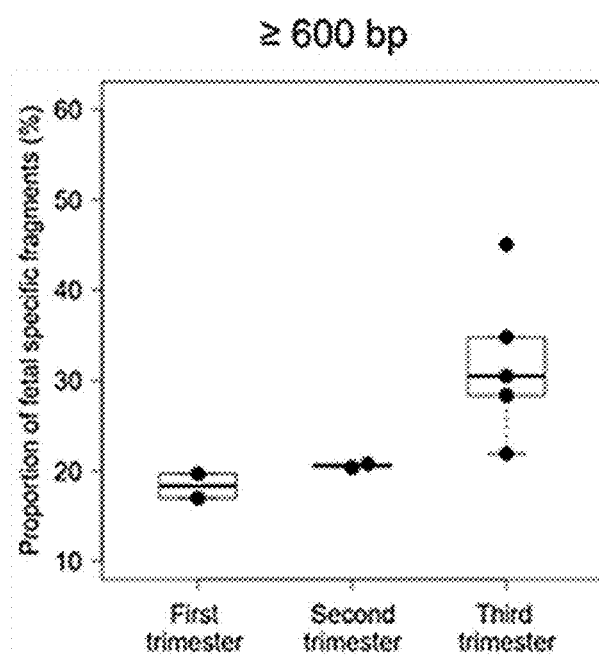

FIGS. 46A, 46B, and 46C show plots of the proportions of fetal-specific plasma DNA fragments of a particular size range across different trimesters. The gestational ages of the assessed pregnant cases were verified by dating ultrasound. FIG. 46A shows results for DNA fragments less than or equal to 150 bp. FIG. 46B shows results for DNA fragments from 150 to 600 bp. FIG. 46C shows results for DNA fragments greater than or equal to 600 bp. The graphs have the proportion of fetal specific fragments on the y-axis and the gestational age on the x-axis. As shown in the graphs, both the proportions of fetal-specific fragments shorter than 150 bp (FIG. 46A) and longer than 600 bp (FIG. 46C) would achieve a certain discriminating power of differentiating the third-trimester samples from the first- and second-trimester samples, compared with the proportion of fetal-specific fragments ranging from 150 to 600 bp (FIG. 46B). The proportions of fetal-specific fragments longer than 600 bp may provide the best discriminating power. This conclusion was evidenced by the fact that the absolute least distance between the third-trimester group and the combined group of the first and second trimesters was 0.38 when using the proportions of fetal-specific fragments shorter than 150 bp, whereas the counterpart value was 3.76 when using the proportions of fetal-specific fragments greater than 600 bp. These results suggested that the use of long DNA molecules for reflecting the pathophysiologic status would be superior to the use of short DNA molecules.

B. Plasma DNA End Analysis

In addition to the size, we determined the first nucleotide at the 5' end of both the Watson and Crick strands separately for each sequenced DNA molecule. This analysis consisted of 4 types of end, namely, A-end, C-end, G-end and T-end. The percentages of plasma DNA molecules with a particular end from maternal plasma samples obtained from each trimester were calculated. The percentages of A-end, C-end, G-end and T-end at each fragment size were further analyzed.

Figure 47A:
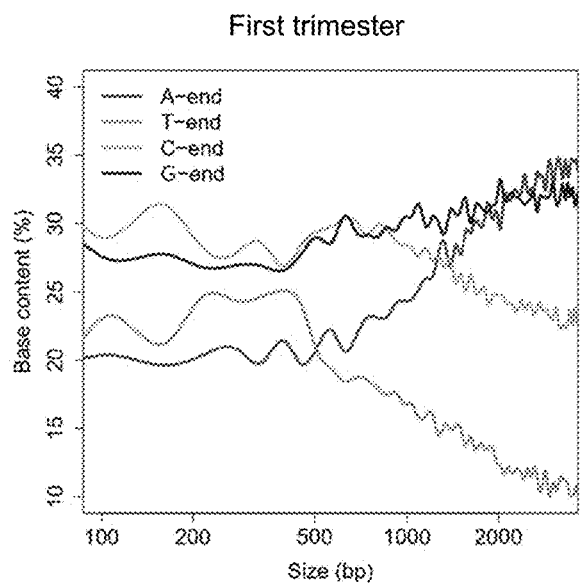
FIGS. 47A, 47B, and 47C show graphs of base content proportions at the 5' end of cell-free DNA molecules from first-, second- and third-trimester maternal plasma across the range of fragment sizes from 0 to 3 kb according to embodiments of the present invention.
Figure 47B:
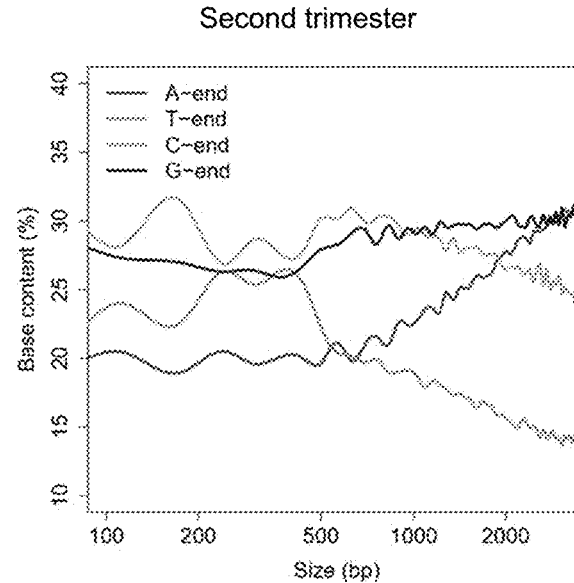
Figure 47C:
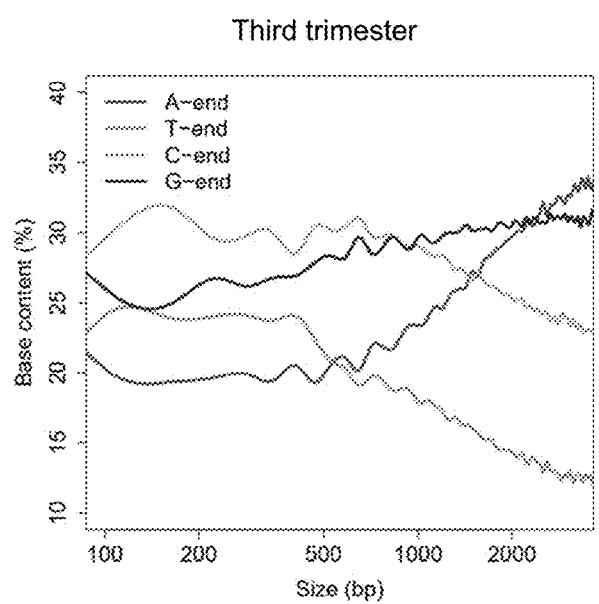

FIGS. 47A, 47B, and 47C show graphs of base content proportions at the 5' end of cell-free DNA molecules from first-, second- and third-trimester maternal plasma across the range of fragment sizes from 0 to 3 kb. FIG. 47A shows first trimester maternal plasma. FIG. 47B shows second trimester maternal plasma. FIG. 47C shows third trimester maternal plasma. The base content as a percentage is shown on the y-axis. The size of the fragment in base pairs is shown on the x-axis. As seen in the graphs, the C-end was over-represented across many size ranges (mostly less than 1 kb) and varied according to different size ranges for first-, second- and third-trimester samples. The plasma DNA end patterns of third-trimester samples appeared to be different from the first- and second-trimester samples. For example, the T-end and G-end curves were mixed together at sizes ranging from 105 to 172 bp, while they were divergent in the first- and second-trimester samples. For longer fragments (e.g., over around 1 kb), C-end fragments are not the most abundant fragment. G-end fragments overtake C-end fragments at around 1 kb, and then A-end fragments become more abundant than G-end fragments at around 2 kb.

FIG. 48 is a table of the end nucleotide base proportions among short and long cell-free DNA molecules from the first-, second-, and third-trimester maternal plasma. The first column shows the base at the end of the molecule. The second column shows the expected proportion point and species. The third column shows the proportion of an end species among fragments less than or equal to 500 bp for first trimester maternal plasma. The fourth column shows the proportion of an end species among fragments greater than 500 bp for first trimester maternal plasma. The fifth column and sixth column are similar to the third column and fourth column, respectively, except for second trimester maternal plasma and instead of first trimester maternal plasma. The seventh column and eighth column are similar to the third column and fourth column, respectively, except for third trimester maternal plasma and instead of first trimester maternal plasma.

If cell-free DNA fragmentation was completely random, the end nucleotide base proportions should reflect the composition of the human genome, which is 29.5% of A, 29.5% of T, 20.5% of C, and 20.5% of G as shown in the second column of FIG. 48. In contrast to the random fragmentation, the 5' end of short cell-free DNA molecules of ≤500 bp showed a substantial overrepresentation of C-end (30.4%, 30.4%, and 31.3% for first-, second-, and third-trimester maternal plasma, respectively), a slight overrepresentation of G-end (27.4%, 26.9%, and 25.3% for first, second and third trimesters, respectively), and an underrepresentation of A-end (19.8%, 19.4%, and 19.3% for first, second and third trimesters, respectively) and T-end (22.4%, 23.3%, and 24.1% for first, second and third trimesters, respectively).

However, when compared with short cell-free DNA molecules, long cell-free DNA molecules of >500 bp showed a substantial increase in the proportion of A-ends (29.6%, 26.0%, and 26.7% for first-, second- and third-trimester maternal plasma, respectively), a slight increase in the proportion of G-ends (31.0%, 29.5%, and 29.9% for first, second and third trimesters respectively), a substantial decrease in the proportion of T-ends (13.9%, 16.9%, and 16.4% for first, second, and third trimesters, respectively), and a slight decrease in the proportion of C-ends (25.5%, 27.5%, and 27.1% for first, second and third trimesters, respectively).

FIG. 49 is a table of the end nucleotide base proportions among short and long cell-free DNA molecules covering a fetal-specific allele from the first-, second-, and third-trimester maternal plasma. FIG. 50 is a table of the end nucleotide base proportions among short and long cell-free DNA molecules covering a maternal-specific allele from the first-, second-, and third-trimester maternal plasma. The first column shows the base at the end of the molecule. The second column shows the expected proportion point and species. The third column shows the proportion of an end species among fragments less than or equal to 500 bp for first trimester maternal plasma. The fourth column shows the proportion of an end species among fragments greater than 500 bp for first trimester maternal plasma. The fifth column and sixth column are similar to the third column and fourth column, respectively, except for second trimester maternal plasma and instead of first trimester maternal plasma. The seventh column and eighth column are similar to the third column and fourth column, respectively, except for third trimester maternal plasma and instead of first trimester maternal plasma. FIGS. 49 and 50 show that such difference in the end nucleotide base proportions among short and long cell-free DNA molecules remained unchanged even when we separately examined DNA molecules covering fetal- and maternal-specific alleles.

Figure 51:
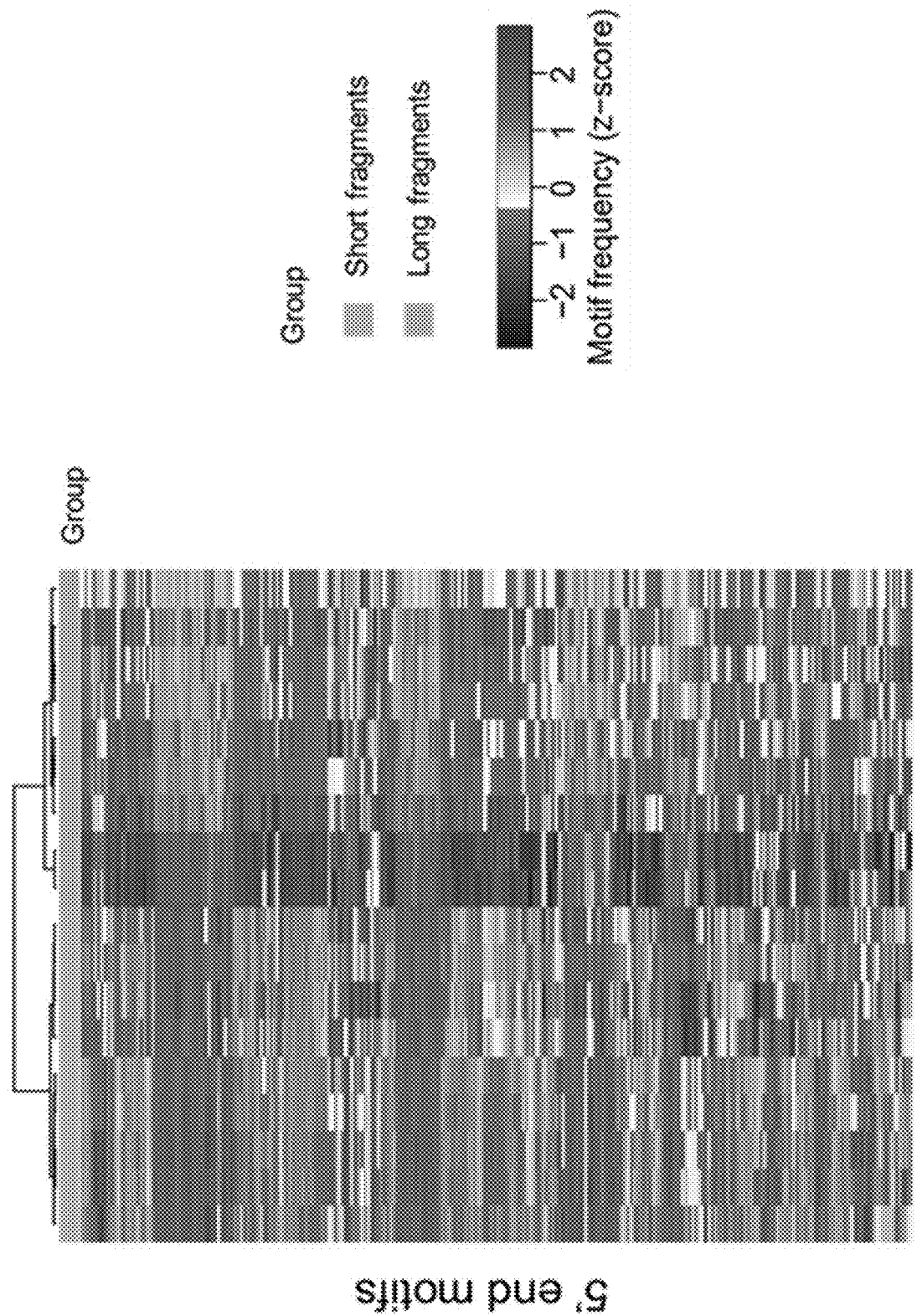
FIG. 51 illustrates hierarchical clustering analysis of short and long plasma cell-free DNA molecules using 256 end motifs according to embodiments of the present invention.

FIG. 51 illustrates hierarchical clustering analysis of short and long plasma cell-free DNA molecules using 256 4-mer end motifs. Each column indicates a sample used for analyzing the end motif frequency based on short (denoted by the cyan in the first row) and long fragments (denoted by the yellow in the first row), respectively. Starting from the second row, each row indicates a type of end motif. The end motif frequencies were presented with a series of color gradients according to the row-normalized frequencies (z-score) (i.e., the number of standard deviations below or above the mean frequency across samples). The redder color indicates a higher frequency of an end motif, while the bluer color indicates a less frequency of an end motif.

In FIG. 51, we characterized short and long cell-free DNA molecules by analyzing their 4-mer end motif profiles. We determined the first 4-nucleotide sequence (a 4-mer motif) at the 5' end of both the Watson and Crick strands separately for each sequenced DNA molecule. For each maternal plasma sample, the frequency of each plasma DNA end motif was calculated separately for short (≤500 bp) and long (>500 bp) plasma DNA molecules. Hierarchical clustering analysis based on frequencies of the 256 4-mer end motifs showed that the end motif profiles of long DNA molecules across different maternal plasma samples formed a cluster which was distinct from that of short DNA molecules. These results suggested that the long and short DNA possessed different fragmentation properties. In embodiments, one would use the relative perturbation of these end motifs between long and short DNA molecules to indicate the contributions of cell-free DNA originating from cell death pathways, such as but not limited to apoptosis and necrosis. Increased activity from these cell death pathways may be related to pregnancy-associated and other disorders.

Figures 52A, 52B:
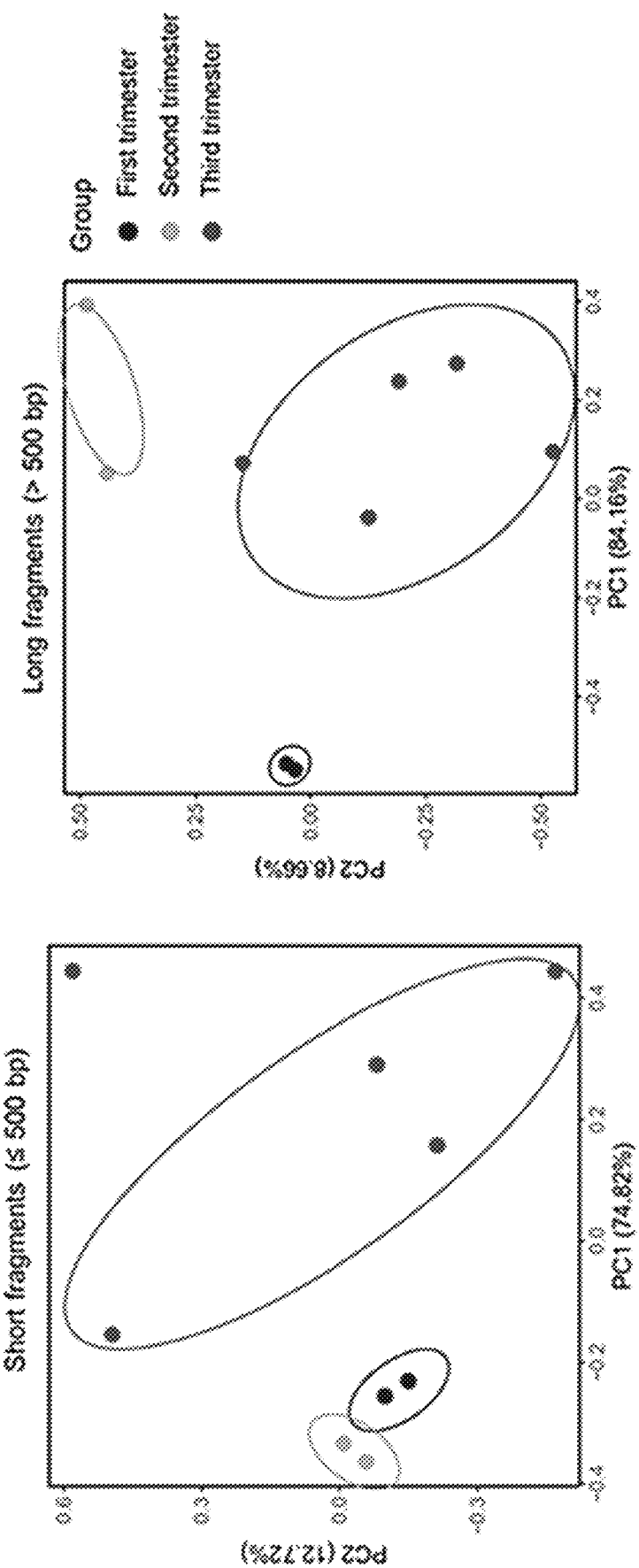
FIGS. 52A and 52B show principal component analysis of 4-mer end motif profiles according to embodiments of the present invention.

FIGS. 52A and 52B show principal component analysis (PCA) using 4-mer end motif profiles of for classification analysis. FIG. 52A shows short cell-free DNA molecules (≤500 bp) from different trimesters. FIG. 52B shows long cell-free DNA molecules (>500 bp) of maternal plasma samples from different trimesters. Percentages in brackets on x- and y-axes represent the amount of variability explained by the corresponding component. Each blue dot represents a first-trimester maternal plasma sample. Each yellow dot represents a second-trimester maternal plasma sample. Each red dot represents a third-trimester maternal plasma sample. Ellipse represents a 95% confidence level to group the datapoints from a particular trimester. Compared with short cell-free DNA molecules (FIG. 52A) (also described in U.S. application Ser. No. 15/787,050), 4-mer end motif profiles of long cell-free DNA molecules (FIG. 52B) gave rise to a clearer separation between first-, second-, and third-trimester maternal plasma samples. In embodiments, one could utilize end motif profiles of long plasma DNA molecules alone or in combination with other maternal plasma DNA characteristics, including but not limited to methylation level and size, for molecular gestational age assessment.

For example, we used the neural networks to train a model to predict the gestational age on basis of the 256 end motifs, overall methylation level and proportion of fragments with size ≥600 bp. Output variables were 1, 2, and 3, representing the $1^{st}$, $2^{nd}$, and $3^{rd}$ trimester. Input variables included 256 end motifs, overall methylation level, and proportion of fragments with size ≥600 bp. We used the leave-one-out approach to assess the performance of predicting gestational age. For a dataset comprising 9 samples, the leave-one-out approach was conducted in a way that one sample was selected as a testing sample and the remaining 8 samples were used for training a model based on neural networks. Such a testing sample were determined to be 1, 2, or 3 based on the established model. Then we repeated this process for other samples which had not yet been tested. In total, we repeated 9 times for such a training-and-testing process. By comparing those testing results with the clinical information about the gestational ages, 8 out of 9 samples (89%) were predicted correctly in term of gestational ages. In another embodiment, such analysis can be performed, for example, but not limited to using Bayes's theorem, logistic regression, multiple regression and support vector machine, random forest analysis, classification and regression tree (CART), K-nearest neighbors algorithm.

Next, all sequenced molecules from samples obtained from each trimester of pregnancy were pooled together for the downstream end motif analyses. The 256 end motifs were ranked according to their frequencies among short and long plasma DNA molecules.

FIGS. 53 to 58 are tables of the 25 end motifs with the highest frequencies for certain lengths of DNA fragments (shorter or longer than 500 bp) and for different trimesters. FIGS. 53, 54, and 55 are tables with end motifs sorted by their rank in short fragments (<500 bp). In FIGS. 53 to 55, the first column shows the end motif. The second column shows the frequency rank of the motif in short fragments. The third column shows the frequency rank of the motif in long fragments. The fourth column shows the frequency of the motif in short fragments. The fifth column shows the frequency of the motif in long fragments. The sixth column shows the fold change (frequency of the motif in short fragments divided by the frequency of the motif in long fragments).

FIGS. 56, 57, and 58 are tables with end motifs sorted by their rank in long fragments (>500 bp). In FIGS. 56 to 58, the first column shows the end motif. The second column shows the frequency rank of the motif in long fragments. The third column shows the frequency rank of the motif in short fragments. The fourth column shows the frequency of the motif in long fragments. The fifth column shows the frequency of the motif in short fragments. The sixth column shows the fold change (frequency of the motif in long fragments divided by the frequency of the motif in short fragments).

FIGS. 53 and 56 are from first trimester samples. FIGS. 54 and 57 are from second trimester samples. FIGS. 55 and 58 are from third trimester samples.

Among the top 25 end motifs with the highest frequencies among short plasma DNA molecules, 11 of them started with CC dinucleotides. End motifs starting with CC together accounted for 14.66%, 14.66%, and 15.13% of short plasma DNA end motifs in the first-, second-, and third-trimester maternal plasma, respectively. Among the top 25 end motifs with the highest frequencies among long plasma DNA molecules, the 4-mer motifs ending with TT dinucleotides accounted for 9 of them in the second- and third-trimester maternal plasma, and 10 of them in first-trimester maternal plasma.

We determined the dinucleotide sequence of the third (X) and fourth nucleotides (Y) from the 5' end of both the Watson and Crick strands separately for each sequenced DNA molecule. X and Y can be one of the four nucleotide bases in DNA. There were 16 possible NNXY motifs, namely NNAA, NNAT, NNAG, NNAC, NNTA, NNTT, NNTG, NNTC, NNGA, NNGT, NNGG, NNGC, NNCA, NNCT, NNCG, and NNCC.

Figure 59C:
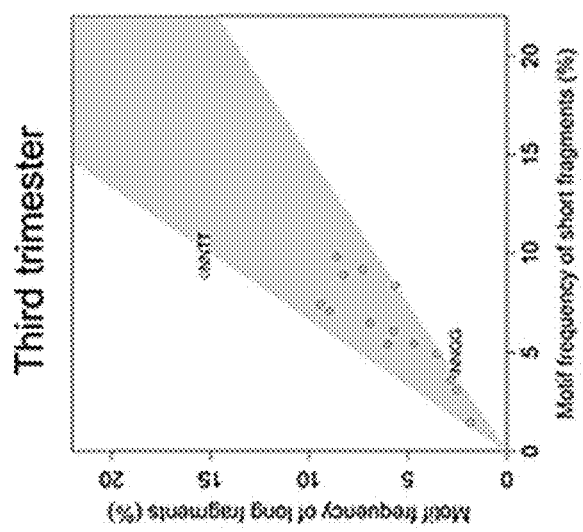
FIGS. 59A, 59B, and 59C show scatterplots of motif frequencies of 16 NNXY motifs among short and long plasma DNA molecules in (A) first-trimester, (B) second-trimester, and (C) third-trimester maternal plasma according to embodiments of the present invention.
Figure 59B:
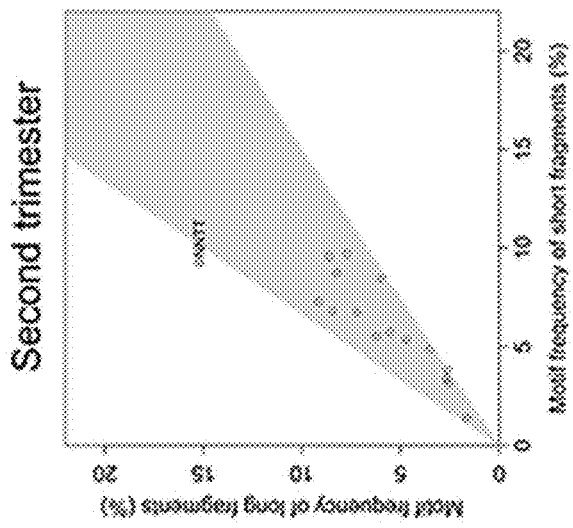
Figure 59A:
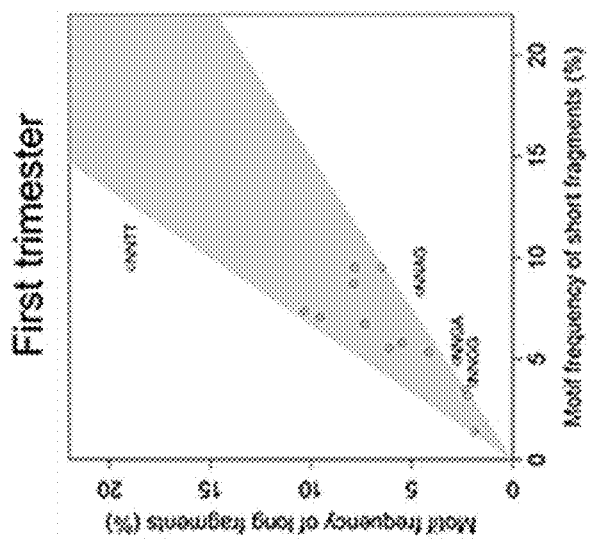

FIGS. 59A, 59B, and 59C show scatterplots of motif frequencies of 16 NNXY motifs among short and long plasma DNA molecules. FIG. 59A shows results for the first trimester. FIG. 59B shows results of the second trimester. FIG. 59C shows results for the third trimester. The motif frequency of long fragments is shown on the y-axis. Motif frequency of short fragments is shown on the x-axis. Each circle represents one of the 16 NNXY motifs. The pair of dotted lines in each scatter plot denote 1.5-fold increase (upper line) and decrease (lower line) in motif frequencies in long plasma DNA molecules (>500 bp) compared to short plasma DNA molecules (≤500 bp). Circles located outside the shaded area represent motifs with fold change of >1.5.

While ends of short plasma DNA molecules showed high frequencies of 4-mer motifs starting with CC dinucleotides (CCNN) (Jiang et al. Cancer Discov 2020; 10(5):664-673; Chan et al. Am J Hum Genet 2020; 107(5):882-894), ends of long plasma DNA molecules showed >1.5-fold increase in frequencies of 4-mer motif ending with TT (NNTT) across all three trimesters (FIG. 11). The NNTT motif accounted for 18.94%, 15.22%, and 15.30% of long plasma DNA end motifs in first-, second-, and third-trimester maternal plasma, respectively. On the contrary, the NNTT motif only accounted for 9.53%, 9.29%, and 8.91% of short plasma DNA end motifs in first-, second-, and third-trimester maternal plasma, respectively.

As previously reported by Han et al., cell-free DNA newly released from dying cells into the plasma was enriched for A-end fragments >150 bp. DNA fragmentation factor beta (DFFB), which is the major intracellular nuclease involved in DNA fragmentation during apoptosis, was found to be responsible for generating such fragments (Han et al. Am J Hum Genet 2020; 106:202-214). In this disclosure, we have shown that long cell-free DNA molecules of >500 bp were also enriched for A-end fragments, suggesting that DFFB might be responsible for generating these fragments as well. In normal pregnancy, trophoblast apoptosis increases with advancing gestation (Sharp et al. Am J Reprod Immuno 2010; 64(3):159-69). Indeed, our finding of increasing proportions of long DNA molecules covering fetal-specific allele with advancing trimesters might reflect increasing trophoblast apoptosis with advancing trimesters.

In embodiments, one could use methods described herein to analyze long cell-free DNA molecules in maternal plasma for the prediction, screening, and progression monitoring of placenta-related pregnancy complications, including but not limited to pre-eclampsia, intrauterine growth restriction (IUGR), preterm labor, and gestational trophoblastic disease. Increased level of trophoblast apoptosis has been reported in placenta-related pregnancy complications such as pre-eclampsia (Leung et al. Am J Obstet Gynecol 2001; 184:1249-1250), IUGR (Smith et al. Am J Obstet Gynecol 1997; 177:1395-1401; Levy et al. Am J Obstet Gynecol 2002; 186:1056-1061), and gestational trophoblastic disease. Moreover, elevated level of fetal DNA in maternal plasma has been reported in pre-eclampsia (Lo et al. Clin Chem 1999; 45(2):184-8; Smid et al. Ann N Y Acad Sci 2001; 945:132-7), IUGR (Sekizawa et al. Am J Obstet Gynecol 2003; 188:480-4), and preterm labor (Leung et al. Lancet 1998; 352(9144):1904-5). We hypothesized that in placenta-related pregnancy complications, there would be increased proportion of long cell-free DNA molecules of placental origin in the maternal plasma samples due to increased placental apoptosis. Hence, long cell-free DNA molecules of placental origin per se, as well as long DNA signatures including but not limited to A-end fragments and NNTT motifs, might serve as biomarkers for placental apoptosis.

While one-nucleotide and 4-nucleotide motifs are used in the above analysis, motif of other lengths, e.g. 2, 3, 5, 6, 7, 8, 9, 10, or more can be used in other embodiments.

C. Example Methods

Long cell-free DNA fragments may be used to determine the gestational age of a female pregnant with a fetus. The amount of long cell-free DNA fragments varies with gestational age and can be used to determine the gestational age. The end motif of the cell-free DNA fragments also varies with gestational age and can be used to determine the gestational age. When the gestational age determined using long cell-free DNA fragments deviates significantly from the gestational age determined through other clinical techniques, then the pregnant female and/or fetus may be considered to have a pregnancy-associated disorder. In some embodiments, the gestational age may not need to be determined to determine the likelihood of a pregnancy-associated disorder.

1. Gestational Age

Figure 60:
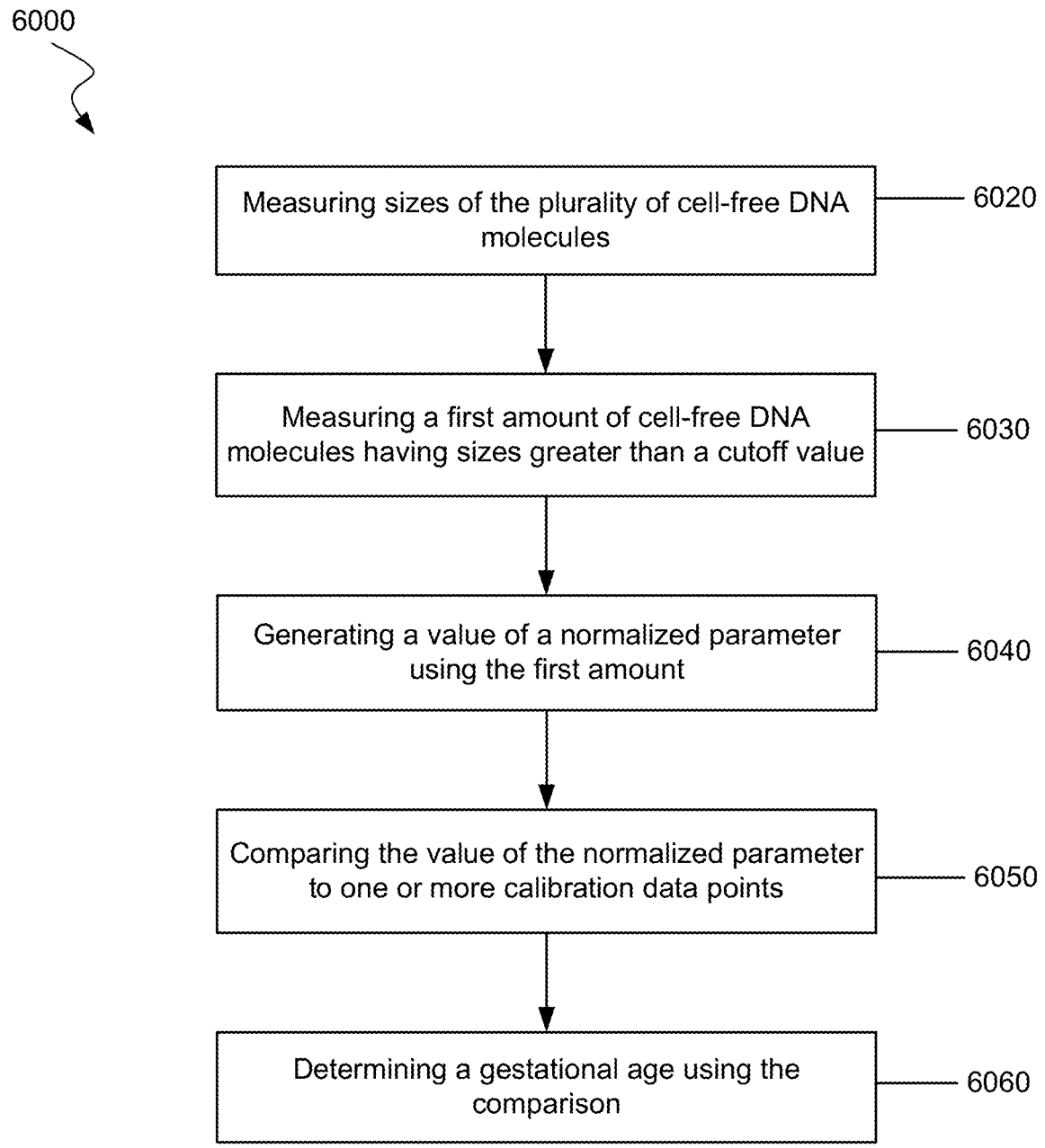
FIG. 60 shows a method of analyzing a biological sample obtained from a female pregnant with a fetus in order to determine a gestational age according to embodiments of the present invention.

FIG. 60 shows a method 6000 of analyzing a biological sample obtained from a female pregnant with a fetus. The gestational age may be determined and may be used to classify the likelihood of a pregnancy-associated disorder. The biological sample may include a plurality of cell-free DNA molecules from the fetus and the female.

Sequence reads corresponding to the plurality of cell-free DNA molecules may be received. In some embodiments, sequencing to obtain the sequence reads may be performed.

At block 6020, sizes of the plurality of cell-free DNA molecules may be measured. Sizes may be measured in a similar manner as described with FIG. 21. The sizes may be measured using the sequence reads.

At block 6030, a first amount of cell-free DNA molecules having sizes greater than a cutoff value may be measured. The amount may be a number, a total length, or a mass of cell-free DNA molecules.

At block 6040, a value of a normalized parameter using the first amount may be generated. The value of the normalized parameter may be the first amount normalized by the total number of cell-free DNA molecules, by the number of cell-free DNA molecules from the fetus or mother, or by a number of DNA molecules from a specific region. For example, the normalized parameter may be a proportion of fetal-specific fragments, as described with FIG. 46A-C.

At block 6050, the value of the normalized parameter may be compared to one or more calibration data points. Each calibration data point may specify a gestational age corresponding to a calibration value of the normalized parameter. For example, a gestational age of a certain trimester or a certain number of weeks may correspond to a calibration value of the normalized parameter. The one or more calibration data points may be determined from a plurality of calibration samples with known gestational ages and including cell-free DNA molecules having sizes greater than the cutoff value. In some embodiments, the calibration data points are determined from a function correlating gestational age with values of the normalized parameter.

At block 6060, a gestational age using the comparison may be determined. The gestational age may be considered to be the age corresponding to the calibration value closest to the value of the normalized parameter. In some embodiments, the gestational age may be considered to be the most advanced age for corresponding to the calibration value exceeded by the value of the normalized parameter.

The method may further include determining a reference gestational age of the fetus using an ultrasound or the date of the last menstrual period of the female. The method may also include comparing the gestational age to the reference gestational age. The method may further include determining a classification of a likelihood of a pregnancy-associated disorder using the comparison of the gestational age to the reference gestational age. For example, a discrepancy between the gestational age and the reference gestational age may indicate a pregnancy-associated disorder. The discrepancy may be a different trimester or a difference in gestational age by a minimum number of weeks (e.g., 1, 2, 3, 4, 5, 6, 7 or more weeks).

The method may further include using end motifs. For example, the method may include determining a first subsequence corresponding to at least one end of the cell-free DNA molecules having sizes greater than the cutoff value. The first amount may be of cell-free DNA molecules having a size greater than the cutoff value and having the first subsequence at one or more ends of the respective cell-free DNA molecule. The first subsequence may be or include 1, 2, 3, 4, 5, or 6 nucleotides. End motifs may be used to determine gestational age through PCA analysis, as described with FIGS. 52A and 52B. Calibration samples may be used with different end motifs and known gestational ages and subjected to PCA analysis. Other classification and regression algorithms may be used on the end motifs, such as linear discriminant analysis, logistic regression, support vector machine, linear regression, non-linear regression, etc. The classification and regression algorithms may relate a gestational age with certain end motifs and/or certain size fragments.

The end motifs may be any motif discussed with FIG. 47-59 or 94. A rank or frequency of an end motif may be compared to ranks or frequencies of the end motif in calibration samples from subjects of known gestational ages. The rank or frequency of the end motif can then be used to determine a gestational age. An end motif present in a rank or frequency deviating from a rank or frequency determined from reference samples of the same gestational age may indicate a pregnancy-associated disorder.

Generating the value of the normalized parameter may include (a) normalizing the first amount by a total amount of cell-free DNA molecules having a size greater than the cutoff value; (b) normalizing the first amount by a second amount of cell-free DNA molecules having a size greater than the cutoff value and ending on a second subsequence, the second subsequence being different than the first subsequence, or (c) normalizing the first amount by a third amount of cell-free DNA molecules having a size less than the cutoff value.

2. Pregnancy-Associated Disorder

Figure 61:
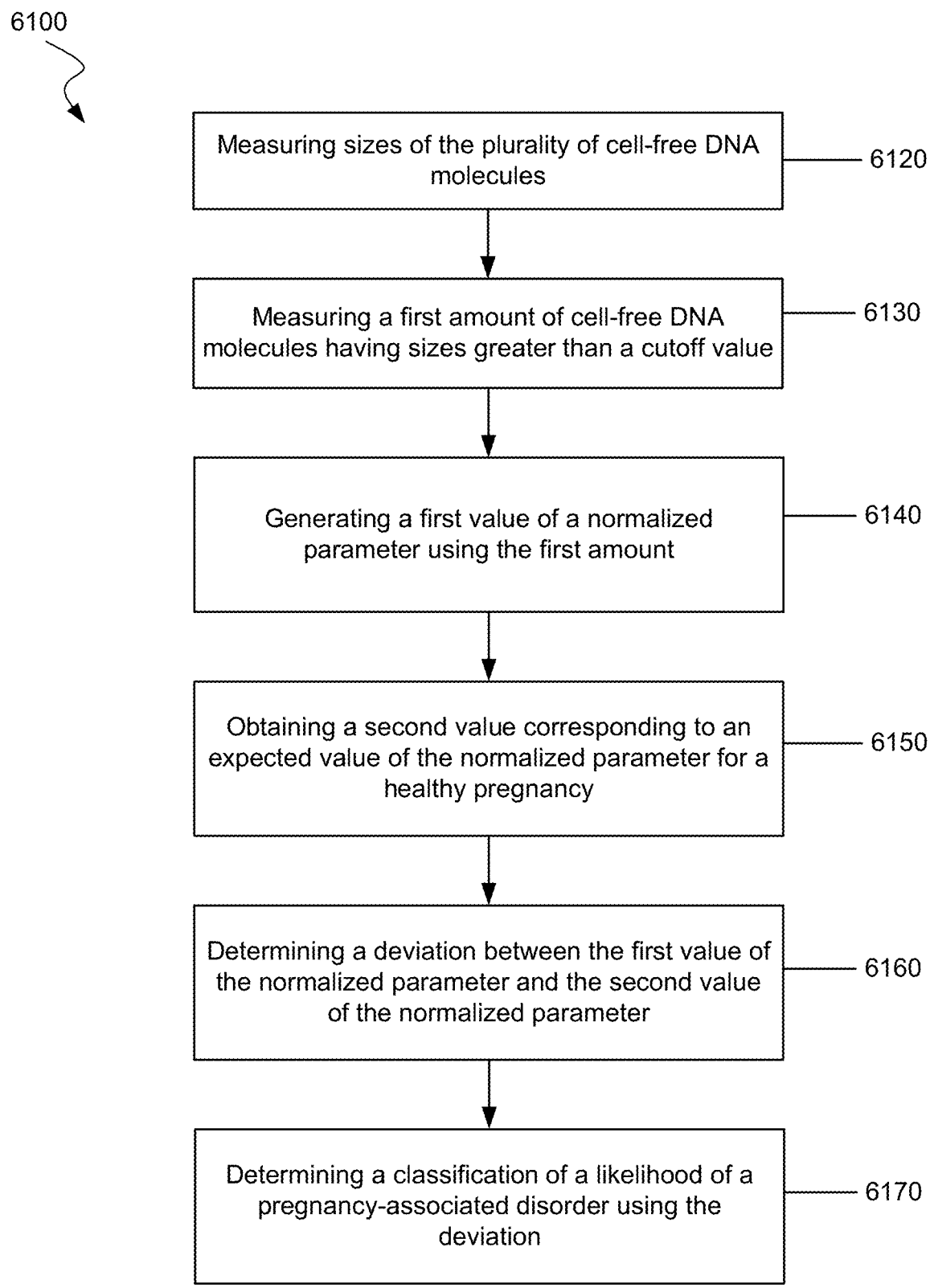
FIG. 61 shows a method of analyzing a biological sample obtained from a female pregnant with a fetus in order to classify a likelihood of a pregnancy-associated disorder according to embodiments of the present invention.

FIG. 61 shows a method 6100 of analyzing a biological sample obtained from a female pregnant with a fetus. Embodiments may include classifying a likelihood of a pregnancy-associated disorder without necessarily determining a gestational age. The biological sample may include a plurality of cell-free DNA molecules from the fetus and the female.

Sequence reads corresponding to the plurality of cell-free DNA molecules may be received. In some embodiments, sequencing to obtain the sequence reads may be performed.

At block 6120, sizes of the plurality of cell-free DNA molecules may be measured. Sizes can be obtained in a similar manner as described with FIG. 21. Measuring sizes may use the sequence reads received.

At block 6130, a first amount of cell-free DNA molecules having sizes greater than a cutoff value may be measured. The cutoff value may be greater than or equal to 200 nt. The cutoff value may be at least 500 nt, including 600 nt, 700 nt, 800 nt, 900 nt, 1 knt, 1.1 knt, 1.2 knt, 1.3 knt, 1.4 knt, 1.5 knt, 1.6 knt, 1.7 knt, 1.8 knt, 1.9 knt, or 2 knt. The cutoff value may be any cutoff value described herein for long cell-free DNA molecules. The first amount may be a number or a frequency.

At block 6140, a first value of a normalized parameter using the first amount may be generated. Generating the value of the normalized parameter may include measuring a second amount of cell-free DNA molecules including sizes less than the cutoff value; and calculating a ratio of the first amount and the second amount. The cutoff value may be a first cutoff value. A second cutoff value may be less than the first cutoff value. The second amount may include cell-free DNA molecules having sizes less than the second cutoff value or the second amount may include all cell-free DNA molecules in the plurality of cell-free DNA molecules. The normalized parameter may be a measure of the frequency of long cell-free DNA molecules.

At block 6150, a second value corresponding to an expected value of the normalized parameter for a healthy pregnancy may be obtained. The second value may be dependent on a gestational age of the fetus. The second value may be the expected value. In some embodiments, the second value may be a cutoff value distinguishing from an abnormal value.

Obtaining the second value may include obtaining the second value from a calibration table relating measurements of pregnant females with calibration values of the normalized parameter. The calibration table may be generated by obtaining a first table relating gestational ages with the measurements of pregnant female subjects. A second table relating gestational ages with calibration values of the normalized parameter may be obtained. The data in the first and second table may be from the same subjects or different subjects. The calibration table relating the measurements with the calibration values may be created from the first table and the second table. A calibration table may include a function that relates calibration values to measurements.

The measurements of the pregnant female subjects may be the time since the last menstrual period or characteristics of an image of the pregnant female subjects (e.g., an ultrasound). Measurements of the pregnant female subjects may be characteristics of images of the pregnant female subjects. For example, the characteristics of the image may include length, size, appearance, or anatomy of a fetus of the female subject. Characteristics may include biometric measurements, e.g., crown-rump length or femur length. The appearance of certain organs may be used, including the appearance of four-chamber heart or vertebrae on the spinal cord. Gestational age may be determined from an ultrasound image by a medical practitioner (e.g., Committee on Obstetric Practice et al., "Methods for estimating the due date," Committee Opinion, No. 700, May 2017).

In some embodiments, a machine learning model may associate one or more calibration data points with characteristics of images. The model may be trained by receiving a plurality of training images. Each training image may be from a female subject known to be without a pregnancy-associated disorder or known to not have a pregnancy-associated disorder. The female subjects may have a range of gestational ages. The training may include storing a plurality of training samples from the female subjects. Each training sample may include a known value of the normalized parameter associated with the training image. The model may be trained by optimizing, using the plurality of training samples, parameters of the model based on outputs of the model matching or not matching the image with the known value of the normalized parameter. The output of the model may specify a value of the normalized parameter corresponding to an image. The second value of the normalized parameter may be generated by inputting an image of the female into the machine learning model.

At block 6160, a deviation between the first value of the normalized parameter and the second value of the normalized parameter may be determined. The deviation may be a separation value.

At block 6170, a classification of a likelihood of a pregnancy-associated disorder may be determined using the deviation. The pregnancy-associated disorder may be likely when the deviation exceeds a threshold. The threshold may indicate a statistically significant difference. The threshold may indicate a difference of 10%, 20%, 30%, 40%, 50%, 60%, 70%, 80%, 90%, or 100%.

The pregnancy-associated disorder may include comprises preeclampsia, intrauterine growth restriction, invasive placentation, pre-term birth, hemolytic disease of the newborn, placental insufficiency, hydrops fetalis, fetal malformation, hemolysis, elevated liver enzymes, and a low platelet count (HELLP) syndrome, or systemic lupus erythematosus.

IV. Size and End Analysis for Pregnancy-Associated Disorders

The size and/or end analysis of long DNA molecules were used to determine a likelihood of preeclampsia. Such methods could also be applied to other pregnancy-associated disorders. DNA extracted from maternal plasma samples of four pregnant women diagnosed with preeclampsia was subjected to single molecule real-time (SMRT) sequencing (PacBio).

FIG. 62 is a table showing clinical information of four preeclamptic cases. The first column shows the case number. The second column shows the gestational age in weeks at the time off blood sampling. The third column shows the fetal sex. The fourth column shows clinical information regarding preeclampsia (PET).

M12804 was a case of severe preeclampsia (PET) and pre-existing IgA nephropathy. M12873 was a case of chronic hypertension with superimposed mild PET. M12876 was a case of severe late-onset PET. M12903 was a case of severe late-onset PET with intrauterine growth restriction (IUGR). Five normotensive third-trimester maternal plasma samples were used as control for subsequent analyses in this disclosure.

For the four preeclamptic and five normotensive third-trimester maternal plasma DNA samples analyzed for this disclosure, DNA extracted from their paired maternal buffy coat and placenta samples was genotyped with the Infinium Omni2.5Exome-8 Beadchip on the iScan System (Illumina).

The plasma DNA concentration of each sample was quantified by the Qubit dsDNA high sensitivity assay with a Qubit Fluorometer (ThermoFisher Scientific). The mean plasma DNA concentrations for the pre-eclamptic and the third-trimester cases were 95.4 ng/mL (range, 52.1-153.8 ng/mL) of plasma and 10.7 ng/mL (6.4-19.1 ng/mL) of plasma, respectively. The mean plasma DNA concentration of the preeclamptic cases was around 9-fold higher than that of the third-trimester cases.

The mean fetal DNA fractions, which was determined from the sequencing data of DNA molecules ≤600 bp that covered the informative single nucleotide polymorphisms (SNPs) for which the mother was homozygous and the fetus was heterozygous, were 22.6% (range, 16.6-25.7%) and 20.0% (range, 15.6-26.7%) for the preeclamptic and normotensive third-trimester maternal plasma samples, respectively.

A. Size Analysis

Figure 63A:
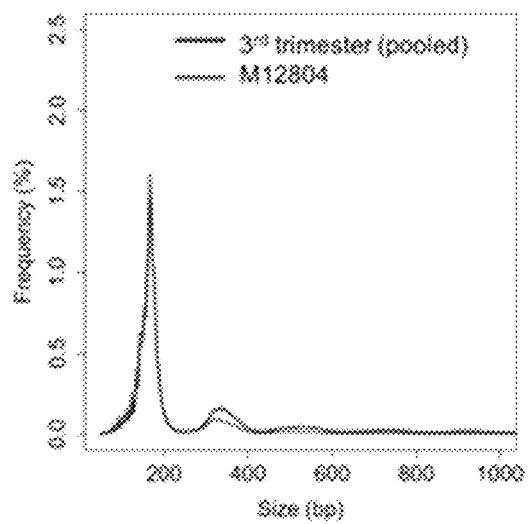
FIGS. 63A-63D are graphs of the size distribution of cell-free DNA molecules from preeclamptic and normotensive third-trimester maternal plasma samples according to embodiments of the present invention.
Figure 63B:
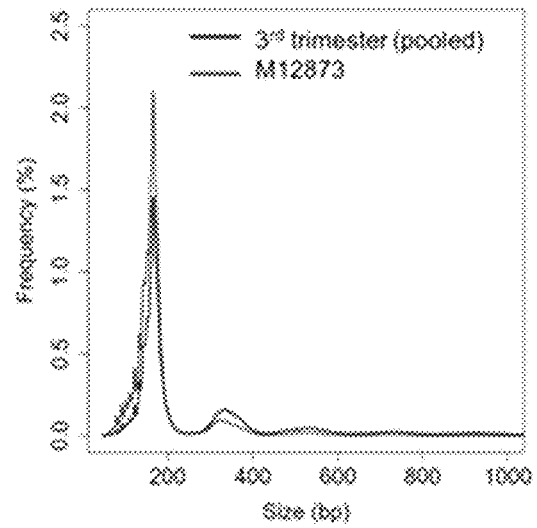
Figure 63C:
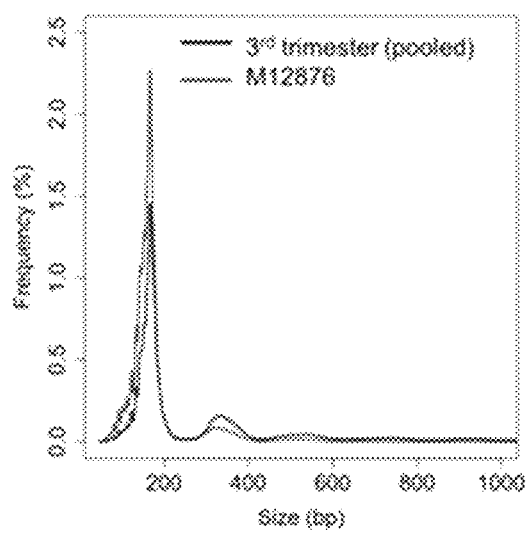
Figure 63D:
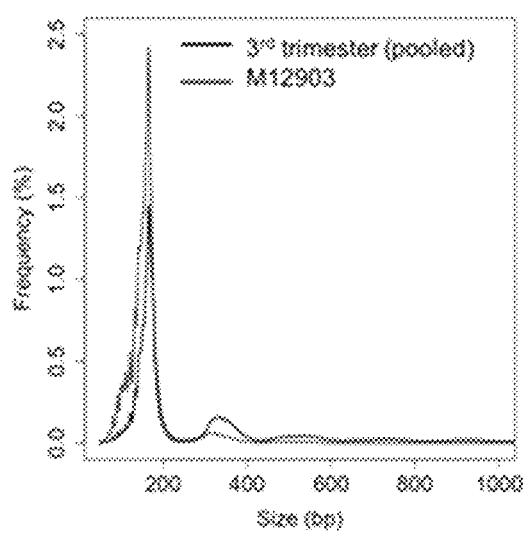
Figure 64A:
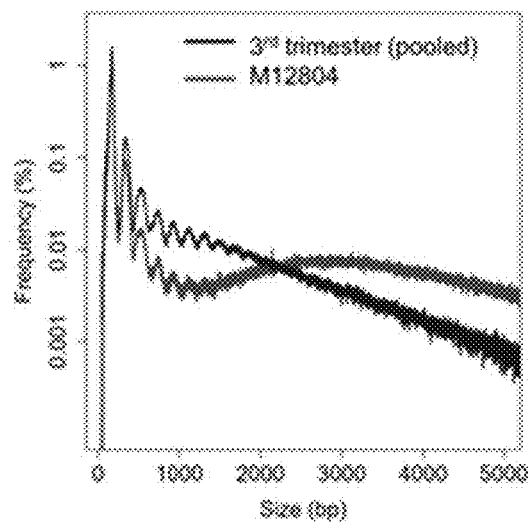
FIGS. 64A-64D are graphs of the size distribution of cell-free DNA molecules from preeclamptic and normotensive third-trimester maternal plasma samples according to embodiments of the present invention.
Figure 64B:
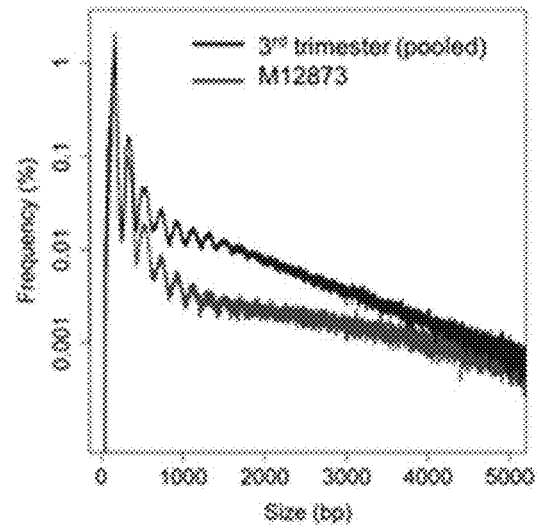
Figure 64C:
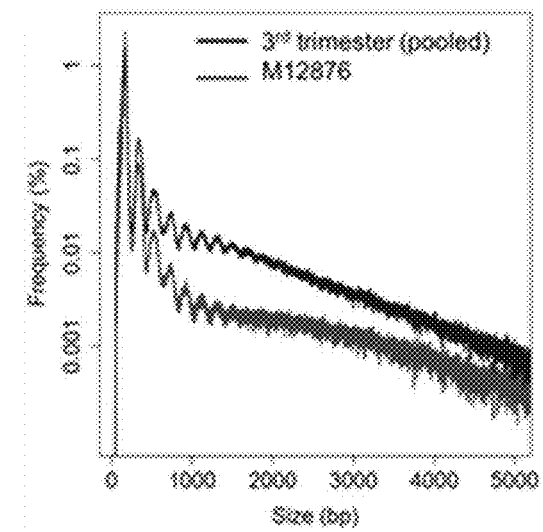
Figure 64D:
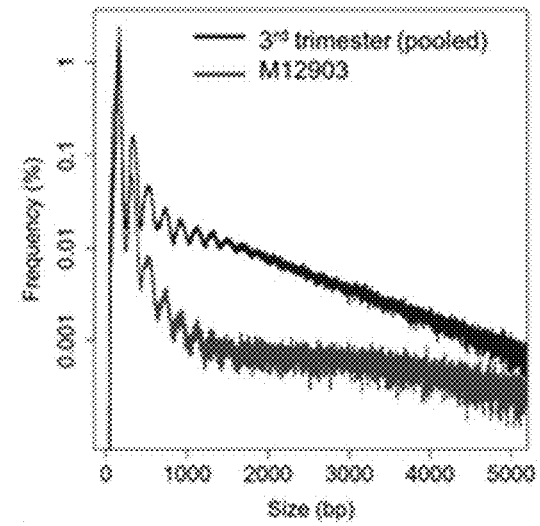

Size analyses were performed on the preeclamptic and normotensive third-trimester maternal plasma samples according to the embodiments in this disclosure. FIGS. 63A-63D and FIGS. 64A-64D show the size distributions of plasma DNA molecules from the preeclamptic and normotensive third-trimester cases. The x-axis shows the size. The y-axis shows the frequency. The size distribution is plotted in the range for FIGS. 63A-63D are from 0 to 1 kb on a linear scale for the x-axis, and for FIGS. 64A-64D, from 0 to 5 kb on a logarithmic scale for the x-axis. FIGS. 63A and 64A show sample M12804. FIGS. 63B and 64B show sample M12873. FIGS. 63C and 64C show sample M12876. FIGS. 63D and 64D show sample M12903.

The blue line represents the size distribution of all sequenced plasma DNA molecules pooled from five normotensive third-trimester cases. The red line represents the size distribution of sequenced plasma DNA molecules from individual preeclamptic case. In FIGS. 63A-63D, the blue line is the line of the shorter peak under 200 bp and the line of the higher peak between 300 and 400 bp. In FIGS. 64A-64D, the blue line corresponds to the line that is higher at 1 kb.

In general, the plasma DNA size profiles of preeclamptic patients were shorter than that of normotensive third-trimester pregnant women with an increased height of the 166-bp peak and an increased proportion of DNA molecules shorter than 166 bp (FIGS. 63A-63D). These changes were more pronounced in the two severe preeclamptic cases M12876 and M12903. The changes were even more dramatic in the preeclamptic case M12903 with intrauterine growth restriction (IUGR).

Three of the four preeclamptic plasma samples showed reduced proportions of long plasma DNA molecules with sizes of 200-5000 bp (FIGS. 64B-64D). The proportions of long plasma DNA molecules of >500 bp in M12873, M12876 and M12903 were 11.7%, 8.9% and 4.5%, respectively, whereas the proportion of long plasma DNA molecules in the pooled sequencing data from five normotensive third-trimester cases were 32.3%. The plasma sample from the case of severe preeclampsia (PET) with pre-existing IgA nephropathy (M12804) showed a decreased proportion of shorter DNA molecules of less than 2000 bp but an increased proportion of longer DNA molecules of greater than 2000 bp compared with the pooled sequencing data from five normotensive third-trimester cases (FIG. 2A). The proportion of long plasma DNA molecules in M12804 was 34.9%.

FIGS. 65A-65D and FIGS. 66A-66D show the size distribution of DNA molecules covering fetal-specific alleles from preeclamptic and normotensive third-trimester maternal plasma samples. Each of the A through D figures shows a different preeclamptic sample. The x-axis shows the size. The y-axis shows the frequency in FIGS. 65A-65D and the cumulative frequency in FIGS. 66A-66D. In FIGS. 66A-66D, the size goes from 0 to 35 kb.

The blue line in each graph represents the size distribution of all sequenced plasma DNA molecules covering fetal-specific alleles pooled from five normotensive third-trimester cases. The red line in each graph represents the size distribution of sequenced plasma DNA molecules covering fetal-specific alleles from individual preeclamptic case. In FIGS. 65A-65D, the blue line is the line of the shorter peak under 200 bp and the line of the higher peak between 300 and 400 bp. In FIGS. 66A-66D, the blue line corresponds to the line that is lower between 100 and 1000 bp.

FIGS. 67A-67D and FIGS. 68A-68D show the size distribution of DNA molecules covering fetal-specific alleles from preeclamptic and normotensive third-trimester maternal plasma samples. Each of the A through D figures shows a different preeclamptic sample. The x-axis shows the size. The y-axis shows the frequency in FIGS. 67A-67D and the cumulative frequency in FIGS. 68A-68D. In FIGS. 68A-68D, the size goes from 0 to 35 kb.

Figure 67A:
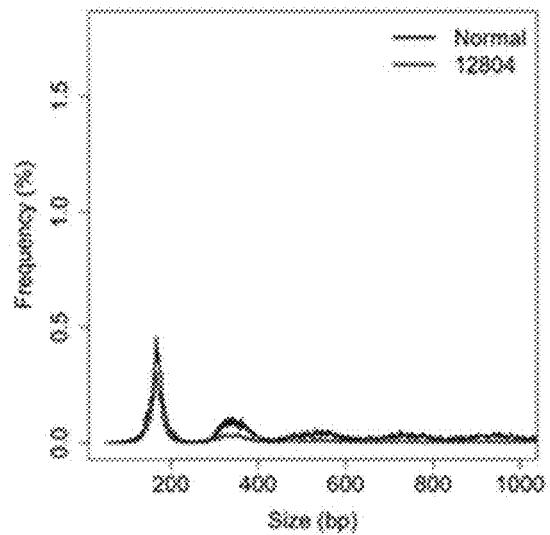
FIGS. 67A-67D are graphs of the size distributions of DNA molecules covering maternal-specific alleles from preeclamptic and normotensive third-trimester maternal plasma samples according to embodiments of the present invention.
Figure 67B:
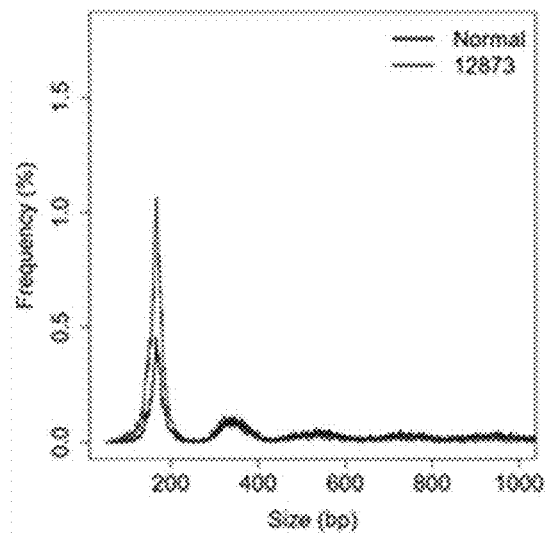
Figure 67C:
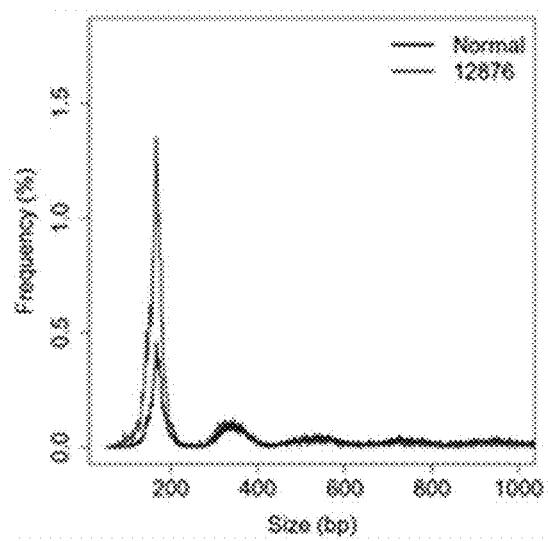
Figure 67D:
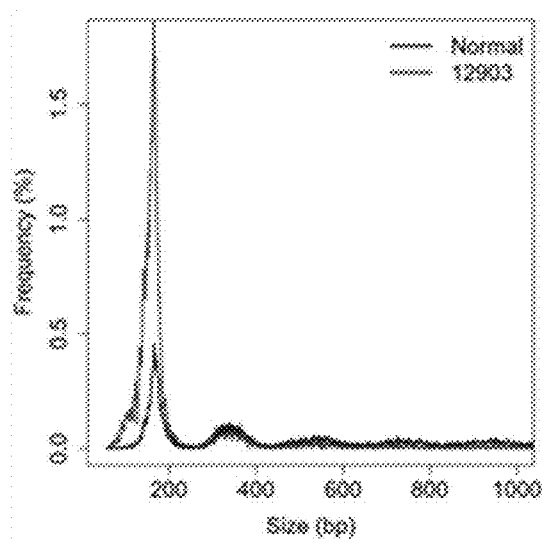
Figure 68A:
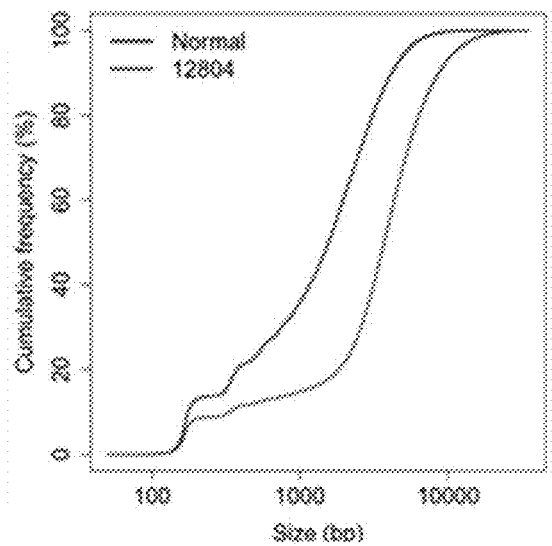
FIGS. 68A-68D are graphs of the size distributions of DNA molecules covering maternal-specific alleles from preeclamptic and normotensive third-trimester maternal plasma samples according to embodiments of the present invention.
Figure 68B:
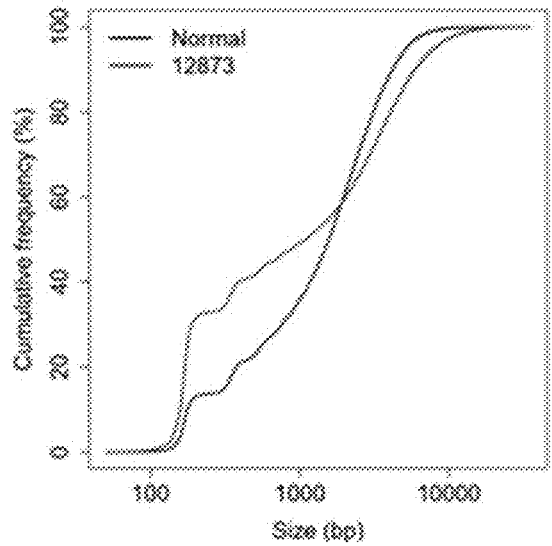
Figure 68C:
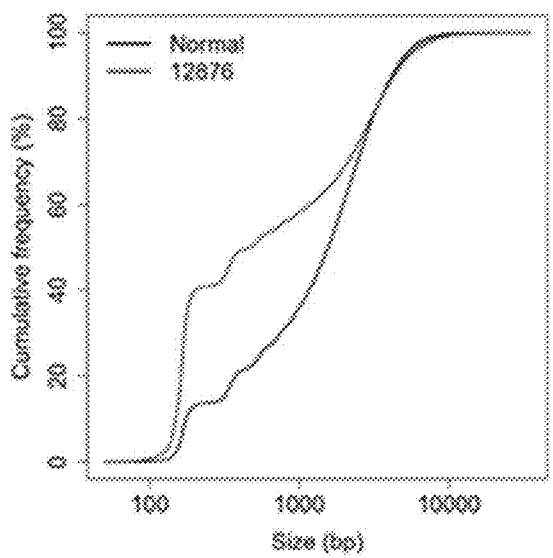
Figure 68D:
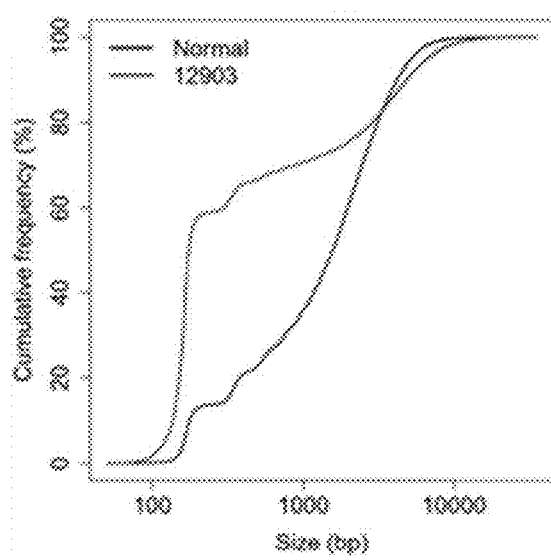

The blue line in each graph represents the size distribution of all sequenced plasma DNA molecules covering maternal-specific alleles pooled from five normotensive third-trimester cases. The red line in each graph represents the size distribution of sequenced plasma DNA molecules covering maternal-specific alleles from individual preeclamptic case. In FIG. 67A, the blue line is the line of the taller peak under 200 bp and the taller peak between 300 and 400 bp. In FIGS. 67B-67D, the blue line is the line of the shorter peak under 200 bp. In FIG. 68A, the blue line corresponds to the line that is higher between 1000 and 10000 bp. In FIGS. 68B-68D, the blue line corresponds to the line that is lower between 100 and 1000 bp.

Figure 65A:
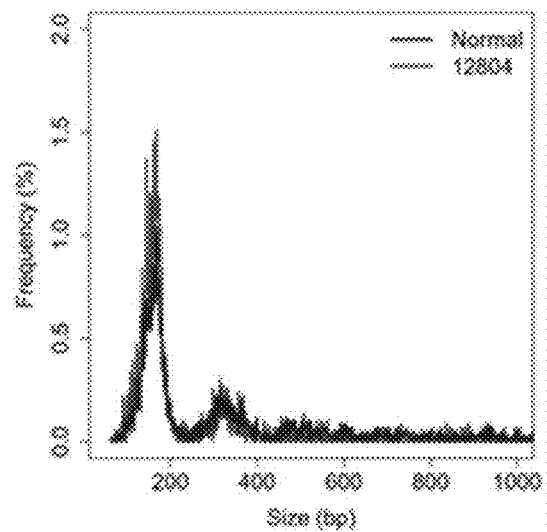
FIGS. 65A-65D are graphs of the size distributions of DNA molecules covering fetal-specific alleles from preeclamptic and normotensive third-trimester maternal plasma samples according to embodiments of the present invention.
Figure 65B:
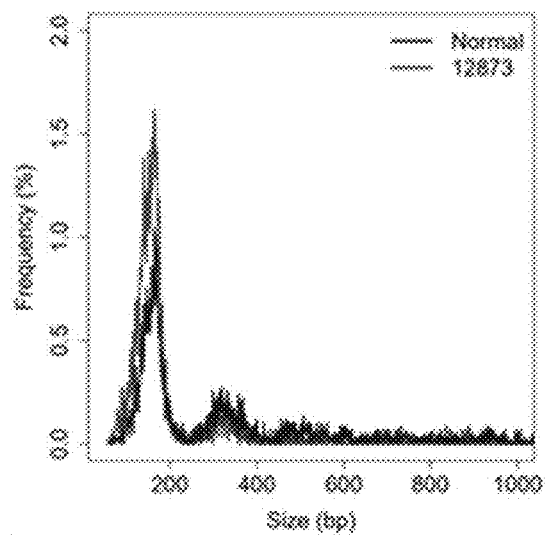
Figure 65C:
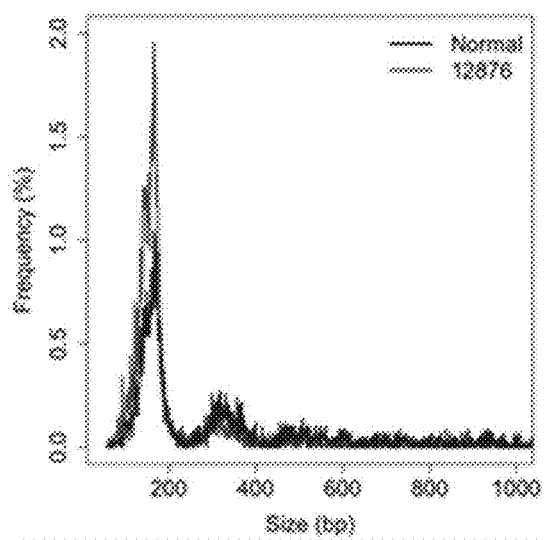
Figure 65D:
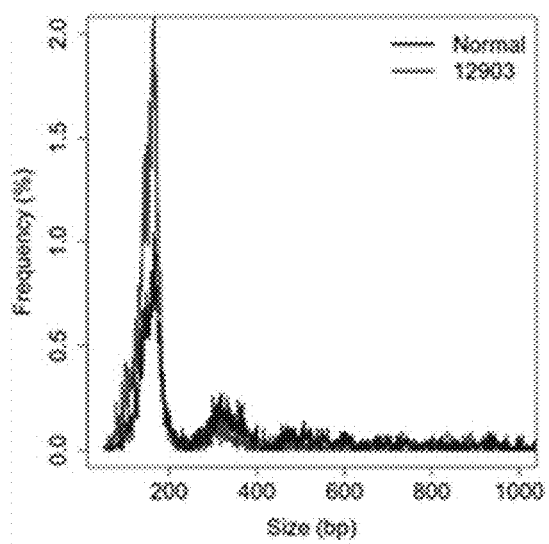
Figure 66A:
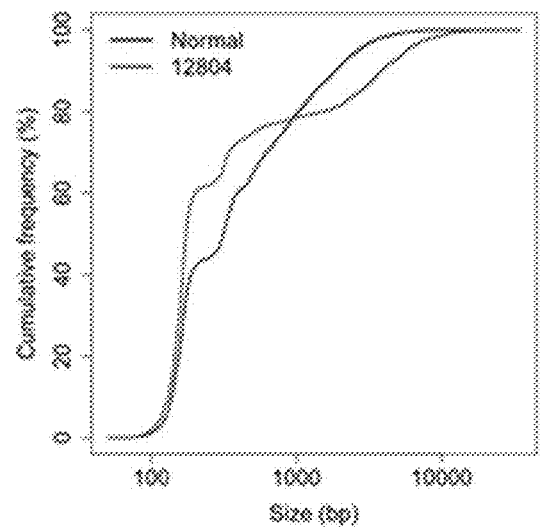
FIGS. 66A-66D are graphs of the size distributions of DNA molecules covering fetal-specific alleles from preeclamptic and normotensive third-trimester maternal plasma samples according to embodiments of the present invention.
Figure 66B:
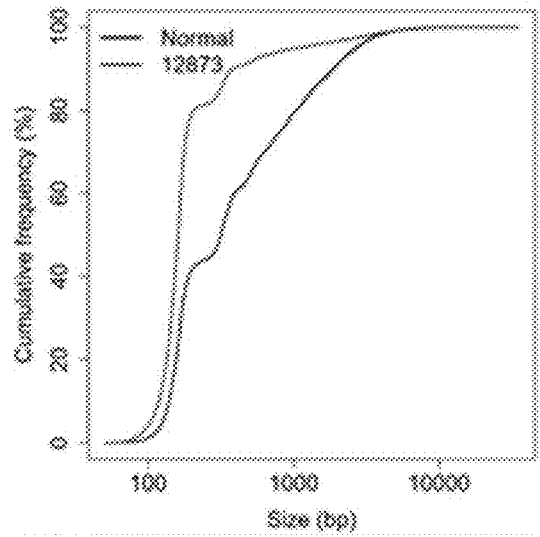
Figure 66C:
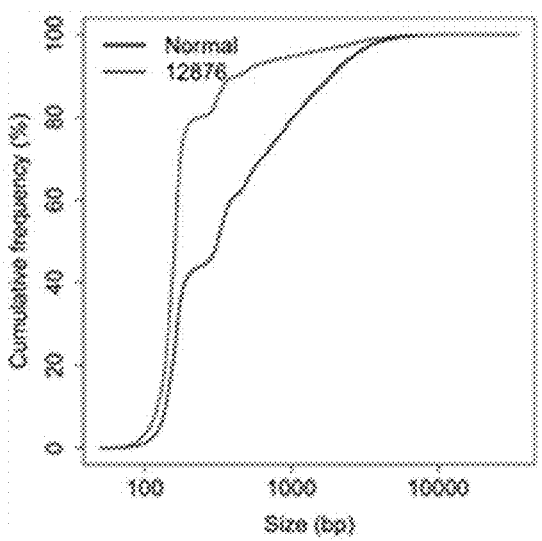
Figure 66D:
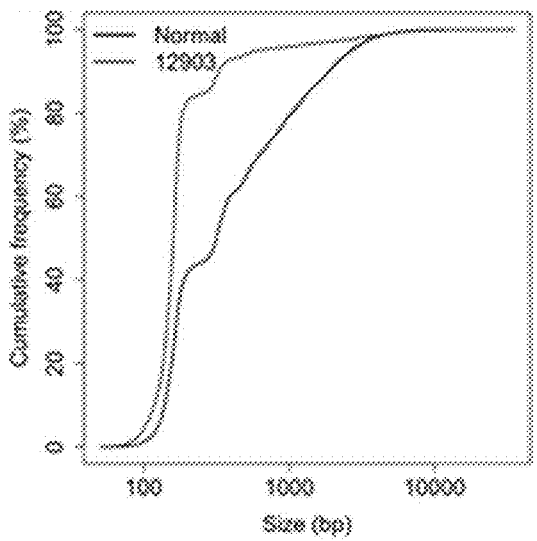

The phenomenon of plasma DNA shortening was observed in both the DNA molecules covering fetal-specific alleles (FIGS. 65B-65D and FIGS. 66B-66D) and those covering the maternal-specific alleles (FIGS. 67B-67D and FIGS. 68B-68D) in three of the four preeclamptic plasma samples when compared with normotensive third-trimester maternal plasma samples. The exception was the case M12804 of severe PET with pre-existing IgA nephropathy which showed an increased proportion of shorter DNA molecules of less than 1 kb and a decreased proportion of longer DNA molecules of greater than 1 kb among those plasma DNA molecules covering the fetal-specific alleles (FIGS. 65A and 66A). Indeed, plasma DNA molecules covering the maternal-specific alleles in case M12804 showed a lengthened size profile (FIGS. 67A and 68A).

Figure 69B:
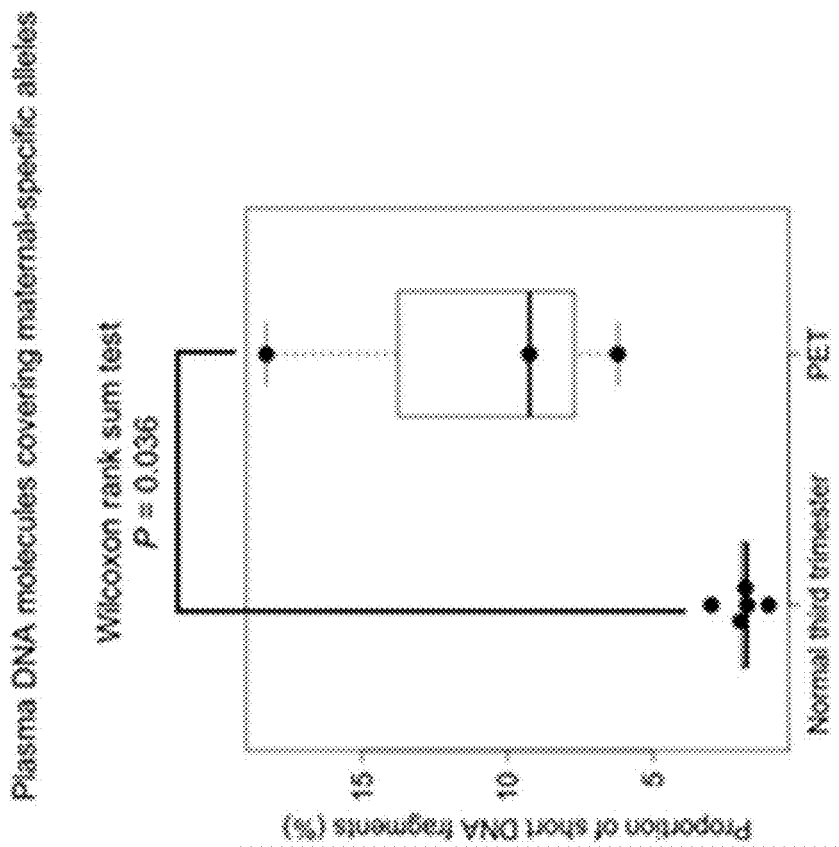
FIGS. 69A and 69B are graphs of the proportion of short DNA molecules covering fetal-specific alleles and maternal-specific alleles in preeclamptic and normotensive maternal plasma samples sequenced with PacBio SMRT sequencing according to embodiments of the present invention.
Figure 69A:
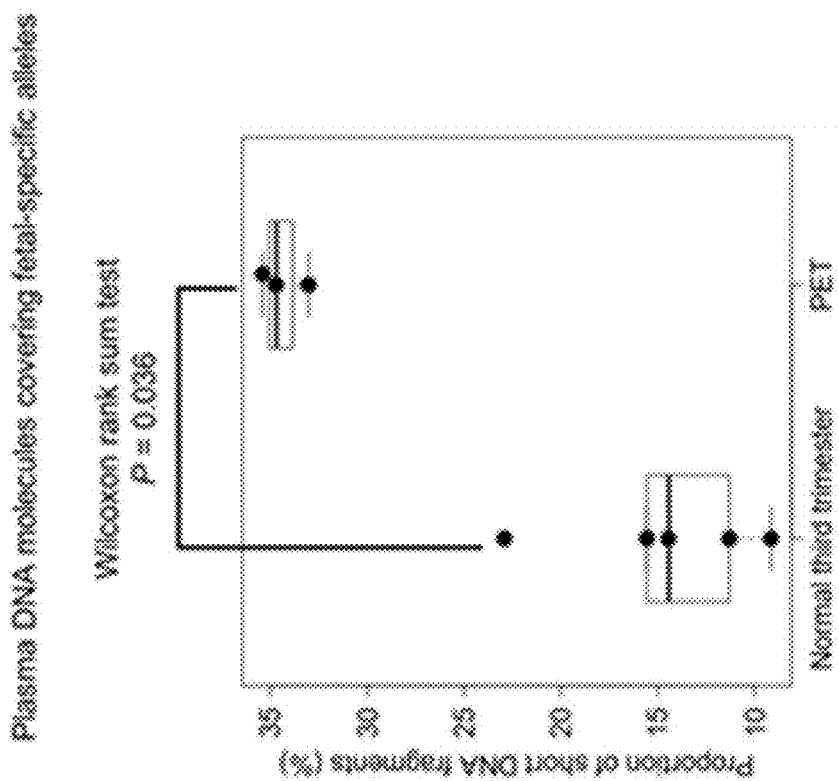

FIGS. 69A and 69B are graphs of the proportion of short DNA molecules covering (A) fetal-specific alleles and (B) maternal-specific alleles, in preeclamptic and normotensive maternal plasma samples sequenced with PacBio SMRT sequencing. The y-axis shows proportion of short DNA fragments of <150 bp. The x-axis shows the normal and PET samples.

In embodiments, the proportion of short DNA molecules was defined as the percentage of maternal plasma DNA molecules with a size of below 150 bp. M12804 was excluded from this analysis as this case had pre-existing IgA nephropathy but other samples did not. The group of preeclamptic plasma samples showed significantly increased proportions of short DNA molecules covering fetal-specific alleles (P=0.036, Wilcoxon rank sum test), and maternal-specific alleles (P=0.036, Wilcoxon rank sum test), when compared to the group of normotensive control plasma samples.

Figure 70B:
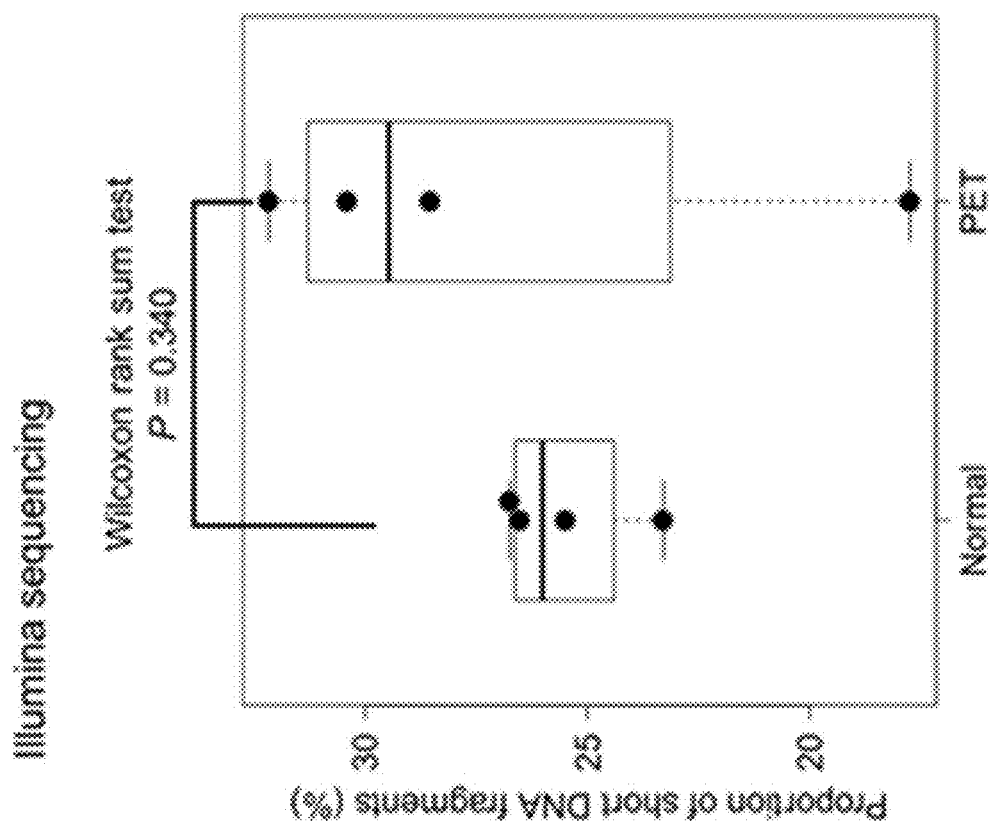
FIGS. 70A and 70B are graphs of the proportion of short DNA molecules in preeclamptic and normotensive maternal plasma samples sequenced with PacBio SMRT sequencing and Illumina sequencing according to embodiments of the present invention.
Figure 70A:
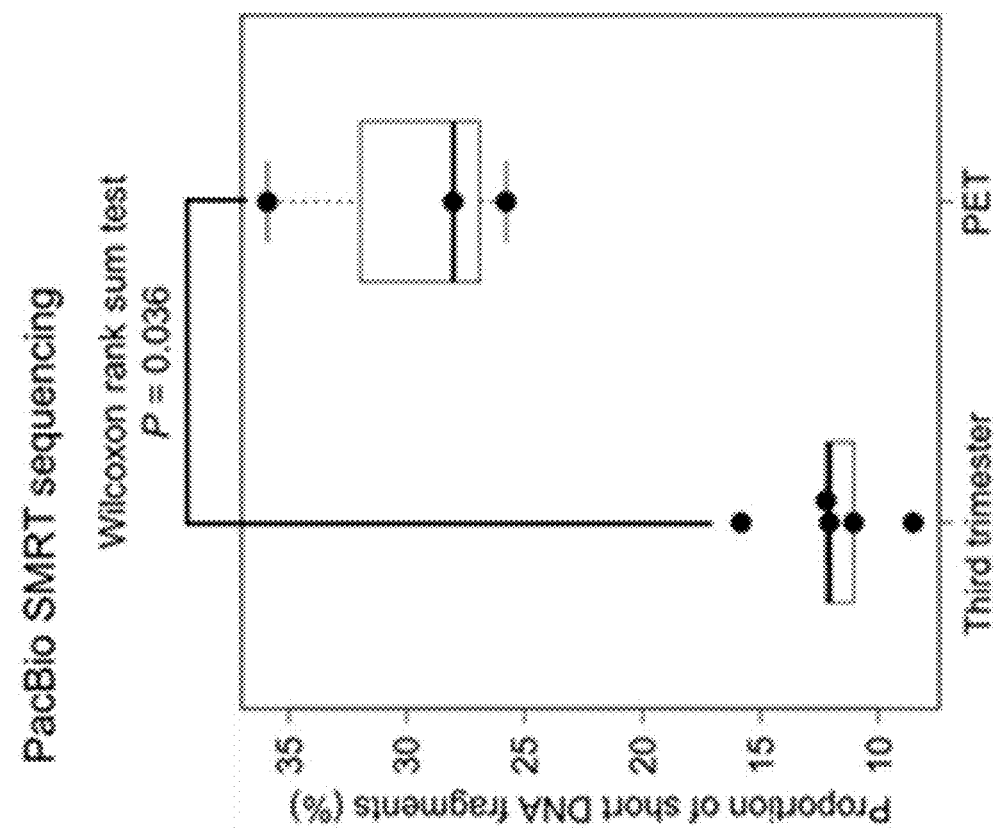

FIGS. 70A and 70B are graphs of the proportion of short DNA molecules in preeclamptic and normotensive maternal plasma samples sequenced with (A) PacBio SMRT sequencing and (B) Illumina sequencing. The y-axis shows proportion of short DNA fragments of <150 bp.

In embodiments, the proportion of short DNA molecules was defined as the percentage of maternal plasma DNA molecules with a size of below 150 bp. M12804 was removed from this analysis as this case showed a different size profile compared with other preeclamptic cases in this cohort, likely due to pre-existing IgA nephropathy in this case. The group of preeclamptic plasma samples showed significantly increased proportions of short DNA molecules (median: 28.0%; range: 25.8-35.1%) when compared to the group of normotensive control plasma samples (median: 12.1%; range: 8.5-15.8%) (P=0.036, Wilcoxon rank sum test). On the contrary, in a previous cohort of four preeclamptic and four gestational age-matched normotensive maternal plasma DNA samples which were subjected to bisulfite conversion and Illumina sequencing, the proportions of short DNA molecules in preeclamptic plasma and control plasma samples were not significantly different (P=0.340, Wilcoxon rank sum test) (FIG. 70B).

In some embodiments, one could use a cutoff of 20% for the proportion of short DNA molecules in a maternal plasma sample sequenced with PacBio SMRT sequencing to determine if a pregnancy was at a high risk or a low risk of developing preeclampsia. A maternal plasma sample with a proportion of short DNA molecules of above 20% would be determined to be at a high risk of developing preeclampsia whereas a maternal plasma sample with a proportion of short DNA molecules of below 20% would be determined to be at low risk of developing preeclampsia. With the use of this cutoff, both the sensitivity and the specificity were 100%. In some other embodiments, the cutoff for the proportion of short DNA molecules used could include but not limited to 5%, 10%, 15%, 20%, 25%, 30%, 35%, 40%, 45%, 50%, 55%, 60%, etc. In another embodiment, the proportion of short DNA molecules in a maternal plasma sample would be used for monitoring and assessing the severity of preeclampsia during pregnancy.

In embodiments, a size ratio indicating the relative proportions of short and long DNA molecules was calculated for each sample using the following equation.

$$\text{Size ratio} = \frac{P(50-150)}{P(200-1000)}$$

where P(50-150) denotes the proportion of sequenced plasma DNA molecules with sizes ranging from 50 bp to 150 bp; and P(200-1000) denotes the proportion of sequenced plasma DNA molecules with sizes ranging from 200 bp to 1000 bp.

Figure 71:
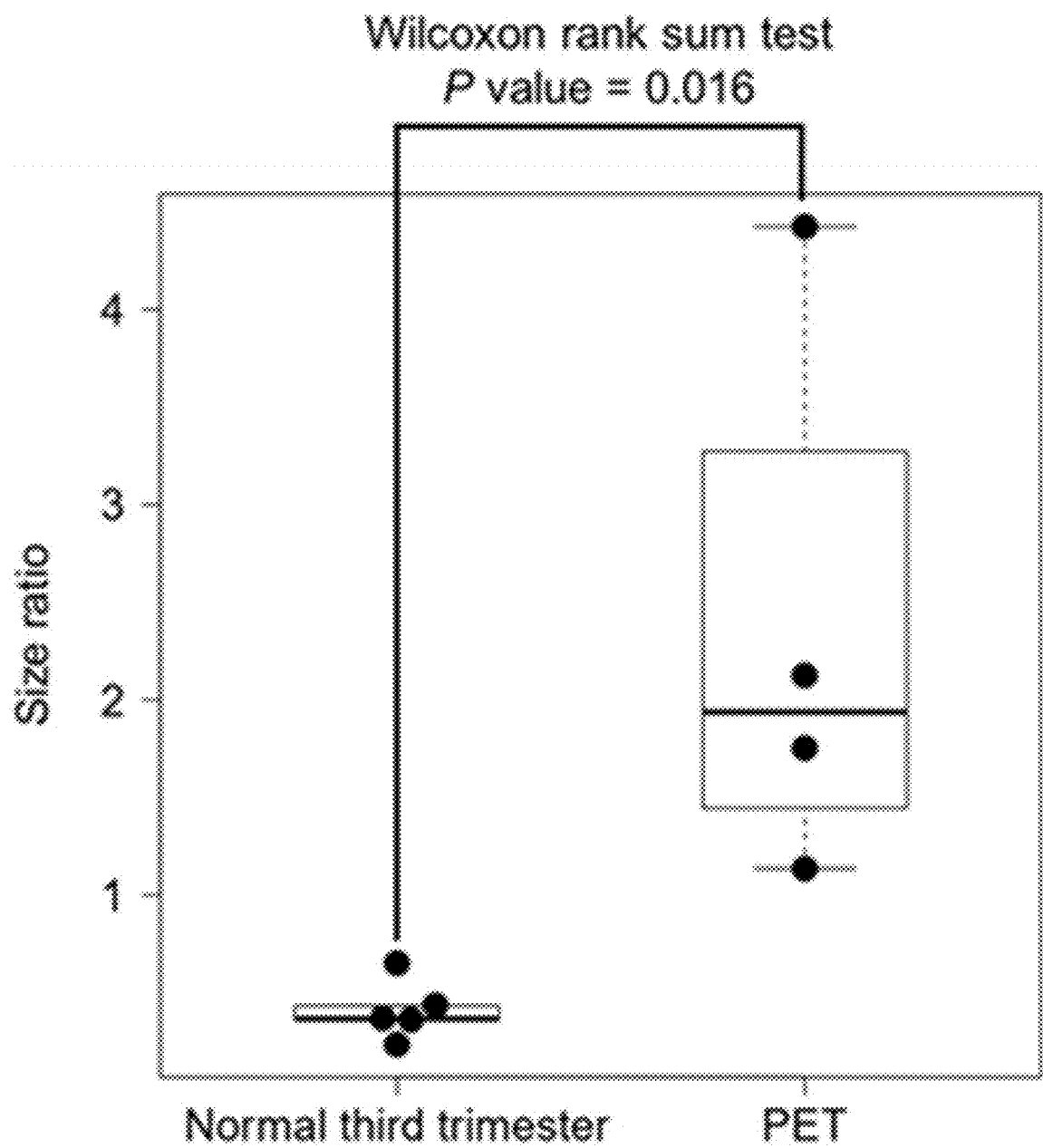
FIG. 71 is graph of the size ratios which indicate the relative proportions of short and long DNA molecules, in preeclamptic and normotensive maternal plasma samples sequenced with PacBio SMRT sequencing according to embodiments of the present invention.

FIG. 71 is graph of the size ratios which indicate the relative proportions of short and long DNA molecules, in preeclamptic and normotensive maternal plasma samples sequenced with PacBio SMRT sequencing. The y-axis shows the size ratio. The x-axis shows normal and PET samples. The group of preeclamptic plasma samples showed a significantly higher size ratio when compared to the group of normotensive control plasma samples (P=0.016, Wilcoxon rank sum test).

In embodiments, one may utilize size profiles generated from long-read sequencing platforms including but not limited to the PacBio SMRT sequencing and the Oxford Nanopore sequencing to predict the development and severity of preeclampsia in pregnancies. In some embodiments, one may monitor the progress of preeclampsia and the development of severe preeclamptic features including but not limited to hepatic and renal impairments by analyzing the size profiles of plasma DNA molecules. In some embodiments, the size parameters used in the analysis could include, but not limited to, the proportion of short or long DNA molecules, and the size ratio which indicated the relative proportions of short and long DNA molecules. The cutoff used for determining the short and long DNA categories could include, but not limited to, 150 bp, 180 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 950 bp, 1 kb, etc. The size ranges used in determining the size ratio of short and long molecules could include, but not limited to, 50-150 bp, 50-166 bp, 50-200 bp, 200-400 bp, 200-1000 bp, 200-5000 bp, or other combinations.

The size end analysis may include using method described with method 6100 in FIG. 61.

B. Fragment End Analysis

Fragment end analyses were performed on the preeclamptic and the normotensive third-trimester maternal plasma samples according to the embodiments in this disclosure. The first nucleotide at the 5' end of both the Watson and Crick strands was determined for each sequenced plasma DNA molecule. The proportions of T-end, C-end, A-end and G-end fragments were determined for each plasma DNA sample.

Figure 72A:
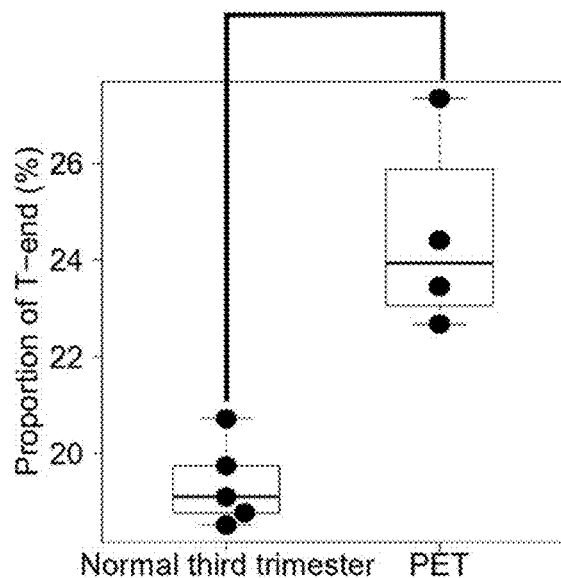
FIGS. 72A-72D show the proportion of different ends of plasma DNA molecules in preeclamptic and normotensive maternal plasma samples sequenced with PacBio SMRT sequencing according to embodiments of the present invention.
Figure 72B:
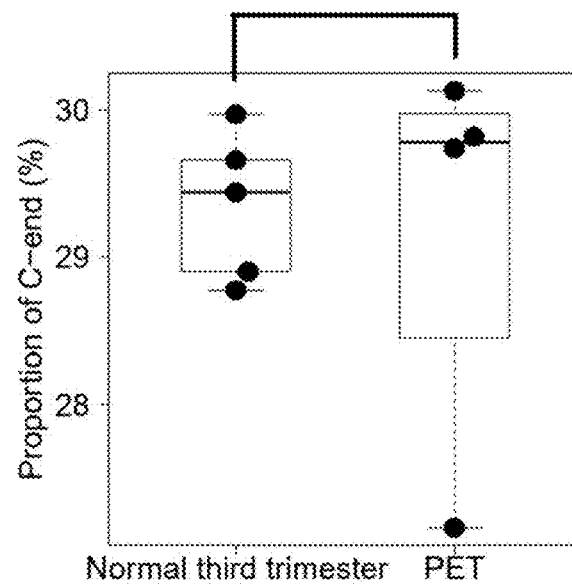
Figure 72C:
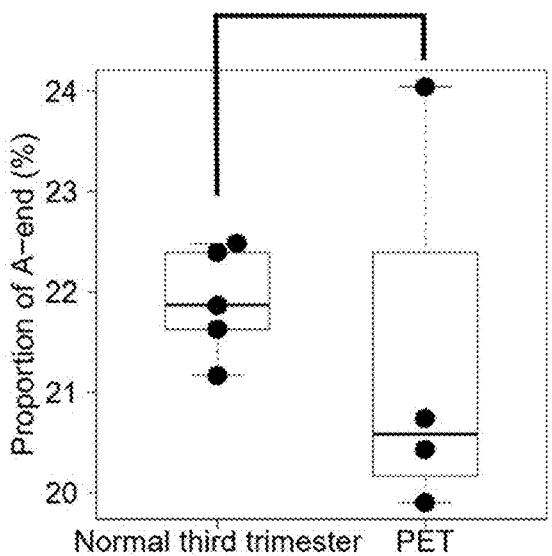
Figure 72D:
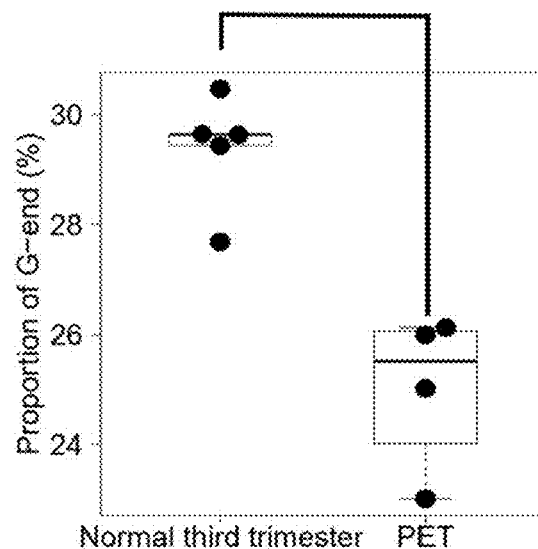

FIGS. 72A-72D show the proportion of different ends of plasma DNA molecules in preeclamptic and normotensive maternal plasma samples sequenced with PacBio SMRT sequencing. The x-axis shows normal third trimester and PET samples. The y-axis shows the proportion of a given end. FIG. 72A shows the proportion of T-end. FIG. 72B shows the proportion of C-end. FIG. 72C shows the proportion of A-end. FIG. 72D shows the proportion of G-end. The group of preeclamptic plasma samples showed significantly increased proportions of T-end plasma DNA molecules (P=0.016, Wilcoxon rank sum test) and significantly reduced proportions of G-end plasma DNA molecules (P=0.016, Wilcoxon rank sum test) when compared to the group of normotensive control plasma samples.

Figure 73:
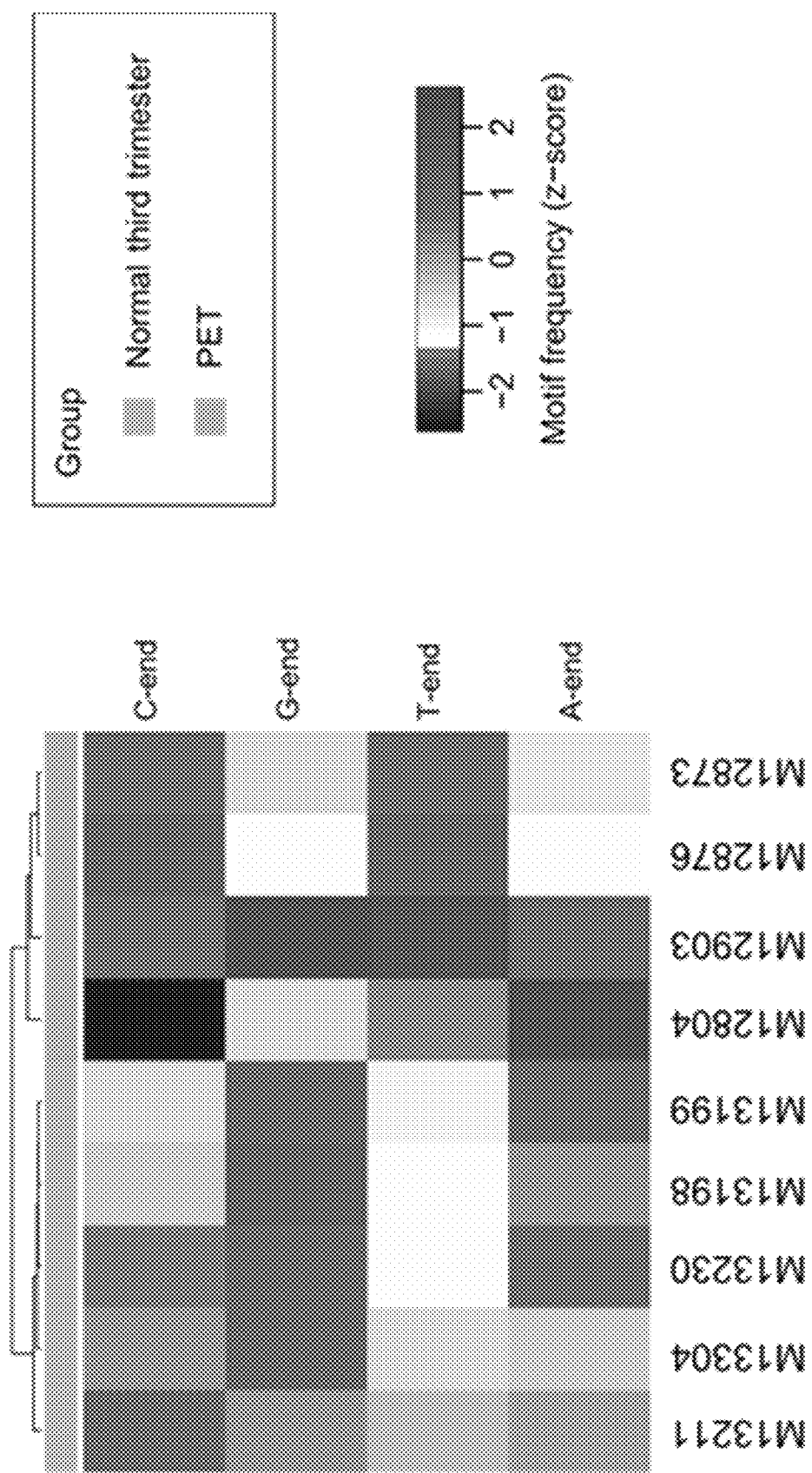
FIG. 73 shows hierarchical clustering analysis of preeclamptic and normotensive third-trimester maternal plasma DNA samples using the frequency of plasma DNA molecules with each of the four types of fragment ends (first nucleotide at the 5' end of each strand), namely C-end, G-end, T-end, and A-end, according to embodiments of the present invention.

FIG. 73 shows the hierarchical clustering analysis of preeclamptic and normotensive third-trimester maternal plasma DNA samples using the four types of fragment ends (first nucleotide at the 5' end of each strand), namely C-end, G-end, T-end and A-end. Each column indicates a plasma DNA sample. The first row indicates which group each sample belonged to, with cyan indicating a normotensive third-trimester maternal plasma DNA sample and orange indicating a preeclamptic plasma DNA sample. Cyan covers the first five columns. Orange covers the last four columns.

Starting from the second row, each row indicates a type of fragment end. The end motif frequencies were presented with a series of color gradients according to the row-normalized frequencies (z-score) (i.e., the number of standard deviations below or above the mean frequency across samples). The redder color indicates a higher frequency of an end motif, while the bluer color indicates a less frequency of an end motif Hierarchical clustering analysis based on frequencies of the 4 types of fragment ends showed that the fragment end profiles of preeclamptic plasma DNA samples formed a cluster which was distinct from that of normotensive third-trimester plasma DNA samples.

In embodiments, one may determine the dinucleotide sequence of the first (X) and second nucleotides (Y) from the 5' end of both the Watson and Crick strands separately for each sequenced DNA molecule. X and Y can be one of the four nucleotide bases in DNA. There are 16 possible two-nucleotide end motifs XYNN, namely AANN, ATNN, AGNN, ACNN, TANN, TTNN, TGNN, TCNN, GANN, GTNN, GGNN, GCNN, CANN, CTNN, CGNN, and CCNN. One can determine the dinucleotide sequence of the third (X) and fourth nucleotides (Y) from the 5' end of both the Watson and Crick strands separately for each sequenced DNA molecules according to the embodiment in this disclosure. There are 16 possible two-nucleotide NNXY motifs. One can also determine the first four-nucleotide sequence (a 4-mer motif) at the 5' end of both the Watson and Crick strands separately for each sequenced DNA molecule.

Figure 74:
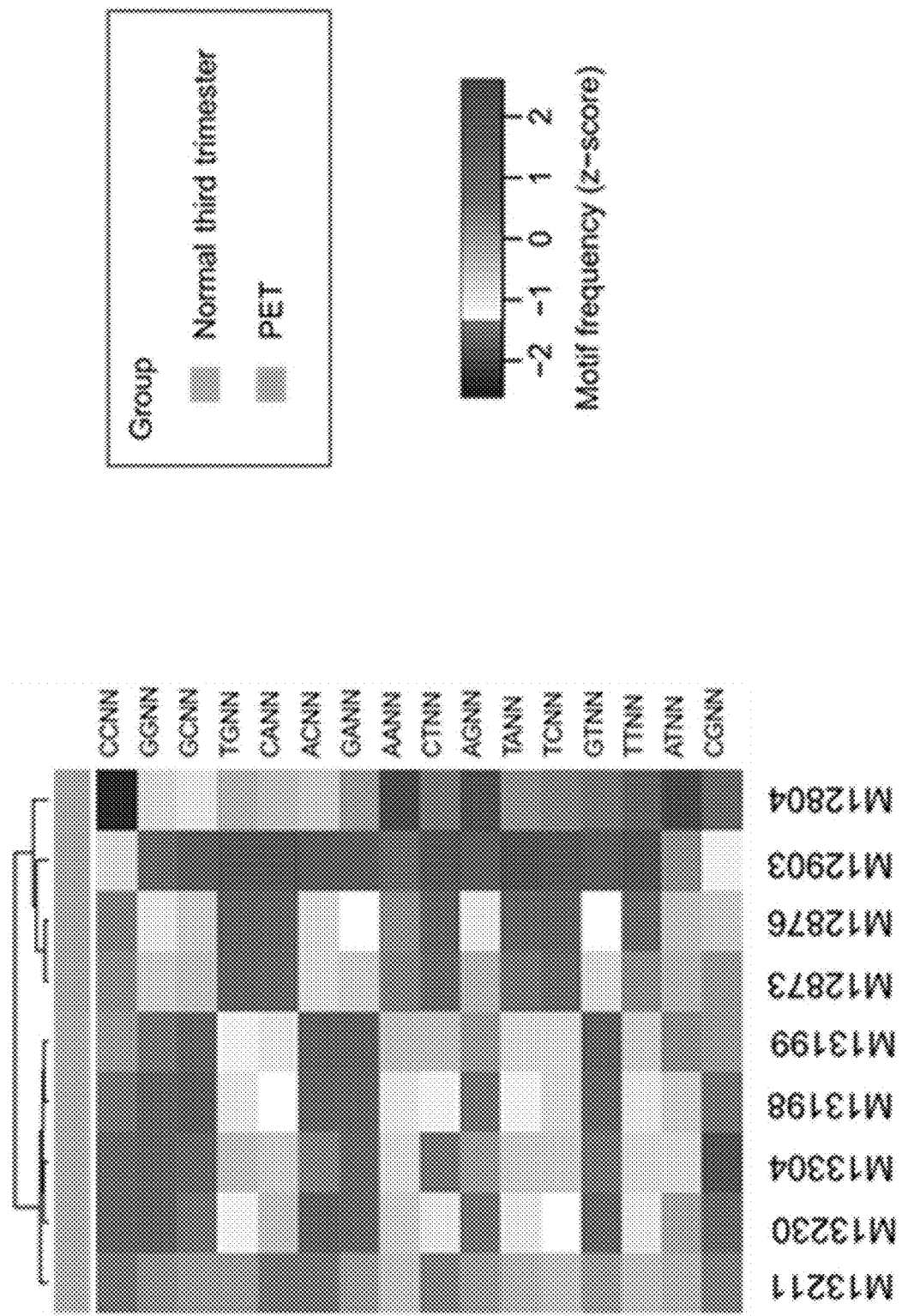
FIG. 74 shows hierarchical clustering analysis of preeclamptic and normotensive third-trimester maternal plasma DNA samples using 16 two-nucleotide motifs XYNN (di-nucleotide sequence of the first and second nucleotides from the 5' end) according to embodiments of the present invention.
Figure 75:
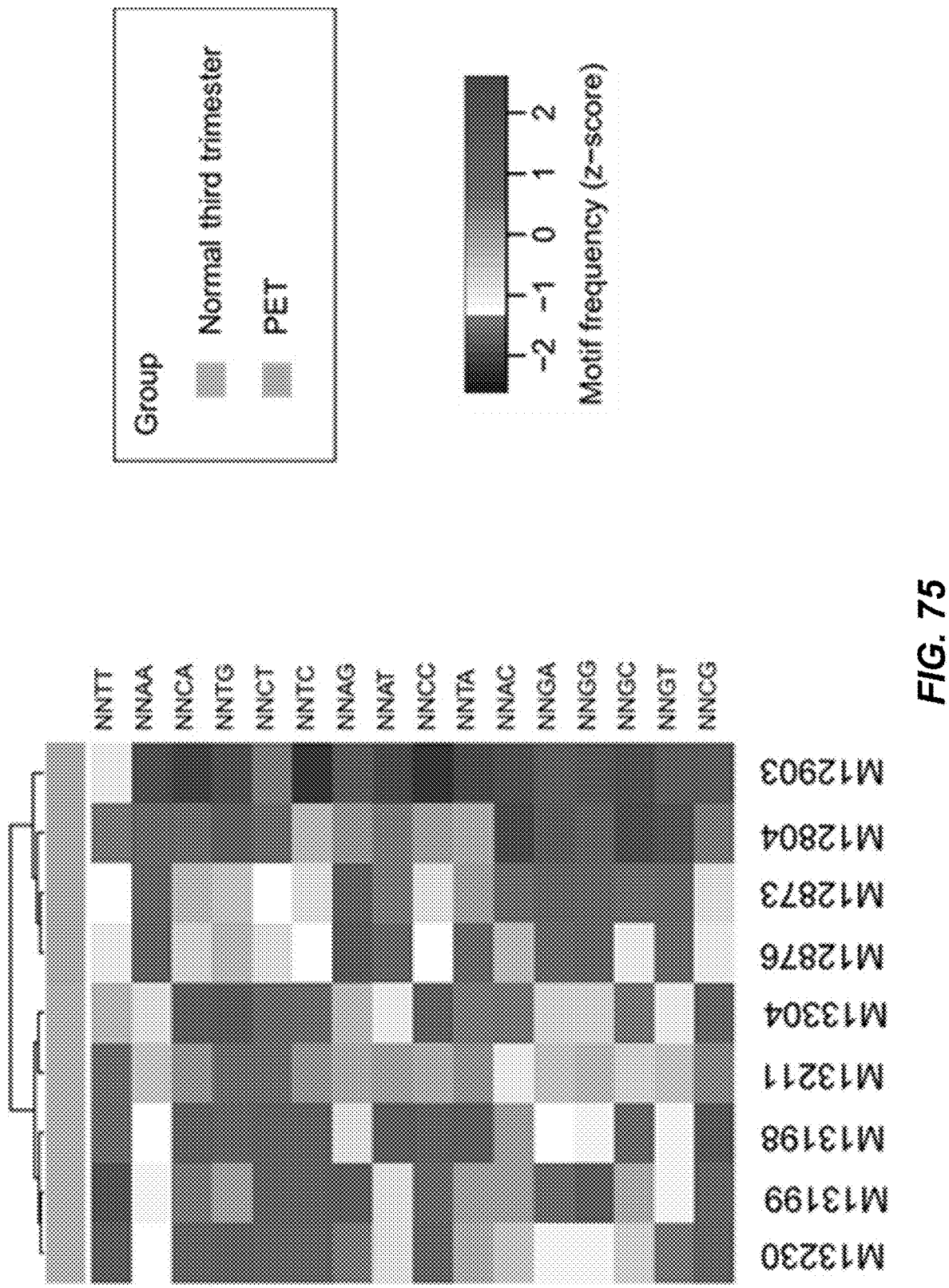
FIG. 75 shows hierarchical clustering analysis of preeclamptic and normotensive third-trimester maternal plasma DNA samples using 16 two-nucleotide motifs NNXY (di-nucleotide sequence of the third and fourth nucleotides from the 5' end) according to embodiments of the present invention.
Figure 76:
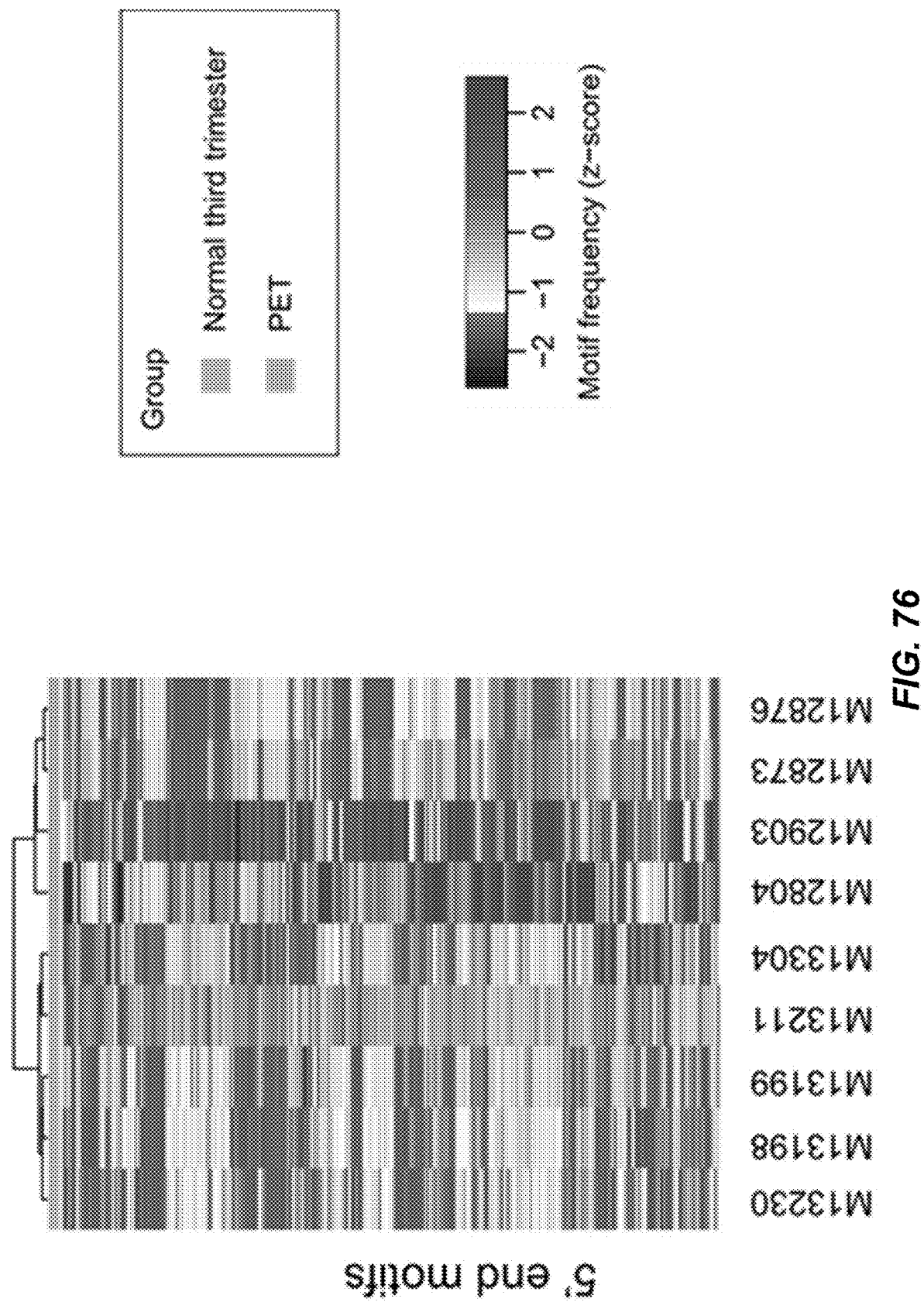
FIG. 76 shows hierarchical clustering analysis of preeclamptic and normotensive third-trimester maternal plasma DNA samples using 256 four-nucleotide motifs (dinucleotide sequence of the first through fourth nucleotides from the 5' end) according to embodiments of the present invention.
Figure 77A:
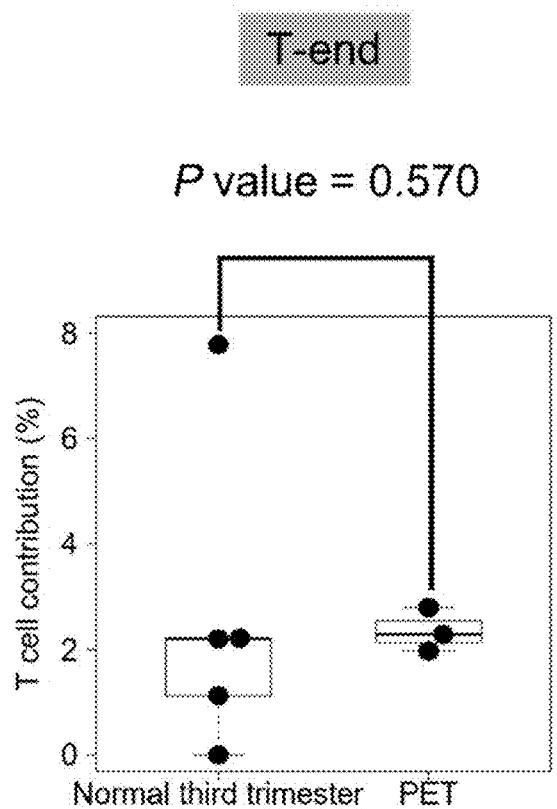
FIGS. 77A-77D show T cell contribution among four types of fragment ends in preeclamptic and normotensive maternal plasma DNA samples according to embodiments of the present invention.
Figure 77B:
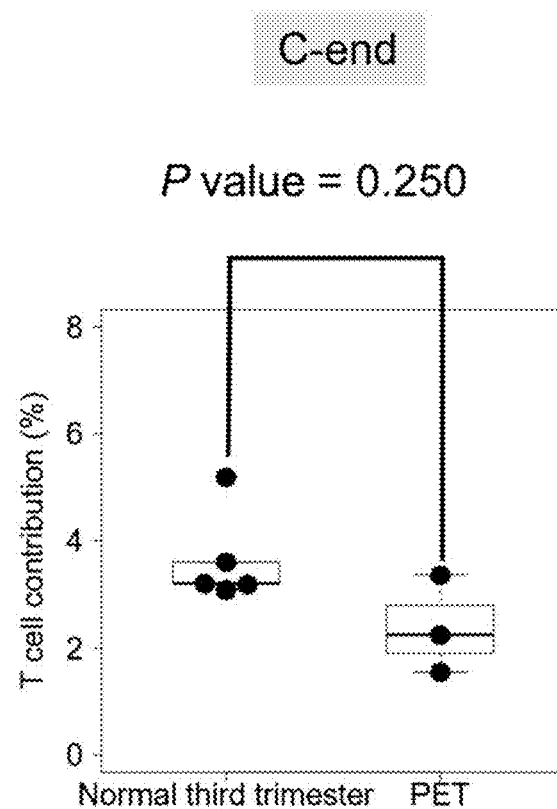
Figure 77C:
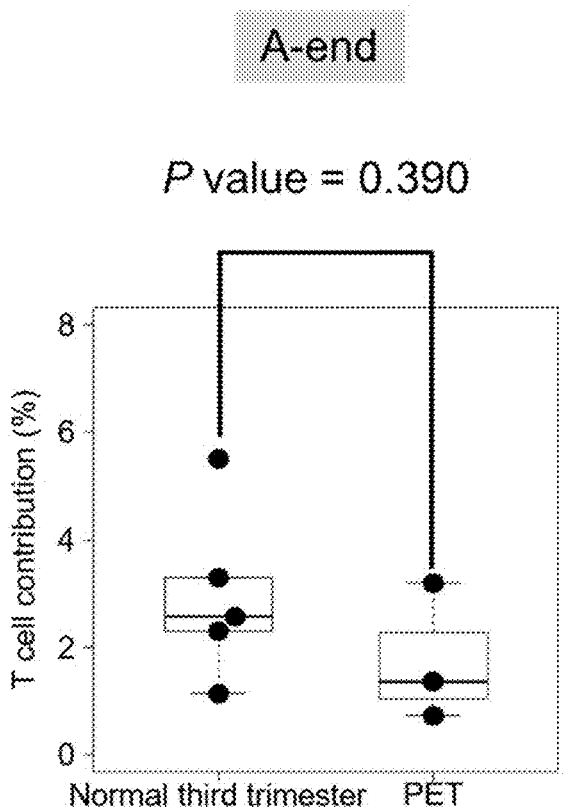
Figure 77D:
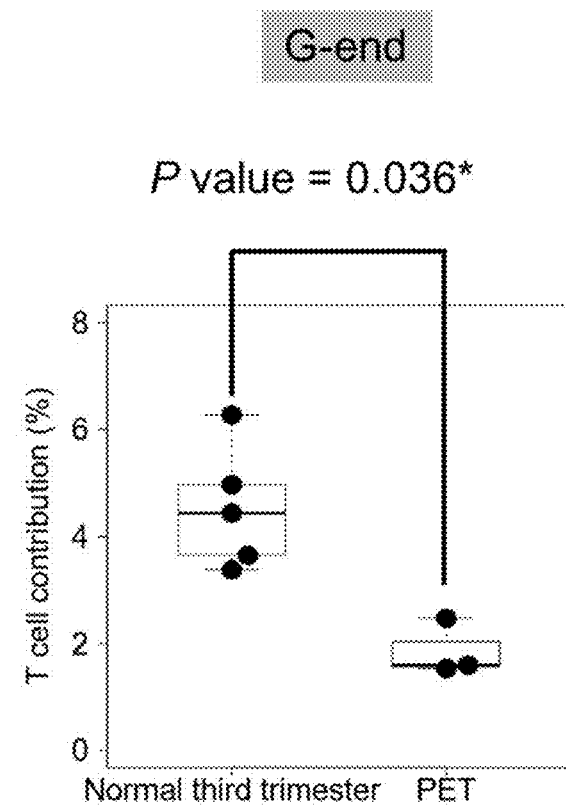

FIG. 74 shows hierarchical clustering analysis of preeclamptic and normotensive third-trimester maternal plasma DNA samples using 16 two-nucleotide motifs XYNN (dinucleotide sequence of the first and second nucleotides from the 5' end). FIG. 75 shows hierarchical clustering analysis of preeclamptic and normotensive third-trimester maternal plasma DNA samples using 16 two-nucleotide motifs NNXY (dinucleotide sequence of the third and fourth nucleotides from the 5' end). FIG. 76 shows hierarchical clustering analysis of preeclamptic and normotensive third-trimester maternal plasma DNA samples using 256 four-nucleotide motifs (dinucleotide sequence of the first through fourth nucleotides from the 5' end).

In FIGS. 74-76, the first row indicates which group each sample belonged to, with cyan indicating a normotensive third-trimester maternal plasma DNA sample and orange indicating a preeclamptic plasma DNA sample. Cyan covers the first five columns. Orange covers the last four columns. Starting from the second row, each row indicates a type of fragment end. The end motif frequencies were presented with a series of color gradients according to the row-normalized frequencies (z-score) (i.e., the number of standard deviations below or above the mean frequency across samples). The redder color indicates a higher frequency of an end motif, while the bluer color indicates a less frequency of an end motif.

These results suggested that plasma DNA in preeclamptic and non-preeclamptic samples possessed different fragmentation properties. In one embodiment, one could utilize end motif profiles generated from long-read sequencing platforms including but not limited to the PacBio SMRT sequencing and the Oxford Nanopore sequencing to predict the development of preeclampsia in pregnancies. While one-nucleotide, two-nucleotide, and four-nucleotide motifs were used in the above analysis, motifs of other lengths, e.g. 3, 5, 6, 7, 8, 9, 10, or more can be used in other embodiments.

In some embodiments, one can combine the fragment end analysis and the tissue-of-origin analysis to improve the performance of the prediction, detection and monitoring of pregnancy-associated conditions including but not limited to preeclampsia. First, one could perform the fragment end analysis for each maternal plasma sample to separate plasma DNA molecules into four fragment end categories, namely, T-end, C-end, A-end, and G-end fragments. One can then perform the tissue-of-origin analysis separately using plasma DNA molecules from each of the fragment end categories for each maternal plasma DNA sample using the methylation status matching analysis according to the embodiments in this disclosure. The proportional contribution of different tissues among one of the fragment end categories was defined as the percentage of plasma DNA molecules in the corresponding fragment end category that was assigned to the corresponding tissue relative to other tissues.

We analyzed three and five plasma DNA samples from pregnant women with and without preeclampsia using single molecule real-time sequencing. We obtained a median of 658,722, 889,900, 851,501, and 607,554 plasma fragments with A-end, C-end, G-end and T-end. For fragments with A-end, we compared methylation patterns of any fragment with at least 10 CpG sites to the reference methylation profiles of neutrophils, T cells, B cells, liver, and placenta according to methylation status matching approach described in this disclosure. A plasma DNA fragment would be assigned to a tissue which corresponded to the maximum scores of methylation status matching among those tissues. Using this method, a median of 2.43% (range: 0.73-5.50%) of A-end fragments was assigned to the T cells (i.e. T-cell contribution) among all samples being analyzed. We further analyzed those fragments with C-end, G-end, and T-end, respectively, in a similar manner. A median T-cell contribution of 3.20% (range: 1.55-5.19%), 3.52% (range: 1.53-6.27%) and 2.22% (0-7.79%) were observed for those fragments with C-end, G-end, and T-end, respectively.

FIGS. 77A-77D show the T cell contribution among DNA molecules belonging to different fragment end categories, namely (A) T-end, (B) C-end, (C) A-end, and (D) G-end, in preeclamptic and normotensive maternal plasma DNA samples. The x-axis shows normal third trimester and PET samples. The y-axis shows the T cell contribution as a percent. The results showed that, among the G-end fragments, the T cell contribution was significantly reduced in preeclamptic plasma samples compared with normotensive third-trimester plasma samples (P=0.036, Wilcoxon rank sum test). In embodiments, one may use a cutoff of 3% for the T cell contribution among the all G-end fragments in a maternal plasma DNA sample to determine if a pregnancy was at a high risk of a low risk of developing preeclampsia.

C. Example Methods

Figure 78:
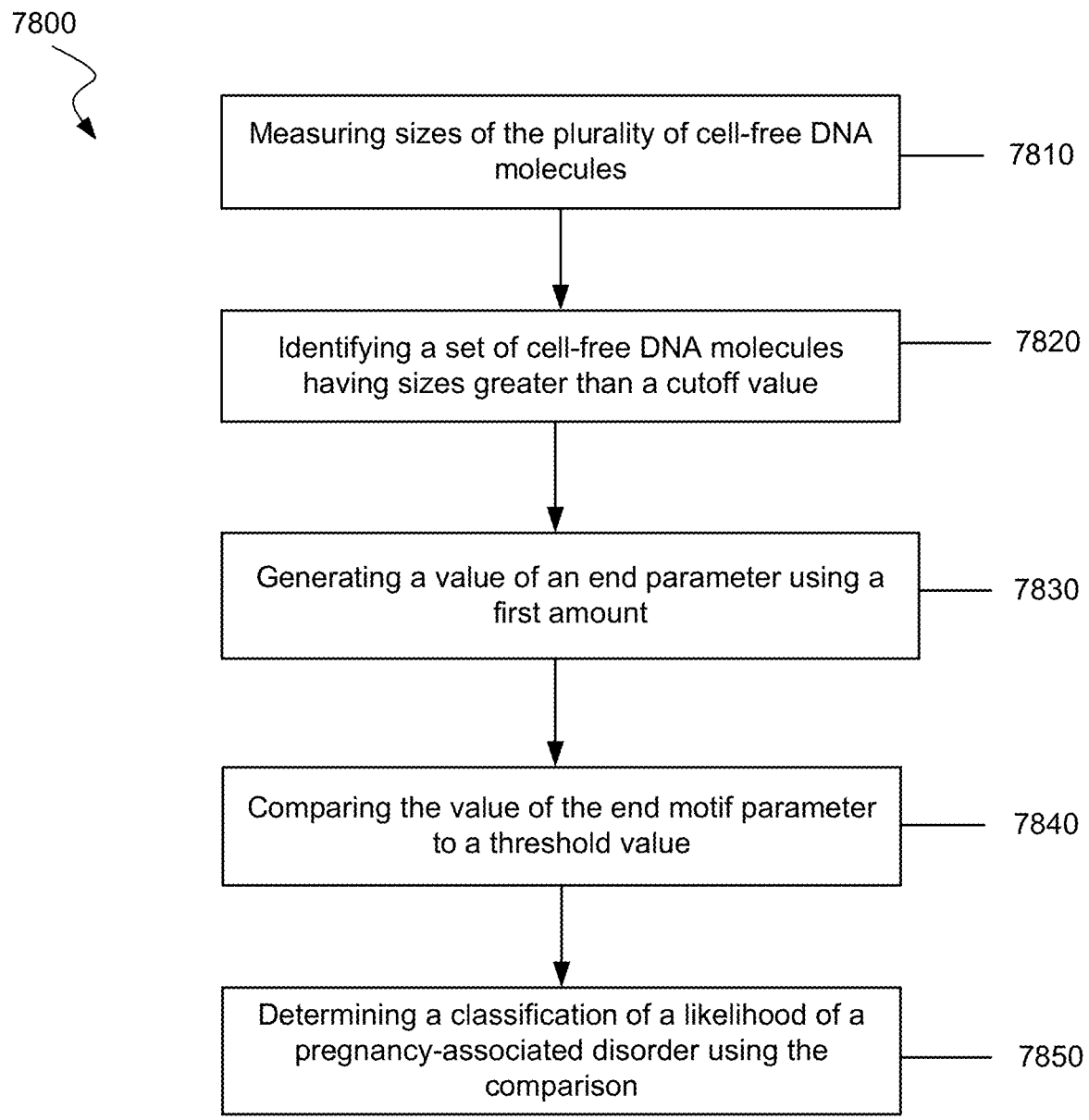
FIG. 78 shows a method of analyzing a biological sample obtained from a female pregnant with a fetus to determine a likelihood of a pregnancy-associate disorder according to embodiments of the present invention.

FIG. 78 shows a method 7800 of analyzing a biological sample obtained from a female pregnant with a fetus. The biological sample may include a plurality of cell-free DNA molecules from the fetus and the female. The method may generate a classification of a likelihood of a pregnancy-associated disorder. The pregnancy-associated disorder may be preeclampsia or any pregnancy-associated disorder described herein.

Sequence reads corresponding to the plurality of cell-free DNA molecules may be received.

At block 7810, sizes of the plurality of cell-free DNA molecules may be measured. Sizes may be measured through alignment or counting the number of nucleotides or any technique described herein, including with FIG. 21.

At block 7820, a set of cell-free DNA molecules having sizes greater than a cutoff value may be identified. The cutoff value may be any cutoff value for long cell-free DNA fragments, including 500 nt, 600 nt, 700 nt, 800 nt, 900 nt, 1 knt, 1.1 knt, 1.2 knt, 1.3 knt, 1.4 knt, 1.5 knt, 1.6 knt, 1.7 knt, 1.8 knt, 1.9 knt, or 2 knt. The cutoff value may be any cutoff value described herein for long cell-free DNA molecules.

At block 7830, a value of an end motif parameter using a first amount may be generated. The first amount of cell-free DNA molecules in the set having a first subsequence at one or more ends of the cell-free DNA molecules in the set may be measured. In some embodiments, the end motif parameter may be the first amount normalized by the total amount of all subsequences at an end. In some embodiments, the end may be the 3' end. In some embodiments, the end may be the 5' end.

The first subsequence may be 1, 2, 3, 4, 5, 6, 7, 8, 9, 10, or more nucleotides in length. The first subsequence may include the last nucleotide at the end of the respective cell-free DNA molecule. For example, the first subsequence may be the XYNN pattern shown in FIG. 74. In some embodiments, the first subsequence may not include the last nucleotide or nucleotides at the end of the respective cell-free DNA molecule. For example, the first subsequence may include the NNXY pattern of FIG. 75.

A second amount of cell-free DNA molecules having a subsequence different from the first subsequence at one or more ends of the cell-free DNA molecules may be measured. The value of the end motif parameter may be generating using a ratio of the second amount and the third amount. For example, the second amount may be divided by the third amount or the third amount may be divided by the second amount.

At block 7840, the value of the end motif parameter may be compared to a threshold value. The threshold value may be value that represents a statistically significant difference from a value of the associated parameter for a subject without the pregnancy-associated disorder. The threshold value may be determined from one or more reference subjects with normal pregnancies or one or more reference subjects with pregnancy-associated disorders.

In some embodiments, the value of the end motif parameter may be compared to the threshold value, and a value of a second end motif parameter may be compared to a second threshold value. A second amount of cell-free DNA molecules having a second subsequence different from the first subsequence at one or more ends of the cell-free DNA molecules may be measured. Amounts of different end motifs may therefore be determined. A value of the second end motif parameter using the second amount may be generated. The value of the second end motif parameter may be compared to a second threshold value. The second threshold value may be the same or different than the first threshold value. Additional subsequences may be used in the same manner as the first and second subsequences. In some embodiments, all possible subsequences may be used for comparisons to threshold values.

At block 7850, a classification of a likelihood of a pregnancy-associated disorder may be determined using the comparison. The pregnancy-associated disorder may be likely when the value of the size parameter or the value of the end motif parameter exceeds the threshold value.

In some embodiments, determining the classification of the likelihood of a pregnancy-associated disorder may use the comparison of the value of the second end motif parameter to the second cutoff value. The pregnancy-associated disorder may be likely when the value of the first end motif parameter exceeds the first threshold value and the value of the second end motif parameter exceeds the second threshold value.

The method may include using a size parameter in addition to the end motif parameter. A second set of cell-free DNA molecules having sizes in a first size range may be identified. The first size range may include sizes greater than the cutoff value. The first size range includes sizes may be greater than the cutoff value. The first size range may be less than 550 nt, 600 nt, 650 nt, 700 nt, 750 nt, 800 nt, 850 nt, 900 nt, 950 nt, 1 nt, 1.5 knt, 2 knt, 3 knt, 5 knt, or more. A value of the size parameter using a second amount of cell-free DNA molecules in the second set may be generated. The value of the size parameter may be compared to a second threshold value. Determining the classification of the likelihood of the pregnancy-associated disorder may use the comparison of the value of the size parameter to the second threshold value. The classification may be likely to have the pregnancy-associated disorder when one or both of the first and second threshold values are exceeded.

The size parameter may be a normalized parameter. For example, a third amount of cell-free DNA molecules in a second size range may be measured. The second size range may include sizes less than the first cutoff value. The second size range may include all sizes. The second size range may include 50-150 nt, 50-166 nt, 50-200 nt, 200-400 nt. The second size range may include any sizes for short cell-free DNA fragments described herein. The second size range may exclude sizes in the first size range. The value of the size parameter may be generated by determining a ratio of the second amount and the third amount. For example, the second amount may be divided by the third amount or the third amount may be divided by the second amount.

Any of the amounts of cell-free DNA molecules may cell-free DNA molecules from a particular tissue of origin. For example, the tissue of origin may be T cells or another tissue of origin described herein. The second amount may be similar to the T cell contribution described with FIGS. 77A-77D. The contribution from the tissue of origin may be determined using methylation status or pattern as described in this disclosure.

V. Repeat Expansion Related Diseases

Long cell-free DNA fragments obtained from pregnant women can be used to identify expansion of repeats in genes. Expansion of repeats in genes can result in neuromuscular diseases. Expansions in tandem repeats have been associated with human diseases, including but not limited to neurodegenerative disorders such as fragile X syndrome, Huntington's disease, and spinocerebellar ataxia. These tandem repeat expansions may occur in protein-coding regions of genes (Machado-Joseph disease, Haw River syndrome, Huntington's disease) or non-coding regions (Friedrich ataxia, myotonic dystrophy, some forms of fragile X syndrome). Expansions involving minisatellite, pentanucleotide, tetranucleotide, and numerous trinucleotide repeats had been associated with fragile sites. The expansions associated with these diseases could be caused by replication slippage or asymmetric recombination or epigenetic aberrations. The number of repeats in the sequence refers to the total number of times a subsequence appears. For example, "CAGCAG" includes two repeats. Because repeats include at least two instances of a subsequence, the number of repeats cannot be 1. The subsequence may be understood to be the repeat unit.

In embodiments, long cell-free DNA analysis in pregnant women could facilitate the detection of repeat-associated diseases. For example, a trinucleotide repeat represents a repetitive stretch of 3-bp motifs in DNA sequences. One example is that the sequence 'CAGCAGCAG' comprises three 3-bp 'CAG' motifs. The expansion of microsatellites, typically trinucleotide repeat expansion, has been reported to play a crucial role in neurological disorders (Kovtun et al. Cell Res. 2008; 18:198-213; McMurray et al. Nat Rev Genet. 2010; 11:786-99). One example is that more than 55 CAG repeats (165 bp in total) in the ATXN3 gene are pathogenic, resulting in spinocerebellar ataxia type 3 (SCA3) disease characterized by progressive problems with movement. This condition is inherited in an autosomal dominant pattern. Thus, one copy of the altered gene is sufficient to cause the disorder. To determine the repeat number of microsatellites, polymerase chain reaction (PCR) is typically used to amplify genomic region of interest and then the PCR product are subjected to a number of different techniques, such as capillary electrophoresis (Lyon et al. J Mol Diagn. 2010; 12:505-11), Southern blot analysis (Hsiao et al. J Clin Lab Anal. 1999; 13:188-93), melting curve analysis (Lim et al. J Mol Diagn. 2014; 17:302-14), and mass spectrometry (Zhang et al. Anal Methods. 2016; 8:5039-44). However, these methods were labor-intensive and time-consuming and were difficult to be applied to high-throughput screening in real clinical practice such as prenatal testing. Sanger sequencing has substantial difficulty in inferring long repeats from the complicate sequence traces through the manual examination. Illumina sequencing technologies and Ion Torrent are well known to have substantial difficulty in sequencing GC-rich (or GC-poor) regions harboring those repeats (Ashely et al. 2016; 17:507-22) and the length of a DNA comprising the expanded repeats easily exceed the length of the sequence reads (Loomis et al. Genome Res. 2013; 23:121-8).

Another example is myotonic dystrophy that is caused by the expansion of CTG repeats, ranging from 50 to 4000 CTG repeats (SEQ ID NO: 6), nearby the DMPK gene and also an autosomal dominant disorder. The molecular diagnosis of DM is routinely performed in prenatal diagnosis by analyzing the CTG number on fetal genomic DNA in an invasive manner.

In contrast to the short-read sequencing (hundreds of bases), the methods described in this disclosure are able to obtain the long DNA molecules from maternal plasma DNA (a number of kilobases). Using the methods described in this disclosure, one could determine whether an unborn fetus inherits this disease from the affected mother in a non-invasive way.

Figure 79:
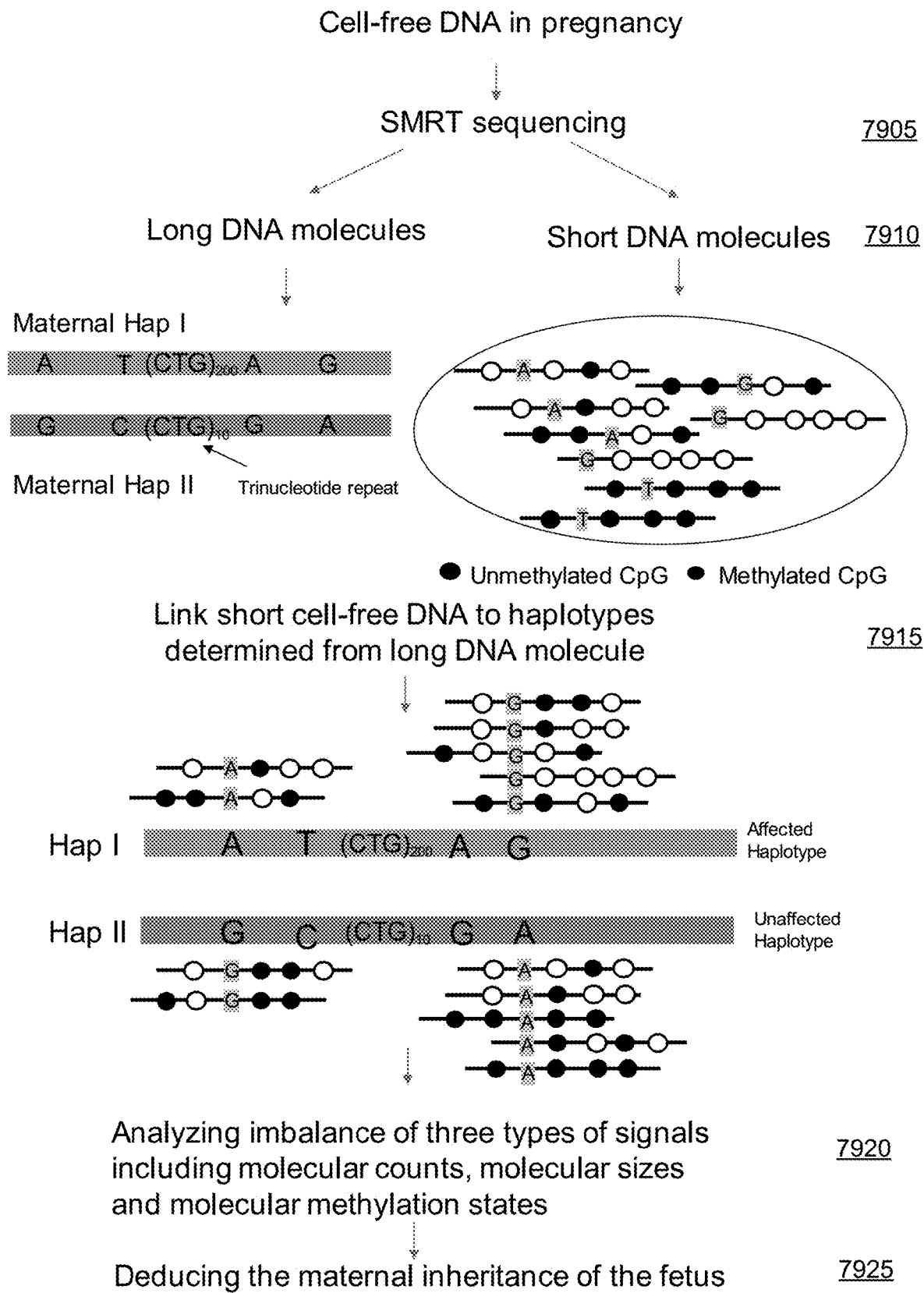
FIG. 79 shows an illustration of deducing the maternal inheritance of the fetus for repeat-associated diseases according to embodiments of the present invention.

FIG. 79 shows an illustration of deducing the maternal inheritance of the fetus for repeat-associated diseases. At stage 7905, the cell-free DNA in pregnancy was subjected to single molecule real-time (e.g., PacBio SMRT) sequencing. At stage 7910, the sequenced results were divided into the long and short DNA categories according to the disclosure.

At stage 7915, the allelic information present in long DNA molecules could be used to construct maternal haplotypes, namely Hap I and Hap II. Hap I and Hap II may each include expanded repeats of a trinucleotide subsequence (e.g., CTG). At stage 7920, an imbalance of haplotypes may be analyzed, similar to as described with FIG. 16. At stage 7925, the maternal inheritance of the fetus may be deduced. The methods described herein allow us to not only determine the haplotypes (e.g., Hap I and Hap II) but also determine which haplotype harbor the expanded repeats (e.g., affected Hap I) that cause the disorder using the sequence information of long DNA molecules according to the disclosure. Using the counts, sizes, or methylation states from short DNA molecules distributing across maternal Hap I and Hap II according to the method described herein, one could determine whether a fetus inherits the maternal Hap I (affected) or Hap II (unaffected) in this example.

Figure 80:
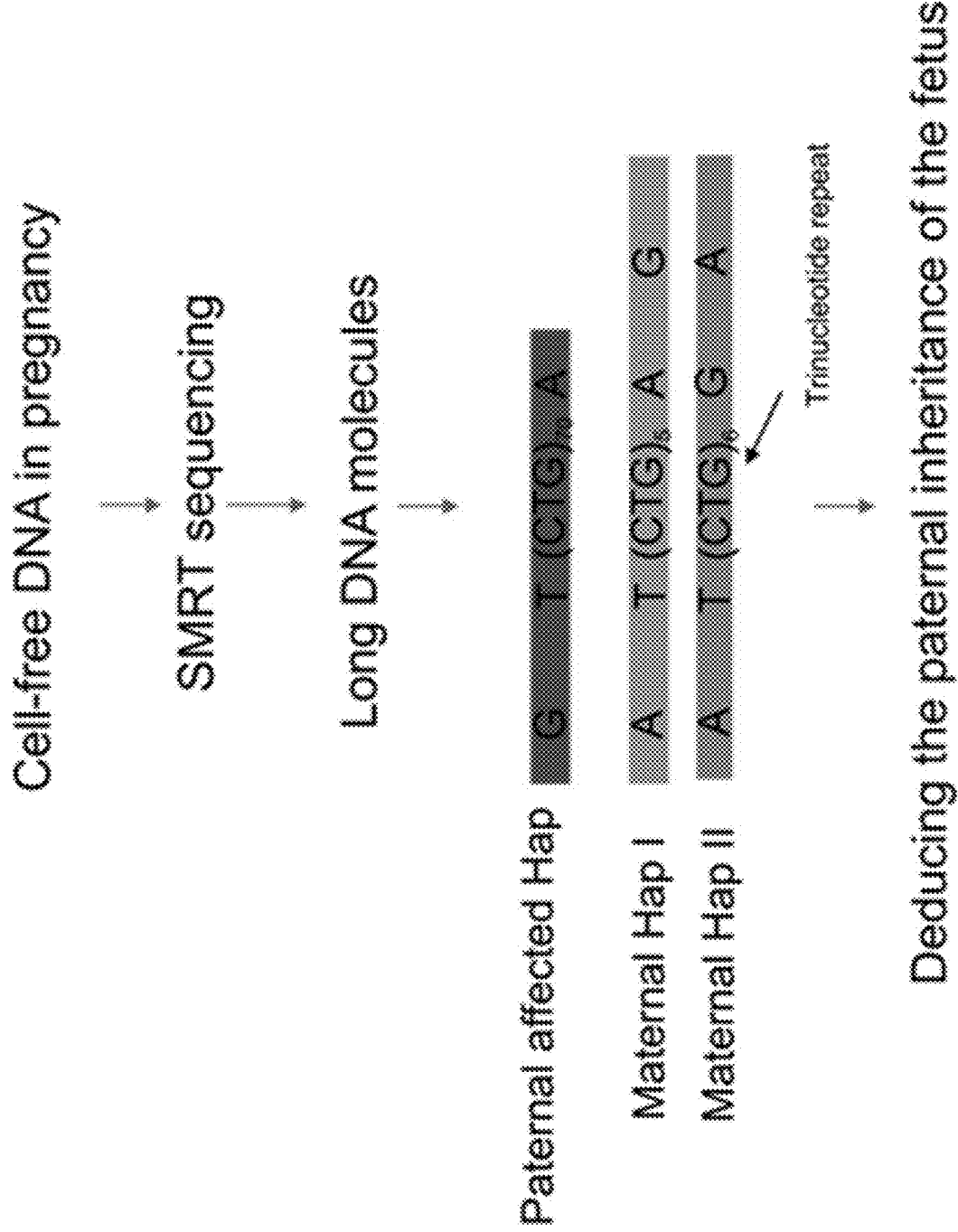
FIG. 80 shows an illustration of deducing the paternal inheritance of the fetus for repeat-associated diseases according to embodiments of the present invention.

FIG. 80 shows an illustration of deducing the paternal inheritance of the fetus for repeat-associated diseases. One could determine whether a fetus inherits an affected paternal haplotype using cell-free DNA in pregnancy. As shown in FIG. 80, cell-free DNA in the pregnancy of an unaffected woman (e.g. 5 CTG repeats (SEQ ID NO: 7) for Hap I and 6 CTG repeats (SEQ ID NO: 8) for Hap II) whose husband was affected by repeat expansion disease (e.g. 70 CTG repeats (SEQ ID NO: 9)) was subjected to PacBio SMRT sequencing, the sequenced long DNA molecules were identified and used for determining the haplotype and the repeat number. If A haplotype harboring a long stretch of CTG repeat (e.g. 70 CTG repeats (SEQ ID NO: 9) in this example) is present in the maternal plasma of the unaffected pregnant woman, it suggests that the fetus inherited an affected paternal haplotype. In some embodiments, the DNA containing the expanded repeats also carries one or more another paternal specific allele which is absent in the maternal genome. This situation would be useful to confirm the paternal inheritance.

In another embodiment, one could determine whether a fetus inherits an affected paternal haplotype using cell-free DNA in pregnancy. As shown in FIG. 80, cell-free DNA in the pregnancy of an unaffected woman (e.g. 5 CTG repeats (SEQ ID NO: 7) for Hap I and 6 CTG repeats (SEQ ID NO: 8) for Hap II) whose husband was affected by repeat expansion disease (e.g. 70 CTG repeats (SEQ ID NO: 9)) was subjected to PacBio SMRT sequencing, the sequenced long DNA molecules were identified and used for determining the haplotype and the repeat number. If a haplotype harboring a long stretch of CTG repeat (e.g. 70 CTG repeats (SEQ ID NO: 9) in this example) is present in the maternal plasma of the unaffected pregnant woman, it suggests that the fetus inherited an affected paternal haplotype. In some embodiments, the DNA containing the expanded repeats also carries one or more another paternal specific allele which is absent in the maternal genome. This situation would be useful to confirm the paternal inheritance.

FIGS. 81, 82, and 83 are tables showing examples of repeat expansion diseases. The first column shows the repeat expansion related disease. The second column shows the repeat subsequence. The third column shows the number of repeats in normal subjects. The fourth column shows the number of repeats in diseased subjects. The fifth column shows the genetic locations related to repeats. The sixth column lists the gene names. The seventh column lists the patterns of inheritance. The table is derived from omicslab-.genetics.ac.cn/dred/index.php.

A. Examples for Repeat Expansion Detection

It was reported that the paternally inherited expanded CAG repeat could be detected in maternal plasma using a direct approach by PCR and subsequent fragment analysis on 3130XL Genetic Analyzer (Oever et al. Prenat Diagn. 2015; 35:945-9). Noninvasive prenatal testing for Huntington was achievable by PCR because the size of the expanded allele only starts from >35 trinucleotide repeats [i.e. a DNA region with 105 bp (35×3) or above in length spanning the repeats]. Many expanded repeats, especially for most trinucleotide repeat disorders (Orr et al. Annu. Rev. Neurosci. 2007; 30:575-621), would involve repeats with 300 bp or above in length, beyond the size of the short fetal DNA molecules which were documented in the previous reports. The DNA with large expanded repeats would cause the difficulty of PCR (Orr et al. Annu. Rev. Neurosci. 2007; 30:575-621). As suggested by Oever et al.'s study, the signal intensity of long CAG repeats is often much lower compared with the signal of smaller repeats, and this phenomenon is observed in both genomic DNA and plasma DNA, leading to a lower sensitivity for detecting those long CAG repeats (Oever et al. Prenat Diagn. 2015; 35:945-9). Another limitation of PCR would be that the methylation signals are not able to be preserved during amplification. In one embodiment, the single molecule real-time sequencing of long DNA molecules would allow the determination of tandem repeat polymorphisms and their associated methylation levels across one or more regions.

FIG. 84 is a table showing examples for repeat expansion detection in the fetus and repeat-associated methylation determination. The first column shows the type of repeat in number of base pairs. The second column shows the repeat unit. The third column shows the genomic locations. The fourth column shows the reference bases, the sequences present in the human reference genome. The fifth column shows the paternal genotypes. The sixth column shows the maternal genotypes. The seventh column shows the fetal genotypes. The eighth column shows the fetal DNA methylation level linked to paternal alleles. The ninth column shows the fetal DNA methylation level linked to maternal alleles.

FIG. 84 shows a number of examples of 1-bp, 2-bp, 3-bp, and 4-bp tandem repeats. For example, at the genomic location of chr3:192384705-192384706, a "GATA" tandem repeat was identified. The genotype of the father at this locus was $T(GATA)_3/T(GATA)_5$ (SEQ ID NOS 10 and 11, respectively) for which the allele 1 had 3 repeat units and the allele 2 had 5 repeat units. Compared with the reference allele $T(GATA)_3$ (SEQ ID NO: 10), the paternal allele 2 suggested a genetic event involving the repeat expansion. The genotype of mother at this locus was T/T, exhibiting a genetic event involving the repeat contraction. The fetal genotype at this locus was $T(GATA)_5/T$ (SEQ ID NO: 11), suggesting that the fetus inherited the paternal allele 2 (i.e. $T(GATA)_5$ (SEQ ID NO: 11)) and the maternal allele T. The methylation levels associated with the paternal allele and the maternal allele were 50.98 and 62.8, respectively. These results suggested that the use of tandem repeat polymorphisms would allow the determination of the maternal and paternal inheritance of the fetus. This technology would allow the identification of different methylation patterns associated with the two alleles. Another example shows that at the genomic location of chr4:73237157-73237158, the fetus had inherited the repeat expansion [$(TAAA)_3$] from the mother. The fetal molecule containing the repeat expansion inherited from the mother showed a higher methylation level (95.65%) compared with the fetal molecule containing the paternal allele (62.84%). These data suggested that we could detect repeats, repeat structures and the associated methylation changes. In one embodiment, one could use a particular cutoff for determining whether the methylation difference between the maternal and paternal inheritance was significant. The cutoff would be the absolute difference in the methylation levels greater than but not limited to 5%, 10%, 15%, 20%, 25%, 30%, 35%, 40%, 45%, 50%, 55%, 60%, 65%, 70%, 75%, 80%, 85%, or 90%, etc. The determination of the maternal inheritance may be similar to methods described with method 2100 of FIG. 21.

B. Example Methods

Subsequence repeats may be used to determine information of a fetus. For example, the presence of subsequence repeats may be used to determine that a molecule is of fetal origin. In addition, subsequence repeats may indicate a likelihood of a genetic disorder. Subsequence repeats can be used to determine the inheritance of maternal and/or paternal haplotypes.

Additionally, the paternity of a fetus may be determined using subsequence repeats.

1. Fetal Origin Analysis Using Subsequence Repeats

Figure 85:
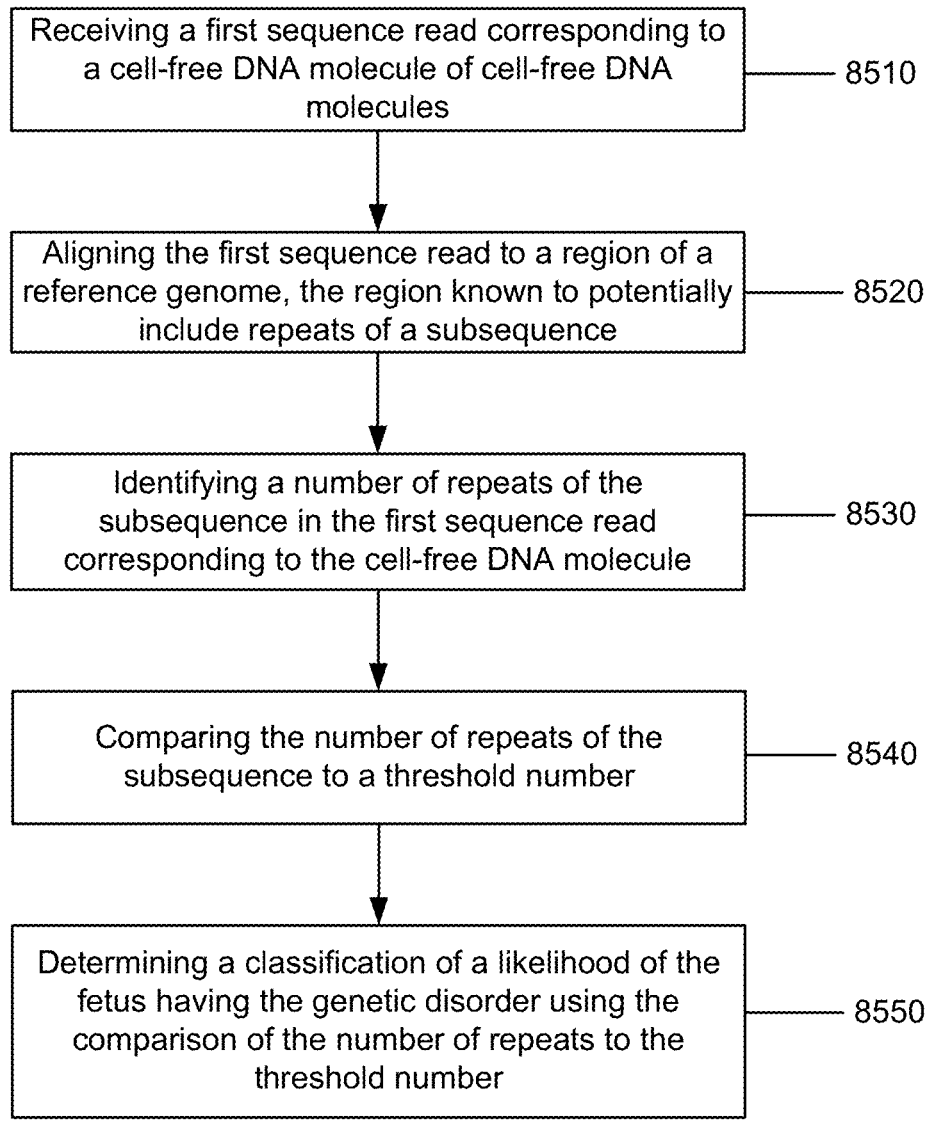
FIG. 85 shows a method of analyzing a biological sample obtained from a female pregnant with a fetus in order to determine a likelihood of a genetic disorder in the fetus according to embodiments of the present invention.

FIG. 85 shows method 8500 of analyzing a biological sample obtained from a female pregnant with a fetus, the biological sample including cell-free DNA molecules from the fetus and the female. A likelihood of a genetic disorder in the fetus may be determined.

At block 8510, a first sequence read corresponding to a cell-free DNA molecule of the cell-free DNA molecules may be received. The cell-free DNA molecules may have a length greater than a cutoff value. The cutoff value may be greater than or equal to 200 nt. The cutoff value may be at least 500 nt, including 600 nt, 700 nt, 800 nt, 900 nt, 1 knt, 1.1 knt, 1.2 knt, 1.3 knt, 1.4 knt, 1.5 knt, 1.6 knt, 1.7 knt, 1.8 knt, 1.9 knt, or 2 knt. The cutoff value may be any cutoff value described herein for long cell-free DNA molecules.

At step 8520, the first sequence read may be aligned to a region of a reference genome. The region may be known to potentially include repeats of a subsequence. The region may correspond to any of the locations or genes in FIGS. 81-83. The subsequence may be a trinucleotide sequence, including any described herein.

At block 8530, a number of repeats of the subsequence in the first sequence read corresponding to the cell-free DNA molecule may be identified.

At block 8540, the number of repeats of the subsequence may be compared to a threshold number. The threshold number may be 55, 60, 75, 100, 150 or more. The threshold number may be different for different genetic disorders. For example, the threshold may reflect the minimum number of repeats in diseased subjects, the maximum number of repeats in normal subjects, or a number between these two numbers (see FIGS. 81-83).

At block 8550, a classification of a likelihood of the fetus having the genetic disorder may be determined using the comparison of the number of repeats to the threshold number. The fetus may be determined as likely to have the genetic disorder when the number of repeats exceeds the threshold number. The genetic disorder may be fragile X syndrome or any disorder listed in FIGS. 81-83.

In some embodiments, the method may include repeating the classification for several different target loci, each known to potentially have a repeat of a subsequence. A plurality of sequence reads corresponding to the cell-free DNA molecules may be received. The plurality of sequence reads may be aligned to a plurality of regions of the reference genome. The plurality of regions may be known to potentially include repeats of subsequences. The plurality of regions may be non-overlapping regions. Each region of a plurality of regions may have a different SNP. The plurality of regions may be from different chromosomal arms or chromosomes. The plurality of regions may cover at least 0.01%, 0.1%, or 1% of the reference genome. Numbers of repeats of the subsequences may be identified in the plurality of sequence reads. The numbers of repeats of the subsequences may be compared to a plurality of threshold numbers. Each threshold number may indicate the presence or likelihood of a different genetic disorder. For each of a plurality of genetic disorders, a classification of a likelihood of the fetus having the respective genetic disorder may be determined using the comparison to a threshold number of the plurality of threshold numbers.

The cell-free DNA molecule may be determined to be of fetal origin. The determination of fetal origin may include receiving a second sequence read corresponding to a cell-free DNA molecule of maternal origin obtained from a buffy coat or a sample of the female before pregnancy. The second sequence read may be aligned to the region of the reference genome. A second number of repeats of the subsequence may be identified in the second sequence read. The second number of repeats may be determined to be less than the first number of repeats.

The determination of fetal origin may include determining a methylation level of the cell-free DNA molecule using the methylated and unmethylated sites of the cell-free DNA molecule. The methylation level may be compared to a reference level. The method may include determining the methylation level exceeds the reference level. The methylation level may be a number or proportion of sites that are methylated.

The determination of fetal origin may include determining a methylation pattern of a plurality of sites of the cell-free molecule. A similarity score may be determined by comparing the methylation pattern to a reference pattern from a maternal or fetal tissue. The similarity score may be compared to one or more threshold values. The similarity score may be any similarity score described herein, including, for example, as described with method 4000.

2. Paternity Analysis Using Subsequence Repeats

Figure 86:
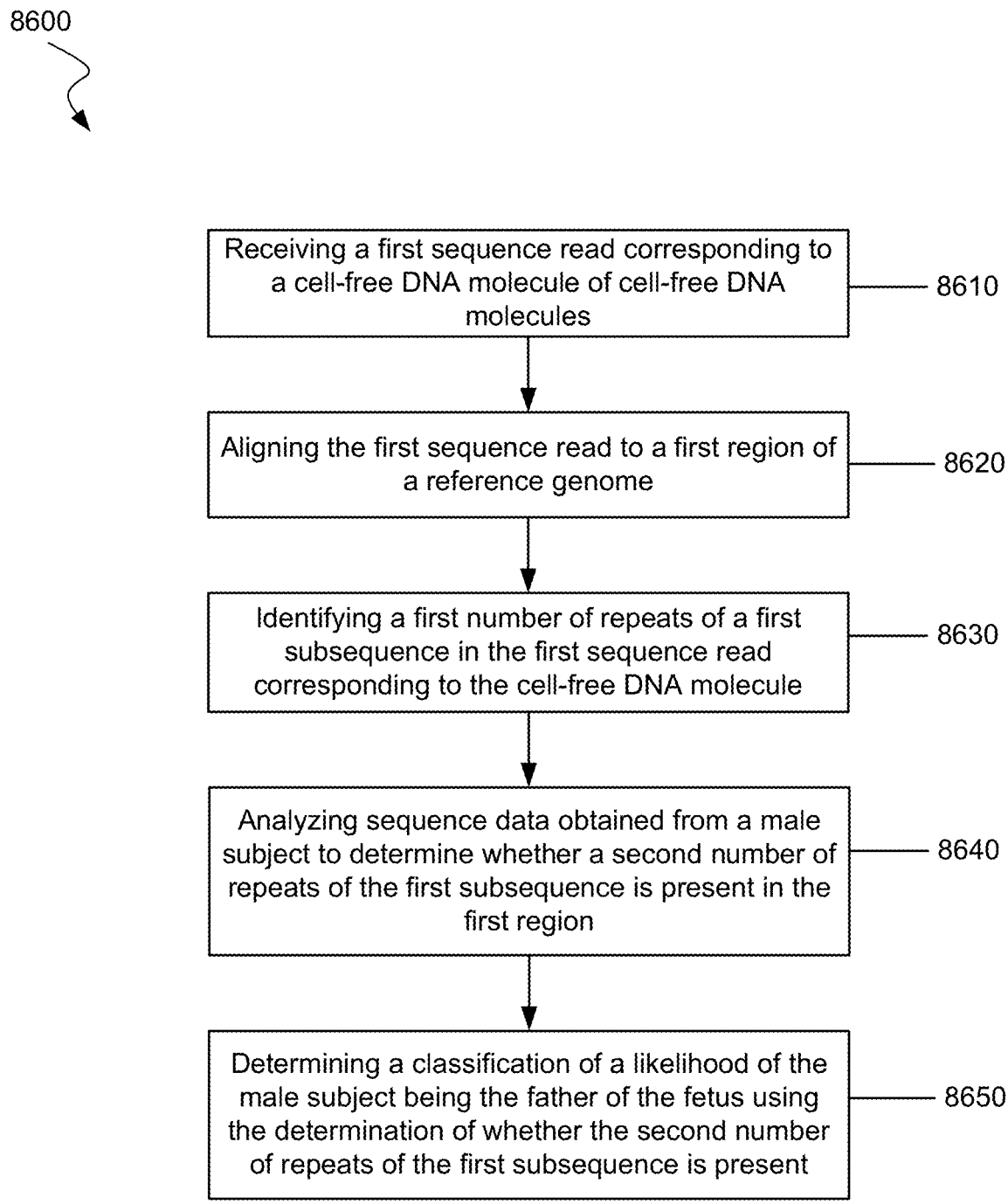
FIG. 86 shows a method of analyzing a biological sample obtained from a female pregnant with a fetus in order to determine paternity according to embodiments of the present invention.

FIG. 86 shows a method 8600 of analyzing a biological sample obtained from a female pregnant with a fetus, the biological sample including cell-free DNA molecules from the fetus and the female. The biological sample may be analyzed to determine the father of the fetus.

At block 8610, a first sequence read corresponding to a cell-free DNA molecule of the cell-free DNA molecules may be received. The method may include determining that the cell-free DNA molecule is of fetal origin. The cell-free DNA molecule may be determined to be of fetal origin by any method described herein, including, for example, as described with method 8500. The cell-free DNA molecules may have sizes greater than a cutoff value. The cutoff value may be greater than or equal to 200 nt. The cutoff value may be at least 500 nt, including 600 nt, 700 nt, 800 nt, 900 nt, 1 knt, 1.1 knt, 1.2 knt, 1.3 knt, 1.4 knt, 1.5 knt, 1.6 knt, 1.7 knt, 1.8 knt, 1.9 knt, or 2 knt. The cutoff value may be any cutoff value described herein for long cell-free DNA molecules.

At block 8620, the first sequence read may be aligned to a first region of a reference genome. The first region may be known to have repeats of a subsequence.

At block 8630, a first number of repeats of a first subsequence in the first sequence read corresponding to the cell-free DNA molecule may be identified. The first subsequence may include an allele.

At block 8640, sequence data obtained from a male subject may be analyzed to determine whether a second number of repeats of the first subsequence is present in the first region. The second number of repeats includes at least two instances of the first subsequence. The sequence data may be obtained by extracting a biological sample from the male subject and performing sequencing on the DNA in the biological sample.

At block 8650, a classification of a likelihood of the male subject being the father of the fetus may be determined using the determination of whether the second number of repeats of the first subsequence is present. The classification may be that the male subject is likely the father when the second number of repeats of the first subsequence is determined to be present. The classification may be that the male subject is likely not the father when the second number of repeats of the first subsequence is determined to be not present.

The method may include comparing the first number of repeats with the second number of repeats. Determining the classification of the likelihood of the male subject being the father may include using the comparison of the first number of repeats with the second number of repeats. The classification may be that the male subject is likely the father when the first number of repeats is within a threshold value of the second number of repeats. The threshold value may be within 10%, 20%, 30%, or 40% of the second number of repeats.

The method may include using multiple regions of repeats. For example, the cell-free DNA molecule is a first cell-free DNA molecule. The method may include receiving a second sequence read corresponding to a second cell-free DNA molecule of the cell-free DNA molecules. The method may also include aligning the second sequence read to a second region of the reference genome. The method may further include identifying a first number of repeats of a second subsequence in the second sequence read corresponding to the second cell-free DNA molecule. The method may include analyzing the sequence data obtained from the male subject to determine whether a second number of repeats of the second subsequence is present in the second region. Determining the classification of the likelihood of the male subject being the father of the fetus may further include using the determination of whether the second number of repeats of the second subsequence is present in the second region. The classification of the likelihood may be a higher likelihood of the male subject being the father of the fetus when repeats are present in both the first region and the second region in sequence data of the male subject.

VI. Size Selection for Enriching Long Plasma DNA Molecules

In embodiments, one could physically select DNA molecules with one or more desired size ranges prior to analysis (e.g., single molecule real-time sequencing). As an example, the size selection can be performed using solid-phase reversible immobilization technology. In other embodiments, the size selection can be performed using electrophoresis (e.g., using the Coastal Genomic system or the Pippin size selection system). Our approach is different from previous work that predominantly focused on shorter DNA (Li et al. JAMA 2005; 293: 843-9) as it is known in the art that fetal DNA is shorter than maternal DNA (Chan et al. Clin Chem 2004; 50: 88-92).

Size selection techniques can be applied to any of the methods described herein and for any sizes described herein. For example, cell-free DNA molecules may be enriched by electrophoresis, magnetic beads, hybridization, immunoprecipitation, amplification, or CRISPR. The resulting enriched sample may have a larger concentration or higher proportion of certain size fragments than the biological sample before enriching.

A. Size Selection with Electrophoresis

In embodiments, making use of the electrophoretic mobilities of DNA depending on DNA sizes, one could use the gel electrophoresis based approaches to select the target DNA molecules with desirable size ranges, for example but not limited to, ≥100 bp, ≥200 bp, ≥300 bp, ≥400 bp, ≥500 bp, ≥600 bp, ≥700 bp, ≥800 bp, ≥900 bp, ≥1 kb, ≥2 kb, ≥3 kb, ≥4 kb, ≥5 kb, ≥6 kb, ≥7 kb, ≥8 kb, ≥9 kb, ≥10 kb, ≥20 kb, ≥30 kb, ≥40 kb, ≥50 kb, ≥60 kb, ≥70 kb, ≥80 kb, ≥90 kb, ≥100 kb, ≥200 kb, or others, including greater than any cutoff described herein. For example, LightBench (Coastal Genomics) an automated gel electrophoresis system for DNA size selection was used. In principle, shorter DNA would move faster than the longer ones during gel electrophoresis. We applied this size selection technology to one plasma DNA sample (M13190), aiming to select the DNA molecules greater than 500 bp. We used a 3% size-selection cassette with an 'In-Channel-Filter' (ICF) collection device and loading buffer with internal size markers for size selection. DNA libraries were loaded into the gel and started electrophoresis. When the target size reached, the first fraction of <500 bp was retrieved from ICF. The running was resumed and allowed for the completion of electrophoresis to obtain a second fraction of ≥500 bp. We used single molecule real-time sequencing (PacBio) to sequence the second fraction with a molecule size of ≥500 bp. We obtained 1,434 high-quality circular consensus sequences (CCS) (i.e. 1,434 molecules). Among them, 97.9% of sequenced molecules were greater than 500 bp. Such a proportion of DNA molecules greater than 500 bp was much higher that the counterpart without size selection (10.6%). The overall methylation of those molecules was determined to be 75.5%.

Figure 87:
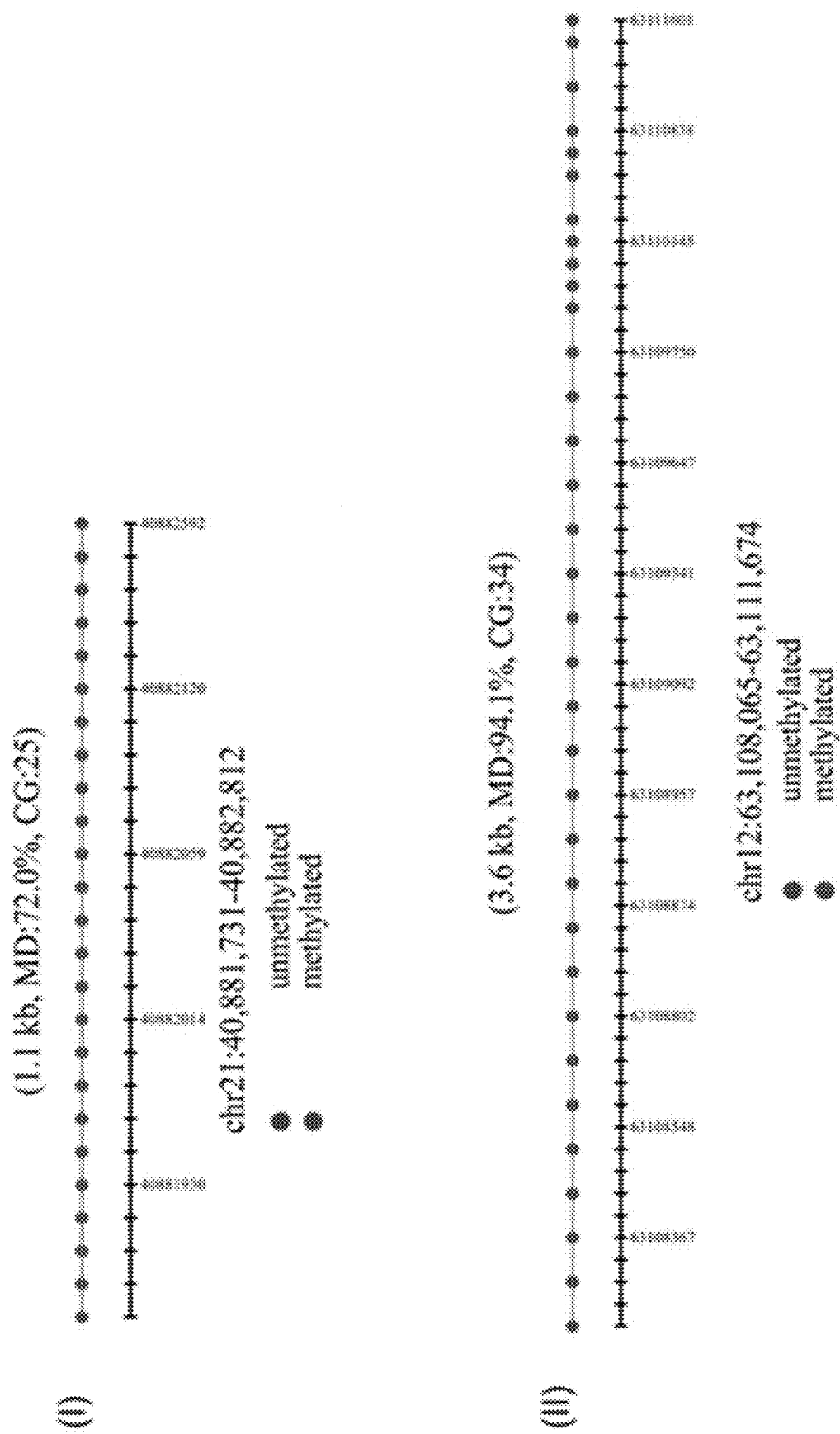
FIG. 87 shows methylation patterns for two representative plasma DNA molecules after size selection.

FIG. 87 shows methylation patterns for two representative plasma DNA molecules after size selection in (I) Molecule I and (II) Molecule II. Molecule I (chr21:40,881,731-40,882,812) was 1.1 kb long, harboring 25 CpG sites. The single molecule methylation level (i.e., the number of methylated sites divided by the total number of sites) of molecule I was determined to be 72.0% using the approaches described in our previous disclosure (U.S. application Ser. No. 16/995,607). Molecule II (chr12:63,108,065-63,111,674) was 3.6 kb long, harboring 34 CpG sites. The single molecule methylation level of molecule II was determined to be 94.1%. It suggested that the size selection-based methylation analysis allowed one to efficiently analyze the methylation of long DNA molecules and compare the methylation status between two or more molecules.

B. Size Selection with Beads

Solid-phase reversible immobilization technology used paramagnetic beads to selectively bind nucleic acids depending on DNA molecule sizes. Such a bead includes a polystyrene core, magnetite, and a carboxylate-modified polymer coating. DNA molecules would selectively bind to beads in the presence of polyethylene glycol (PEG) and salt, depending on the concentration of PEG and salt in the reaction. PEG caused the negatively-charged DNA to bind with the carboxyl groups on the bead surface, which would be collected in the presence of the magnetic field. The molecules with desired sizes were eluted from the magnetic beads using elution buffers, for example, 10 mM Tris-HCl, pH 8 buffer, or water. The volumetric ratio of PEG to DNA would determine the sizes of DNA molecules that one could obtain. The lower the ratio of PEG:DNA, the more long molecules would be retained on the beads.

1. Sample Processing

Peripheral blood samples from two third-trimester pregnant women were collected in EDTA blood tubes. The peripheral blood samples were collected and centrifuged at 1,600×g for 10 min at 4° C. The plasma portion was further centrifuged at 16,000×g for 10 min at 4° C. to remove residual cells and debris. The buffy coat portion was centrifuged at 5,000×g for 5 min at room temperature to remove residual plasma. Placental tissues were collected immediately after delivery. Plasma DNA extractions were performed using the QIAamp Circulating Nucleic Acid Kit (Qiagen). Buffy coat and placental tissue DNA extractions were performed using QIAamp DNA Mini Kit (Qiagen).

2. Plasma DNA Size Selection

Post-extraction plasma DNA samples were divided into two aliquots. One aliquot from each patient was subjected to size selection with AMPure XP SPRI beads (Beckman Coulter, Inc.). 50 µL of each extracted plasma DNA sample was thoroughly mixed with 25 µL of AMPureXP solution and incubated at room temperature for 5 minutes. Beads were separated from the solution with magnets and washed with 180 µL 80% ethanol. The beads were then resuspended in 50 µL water and vortexed for 1 minute to elute the size-selected DNA from beads. Beads were subsequently removed to obtain the size-selected DNA solution.

3. Single-Nucleotide Polymorphism Identification

Fetal and maternal genomic DNA samples were genotyped with the iScan System (Illumina). Single-nucleotide polymorphisms (SNPs) were called. The genotypes of the placenta were compared with those of the mothers to identify the fetal-specific and maternal-specific alleles. The fetal-specific allele was defined as an allele that was present in the fetal genome but absent in the maternal genome. In one embodiment, those fetal-specific alleles could be determined by analyzing those SNP sites for which the mother was homozygous and the fetus was heterozygous. The maternal-specific allele was defined by an allele that was present in the maternal genome but absent in the fetal genome. In one embodiment, those fetal-specific alleles could be determined by analyzing those SNP sites for which the mother was heterozygous and the fetus was homozygous.

4. Single-Molecule Real-Time Sequencing

Two size-selected samples, along with their corresponding unselected samples, were subjected to single-molecule real-time (SMRT) sequencing template construction using a SMRTbell Template Prep Kit 1.0—SPv3 (Pacific Biosciences). DNA was purified with 1.8× AMPure PB beads, and library size was estimated using a TapeStation instrument (Agilent). Sequencing primer annealing and polymerase binding conditions were calculated with the SMRT Link v5.1.0 software (Pacific Biosciences). Briefly, sequencing primer v3 was annealed to the sequencing template, and then polymerase was bound to templates using a Sequel Binding and Internal Control Kit 2.1 (Pacific Biosciences). Sequencing was performed on a Sequel SMRT Cell 1M v2. Sequencing movies were collected on the Sequel system for 20 hours with a Sequel Sequencing Kit 2.1 (Pacific Biosciences).

5. Size Analysis

FIG. 88 is a table of sequencing information for samples with and without size selection. The first column is the sample identifier. The second column lists the group of the sample—whether or not there was size selection. The third column lists the number of sequenced molecules. The fourth column lists the mean subread depths. The fifth column lists the median fragment size. The sixth column shows the proportion of fragments greater than or equal to 500 bp.

We analyzed two samples (299 and 300) with and without bead-based size selection. As shown in FIG. 88, we obtained 2.5 million and 3.1 million sequenced molecules for samples 299 and 300, respectively without size selection, using single molecule real-time sequencing (e.g. PacBio SMRT sequencing). The mean subread depths were 91× and 67×. The median fragment sizes were 176 and 512 bp.

For paired samples (B299 and B300) with solid-phase reversible immobilization-based size selection aiming to select DNA fragments ≥500 bp, we obtained respectively 4.1 million and 2.0 million sequenced molecules, with mean subread depths of 18× and 19×. The median fragment sizes were found to be 2.5 kb and 2.2 kb for samples B299 and B300, respectively. The mean fragment size was 4 to 14 folds longer than the corresponding samples without size selection. The proportion of fragments ≥500 bp after the size selection was increased from 27.3% to 97.6% for sample B299 and from 50.5% to 97.4% for sample B300.

Figure 89A:
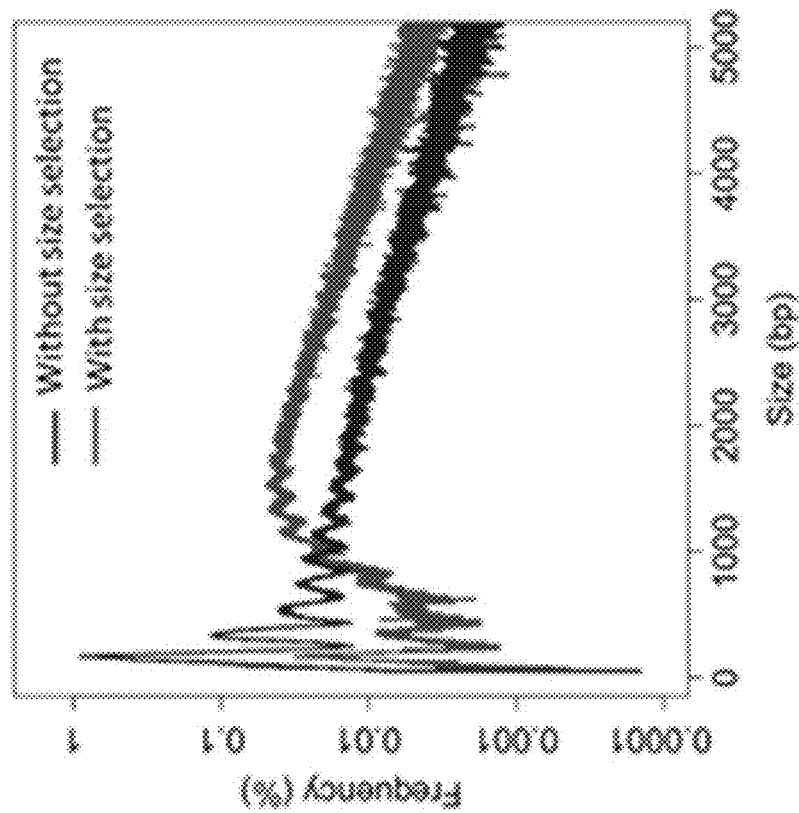
FIGS. 89A and 89B show graphs of plasma DNA size profiles for samples with and without bead-based size selection according to embodiments of the present invention.
Figure 89B:
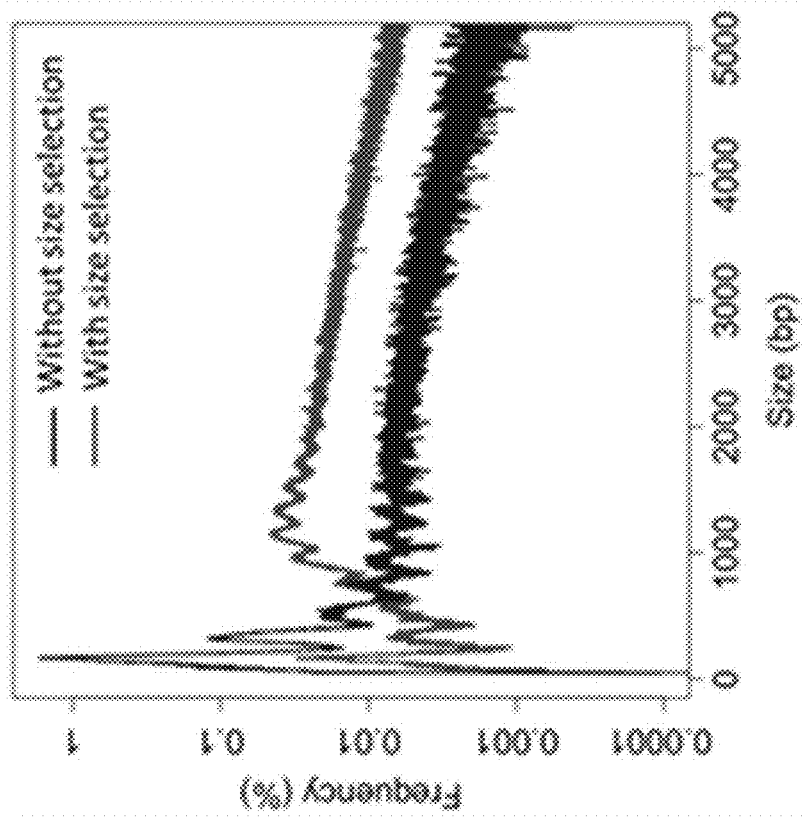

FIGS. 89A and 89B show size distributions for DNA samples from pregnant females with and without bead-based size selection. FIG. 89A shows sample 299, and FIG. 89B shows sample 300. The x-axis shows size of the fragments. The y-axis shows the frequency for each fragment size on a logarithmic scale. Higher frequencies were present across long DNA molecules above 1 kb in DNA samples after bead-based size selection. These data suggested that the bead-based size selection could enrich more long DNA molecules for downstream analysis. Such enrichment would make the analysis more cost effective through maximizing the number of long DNA molecules sequenced per sequencing run. Such enrichment of long DNA molecules would also improve the informativeness when analyzing the tissues of origin for each DNA molecule, as there would be more accessible CpG sites of each plasma DNA molecules for methylation pattern matching analysis. In one embodiment, the methylation analysis can be performed using the method described in U.S. application Ser. No. 16/995,607. The nucleosomal patterns were preserved in samples with size selection, suggesting that the size-selected plasma DNA molecules would be suited for studying nucleosome structures.

For sample 299, we obtained the genotype information for maternal buffy coat DNA and placenta DNA using microarray technology (Infinium Omni2.5). The sequenced plasma DNA molecules were differentiated into the maternal-specific and fetal-specific DNA molecules according to the genotype information.

Figure 90B:
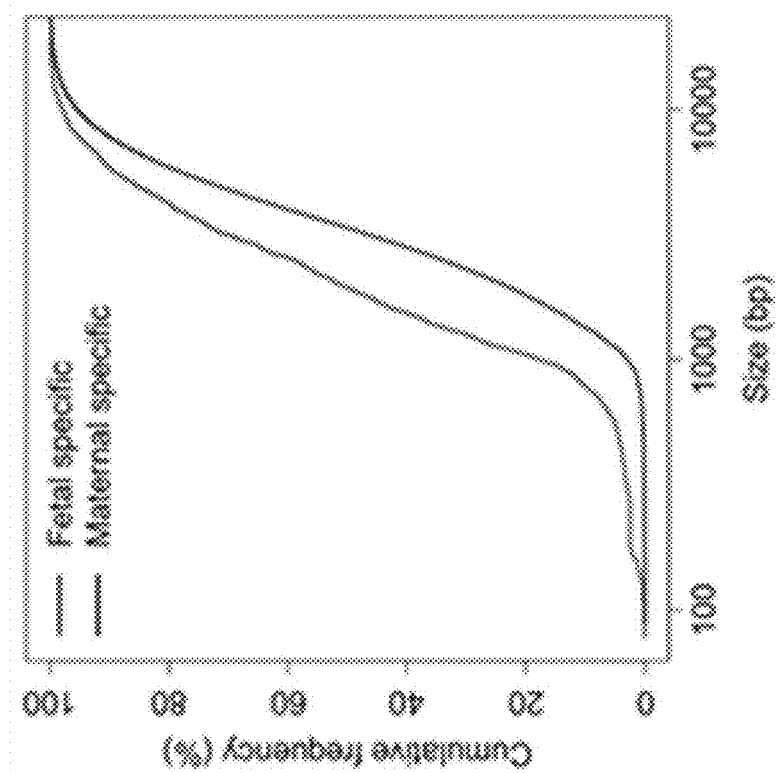
FIGS. 90A and 90B show size profiles between fetal and maternal DNA molecules in a sample with size selection according to embodiments of the present invention.
Figure 90A:
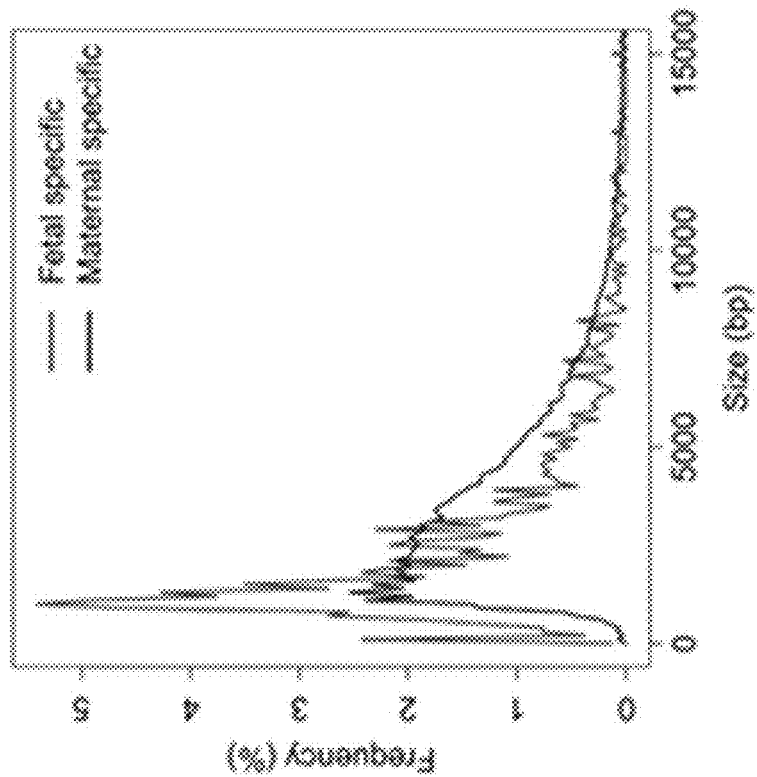

FIGS. 90A and 90B show the size distributions between fetal-specific and maternal-specific DNA molecules. The size is shown on the x-axis. In FIG. 90A, frequency is shown on the y-axis. In FIG. 90B, cumulative frequency is shown on the y-axis. In FIG. 90A, the fetal DNA size distribution showed higher frequencies in relative smaller molecules, in comparison with the maternal DNA size distribution. In FIG. 90B, such size shortening of fetal DNA molecule was shown in the cumulative frequency plot, i.e., the fetal DNA cumulative size distribution was located in the left hand of the maternal one.

C. Enhancing the Informativeness of Plasma DNA with Size Selection

In embodiments, informative SNPs could be defined by those SNPs that contain an allele specific to the fetal or maternal genome. Those SNPs provided a means for differentiating the fetal and maternal DNA molecules. We identified 419,539 informative SNPs. In other embodiments, informative SNPs could be defined by those SNPs that were heterozygous in the maternal genome. In other embodiments, informative SNPs could be defined by those SNPs in the maternal genome that were heterozygous and that were grouped together in the form of a haplotype.

FIG. 91 is a table of statistics for the number of plasma DNA molecules carrying informative SNPs between samples with and without size selection. The first column shows the sample identification and group. The second column shows the total number of plasma DNA molecules being analyzed. The third column shows the number of plasma DNA molecules carrying informative SNPs. The fourth column shows the percentage of plasma DNA molecules carrying informative SNPs.

As shown in FIG. 91, there was only 6.5% of plasma DNA molecules carrying informative SNPs in a sample without size selection, whereas the proportion of plasma DNA molecules carrying informative SNPs increased up to 20.6%. Thus, making use of size selection would greatly improve the yield of long DNA molecules suitable for the utilities present in this disclosure. We identified 260 fetal DNA molecules >500 bp in sample 299 without size selection, whereas 918 fetal DNA molecules >500 bp in the sample B299 with size selection. By normalizing the sequencing throughput, these data suggested that there was approximately a 3-fold enrichment in the obtaining fetal-specific DNA molecules >500 bp, by making use of bead-based size selection. Through the size selection, we would substantially increase the number of long fetal DNA molecules for analysis.

D. Methylation

FIG. 92 is a table of the methylation level in size-selected and non-size selected plasma DNA samples. The first column shows the sample identification. The second column shows the group. The third column shows the number of methylated CpG sites. The fourth column shows the number of unmethylated CpG sites. The fifth column shows the methylation level based on the number of methylated sites and total sites. As shown in FIG. 92, overall methylation level was shown to be higher in the size-selected samples compared to the corresponding non-selected samples (71.5% vs 69.1% for sample 299 and B299 in all CpG sites; 71.4% vs 69.3% for sample 300 and B300).

FIG. 93 is a table of methylation level in maternal- or fetal-specific cell-free DNA molecules. The first column shows the sample identification. The second column shows the group. The third column shows the number of methylated CpG sites. The fourth column shows the number of unmethylated CpG sites. The fifth column shows the methylation level based on the number of methylated sites and total sites.

As shown in FIG. 93, an increase in methylation level was also observed in both fetal-specific and maternal-specific plasma DNA molecules in the sample with size selection, when comparing with the sample without size selection. Those fetal-specific fragments tend to be hypomethylated compared to maternal-specific DNA molecules in plasma in both size-selected and non-size selected samples.

E. End Motifs

FIG. 94 is a table of the top 10 end motifs in samples with and without size selection. The first column shows the rank. The second through fifth columns are for samples without size selection. The sixth through ninth columns are for samples with size selection. The second row lists sample identifications. The second, fourth, sixth, and eighth columns list the end motif. The third, fifth, seventh, and ninth columns list the frequency of the end motif.

As shown in FIG. 94, without size selection, plasma DNA molecules sequenced by single molecule real-time sequencing displayed end motifs preferentially starting with C, suggesting a cleavage signature of the nuclease DNASE1L3 (Han et al., Am J Hum Genet 2020; 106: 202-214). In contrast, for those samples with size selection, plasma DNA sequenced by single molecule real-time sequencing carry end motifs predominately starting with A or G, suggesting a cleavage signature of the nuclease DFFB (Han et al. Am J Hum Genet 2020; 106: 202-214). These data suggested that the size selection would allow one to selectively enrich for plasma DNA molecules derived from different enzymatic processes in the fragmentation of cell-free DNA. Such selective targeting would be useful in the analysis, detection or monitoring of disorders associated with aberrant levels of one or more nucleases. In one embodiment, the size selection of plasma DNA would enhance the performance for monitoring DFFB activity or DFFB mediated DNA degradation kinetics.

In some embodiments, the DNA bound to beads enriching for long plasma DNA and the DNA retained in supernatant enriching for short plasma DNA were sequenced. The long DNA would be useful for constructing the haplotype information. The short plasma DNA would be useful for monitoring DNASE1L3 activity. In embodiments, one would perform a synergistic combined analysis of long and short DNA molecules. For example, aligning the short DNA plasma DNA to the maternal haplotypes (i.e., Hap I and Hap II), one maternal haplotype exhibiting more short DNA and/or more hypomethylation and/or relative higher dosage would be likely inherited by the fetus, comparing with the other haplotype.

In some embodiments, the size selection could be based on, but not limited to, gel electrophoresis-based technologies such as PippinHT DNA Size selection, BluePippin DNA Size Selection, Pippin Prep DNA Size Selection System, SageELF Whole Sample Fractionation System, Pippin Pulse Electrophoresis, SageHLS HMW Library System, etc.

Figure 95:
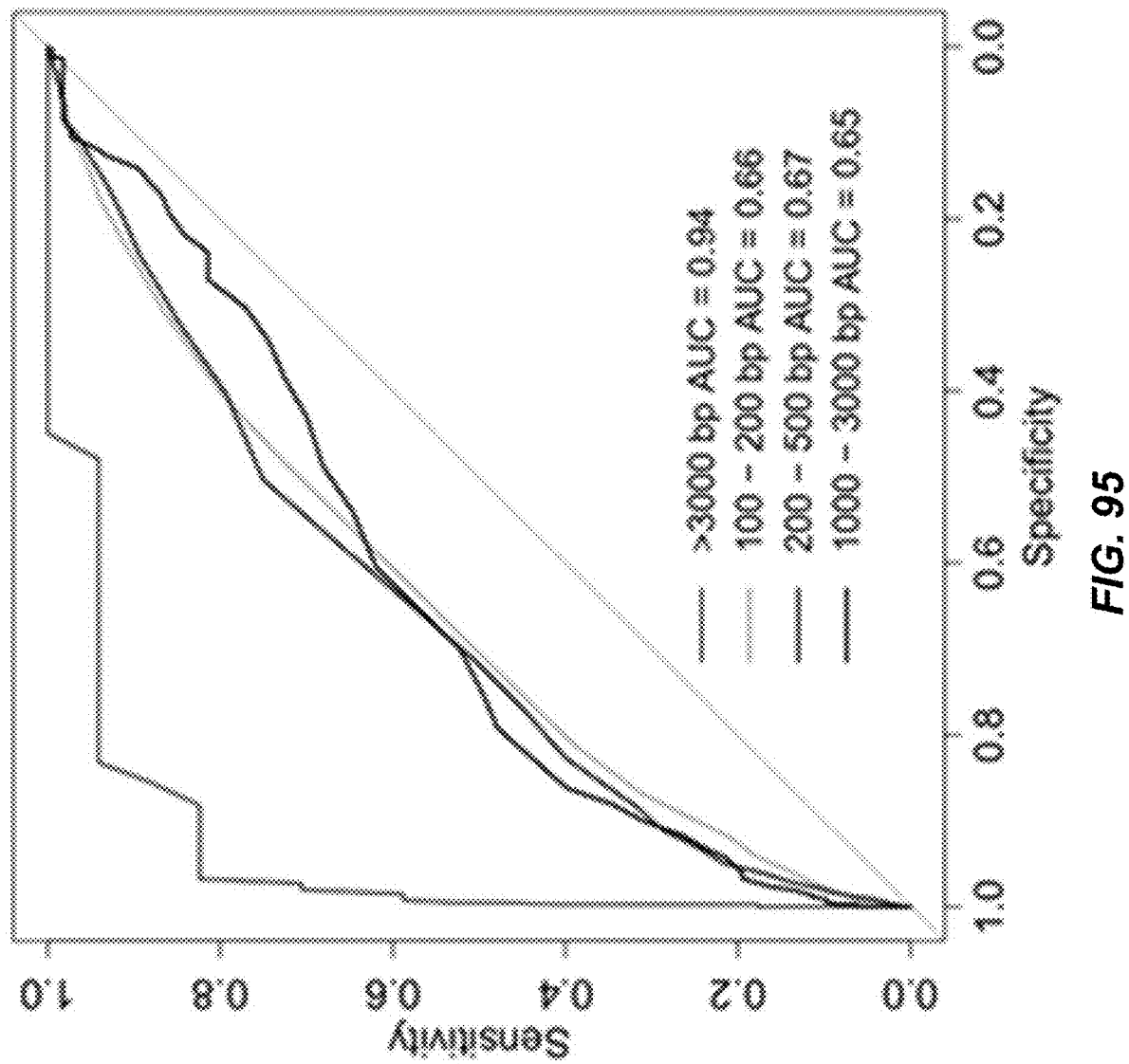
FIG. 95 is a receiver operating characteristic (ROC) graph showing that long plasma DNA molecules enhance the performance of tissue-of-origin analysis according to embodiments of the present invention.

F. Long Plasma DNA Molecules Enhance the Performance of Tissue-of-Origin Analysis FIG. 95 is a receiver operating characteristic (ROC) graph showing that long plasma DNA molecules enhance the performance of tissue-of-origin analysis. The y-axis shows sensitivity. The x-axis shows specificity. The different lines show results for different size fragments. The red line, with the highest area under the curve (AUC), is for fragments greater than 3,000 bp.

As shown in FIG. 95, when differentiating between fetal and maternal DNA molecules in plasma of pregnant women, the performance based on long plasma DNA molecules (e.g. >3000 bp) (AUC: 0.94) according to the embodiments in this disclosure was much higher than those analyses based on relatively short DNA molecules such as with 100-200 bp (AUC: 0.66) and 200-500 bp (AUC: 0.67). These data suggested that the use of long plasma DNA would greatly enhance the accuracy in differentiating the fetal and maternal DNA molecules, thus leading to a higher performance in determining the fetal inheritance in a noninvasive manner.

VII. Nanopore Sequencing for Long DNA Analysis of Maternal Plasma DNA

In addition to using single-molecule, real-time sequencing technology, nanopore sequencing may be used to sequence long cell-free DNA fragments from maternal plasma. Methylation and SNP information may improve the accuracy of nanopore sequencing of long cell-free DNA fragments.

Figure 96:
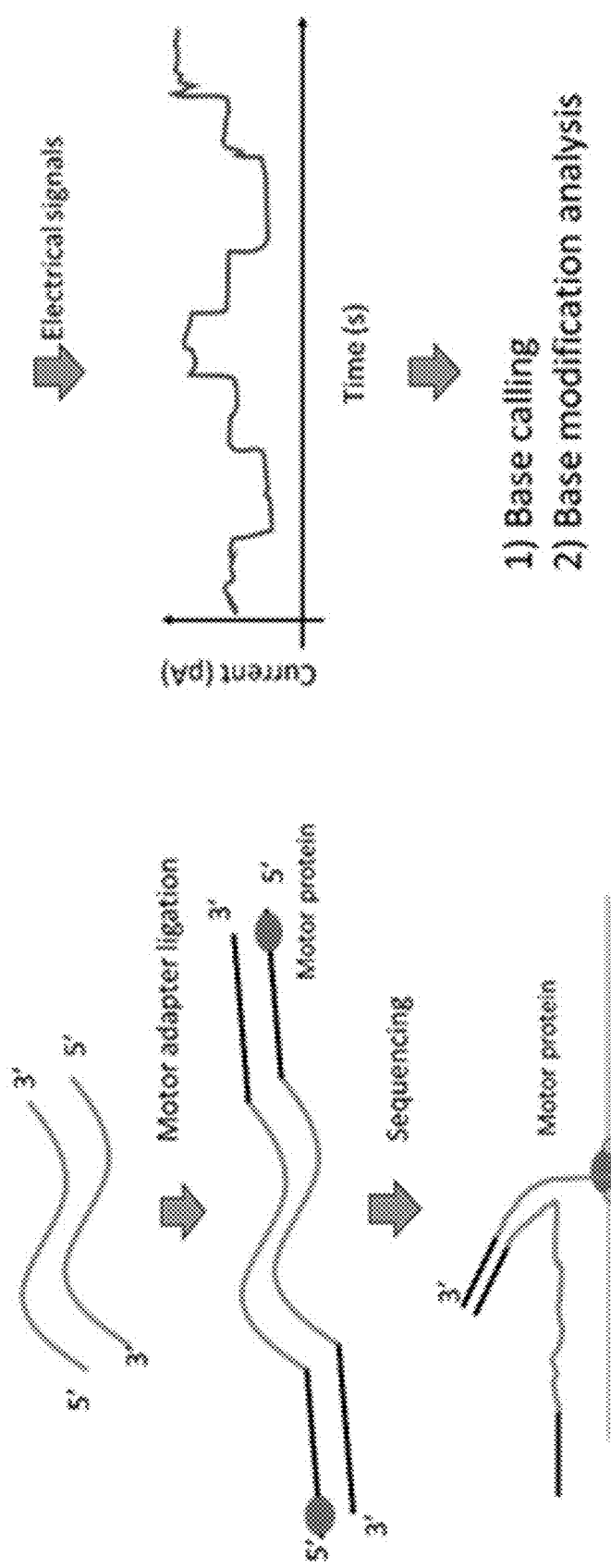
FIG. 96 illustrates the principle of an airport sequencing for plasma DNA molecules according to embodiments of the present invention.

FIG. 96 shows the principle for nanopore sequencing of plasma DNA obtained from a pregnant woman, in which the sequence of nucleic acids is inferred from changes in the ionic current across a membrane as a single DNA molecule passes through a pore of nanometer size. Such a pore may, for example but not limited to, be created by a protein (e.g. alpha hemolysin, aerolysin, and *Mycobacterium smegmatis* porin A (MspA)) or synthetic materials such as silicon or graphene (Magi et al, Brief Bioinform. 2018; 19:1256-1272). In embodiments, double-stranded plasma DNA molecules are subjected to an end-repair process. Such a process would convert plasma DNA into blunt-end DNA that is followed by addition of A tail. Sequence adapters each carrying a motor protein (i.e. motor adapter) are ligated to either end of a plasma DNA molecule, as shown in FIG. 96. The process of sequencing starts as the motor protein unwinds a double-stranded DNA, enabling the first strand to pass through the nanopore. When the DNA strand passes through the nanopore, a sensor measures the ionic current changes (pA) over time that depends on the sequence context and the associated base modifications (called 1D read). In other embodiments, hairpin sequence adaptors would be used for covalently tethering the first strand and the complementary strand together. During sequencing, a strand of a double-stranded DNA molecule is sequenced, followed by the complementary strand (called $1D^2$ or 2D read), which could potentially improve the sequencing accuracy. Raw current signals are used for base calling and base modification analyses. In other embodiments, the base calling and base modification analyses are conducted by means of a machine learning approach, for example but not limited to, recurrent neural network (RNN), or hidden Markov model (HMM). In this disclosure, we presented the methods for characterizing properties of plasma DNA molecules, including but not limited to, molecule counts, base compositions, molecular sizes, end motifs, and base modifications, using nanopore sequencing.

For illustrative purposes, we used nanopore sequencing (Oxford Nanopore Technologies) to sequence three maternal plasma DNA samples (M12970, M12985, and M12969) of pregnant women at a gestational age of 38 weeks. Plasma DNA extracted from 4 mL of maternal plasma was subjected to library preparation using Ligation Sequencing Kit (Oxford Nanopore). In brief, DNA was repaired with FFPE Repair Mix (NEB), then end-repaired and A-tailed with NEBNext End Prep module (NEB). Then, adapter mix was added to repaired DNA and ligated with blunt/TA master mix. After cleanup with AMPure XP beads (Beckman), the adaptor-ligated library was mixed with sequencing buffer and loading beads, and loaded onto PromethION R9 flow cell. The flow cell was sequenced on PromethION beta device (Oxford Nanopore) for 64 hours.

A. Alignment

The sequenced reads were aligned to a human reference genome (hg19) using Minimap2 (Li H, Bioinformatics. 2018; 34(18):3094-3100). In some embodiments, BLASR (Mark J Chaisson et al, BMC Bioinformatics. 2012; 13: 238), BLAST (Altschul S F et al, J Mol Biol. 1990; 215(3):403-410), BLAT (Kent W J, Genome Res. 2002; 12(4):656-664), BWA (Li H et al, Bioinformatics. 2010; 26(5):589-595), NGMLR (Sedlazeck F J et al, Nat Methods. 2018; 15(6):461-468), and LAST (Kielbasa S M et al, Genome Res. 2011; 21(3):487-493) could be used for aligning sequenced reads to a reference genome. We obtained 11.31, 12.30, and 21.28 million sequenced molecules for samples M12970, M12985 and M12969, respectively. Among them, the number of mapped fragments were 3.67, 2.63, and 4.33 million, respectively.

B. Size and Methylation

The number of nucleotides of a plasma DNA molecule determined by nanopore sequencing was used for deducing the size of that DNA molecule. The current signals of a DNA molecule could be used for determining base modifications. In embodiments, the methylation status for each CpG site was determined by the open-source software Nanopolish (Simpson et al, Nat Methods. 2017; 14:407-410). In another embodiment, the methylation status could be determined by using other software including but not limited to DeepMod (Liu et al, Nat Commun. 2019; 10:2449), Tomo (Stoiber et al, BioRxiv. 2017:p. 094672), DeepSignal (Ni et al, Bioinformatics. 2019; 35:4586-4595), Guppy (github.com/nanoporetech), Megalodon (github.com/nanoporetech/megalodon), etc.

FIG. 97 is a table of the percentage of the plasma DNA molecules in a particular size range and their corresponding methylation levels. Three samples are shown: M12970, M12985, and M12969. The first column shows the fragment size. The second column shows the number of fragments of that fragment size. The third column shows the frequency of the fragment size. The fourth column shows the number of methylated CpG sites of the fragment size. The fifth column shows the number of unmethylated CpG sites of the fragment size. The sixth column shows the methylation level as a percentage.

As shown in FIG. 97, the proportions of DNA molecules with a size of ≥500 bp were 16.6%, 7.6% and 12.6% for samples M12970, M12985 and M12969, respectively. The proportion of DNA molecules with a size of ≥500 bp was much higher than data generated by Illumina sequencing (0.2%). The methylation levels of DNA molecules with a size of ≥500 bp were 64.12%, 65.05%, and 63.30% for samples M12970, M12985, and M12969, respectively. In addition, the methylation level increased in the population with more long plasma DNA. As an example, for sample M12970, the methylation level was 70.7% in those molecules with a size of ≥2000 bp, which was equivalent to a 10.3% increase of methylation level relative to those with a size of ≥500 bp. A similar increasing trend in the population with more long DNA was also observed in sample M12985 and M12969. The plasma DNA molecules with different sizes would reflect different pathways which contributed cell-free DNA into the blood circulation, such as but not limited to, senescence, apoptosis, necrosis, active secretion etc. The methylation status of a long DNA molecule would further allow one to infer the tissues of origin of those long DNA molecules. Therefore, combined analysis of long DNA molecule fragmentation patterns and methylation patterns would allow one to infer the relative ratios of senescence, apoptosis, necrosis and active secretion for a particular organ. The relative ratios of cell-free DNA generations by different pathways would reflect the underlying pathophysiological conditions such as pregnancy, preeclampsia, premature birth, intrauterine growth restriction, etc.

Figure 98:
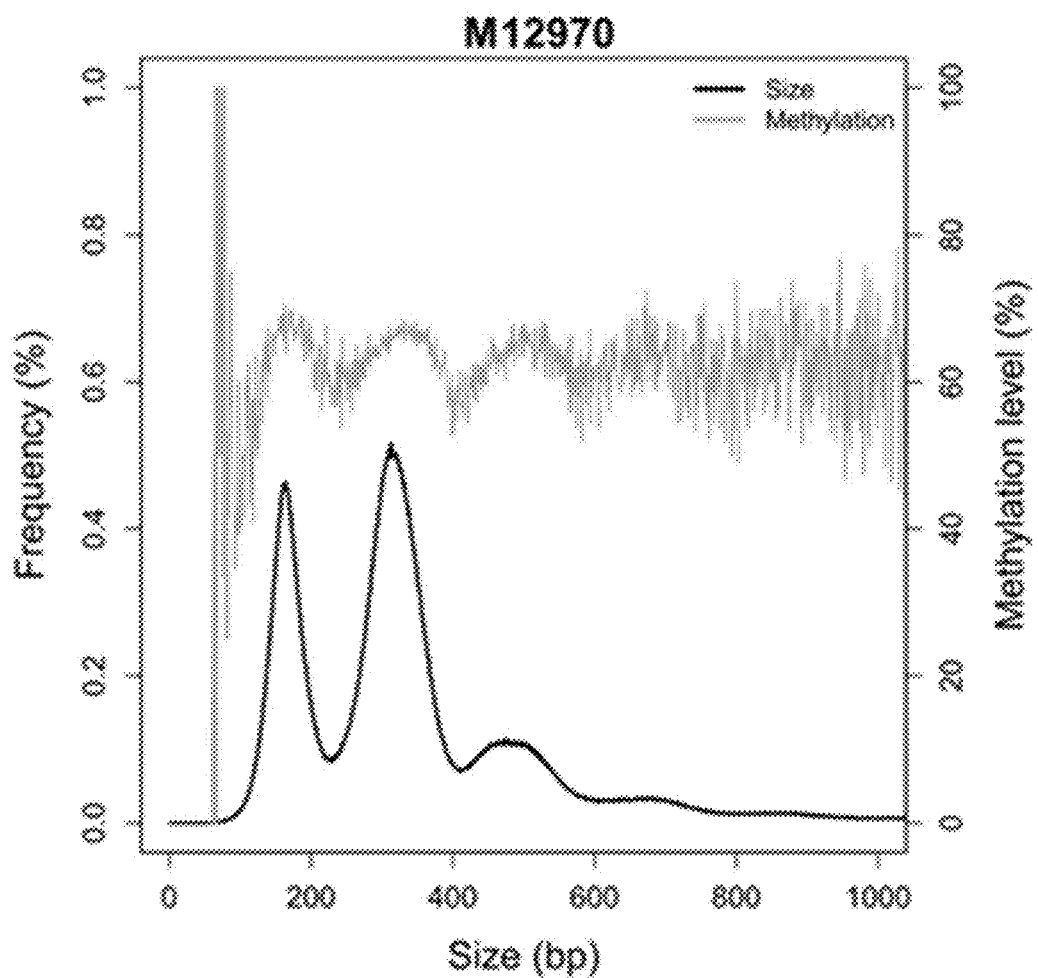
FIG. 98 is a graph of the size distribution and methylation patterns across different sizes according to embodiments of the present invention.

FIG. 98 is a graph of the size distribution and methylation patterns across different sizes. Size is shown on the x-axis. Frequency is shown on the left y-axis. Methylation level is shown on the right y-axis. The size distribution (frequency) data is shown as a black line. The methylation level shown is shown as a yellow line.

FIG. 98 shows the size distribution and the methylation levels across different fragment sizes. The size distribution harbored multiple peaks at 164 bp, 313 bp, and 473 bp, with an average interval of 154 bp. Such patterns of size distribution were reminiscent of nuclease-cleaved nucleosomes, suggesting that the nonrandom process of plasma DNA fragmentation could be identified by nanopore sequencing. In contrast to the plasma DNA size patterns with a major peak at 166 bp based on Illumina sequencing data, the major peak was at 380 bp. These data indicated that nanopore sequencing would enrich more long DNA fragments. Such a characteristic of nanopore sequencing of plasma DNA would be particularly useful for detecting those variants that were hard to be solved by short-read sequencing technologies. In embodiments, nanopore sequencing would be useful for analyzing a triplet repeat expansion. The number of trinucleotide repeats would be used for predicting the progression, severity and age of onset of trinucleotide repeat disorders such as fragile X syndrome, Huntington's disease, spinocerebellar ataxias, myotonic dystrophy and Friedreich's ataxia. FIG. 98 also shows the methylation levels varied according to different sizes. A series of methylation peak values coincided with the peaks in size distribution.

C. Fetal and Maternal DNA

By genotyping DNA extracted from the maternal buffy coat and the placenta using the iScan platform (Illumina), we identified a median of 204,410 informative SNPs (range: 199,420-205,597) for which the mother was homozygous (AA) and the fetus was heterozygous (AB), which were used for determining the fetal-specific alleles (B) and the shared alleles (A).

FIG. 99 is a table of the fetal DNA fraction determined using nanopore sequencing. The first column shows the sample identifier. The second column shows the number of molecules carrying shared alleles. The third column shows the number of molecules carrying fetal-specific alleles. The fourth column shows the fetal DNA fraction, calculated by the value in the third column multiplied by two and divided by the sum of the second column and the third column. As shown in FIG. 99, we identified 84,911, 52,059 and 95,273 molecules carrying shared alleles and 17,776, 7,385 and 17,007 molecules carrying fetal-specific alleles for samples M12970, M12985 and M12969, respectively. The fetal DNA fractions were determined to be 34.6%, 24.9% and 30.3% for samples M12970, M12985 and M12969, respectively. In addition, we identified a median of 212,330 informative SNPs (range: 210,411-214,744) for which the mother was heterozygous (AB) and the fetus was homozygous (AA), which were used for determining the maternal-specific alleles (B). We identified 65,349, 34,017 and 65,481 molecules carrying shared alleles, and 43,594, 26,704 and 48,337 molecules carrying maternal-specific alleles for samples M12970, M12985 and M12969, respectively.

FIG. 100 is a table of the methylation levels between fetal-specific and maternal-specific DNA molecules. The first column shows the sample identifier. The second, third, and fourth column show results for fetal-specific DNA. The fifth, sixth, and seventh columns show results for maternal-specific DNA. The second and fifth columns show the number of methylated CpG sites. The third and sixth columns show the number of unmethylated CpG sites. The fourth and seventh columns show the methylation level based on the percentage of methylated sites.

According to the embodiments in this disclosure, the methylation patterns for each fetal-specific DNA molecule were determined. The proportion of sequenced CpG sites determined to be methylated (i.e., overall methylation levels) were to be 62.43%, 62.39%, and 61.48% for samples M12970, M12985 and M12969, respectively, as shown in FIG. 100. Such overall methylation levels of fetal-specific DNA were on average 8% lower than the counterparts of maternal-specific DNA. These results suggested that one would be able to differentiate fetal DNA molecules from the maternal DNA molecules based on differential methylation patterns between fetal and maternal DNA molecules according to the embodiments in this disclosure using the nanopore sequencing results.

FIG. 101 is a table of the percentages of the plasma DNA molecules in a particular size range and their corresponding methylation levels for fetal and maternal DNA molecules. Three samples are shown: M12970, M12985, and M12969. The first column shows the fragment size. The second through sixth columns show results for fetal-specific DNA. The seventh through eleventh columns show results for maternal-specific DNA. The second and seventh columns show the number of fragments of that fragment size. The third and eighth columns show the frequency of the fragment size. The fourth and ninth columns show the number of methylated CpG sites of the fragment size. The fifth and tenth columns shows the number of unmethylated CpG sites of the fragment size. The sixth and eleventh columns show the methylation level as a percentage.

As seen in FIG. 101, the properties of fetal-specific and maternal-specific DNA molecules were analyzed with different size ranges, including but not limited to, ≥500 bp, ≥600 bp, ≥1000 bp and ≥2000 bp. Compared with maternal DNA molecules, we obtained a relatively smaller proportion of fetal DNA molecules above 1 kb in size. However, the amount of such long fetal DNA molecules (e.g. ≥1000 bp) in the plasma of pregnant women (range: 4.9%-9.3%) was significantly higher than the expected value by Illumina sequencing (<0.2%). Such long fetal DNA fragments are not readily revealed in conventional short-read sequencing technologies such as Illumina sequencing platforms (for example but not limited to MiSeq, NextSeq, HiSeq, NovaSeq, etc) as the insert sizes of DNA library are restricted to be less than 550 bp (e.g. Illumina NextSeq system, support.illumina.com/sequencing/sequencing_instruments/nextseq-550/questions.html). In embodiments, the analysis of long fetal and maternal DNA fragments, including but not limited to sizes and methylation profiles, could provide a new tool for assessing different diseases. For example, DNASE1L3 deficiency causes monogenic systemic lupus erythematosus. Such DNASE1L3 deficiency would result in the generation of more long DNA molecules (Chan et al, Am J Hum Genet. 2020; 107:882-894). Thus, embodiments described herein would be particularly sensitive to monitor the disease severity of those patients during pregnancy and assess whether the unborn fetus would be affected by the same condition by analyzing the characteristics of those long DNA molecules.

Figure 102A:
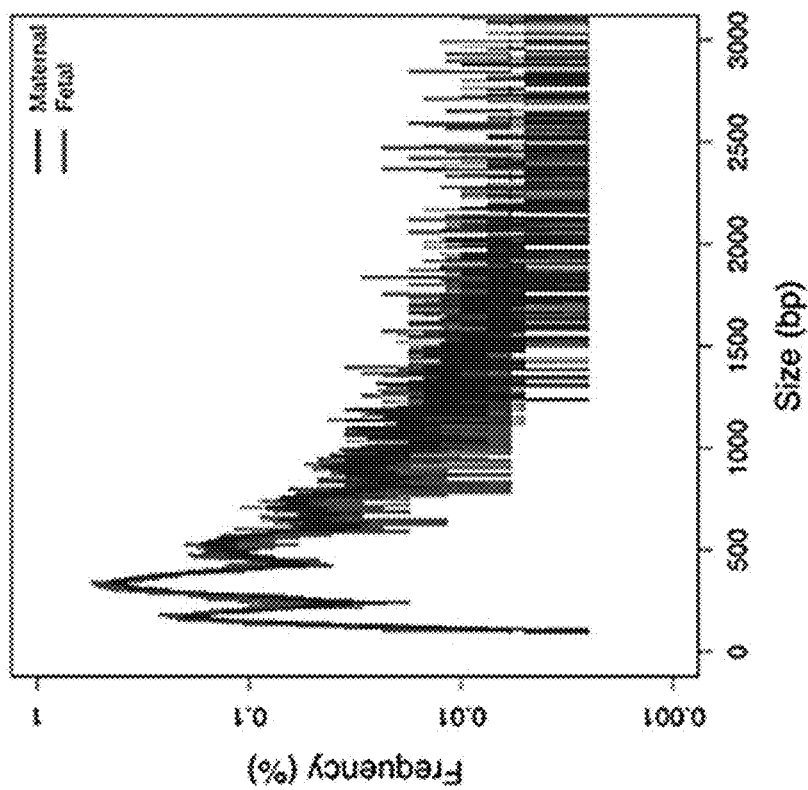
FIGS. 102A and 102B are graphs of the size distributions of fetal and maternal DNA molecules determined by nanopore sequencing according to embodiments of the present invention.
Figure 102B:
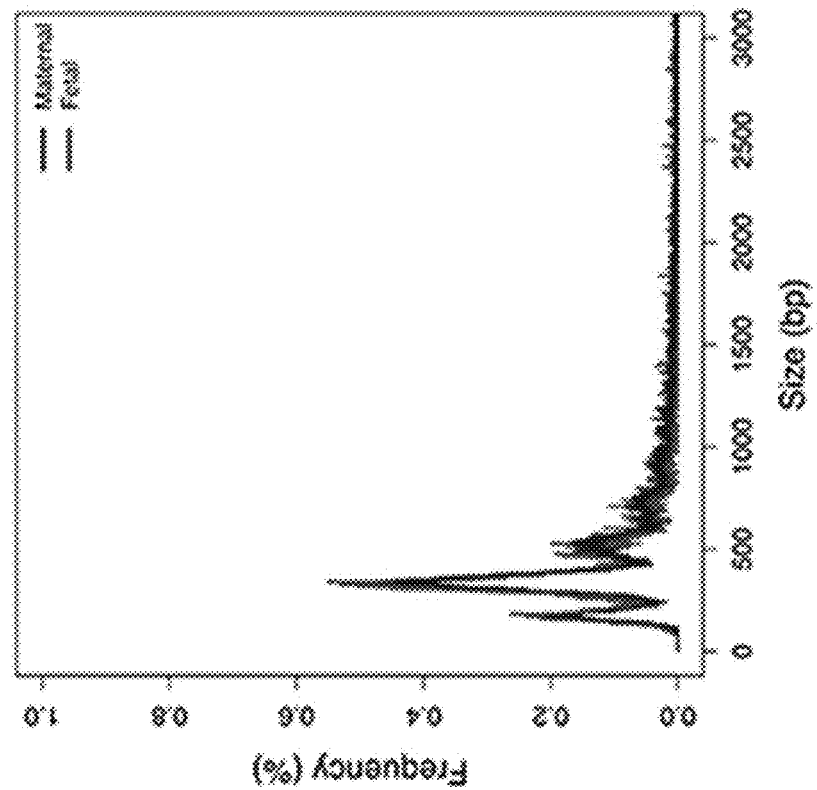

FIGS. 102A and 102B are graphs of the size distributions of fetal and maternal DNA molecules determined by nanopore sequencing. The size of the fragments is shown on the x-axis. The frequency is shown on the y-axis in a linear scale in FIG. 102A and a logarithmic scale in FIG. 102B. The maternal DNA is shown with a blue line. The fetal DNA is shown with a red line.

As shown in FIGS. 102A and 102B, both maternal and fetal DNA molecules contained more long DNA molecules than previously reported (Lo et al, Sci Transl Med. 2020; 2:61ra91) in an Illumina short-read sequencing platform. These results suggested that the analysis of plasma DNA by nanopore sequencing revealed a set of new characteristics of cell-free DNA that was not appreciated before. Such characteristics can be used in noninvasive prenatal testing.

D. Improved Accuracy for the Determination of Fetal and Maternal DNA Molecules As nanopore sequencing would be accompanied by a higher sequencing error (between ~5% and 40%) (Goodwin et al, Genome Res. 2015; 25:1750-1756), it may cause an inaccurate classification of fetal and maternal DNA molecules based on SNP genotype information. In embodiments, one could use two or more informative SNPs to score a fragment and determine whether that fragment was derived from the placenta or not. For example, for a fragment carrying two informative SNPs for which the mother was homozygous (AA) and the fetus was heterozygous (AB), only when two informative SNPs both supported a conclusion that such a fragment was originating from the fetus, it would be determined to be of fetal origin. Similarly, for a fragment carrying two informative SNPs, only when two informative SNPs both supported that such a fragment was originating from the mother, it would be determined to be of maternal origin.

Figure 103:
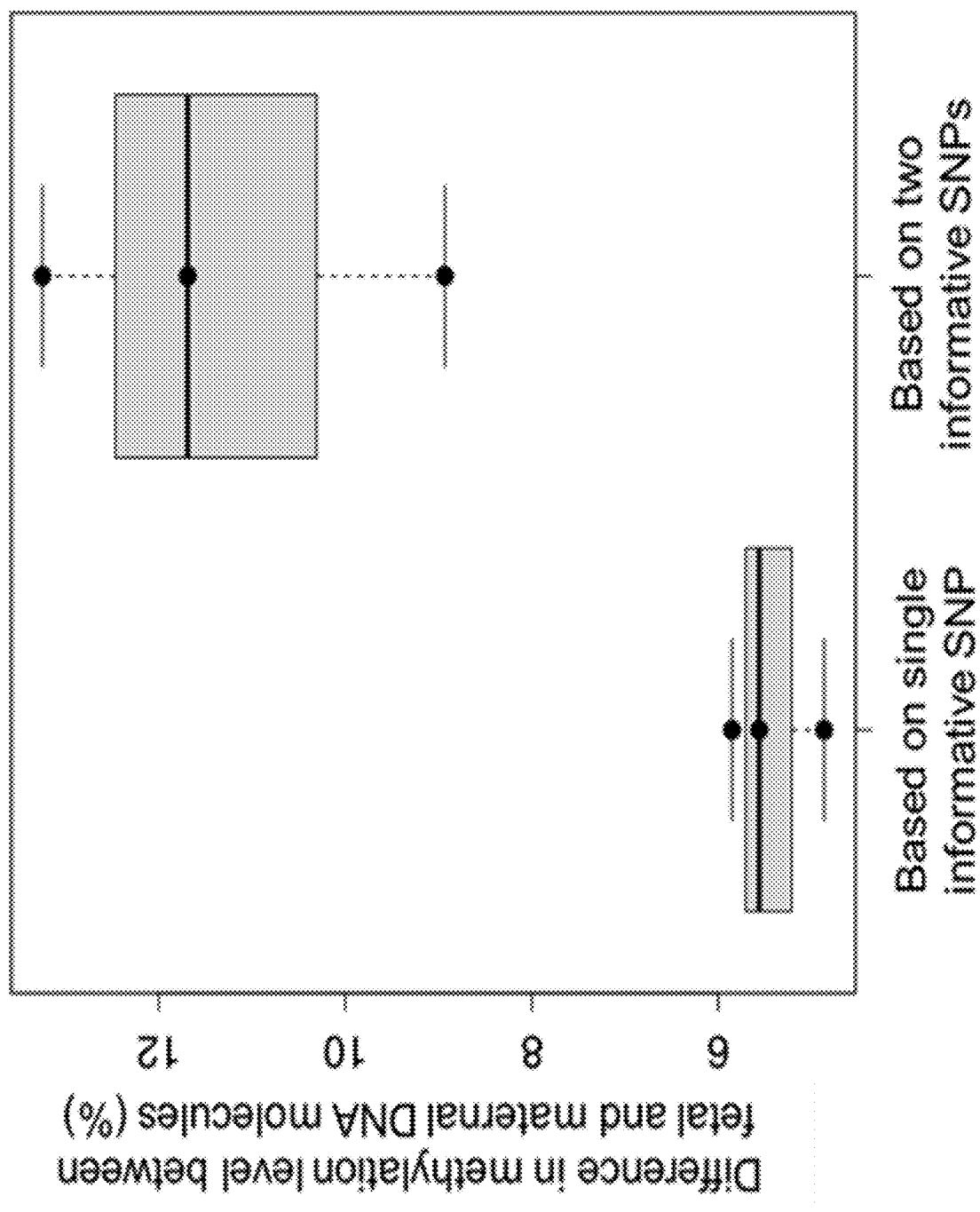
FIG. 103 is a graph showing the difference in methylation levels between fetal and maternal DNA molecules on the basis of single informative SNP and two informative SNPs according to embodiments of the present invention.

FIG. 103 is a graph showing the difference in methylation levels between fetal and maternal DNA molecules on the basis of single informative SNP and two informative SNPs. The y-axis shows the difference in methylation level as a percentage between fetal and maternal DNA molecules. The x-axis shows using a single informative SNP versus using two informative SNPs for the difference in methylation levels.

As shown in FIG. 103, using two informative SNPs to differentiate the fetal and maternal DNA molecules, the difference in methylation levels between fetal and maternal DNA molecules was much larger than the results based on one informative SNP. The mean difference in methylation level between fetal-specific and maternal-specific molecules increased from 5.4% to 11.3%, equivalent to a 109% increment. These results suggested that the use of multiple SNPs would greatly improve the accuracy for differentiating fetal-specific and maternal-specific DNA molecules.

FIG. 104 is a table of the difference in methylation levels between fetal and maternal DNA molecules. The first column shows the sample identifier. The second, third, and fourth column show results for fetal-specific DNA. The fifth, sixth, and seventh columns show results for maternal-specific DNA. The second and fifth columns show the number of methylated CpG sites. The third and sixth columns show the number of unmethylated CpG sites. The fourth and seventh columns show the methylation level based on the percentage of methylated sites.

As seen in FIG. 104, such overall methylation levels of fetal-specific DNA were on average 16.3% lower than the counterparts of maternal-specific DNA. In embodiments, the use of methylation signals would in turn enhance the accuracy of fetal and maternal DNA classification. For example, for a fragment carrying a putative fetal-specific allele, when the methylation level of that fragment was determined to be lower than a threshold, such a fragment would have a higher likelihood of being derived from the fetus. Such a threshold could be, but not limited to, 60%, 50%, 40%, 30%, 20%, 10%, etc. For a fragment carrying a putative maternal-specific allele, when the methylation level of that fragment was determined to be higher than a threshold, such a fragment would have a higher likelihood of being derived from the mother. Such a threshold could be, but not limited to, 90%, 80%, 70%, 60%, 50%, 40%, etc.

In some other embodiments, the total number of informative SNPs would be required to be at least, for example but not limited to, 3, 4, 5, 6, 7, 8, 9, 10, etc. The number of informative SNPs supporting a fragment originating from the fetus would be required to be at least, for example but not limited to, 3, 4, 5, 6, 7, 8, 9, 10, etc. The number of informative SNPs supporting a fragment originating from the mother would be required to be at least, for example but not limited to, 3, 4, 5, 6, 7, 8, 9, 10, etc. In embodiments, the percentage of informative SNPs supporting a fragment originating from the fetus would be required to reach a certain threshold, for example, 1%, 5%, 10%, 20%, 30%, 40%, 50%, 60%, 70%, 80%, 90%, or 100%. The percentage of informative SNPs supporting a fragment originating from the mother would be required to reach a certain threshold, for example, 1%, 5%, 10%, 20%, 30%, 40%, 50%, 60%, 70%, 80%, 90%, or 100%.

In some other embodiments, one could circularize plasma DNA molecules, followed by the rolling-circle amplification. The amplified DNA could be sequenced by nanopore sequencing, thus the template DNA information could be sequenced multiple times. The consensus sequence could be deduced from the repeatedly sequenced information.

VIII. Example Systems

Figure 105:
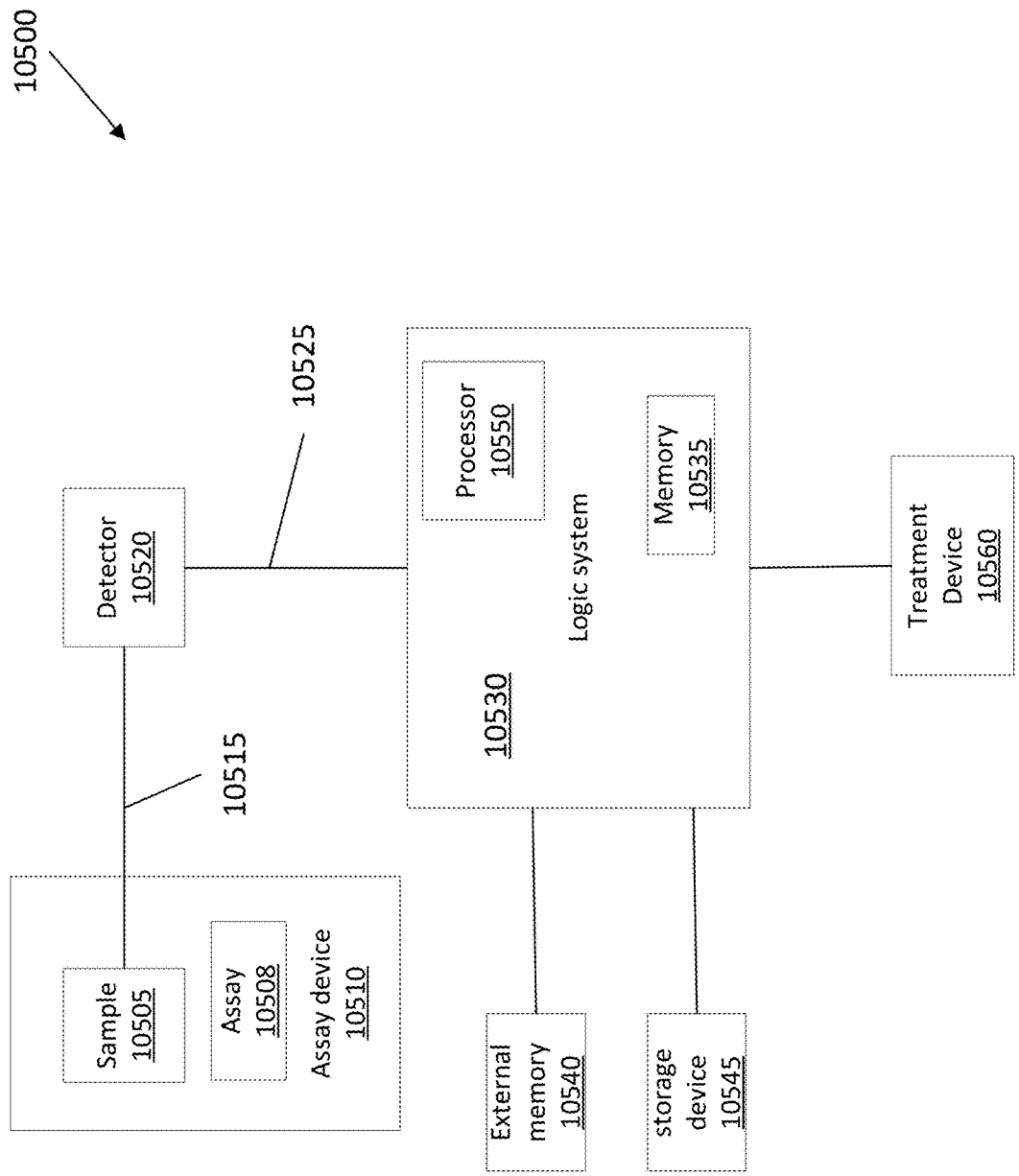
FIG. 105 illustrates a measurement system according to embodiments of the present invention.

FIG. 105 illustrates a measurement system 10500 according to an embodiment of the present disclosure. The system as shown includes a sample 10505, such as cell-free DNA molecules within an assay device 10510, where an assay 10508 can be performed on sample 10505. For example, sample 10505 can be contacted with reagents of assay 10508 to provide a signal of a physical characteristic 10515. An example of an assay device can be a flow cell that includes probes and/or primers of an assay or a tube through which a droplet moves (with the droplet including the assay). Physical characteristic 10515 (e.g., a fluorescence intensity, a voltage, or a current), from the sample is detected by detector 10520. Detector 10520 can take a measurement at intervals (e.g., periodic intervals) to obtain data points that make up a data signal. In one embodiment, an analog-to-digital converter converts an analog signal from the detector into digital form at a plurality of times. Assay device 10510 and detector 10520 can form an assay system, e.g., a sequencing system that performs sequencing according to embodiments described herein. A data signal 10525 is sent from detector 10520 to logic system 10530. As an example, data signal 10525 can be used to determine sequences and/or locations in a reference genome of DNA molecules. Data signal 10525 can include various measurements made at a same time, e.g., different colors of fluorescent dyes or different electrical signals for different molecule of sample 10505, and thus data signal 10525 can correspond to multiple signals. Data signal 10525 may be stored in a local memory 10535, an external memory 10540, or a storage device 10545.

Logic system 10530 may be, or may include, a computer system, ASIC, microprocessor, graphics processing unit (GPU), etc. It may also include or be coupled with a display (e.g., monitor, LED display, etc.) and a user input device (e.g., mouse, keyboard, buttons, etc.). Logic system 10530 and the other components may be part of a stand-alone or network connected computer system, or they may be directly attached to or incorporated in a device (e.g., a sequencing device) that includes detector 10520 and/or assay device 10510. Logic system 10530 may also include software that executes in a processor 10550. Logic system 10530 may include a computer readable medium storing instructions for controlling measurement system 10500 to perform any of the methods described herein. For example, logic system 10530 can provide commands to a system that includes assay device 10510 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Measurement system 10500 may also include a treatment device 10560, which can provide a treatment to the subject. Treatment device 10560 can determine a treatment and/or be used to perform a treatment. Examples of such treatment can include surgery, radiation therapy, chemotherapy, immunotherapy, targeted therapy, hormone therapy, and stem cell transplant. Logic system 10530 may be connected to treatment device 10560, e.g., to provide results of a method described herein. The treatment device may receive inputs from other devices, such as an imaging device and user inputs (e.g., to control the treatment, such as controls over a robotic system).

Figure 106:
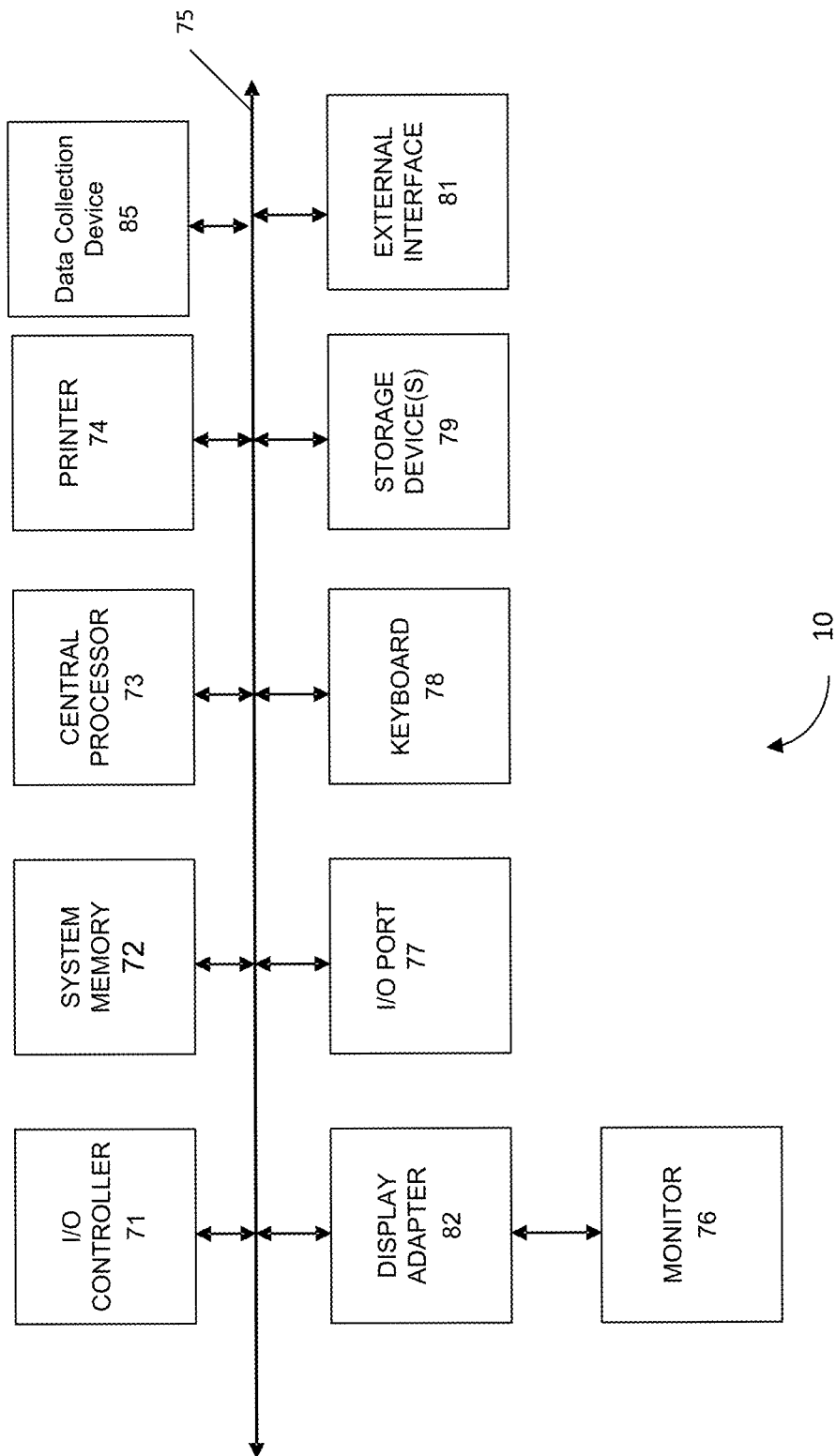
FIG. 106 shows a computer system according to embodiments of the present invention.

Any of the computer systems mentioned herein may utilize any suitable number of subsystems. Examples of such subsystems are shown in FIG. 106 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 106 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order that is logically possible. Additionally, portions of these steps may be used with portions of other steps from other methods. Also, all or portions of a step may be optional. Additionally, any of the steps of any of the methods can be performed with modules, units, circuits, or other means of a system for performing these steps.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The above description of example embodiments of the present disclosure has been presented for the purposes of illustration and description and are set forth so as to provide those of ordinary skill in the art with a complete disclosure and description of how to make and use embodiments of the present disclosure. It is not intended to be exhaustive or to limit the disclosure to the precise form described nor are they intended to represent that the experiments are all or the only experiments performed. Although the disclosure has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the disclosure being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

The claims may be drafted to exclude any element which may be optional. As such, this statement is intended to serve as antecedent basis for use of such exclusive terminology as "solely", "only", and the like in connection with the recitation of claim elements, or the use of a "negative" limitation.

All patents, patent applications, publications, and descriptions mentioned herein are hereby incorporated by reference in their entirety for all purposes as if each individual publication or patent were specifically and individually indicated to be incorporated by reference and are incorporated herein by reference to disclose and describe the methods and/or materials in connection with which the publications are cited. None is admitted to be prior art.

What is claimed is:

1. A method of analyzing a biological sample obtained from a female pregnant with a fetus, the biological sample including a plurality of cell-free DNA molecules from the fetus and the female, the method comprising:
measuring sizes of the plurality of cell-free DNA molecules;
measuring a first amount of cell-free DNA molecules having sizes greater than a cutoff value, wherein the cutoff value is at least 500 nt;
generating a first value of a normalized parameter using the first amount;
obtaining a second value corresponding to an expected value of the normalized parameter for a healthy pregnancy, wherein the second value is dependent on a gestational age of the fetus;
determining a deviation between the first value of the normalized parameter and the second value of the normalized parameter; and
determining a classification of a likelihood of a pregnancy-associated disorder using the deviation.

2. The method of claim 1, wherein obtaining the second value comprises:
obtaining the second value from a calibration table relating measurements of pregnant females with calibration values of the normalized parameter, wherein the calibration table is generated by:
obtaining a first table relating gestational ages with the measurements of pregnant female subjects,
obtaining a second table relating gestational ages with calibration values of the normalized parameter, and
creating the calibration table relating the measurements with the calibration values from the first table and the second table.

3. The method of claim 2, wherein the measurements of the pregnant female subjects are the time since the last menstrual period.

4. The method of claim 2, wherein the measurements of the pregnant female subjects are characteristics of images of the pregnant female subjects.

5. The method of claim 4, wherein characteristics of the image comprise length, size, appearance, or anatomy of a fetus of the female subject.

6. The method of claim 1, wherein the pregnancy-associated disorder comprises preeclampsia, intrauterine growth restriction, invasive placentation, pre-term birth, hemolytic disease of the newborn, placental insufficiency, hydrops fetalis, fetal malformation, hemolysis, elevated liver enzymes, and a low platelet count (HELLP) syndrome, or systemic lupus erythematosus.

7. The method of claim 1, wherein the cutoff value is 600 nt or more.

8. The method of claim 1, wherein the cutoff value is 1,000 nt or more.

9. The method of claim 1, wherein the first amount is a number or a frequency.

10. The method of claim 1, wherein generating the value of the normalized parameter using the first amount comprises:
measuring a second amount of cell-free DNA molecules including sizes less than the cutoff value; and
calculating a ratio of the first amount and the second amount.

11. The method of claim 10, wherein:
the cutoff value is a first cutoff value,
a second cutoff value is less than the first cutoff value, and the second amount comprises cell-free DNA molecules having sizes less than the second cutoff value or the second amount comprises all cell-free DNA molecules in the plurality of cell-free DNA molecules.

12. The method of claim 1, wherein:
the plurality of cell-free DNA molecules is enriched for sizes greater than or equal to the cutoff value relative to the biological sample, wherein over 20% of the cell-free DNA molecules in the biological sample have sizes greater than 200 nt.

13. The method of claim 12, further comprising:
enriching for the plurality of cell-free DNA molecules using electrophoresis.

14. The method of claim 12, further comprising:
enriching for the plurality of cell-free DNA molecules using magnetic beads to selectively bind cell-free DNA molecules based on size.

15. The method of claim 12, further comprising:
enriching for the plurality of cell-free DNA molecules using hybridization, immunoprecipitation, amplification or CRISPR.

16. The method of claim 12, further comprising enriching the biological sample for sizes greater than 500 nt.

17. The method of claim 1, wherein the plurality of cell-free DNA molecules is enriched for a methylation profile relative to the biological sample,
the method further comprising:
enriching for the plurality of cell-free DNA molecules using immunoprecipitation.

18. The method of claim 1, wherein the classification is that the pregnancy-associated disorder exists, the method further comprising treating the fetus or the female for the pregnancy-associated disorder.

19. The method of claim 1, wherein the plurality of cell-free DNA molecules comprises at least 10,000 molecules.

20. The method of claim 1, further comprising receiving reads corresponding to the plurality of cell-free DNA molecules, wherein the reads are obtained by single molecule sequencing.

21. The method of claim 20, wherein the single molecule sequencing comprises optical monitoring of a DNA polymerase incorporating a new base into a complementary strand of a cell-free DNA molecule of the plurality of cell-free DNA molecules.

22. A computer product comprising a non-transitory computer readable medium storing instructions that, when executed, control a computing system to perform a method of analyzing a biological sample obtained from a female pregnant with a fetus, the biological sample including a plurality of cell-free DNA molecules from the fetus and the female, the method comprising:
measuring sizes of the plurality of cell-free DNA molecules;
measuring a first amount of cell-free DNA molecules having sizes greater than a cutoff value, wherein the cutoff value is at least 500 nt;
generating a first value of a normalized parameter using the first amount;
obtaining a second value corresponding to an expected value of the normalized parameter for a healthy pregnancy, wherein the second value is dependent on a gestational age of the fetus;
determining a deviation between the first value of the normalized parameter and the second value of the normalized parameter; and
determining a classification of a likelihood of a pregnancy-associated disorder using the deviation.

\* \* \* \* \*

SEQUENCE LISTING

```
<160> NUMBER OF SEQ ID NOS: 93

<210> SEQ ID NO 1
<211> LENGTH: 600
<212> TYPE: DNA
<213> ORGANISM: Homo sapiens
<220> FEATURE:
<221> NAME/KEY: misc_feature
<222> LOCATION: (1)..(600)
<223> OTHER INFORMATION: This sequence may encompass 55-200 "cgg"
      repeating units

<400> SEQUENCE: 1
cggcggcggc ggcggcggcg gcggcggcgg cggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
cggcggcggc ggcggcggcg gcggcggcgg cggcggcggc ggcggcggcg gcggcggcgg     240
cggcggcggc ggcggcggcg gcggcggcgg cggcggcggc ggcggcggcg gcggcggcgg     300
cggcggcggc ggcggcggcg gcggcggcgg cggcggcggc ggcggcggcg gcggcggcgg     360
cggcggcggc ggcggcggcg gcggcggcgg cggcggcggc ggcggcggcg gcggcggcgg     420
```

| | |
|---|---|
| cggcggcggc ggcggcggcg gcggcggcgg cggcggcggc ggcggcggcg gcggcggcgg | 480 |
| cggcggcggc ggcggcggcg gcggcggcgg cggcggcggc ggcggcggcg gcggcggcgg | 540 |
| cggcggcggc ggcggcggcg gcggcggcgg cggcggcggc ggcggcggcg gcggcggcgg | 600 |

<210> SEQ ID NO 2
<211> LENGTH: 600
<212> TYPE: DNA
<213> ORGANISM: Homo sapiens
<220> FEATURE:
<223> OTHER INFORMATION: See specification as filed for detailed
      description of substitutions and preferred embodiments

<400> SEQUENCE: 2

| | |
|---|---|
| cggcggcggc ggcggcggcg gcggcggcgg cggcggcggc ggcggcggcg gcggcggcgg | 60 |
| cggcggcggc ggcggcggcg gcggcggcgg cggcggcggc ggcggcggcg gcggcggcgg | 120 |
| cggcggcggc ggcggcggcg gcggcggcgg cggcggcggc ggcggcggcg gcggcggcgg | 180 |
| cggcggcggc ggcggcggcg gcggcggcgg cggcggcggc ggcggcggcg gcggcggcgg | 240 |
| cggcggcggc ggcggcggcg gcggcggcgg cggcggcggc ggcggcggcg gcggcggcgg | 300 |
| cggcggcggc ggcggcggcg gcggcggcgg cggcggcggc ggcggcggcg gcggcggcgg | 360 |
| cggcggcggc ggcggcggcg gcggcggcgg cggcggcggc ggcggcggcg gcggcggcgg | 420 |
| cggcggcggc ggcggcggcg gcggcggcgg cggcggcggc ggcggcggcg gcggcggcgg | 480 |
| cggcggcggc ggcggcggcg gcggcggcgg cggcggcggc ggcggcggcg gcggcggcgg | 540 |
| cggcggcggc ggcggcggcg gcggcggcgg cggcggcggc ggcggcggcg gcggcggcgg | 600 |

<210> SEQ ID NO 3
<211> LENGTH: 351
<212> TYPE: DNA
<213> ORGANISM: Homo sapiens
<220> FEATURE:
<221> NAME/KEY: misc_feature
<222> LOCATION: (1)..(351)
<223> OTHER INFORMATION: This sequence may encompass 113-117 "cgg"
      repeating units

<400> SEQUENCE: 3

| | |
|---|---|
| cggcggcggc ggcggcggcg gcggcggcgg cggcggcggc ggcggcggcg gcggcggcgg | 60 |
| cggcggcggc ggcggcggcg gcggcggcgg cggcggcggc ggcggcggcg gcggcggcgg | 120 |
| cggcggcggc ggcggcggcg gcggcggcgg cggcggcggc ggcggcggcg gcggcggcgg | 180 |
| cggcggcggc ggcggcggcg gcggcggcgg cggcggcggc ggcggcggcg gcggcggcgg | 240 |
| cggcggcggc ggcggcggcg gcggcggcgg cggcggcggc ggcggcggcg gcggcggcgg | 300 |
| cggcggcggc ggcggcggcg gcggcggcgg cggcggcggc ggcggcggcg g | 351 |

<210> SEQ ID NO 4
<211> LENGTH: 372
<212> TYPE: DNA
<213> ORGANISM: Homo sapiens

<400> SEQUENCE: 4

| | |
|---|---|
| cggcggcggc ggcggcggcg gcggcggcgg cggcggcggc ggcggcggcg gcggcggcgg | 60 |
| cggcggcggc ggcggcggcg gcggcggcgg cggcggcggc ggcggcggcg gcggcggcgg | 120 |
| cggcggcggc ggcggcggcg gcggcggcgg cggcggcggc ggcggcggcg gcggcggcgg | 180 |
| cggcggcggc ggcggcggcg gcggcggcgg cggcggcggc ggcggcggcg gcggcggcgg | 240 |
| cggcggcggc ggcggcggcg gcggcggcgg cggcggcggc ggcggcggcg gcggcggcgg | 300 |

-continued

```
cggcggcggc ggcggcggcg gcggcggcgg cggcggcggc ggcggcggcg gcggcggcgg     360
cggcggcggc gg                                                          372
```

<210> SEQ ID NO 5
<211> LENGTH: 129
<212> TYPE: DNA
<213> ORGANISM: Homo sapiens

<400> SEQUENCE: 5

```
cggcggcggc ggcggcggcg gcggcggcgg cggcggcggc ggcggcggcg gcggcggcgg      60
cggcggcggc ggcggcggcg gcggcggcgg cggcggcggc ggcggcggcg gcggcggcgg     120
cggcggcgg                                                             129
```

<210> SEQ ID NO 6
<211> LENGTH: 12000
<212> TYPE: DNA
<213> ORGANISM: Homo sapiens
<220> FEATURE:
<221> NAME/KEY: misc_feature
<222> LOCATION: (1)..(12000)
<223> OTHER INFORMATION: This sequence may encompass 50-4000 "ctg" repeating units

<400> SEQUENCE: 6

```
ctgctgctgc tgctgctgct gctgctgctg ctgctgctgc tgctgctgct gctgctgctg      60
ctgctgctgc tgctgctgct gctgctgctg ctgctgctgc tgctgctgct gctgctgctg     120
ctgctgctgc tgctgctgct gctgctgctg ctgctgctgc tgctgctgct gctgctgctg     180
ctgctgctgc tgctgctgct gctgctgctg ctgctgctgc tgctgctgct gctgctgctg     240
ctgctgctgc tgctgctgct gctgctgctg ctgctgctgc tgctgctgct gctgctgctg     300
ctgctgctgc tgctgctgct gctgctgctg ctgctgctgc tgctgctgct gctgctgctg     360
ctgctgctgc tgctgctgct gctgctgctg ctgctgctgc tgctgctgct gctgctgctg     420
ctgctgctgc tgctgctgct gctgctgctg ctgctgctgc tgctgctgct gctgctgctg     480
ctgctgctgc tgctgctgct gctgctgctg ctgctgctgc tgctgctgct gctgctgctg     540
ctgctgctgc tgctgctgct gctgctgctg ctgctgctgc tgctgctgct gctgctgctg     600
ctgctgctgc tgctgctgct gctgctgctg ctgctgctgc tgctgctgct gctgctgctg     660
ctgctgctgc tgctgctgct gctgctgctg ctgctgctgc tgctgctgct gctgctgctg     720
ctgctgctgc tgctgctgct gctgctgctg ctgctgctgc tgctgctgct gctgctgctg     780
ctgctgctgc tgctgctgct gctgctgctg ctgctgctgc tgctgctgct gctgctgctg     840
ctgctgctgc tgctgctgct gctgctgctg ctgctgctgc tgctgctgct gctgctgctg     900
ctgctgctgc tgctgctgct gctgctgctg ctgctgctgc tgctgctgct gctgctgctg     960
ctgctgctgc tgctgctgct gctgctgctg ctgctgctgc tgctgctgct gctgctgctg    1020
ctgctgctgc tgctgctgct gctgctgctg ctgctgctgc tgctgctgct gctgctgctg    1080
ctgctgctgc tgctgctgct gctgctgctg ctgctgctgc tgctgctgct gctgctgctg    1140
ctgctgctgc tgctgctgct gctgctgctg ctgctgctgc tgctgctgct gctgctgctg    1200
ctgctgctgc tgctgctgct gctgctgctg ctgctgctgc tgctgctgct gctgctgctg    1260
ctgctgctgc tgctgctgct gctgctgctg ctgctgctgc tgctgctgct gctgctgctg    1320
ctgctgctgc tgctgctgct gctgctgctg ctgctgctgc tgctgctgct gctgctgctg    1380
ctgctgctgc tgctgctgct gctgctgctg ctgctgctgc tgctgctgct gctgctgctg    1440
```

-continued

| | |
|---|---|
| ctgctgctgc tgctgctgct gctgctgctg ctgctgctgc tgctgctgct gctgctgctg | 1500 |
| ctgctgctgc tgctgctgct gctgctgctg ctgctgctgc tgctgctgct gctgctgctg | 1560 |
| ctgctgctgc tgctgctgct gctgctgctg ctgctgctgc tgctgctgct gctgctgctg | 1620 |
| ctgctgctgc tgctgctgct gctgctgctg ctgctgctgc tgctgctgct gctgctgctg | 1680 |
| ctgctgctgc tgctgctgct gctgctgctg ctgctgctgc tgctgctgct gctgctgctg | 1740 |
| ctgctgctgc tgctgctgct gctgctgctg ctgctgctgc tgctgctgct gctgctgctg | 1800 |
| ctgctgctgc tgctgctgct gctgctgctg ctgctgctgc tgctgctgct gctgctgctg | 1860 |
| ctgctgctgc tgctgctgct gctgctgctg ctgctgctgc tgctgctgct gctgctgctg | 1920 |
| ctgctgctgc tgctgctgct gctgctgctg ctgctgctgc tgctgctgct gctgctgctg | 1980 |
| ctgctgctgc tgctgctgct gctgctgctg ctgctgctgc tgctgctgct gctgctgctg | 2040 |
| ctgctgctgc tgctgctgct gctgctgctg ctgctgctgc tgctgctgct gctgctgctg | 2100 |
| ctgctgctgc tgctgctgct gctgctgctg ctgctgctgc tgctgctgct gctgctgctg | 2160 |
| ctgctgctgc tgctgctgct gctgctgctg ctgctgctgc tgctgctgct gctgctgctg | 2220 |
| ctgctgctgc tgctgctgct gctgctgctg ctgctgctgc tgctgctgct gctgctgctg | 2280 |
| ctgctgctgc tgctgctgct gctgctgctg ctgctgctgc tgctgctgct gctgctgctg | 2340 |
| ctgctgctgc tgctgctgct gctgctgctg ctgctgctgc tgctgctgct gctgctgctg | 2400 |
| ctgctgctgc tgctgctgct gctgctgctg ctgctgctgc tgctgctgct gctgctgctg | 2460 |
| ctgctgctgc tgctgctgct gctgctgctg ctgctgctgc tgctgctgct gctgctgctg | 2520 |
| ctgctgctgc tgctgctgct gctgctgctg ctgctgctgc tgctgctgct gctgctgctg | 2580 |
| ctgctgctgc tgctgctgct gctgctgctg ctgctgctgc tgctgctgct gctgctgctg | 2640 |
| ctgctgctgc tgctgctgct gctgctgctg ctgctgctgc tgctgctgct gctgctgctg | 2700 |
| ctgctgctgc tgctgctgct gctgctgctg ctgctgctgc tgctgctgct gctgctgctg | 2760 |
| ctgctgctgc tgctgctgct gctgctgctg ctgctgctgc tgctgctgct gctgctgctg | 2820 |
| ctgctgctgc tgctgctgct gctgctgctg ctgctgctgc tgctgctgct gctgctgctg | 2880 |
| ctgctgctgc tgctgctgct gctgctgctg ctgctgctgc tgctgctgct gctgctgctg | 2940 |
| ctgctgctgc tgctgctgct gctgctgctg ctgctgctgc tgctgctgct gctgctgctg | 3000 |
| ctgctgctgc tgctgctgct gctgctgctg ctgctgctgc tgctgctgct gctgctgctg | 3060 |
| ctgctgctgc tgctgctgct gctgctgctg ctgctgctgc tgctgctgct gctgctgctg | 3120 |
| ctgctgctgc tgctgctgct gctgctgctg ctgctgctgc tgctgctgct gctgctgctg | 3180 |
| ctgctgctgc tgctgctgct gctgctgctg ctgctgctgc tgctgctgct gctgctgctg | 3240 |
| ctgctgctgc tgctgctgct gctgctgctg ctgctgctgc tgctgctgct gctgctgctg | 3300 |
| ctgctgctgc tgctgctgct gctgctgctg ctgctgctgc tgctgctgct gctgctgctg | 3360 |
| ctgctgctgc tgctgctgct gctgctgctg ctgctgctgc tgctgctgct gctgctgctg | 3420 |
| ctgctgctgc tgctgctgct gctgctgctg ctgctgctgc tgctgctgct gctgctgctg | 3480 |
| ctgctgctgc tgctgctgct gctgctgctg ctgctgctgc tgctgctgct gctgctgctg | 3540 |
| ctgctgctgc tgctgctgct gctgctgctg ctgctgctgc tgctgctgct gctgctgctg | 3600 |
| ctgctgctgc tgctgctgct gctgctgctg ctgctgctgc tgctgctgct gctgctgctg | 3660 |
| ctgctgctgc tgctgctgct gctgctgctg ctgctgctgc tgctgctgct gctgctgctg | 3720 |
| ctgctgctgc tgctgctgct gctgctgctg ctgctgctgc tgctgctgct gctgctgctg | 3780 |

```
ctgctgctgc tgctgctgct gctgctgctg ctgctgctgc tgctgctgct gctgctgctg    3840
ctgctgctgc tgctgctgct gctgctgctg ctgctgctgc tgctgctgct gctgctgctg    3900
ctgctgctgc tgctgctgct gctgctgctg ctgctgctgc tgctgctgct gctgctgctg    3960
ctgctgctgc tgctgctgct gctgctgctg ctgctgctgc tgctgctgct gctgctgctg    4020
ctgctgctgc tgctgctgct gctgctgctg ctgctgctgc tgctgctgct gctgctgctg    4080
ctgctgctgc tgctgctgct gctgctgctg ctgctgctgc tgctgctgct gctgctgctg    4140
ctgctgctgc tgctgctgct gctgctgctg ctgctgctgc tgctgctgct gctgctgctg    4200
ctgctgctgc tgctgctgct gctgctgctg ctgctgctgc tgctgctgct gctgctgctg    4260
ctgctgctgc tgctgctgct gctgctgctg ctgctgctgc tgctgctgct gctgctgctg    4320
ctgctgctgc tgctgctgct gctgctgctg ctgctgctgc tgctgctgct gctgctgctg    4380
ctgctgctgc tgctgctgct gctgctgctg ctgctgctgc tgctgctgct gctgctgctg    4440
ctgctgctgc tgctgctgct gctgctgctg ctgctgctgc tgctgctgct gctgctgctg    4500
ctgctgctgc tgctgctgct gctgctgctg ctgctgctgc tgctgctgct gctgctgctg    4560
ctgctgctgc tgctgctgct gctgctgctg ctgctgctgc tgctgctgct gctgctgctg    4620
ctgctgctgc tgctgctgct gctgctgctg ctgctgctgc tgctgctgct gctgctgctg    4680
ctgctgctgc tgctgctgct gctgctgctg ctgctgctgc tgctgctgct gctgctgctg    4740
ctgctgctgc tgctgctgct gctgctgctg ctgctgctgc tgctgctgct gctgctgctg    4800
ctgctgctgc tgctgctgct gctgctgctg ctgctgctgc tgctgctgct gctgctgctg    4860
ctgctgctgc tgctgctgct gctgctgctg ctgctgctgc tgctgctgct gctgctgctg    4920
ctgctgctgc tgctgctgct gctgctgctg ctgctgctgc tgctgctgct gctgctgctg    4980
ctgctgctgc tgctgctgct gctgctgctg ctgctgctgc tgctgctgct gctgctgctg    5040
ctgctgctgc tgctgctgct gctgctgctg ctgctgctgc tgctgctgct gctgctgctg    5100
ctgctgctgc tgctgctgct gctgctgctg ctgctgctgc tgctgctgct gctgctgctg    5160
ctgctgctgc tgctgctgct gctgctgctg ctgctgctgc tgctgctgct gctgctgctg    5220
ctgctgctgc tgctgctgct gctgctgctg ctgctgctgc tgctgctgct gctgctgctg    5280
ctgctgctgc tgctgctgct gctgctgctg ctgctgctgc tgctgctgct gctgctgctg    5340
ctgctgctgc tgctgctgct gctgctgctg ctgctgctgc tgctgctgct gctgctgctg    5400
ctgctgctgc tgctgctgct gctgctgctg ctgctgctgc tgctgctgct gctgctgctg    5460
ctgctgctgc tgctgctgct gctgctgctg ctgctgctgc tgctgctgct gctgctgctg    5520
ctgctgctgc tgctgctgct gctgctgctg ctgctgctgc tgctgctgct gctgctgctg    5580
ctgctgctgc tgctgctgct gctgctgctg ctgctgctgc tgctgctgct gctgctgctg    5640
ctgctgctgc tgctgctgct gctgctgctg ctgctgctgc tgctgctgct gctgctgctg    5700
ctgctgctgc tgctgctgct gctgctgctg ctgctgctgc tgctgctgct gctgctgctg    5760
ctgctgctgc tgctgctgct gctgctgctg ctgctgctgc tgctgctgct gctgctgctg    5820
ctgctgctgc tgctgctgct gctgctgctg ctgctgctgc tgctgctgct gctgctgctg    5880
ctgctgctgc tgctgctgct gctgctgctg ctgctgctgc tgctgctgct gctgctgctg    5940
ctgctgctgc tgctgctgct gctgctgctg ctgctgctgc tgctgctgct gctgctgctg    6000
ctgctgctgc tgctgctgct gctgctgctg ctgctgctgc tgctgctgct gctgctgctg    6060
ctgctgctgc tgctgctgct gctgctgctg ctgctgctgc tgctgctgct gctgctgctg    6120
ctgctgctgc tgctgctgct gctgctgctg ctgctgctgc tgctgctgct gctgctgctg    6180
```

```
ctgctgctgc tgctgctgct gctgctgctg ctgctgctgc tgctgctgct gctgctgctg    6240
ctgctgctgc tgctgctgct gctgctgctg ctgctgctgc tgctgctgct gctgctgctg    6300
ctgctgctgc tgctgctgct gctgctgctg ctgctgctgc tgctgctgct gctgctgctg    6360
ctgctgctgc tgctgctgct gctgctgctg ctgctgctgc tgctgctgct gctgctgctg    6420
ctgctgctgc tgctgctgct gctgctgctg ctgctgctgc tgctgctgct gctgctgctg    6480
ctgctgctgc tgctgctgct gctgctgctg ctgctgctgc tgctgctgct gctgctgctg    6540
ctgctgctgc tgctgctgct gctgctgctg ctgctgctgc tgctgctgct gctgctgctg    6600
ctgctgctgc tgctgctgct gctgctgctg ctgctgctgc tgctgctgct gctgctgctg    6660
ctgctgctgc tgctgctgct gctgctgctg ctgctgctgc tgctgctgct gctgctgctg    6720
ctgctgctgc tgctgctgct gctgctgctg ctgctgctgc tgctgctgct gctgctgctg    6780
ctgctgctgc tgctgctgct gctgctgctg ctgctgctgc tgctgctgct gctgctgctg    6840
ctgctgctgc tgctgctgct gctgctgctg ctgctgctgc tgctgctgct gctgctgctg    6900
ctgctgctgc tgctgctgct gctgctgctg ctgctgctgc tgctgctgct gctgctgctg    6960
ctgctgctgc tgctgctgct gctgctgctg ctgctgctgc tgctgctgct gctgctgctg    7020
ctgctgctgc tgctgctgct gctgctgctg ctgctgctgc tgctgctgct gctgctgctg    7080
ctgctgctgc tgctgctgct gctgctgctg ctgctgctgc tgctgctgct gctgctgctg    7140
ctgctgctgc tgctgctgct gctgctgctg ctgctgctgc tgctgctgct gctgctgctg    7200
ctgctgctgc tgctgctgct gctgctgctg ctgctgctgc tgctgctgct gctgctgctg    7260
ctgctgctgc tgctgctgct gctgctgctg ctgctgctgc tgctgctgct gctgctgctg    7320
ctgctgctgc tgctgctgct gctgctgctg ctgctgctgc tgctgctgct gctgctgctg    7380
ctgctgctgc tgctgctgct gctgctgctg ctgctgctgc tgctgctgct gctgctgctg    7440
ctgctgctgc tgctgctgct gctgctgctg ctgctgctgc tgctgctgct gctgctgctg    7500
ctgctgctgc tgctgctgct gctgctgctg ctgctgctgc tgctgctgct gctgctgctg    7560
ctgctgctgc tgctgctgct gctgctgctg ctgctgctgc tgctgctgct gctgctgctg    7620
ctgctgctgc tgctgctgct gctgctgctg ctgctgctgc tgctgctgct gctgctgctg    7680
ctgctgctgc tgctgctgct gctgctgctg ctgctgctgc tgctgctgct gctgctgctg    7740
ctgctgctgc tgctgctgct gctgctgctg ctgctgctgc tgctgctgct gctgctgctg    7800
ctgctgctgc tgctgctgct gctgctgctg ctgctgctgc tgctgctgct gctgctgctg    7860
ctgctgctgc tgctgctgct gctgctgctg ctgctgctgc tgctgctgct gctgctgctg    7920
ctgctgctgc tgctgctgct gctgctgctg ctgctgctgc tgctgctgct gctgctgctg    7980
ctgctgctgc tgctgctgct gctgctgctg ctgctgctgc tgctgctgct gctgctgctg    8040
ctgctgctgc tgctgctgct gctgctgctg ctgctgctgc tgctgctgct gctgctgctg    8100
ctgctgctgc tgctgctgct gctgctgctg ctgctgctgc tgctgctgct gctgctgctg    8160
ctgctgctgc tgctgctgct gctgctgctg ctgctgctgc tgctgctgct gctgctgctg    8220
ctgctgctgc tgctgctgct gctgctgctg ctgctgctgc tgctgctgct gctgctgctg    8280
ctgctgctgc tgctgctgct gctgctgctg ctgctgctgc tgctgctgct gctgctgctg    8340
ctgctgctgc tgctgctgct gctgctgctg ctgctgctgc tgctgctgct gctgctgctg    8400
ctgctgctgc tgctgctgct gctgctgctg ctgctgctgc tgctgctgct gctgctgctg    8460
ctgctgctgc tgctgctgct gctgctgctg ctgctgctgc tgctgctgct gctgctgctg    8520
```

```
ctgctgctgc tgctgctgct gctgctgctg ctgctgctgc tgctgctgct gctgctgctg   8580
ctgctgctgc tgctgctgct gctgctgctg ctgctgctgc tgctgctgct gctgctgctg   8640
ctgctgctgc tgctgctgct gctgctgctg ctgctgctgc tgctgctgct gctgctgctg   8700
ctgctgctgc tgctgctgct gctgctgctg ctgctgctgc tgctgctgct gctgctgctg   8760
ctgctgctgc tgctgctgct gctgctgctg ctgctgctgc tgctgctgct gctgctgctg   8820
ctgctgctgc tgctgctgct gctgctgctg ctgctgctgc tgctgctgct gctgctgctg   8880
ctgctgctgc tgctgctgct gctgctgctg ctgctgctgc tgctgctgct gctgctgctg   8940
ctgctgctgc tgctgctgct gctgctgctg ctgctgctgc tgctgctgct gctgctgctg   9000
ctgctgctgc tgctgctgct gctgctgctg ctgctgctgc tgctgctgct gctgctgctg   9060
ctgctgctgc tgctgctgct gctgctgctg ctgctgctgc tgctgctgct gctgctgctg   9120
ctgctgctgc tgctgctgct gctgctgctg ctgctgctgc tgctgctgct gctgctgctg   9180
ctgctgctgc tgctgctgct gctgctgctg ctgctgctgc tgctgctgct gctgctgctg   9240
ctgctgctgc tgctgctgct gctgctgctg ctgctgctgc tgctgctgct gctgctgctg   9300
ctgctgctgc tgctgctgct gctgctgctg ctgctgctgc tgctgctgct gctgctgctg   9360
ctgctgctgc tgctgctgct gctgctgctg ctgctgctgc tgctgctgct gctgctgctg   9420
ctgctgctgc tgctgctgct gctgctgctg ctgctgctgc tgctgctgct gctgctgctg   9480
ctgctgctgc tgctgctgct gctgctgctg ctgctgctgc tgctgctgct gctgctgctg   9540
ctgctgctgc tgctgctgct gctgctgctg ctgctgctgc tgctgctgct gctgctgctg   9600
ctgctgctgc tgctgctgct gctgctgctg ctgctgctgc tgctgctgct gctgctgctg   9660
ctgctgctgc tgctgctgct gctgctgctg ctgctgctgc tgctgctgct gctgctgctg   9720
ctgctgctgc tgctgctgct gctgctgctg ctgctgctgc tgctgctgct gctgctgctg   9780
ctgctgctgc tgctgctgct gctgctgctg ctgctgctgc tgctgctgct gctgctgctg   9840
ctgctgctgc tgctgctgct gctgctgctg ctgctgctgc tgctgctgct gctgctgctg   9900
ctgctgctgc tgctgctgct gctgctgctg ctgctgctgc tgctgctgct gctgctgctg   9960
ctgctgctgc tgctgctgct gctgctgctg ctgctgctgc tgctgctgct gctgctgctg  10020
ctgctgctgc tgctgctgct gctgctgctg ctgctgctgc tgctgctgct gctgctgctg  10080
ctgctgctgc tgctgctgct gctgctgctg ctgctgctgc tgctgctgct gctgctgctg  10140
ctgctgctgc tgctgctgct gctgctgctg ctgctgctgc tgctgctgct gctgctgctg  10200
ctgctgctgc tgctgctgct gctgctgctg ctgctgctgc tgctgctgct gctgctgctg  10260
ctgctgctgc tgctgctgct gctgctgctg ctgctgctgc tgctgctgct gctgctgctg  10320
ctgctgctgc tgctgctgct gctgctgctg ctgctgctgc tgctgctgct gctgctgctg  10380
ctgctgctgc tgctgctgct gctgctgctg ctgctgctgc tgctgctgct gctgctgctg  10440
ctgctgctgc tgctgctgct gctgctgctg ctgctgctgc tgctgctgct gctgctgctg  10500
ctgctgctgc tgctgctgct gctgctgctg ctgctgctgc tgctgctgct gctgctgctg  10560
ctgctgctgc tgctgctgct gctgctgctg ctgctgctgc tgctgctgct gctgctgctg  10620
ctgctgctgc tgctgctgct gctgctgctg ctgctgctgc tgctgctgct gctgctgctg  10680
ctgctgctgc tgctgctgct gctgctgctg ctgctgctgc tgctgctgct gctgctgctg  10740
ctgctgctgc tgctgctgct gctgctgctg ctgctgctgc tgctgctgct gctgctgctg  10800
ctgctgctgc tgctgctgct gctgctgctg ctgctgctgc tgctgctgct gctgctgctg  10860
ctgctgctgc tgctgctgct gctgctgctg ctgctgctgc tgctgctgct gctgctgctg  10920
```

```
ctgctgctgc tgctgctgct gctgctgctg ctgctgctgc tgctgctgct gctgctgctg   10980
ctgctgctgc tgctgctgct gctgctgctg ctgctgctgc tgctgctgct gctgctgctg   11040
ctgctgctgc tgctgctgct gctgctgctg ctgctgctgc tgctgctgct gctgctgctg   11100
ctgctgctgc tgctgctgct gctgctgctg ctgctgctgc tgctgctgct gctgctgctg   11160
ctgctgctgc tgctgctgct gctgctgctg ctgctgctgc tgctgctgct gctgctgctg   11220
ctgctgctgc tgctgctgct gctgctgctg ctgctgctgc tgctgctgct gctgctgctg   11280
ctgctgctgc tgctgctgct gctgctgctg ctgctgctgc tgctgctgct gctgctgctg   11340
ctgctgctgc tgctgctgct gctgctgctg ctgctgctgc tgctgctgct gctgctgctg   11400
ctgctgctgc tgctgctgct gctgctgctg ctgctgctgc tgctgctgct gctgctgctg   11460
ctgctgctgc tgctgctgct gctgctgctg ctgctgctgc tgctgctgct gctgctgctg   11520
ctgctgctgc tgctgctgct gctgctgctg ctgctgctgc tgctgctgct gctgctgctg   11580
ctgctgctgc tgctgctgct gctgctgctg ctgctgctgc tgctgctgct gctgctgctg   11640
ctgctgctgc tgctgctgct gctgctgctg ctgctgctgc tgctgctgct gctgctgctg   11700
ctgctgctgc tgctgctgct gctgctgctg ctgctgctgc tgctgctgct gctgctgctg   11760
ctgctgctgc tgctgctgct gctgctgctg ctgctgctgc tgctgctgct gctgctgctg   11820
ctgctgctgc tgctgctgct gctgctgctg ctgctgctgc tgctgctgct gctgctgctg   11880
ctgctgctgc tgctgctgct gctgctgctg ctgctgctgc tgctgctgct gctgctgctg   11940
ctgctgctgc tgctgctgct gctgctgctg ctgctgctgc tgctgctgct gctgctgctg   12000

<210> SEQ ID NO 7
<211> LENGTH: 15
<212> TYPE: DNA
<213> ORGANISM: Homo sapiens

<400> SEQUENCE: 7
ctgctgctgc tgctg                                                    15

<210> SEQ ID NO 8
<211> LENGTH: 18
<212> TYPE: DNA
<213> ORGANISM: Homo sapiens

<400> SEQUENCE: 8
ctgctgctgc tgctgctg                                                 18

<210> SEQ ID NO 9
<211> LENGTH: 210
<212> TYPE: DNA
<213> ORGANISM: Homo sapiens

<400> SEQUENCE: 9
ctgctgctgc tgctgctgct gctgctgctg ctgctgctgc tgctgctgct gctgctgctg   60
ctgctgctgc tgctgctgct gctgctgctg ctgctgctgc tgctgctgct gctgctgctg   120
ctgctgctgc tgctgctgct gctgctgctg ctgctgctgc tgctgctgct gctgctgctg   180
ctgctgctgc tgctgctgct gctgctgctg                                    210

<210> SEQ ID NO 10
<211> LENGTH: 13
<212> TYPE: DNA
<213> ORGANISM: Homo sapiens
```

```
<400> SEQUENCE: 10
tgatagatag ata                                                          13

<210> SEQ ID NO 11
<211> LENGTH: 21
<212> TYPE: DNA
<213> ORGANISM: Homo sapiens

<400> SEQUENCE: 11
tgatagatag atagatagat a                                                 21

<210> SEQ ID NO 12
<211> LENGTH: 39
<212> TYPE: DNA
<213> ORGANISM: Homo sapiens
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: May or may not be present
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: misc_feature
<222> LOCATION: (10)..(11)
<223> OTHER INFORMATION: May or may not be present
<220> FEATURE:
<221> NAME/KEY: modified_base
<222> LOCATION: (14)..(24)
<223> OTHER INFORMATION: a, c, t, g, unknown or other
<220> FEATURE:
<221> NAME/KEY: misc_feature
<222> LOCATION: (14)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: misc_feature
<222> LOCATION: (39)..(39)
<223> OTHER INFORMATION: May or may not be present

<400> SEQUENCE: 12
nntnggnttn nccnnnnnnn nnnnaaagta tgntttaan                              39
```

```
<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: May or may not be present
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: misc_feature
<222> LOCATION: (10)..(11)
<223> OTHER INFORMATION: May or may not be present
<220> FEATURE:
<221> NAME/KEY: modified_base
<222> LOCATION: (14)..(24)
<223> OTHER INFORMATION: a, c, t, g, unknown or other
<220> FEATURE:
<221> NAME/KEY: misc_feature
<222> LOCATION: (14)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: misc_feature
<222> LOCATION: (39)..(39)
<223> OTHER INFORMATION: May or may not be present

<400> SEQUENCE: 13
nntnggtttn nacnnnnnnn nnnnaaagta tgngttaan                           39

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: May or may not be present
<220> FEATURE:
```

<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: misc_feature
<222> LOCATION: (10)..(11)
<223> OTHER INFORMATION: May or may not be present
<220> FEATURE:
<221> NAME/KEY: modified_base
<222> LOCATION: (14)..(24)
<223> OTHER INFORMATION: a, c, t, g, unknown or other
<220> FEATURE:
<221> NAME/KEY: misc_feature
<222> LOCATION: (14)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: misc_feature
<222> LOCATION: (39)..(39)
<223> OTHER INFORMATION: May or may not be present

<400> SEQUENCE: 14
nntnggnttn nacnnnnnnn nnnnaaagta tgntttaan                                39

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: May or may not be present
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (5)..(5)

-continued

```
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: misc_feature
<222> LOCATION: (10)..(11)
<223> OTHER INFORMATION: May or may not be present
<220> FEATURE:
<221> NAME/KEY: modified_base
<222> LOCATION: (14)..(24)
<223> OTHER INFORMATION: a, c, t, g, unknown or other
<220> FEATURE:
<221> NAME/KEY: misc_feature
<222> LOCATION: (14)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: misc_feature
<222> LOCATION: (39)..(39)
<223> OTHER INFORMATION: May or may not be present

<400> SEQUENCE: 15
nntnngnttn nacnnnnnnn nnnnaaagta tgntttaan                              39

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: May or may not be present
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
```

```
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present

<400> SEQUENCE: 16
nnanccnaat aggaaaaaaa aaaatttcat acnaaattt                    39

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: May or may not be present
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: misc_feature
<222> LOCATION: (10)..(11)
<223> OTHER INFORMATION: May or may not be present
<220> FEATURE:
<221> NAME/KEY: modified_base
<222> LOCATION: (14)..(24)
<223> OTHER INFORMATION: a, c, t, g, unknown or other
<220> FEATURE:
<221> NAME/KEY: misc_feature
<222> LOCATION: (14)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present

<400> SEQUENCE: 17
nnagccnaan nagnnnnnnn nnnntttcat acnaaattt                    39

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
```

```
<222> LOCATION: (4)..(4)
<223> OTHER INFORMATION: May or may not be present
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: misc_feature
<222> LOCATION: (10)..(11)
<223> OTHER INFORMATION: May or may not be present
<220> FEATURE:
<221> NAME/KEY: modified_base
<222> LOCATION: (14)..(24)
<223> OTHER INFORMATION: a, c, t, g, unknown or other
<220> FEATURE:
<221> NAME/KEY: misc_feature
<222> LOCATION: (14)..(24)
<223> OTHER INFORMATION: May or may not be present
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: misc_feature
<222> LOCATION: (39)..(39)
<223> OTHER INFORMATION: May or may not be present

<400> SEQUENCE: 18
tatnggnttn nacnnnnnnn nnnnaaagta tgctttaan                    39

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: May or may not be present
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
```

```
<220> FEATURE:
<221> NAME/KEY: misc_feature
<222> LOCATION: (10)..(11)
<223> OTHER INFORMATION: May or may not be present
<220> FEATURE:
<221> NAME/KEY: modified_base
<222> LOCATION: (14)..(24)
<223> OTHER INFORMATION: a, c, t, g, unknown or other
<220> FEATURE:
<221> NAME/KEY: misc_feature
<222> LOCATION: (14)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: misc_feature
<222> LOCATION: (39)..(39)
<223> OTHER INFORMATION: May or may not be present

<400> SEQUENCE: 19
nnanccnnan nagnnnnnnn nnnntttcat acnaaattn                              39

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: May or may not be present
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: misc_feature
<222> LOCATION: (10)..(11)
<223> OTHER INFORMATION: May or may not be present
<220> FEATURE:
<221> NAME/KEY: modified_base
<222> LOCATION: (14)..(24)
<223> OTHER INFORMATION: a, c, t, g, unknown or other
<220> FEATURE:
<221> NAME/KEY: misc_feature
```

```
<222> LOCATION: (14)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: misc_feature
<222> LOCATION: (39)..(39)
<223> OTHER INFORMATION: May or may not be present

<400> SEQUENCE: 20
nnanccnaan nagnnnnnnn nnntttcat acnaaattn                              39

<210> SEQ ID NO 21
<211> LENGTH: 40
<212> TYPE: DNA
<213> ORGANISM: Homo sapiens
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: misc_feature
<222> LOCATION: (25)..(25)
<223> OTHER INFORMATION: May or may not be present
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: May or may not be present
<220> FEATURE:
<221> NAME/KEY: modified_base
<222> LOCATION: (35)..(35)
```

```
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present

<400> SEQUENCE: 21
aaaanttctg nccatttatt atgtnancna nntantacat                              40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: misc_feature
<222> LOCATION: (25)..(25)
<223> OTHER INFORMATION: May or may not be present
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present

<400> SEQUENCE: 22
aacanttctg nccatttatc atgtnancna nntantacat                              40
```

```
<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: misc_feature
<222> LOCATION: (25)..(25)
<223> OTHER INFORMATION: May or may not be present
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: misc_feature
<222> LOCATION: (28)..(28)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: misc_feature
<222> LOCATION: (34)..(34)
<223> OTHER INFORMATION: May or may not be present
<220> FEATURE:
<221> NAME/KEY: modified_base
<222> LOCATION: (39)..(39)
<223> OTHER INFORMATION: a, c, t, g, unknown or other

<400> SEQUENCE: 23
aatangtctg nccanttatc atgtnacnan ntantacan                              39

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: misc_feature
<222> LOCATION: (25)..(25)
<223> OTHER INFORMATION: May or may not be present
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present

<400> SEQUENCE: 24
aaaanttctg nccatttata atgtnancna nnaantacat                              40

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
```

```
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: misc_feature
<222> LOCATION: (28)..(28)
<223> OTHER INFORMATION: May or may not be present
<220> FEATURE:
<221> NAME/KEY: modified_base
<222> LOCATION: (32)..(32)
<223> OTHER INFORMATION: a, c, t, g, unknown or other
<220> FEATURE:
<221> NAME/KEY: misc_feature
<222> LOCATION: (32)..(32)
<223> OTHER INFORMATION: May or may not be present

<400> SEQUENCE: 25
ttttnaagac nggtaagtac tgcatngnta tnatgta                               37

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: misc_feature
<222> LOCATION: (28)..(28)
<223> OTHER INFORMATION: May or may not be present
<220> FEATURE:
<221> NAME/KEY: modified_base
<222> LOCATION: (32)..(32)
<223> OTHER INFORMATION: a, c, t, g, unknown or other
<220> FEATURE:
<221> NAME/KEY: misc_feature
```

```
<222> LOCATION: (32)..(32)
<223> OTHER INFORMATION: May or may not be present

<400> SEQUENCE: 26
ttttaagacn ggtaaatact acantngnta tnatgta                                    37

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: misc_feature
<222> LOCATION: (28)..(28)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: misc_feature
<222> LOCATION: (34)..(34)
<223> OTHER INFORMATION: May or may not be present

<400> SEQUENCE: 27
aaaanttctg ccatttatca tntnancnan ntantactt                                  39

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: misc_feature
<222> LOCATION: (25)..(25)
<223> OTHER INFORMATION: May or may not be present
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present

<400> SEQUENCE: 28
ttttnaagac nagtaaatac tacantngnt nnatnatgca                          40

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
```

```
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: misc_feature
<222> LOCATION: (25)..(25)
<223> OTHER INFORMATION: May or may not be present
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present

<400> SEQUENCE: 29
ttttnaagac nggnaaataa tatantngtn natatgta                              38

<210> SEQ ID NO 30
<211> LENGTH: 45
<212> TYPE: DNA
<213> ORGANISM: Homo sapiens
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: misc_feature
<222> LOCATION: (39)..(40)
<223> OTHER INFORMATION: May or may not be present

<400> SEQUENCE: 30
```
tctctgnttn ctcactaacc cctcaantag cagaaacann gccca                    45

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: misc_feature
<222> LOCATION: (39)..(40)
<223> OTHER INFORMATION: May or may not be present

<400> SEQUENCE: 31
tctctgnttn ctcactaacc cttcaantag cagaaacann gccca                    45

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)

```
<223> OTHER INFORMATION: May or may not be present
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: misc_feature
<222> LOCATION: (39)..(40)
<223> OTHER INFORMATION: May or may not be present
<220> FEATURE:
<221> NAME/KEY: modified_base
<222> LOCATION: (41)..(41)
<223> OTHER INFORMATION: a, c, t, g, unknown or other

<400> SEQUENCE: 32
tctctgnttn ctcactaacc cttcaantag cagaaacann nccca            45

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: misc_feature
<222> LOCATION: (39)..(40)
<223> OTHER INFORMATION: May or may not be present

<400> SEQUENCE: 33
tctctgnttn ctcacnaacc ccttcantag nagaaactnn gccca            45

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: May or may not be present
<220> FEATURE:
<221> NAME/KEY: modified_base
<222> LOCATION: (41)..(41)
<223> OTHER INFORMATION: a, c, t, g, unknown or other

<400> SEQUENCE: 34
agagacaang agtgattngg tagttnatcg tctttgtnnc nggt                    44

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present

<400> SEQUENCE: 35
agagacnnan gagtgattgg gtagttnatc gtctttgtcg ggt                     43
```

-continued

```
<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: misc_feature
<222> LOCATION: (39)..(40)
<223> OTHER INFORMATION: May or may not be present

<400> SEQUENCE: 36
tctctgnttn ctcactaanc cctcaantag cagnaacann gccca            45

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (27)..(27)
```

```
<223> OTHER INFORMATION: a, c, t, g, unknown or other
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: misc_feature
<222> LOCATION: (39)..(40)
<223> OTHER INFORMATION: May or may not be present

<400> SEQUENCE: 37
agagacnaan gagtgattgg gtagttnatc gtctttgtnn cgggt                45

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: misc_feature
<222> LOCATION: (37)..(37)
<223> OTHER INFORMATION: May or may not be present

<400> SEQUENCE: 38
agagacnaag agtgattggg tagttatcgt ctctgtncga gt                   42

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: misc_feature
<222> LOCATION: (7)..(7)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
```

```
<220> FEATURE:
<221> NAME/KEY: misc_feature
<222> LOCATION: (27)..(27)
<223> OTHER INFORMATION: May or may not be present
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: misc_feature
<222> LOCATION: (39)..(40)
<223> OTHER INFORMATION: May or may not be present

<400> SEQUENCE: 39
agagacnaan gagtgattng gtagttnatc gtctttgtnn cgggt          45

<210> SEQ ID NO 40
<211> LENGTH: 46
<212> TYPE: DNA
<213> ORGANISM: Homo sapiens
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: misc_feature
<222> LOCATION: (13)..(13)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: May or may not be present
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: misc_feature
<222> LOCATION: (36)..(36)
<223> OTHER INFORMATION: May or may not be present
<220> FEATURE:
```

<221> NAME/KEY: modified_base
<222> LOCATION: (38)..(38)
<223> OTHER INFORMATION: a, c, t, g, unknown or other
<220> FEATURE:
<221> NAME/KEY: misc_feature
<222> LOCATION: (38)..(38)
<223> OTHER INFORMATION: May or may not be present
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: misc_feature
<222> LOCATION: (44)..(44)
<223> OTHER INFORMATION: May or may not be present

<400> SEQUENCE: 40
tgtnctttna agncnagagt gatnctttat aanttnanaa accntt           46

<210> SEQ ID NO 41
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: misc_feature
<222> LOCATION: (13)..(13)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: May or may not be present
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: misc_feature
<222> LOCATION: (36)..(36)
<223> OTHER INFORMATION: May or may not be present
<220> FEATURE:
<221> NAME/KEY: modified_base
<222> LOCATION: (38)..(38)

```
<223> OTHER INFORMATION: a, c, t, g, unknown or other
<220> FEATURE:
<221> NAME/KEY: misc_feature
<222> LOCATION: (38)..(38)
<223> OTHER INFORMATION: May or may not be present
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: misc_feature
<222> LOCATION: (44)..(44)
<223> OTHER INFORMATION: May or may not be present

<400> SEQUENCE: 41
tgtactttna agncnagact gatnctttat aanttnanga aacntt          46

<210> SEQ ID NO 42
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: misc_feature
<222> LOCATION: (13)..(13)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: May or may not be present
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(36)
<223> OTHER INFORMATION: a, c, t, g, unknown or other
<220> FEATURE:
```

```
<221> NAME/KEY: misc_feature
<222> LOCATION: (36)..(36)
<223> OTHER INFORMATION: May or may not be present
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: misc_feature
<222> LOCATION: (38)..(38)
<223> OTHER INFORMATION: May or may not be present
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: misc_feature
<222> LOCATION: (44)..(44)
<223> OTHER INFORMATION: May or may not be present

<400> SEQUENCE: 42 tgtncttna agncnagacg gagnctttat aanttnanaa accnat            46

<210> SEQ ID NO 43
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: misc_feature
<222> LOCATION: (13)..(13)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: May or may not be present
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: misc_feature
<222> LOCATION: (36)..(36)
<223> OTHER INFORMATION: May or may not be present
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: misc_feature
<222> LOCATION: (38)..(38)
<223> OTHER INFORMATION: May or may not be present
<220> FEATURE:
<221> NAME/KEY: modified_base
<222> LOCATION: (44)..(44)
```

```
<223> OTHER INFORMATION: a, c, t, g, unknown or other
<220> FEATURE:
<221> NAME/KEY: misc_feature
<222> LOCATION: (44)..(44)
<223> OTHER INFORMATION: May or may not be present
<220> FEATURE:
<221> NAME/KEY: modified_base
<222> LOCATION: (46)..(46)
<223> OTHER INFORMATION: a, c, t, g, unknown or other

<400> SEQUENCE: 43
tgtnctttaa agncnaganc gatcctttat aatttnanaa accntn            46

<210> SEQ ID NO 44
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: misc_feature
<222> LOCATION: (13)..(13)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(36)
<223> OTHER INFORMATION: a, c, t, g, unknown or other
<220> FEATURE:
```

<221> NAME/KEY: misc_feature
<222> LOCATION: (36)..(36)
<223> OTHER INFORMATION: May or may not be present
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: misc_feature
<222> LOCATION: (38)..(38)
<223> OTHER INFORMATION: May or may not be present
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: misc_feature
<222> LOCATION: (44)..(44)
<223> OTHER INFORMATION: May or may not be present

<400> SEQUENCE: 44
acangaaant tcngnnctca ctangaaata ttnaannntt tggnaa        46

<210> SEQ ID NO 45
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: May or may not be present
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(36)

```
<223> OTHER INFORMATION: a, c, t, g, unknown or other
<220> FEATURE:
<221> NAME/KEY: misc_feature
<222> LOCATION: (36)..(36)
<223> OTHER INFORMATION: May or may not be present
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: misc_feature
<222> LOCATION: (38)..(38)
<223> OTHER INFORMATION: May or may not be present
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: misc_feature
<222> LOCATION: (44)..(44)
<223> OTHER INFORMATION: May or may not be present

<400> SEQUENCE: 45 acangaaaant tccgntctaa ttangaaata ttnaantntt tggnaa          46

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: misc_feature
<222> LOCATION: (13)..(13)
<223> OTHER INFORMATION: May or may not be present
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
```

```
<221> NAME/KEY: modified_base
<222> LOCATION: (38)..(38)
<223> OTHER INFORMATION: a, c, t, g, unknown or other
<220> FEATURE:
<221> NAME/KEY: misc_feature
<222> LOCATION: (38)..(38)
<223> OTHER INFORMATION: May or may not be present

<400> SEQUENCE: 46
tgtncnttna agnctagact gatncttat aanttaanaa accttt           46

<210> SEQ ID NO 47
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: May or may not be present
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: misc_feature
<222> LOCATION: (36)..(36)
<223> OTHER INFORMATION: May or may not be present
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: misc_feature
<222> LOCATION: (38)..(38)
```

<223> OTHER INFORMATION: May or may not be present
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: misc_feature
<222> LOCATION: (44)..(44)
<223> OTHER INFORMATION: May or may not be present

<400> SEQUENCE: 47
acangaaant tccgntctca ccangaaata ttnaannntt tggnaa                46

<210> SEQ ID NO 48
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: misc_feature
<222> LOCATION: (13)..(13)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: May or may not be present
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(36)
<223> OTHER INFORMATION: a, c, t, g, unknown or other
<220> FEATURE:

```
<221> NAME/KEY: misc_feature
<222> LOCATION: (36)..(36)
<223> OTHER INFORMATION: May or may not be present
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: misc_feature
<222> LOCATION: (44)..(44)
<223> OTHER INFORMATION: May or may not be present

<400> SEQUENCE: 48
acangaaant tcngntctna ctangaaata ttnaantctt tggnaa          46

<210> SEQ ID NO 49
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: May or may not be present
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: misc_feature
<222> LOCATION: (13)..(13)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: May or may not be present
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: misc_feature
<222> LOCATION: (36)..(36)
```

-continued

```
<223> OTHER INFORMATION: May or may not be present
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: misc_feature
<222> LOCATION: (38)..(38)
<223> OTHER INFORMATION: May or may not be present
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: misc_feature
<222> LOCATION: (44)..(44)
<223> OTHER INFORMATION: May or may not be present

<400> SEQUENCE: 49
acangaaant tcngntctca ctangaaata ttnaantntt tggnaa          46

<210> SEQ ID NO 50
<211> LENGTH: 38
<212> TYPE: DNA
<213> ORGANISM: Homo sapiens
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: May or may not be present
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: misc_feature
<222> LOCATION: (23)..(23)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
```

```
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: misc_feature
<222> LOCATION: (36)..(37)
<223> OTHER INFORMATION: May or may not be present

<400> SEQUENCE: 50
tgncnctcag ncctcnccga gtnagnctng ggnacnnt                              38

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: misc_feature
<222> LOCATION: (23)..(23)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
```

```
<222> LOCATION: (30)..(30)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present

<400> SEQUENCE: 51
tgccnctcag ncctctctga ntnagnctnn ggnactat                    38

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: May or may not be present
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
```

```
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: misc_feature
<222> LOCATION: (36)..(37)
<223> OTHER INFORMATION: May or may not be present

<400> SEQUENCE: 52
tgngnaaggg ngggngtaa ttgaanttng ggnatnnt                              38

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: May or may not be present
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: misc_feature
<222> LOCATION: (23)..(23)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
```

```
<222> LOCATION: (33)..(33)
<223> OTHER INFORMATION: May or may not be present
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: misc_feature
<222> LOCATION: (36)..(37)
<223> OTHER INFORMATION: May or may not be present

<400> SEQUENCE: 53
tgncnctcan ncctcnctga gtnagnctgg ggnacnnt                              38

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: May or may not be present
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: misc_feature
<222> LOCATION: (23)..(23)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
```

```
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: misc_feature
<222> LOCATION: (36)..(37)
<223> OTHER INFORMATION: May or may not be present

<400> SEQUENCE: 54
acngngagtc nngagngtcc cantcnganc ccntgnna                              38

<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: May or may not be present
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: misc_feature
<222> LOCATION: (23)..(23)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
```

```
<222> LOCATION: (26)..(26)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: misc_feature
<222> LOCATION: (36)..(37)
<223> OTHER INFORMATION: May or may not be present

<400> SEQUENCE: 55
acngngagtc nggagnggct cantcnganc ccntgnna                              38

<210> SEQ ID NO 56
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: May or may not be present
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (23)..(23)
<223> OTHER INFORMATION: a, c, t, g, unknown or other
```

```
<220> FEATURE:
<221> NAME/KEY: misc_feature
<222> LOCATION: (23)..(23)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: misc_feature
<222> LOCATION: (36)..(37)
<223> OTHER INFORMATION: May or may not be present

<400> SEQUENCE: 56
tgncnctcag nccncnctga ggnagnctng ggnacnnt                             38

<210> SEQ ID NO 57
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: May or may not be present
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
```

```
<222> LOCATION: (23)..(23)
<223> OTHER INFORMATION: a, c, t, g, unknown or other
<220> FEATURE:
<221> NAME/KEY: misc_feature
<222> LOCATION: (23)..(23)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: misc_feature
<222> LOCATION: (37)..(37)
<223> OTHER INFORMATION: May or may not be present

<400> SEQUENCE: 57
acngngagtc tgganngtct cantccganc ccntgana                              38

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: May or may not be present
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (23)..(23)
<223> OTHER INFORMATION: a, c, t, g, unknown or other
```

```
<220> FEATURE:
<221> NAME/KEY: misc_feature
<222> LOCATION: (23)..(23)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: May or may not be present
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: misc_feature
<222> LOCATION: (33)..(33)
<223> OTHER INFORMATION: May or may not be present
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: misc_feature
<222> LOCATION: (36)..(37)
<223> OTHER INFORMATION: May or may not be present

<400> SEQUENCE: 58
acngngagtc nggagngtct cantcngagc ccntgnna                            38

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: misc_feature
<222> LOCATION: (23)..(23)
<223> OTHER INFORMATION: May or may not be present
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
```

```
<222> LOCATION: (26)..(26)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: misc_feature
<222> LOCATION: (36)..(37)
<223> OTHER INFORMATION: May or may not be present

<400> SEQUENCE: 59
acngagagtc nggagngtct cantcnganc ccttgnna                               38

<210> SEQ ID NO 60
<211> LENGTH: 60
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (12)..(14)
<223> OTHER INFORMATION: a, c, t, g, unknown or other
<220> FEATURE:
<221> NAME/KEY: misc_feature
<222> LOCATION: (12)..(14)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (35)..(35)
```

```
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present
<220> FEATURE:
<221> NAME/KEY: modified_base
<222> LOCATION: (37)..(39)
<223> OTHER INFORMATION: a, c, t, g, unknown or other
<220> FEATURE:
<221> NAME/KEY: misc_feature
<222> LOCATION: (37)..(39)
<223> OTHER INFORMATION: May or may not be present
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: misc_feature
<222> LOCATION: (42)..(42)
<223> OTHER INFORMATION: May or may not be present
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: misc_feature
<222> LOCATION: (47)..(49)
<223> OTHER INFORMATION: May or may not be present
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: misc_feature
<222> LOCATION: (53)..(53)
<223> OTHER INFORMATION: May or may not be present
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: May or may not be present

<400> SEQUENCE: 60
cngctaccan tnnngncccn nagctaatnt ttttntnnng tnatttnnnt cangnntaga         60

<210> SEQ ID NO 61
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (12)..(14)
<223> OTHER INFORMATION: a, c, t, g, unknown or other
<220> FEATURE:
```

```
<221> NAME/KEY: misc_feature
<222> LOCATION: (12)..(14)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present
<220> FEATURE:
<221> NAME/KEY: modified_base
<222> LOCATION: (37)..(39)
<223> OTHER INFORMATION: a, c, t, g, unknown or other
<220> FEATURE:
<221> NAME/KEY: misc_feature
<222> LOCATION: (37)..(39)
<223> OTHER INFORMATION: May or may not be present
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: misc_feature
<222> LOCATION: (42)..(42)
<223> OTHER INFORMATION: May or may not be present
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: misc_feature
<222> LOCATION: (47)..(49)
<223> OTHER INFORMATION: May or may not be present
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: misc_feature
<222> LOCATION: (53)..(53)
<223> OTHER INFORMATION: May or may not be present
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: May or may not be present

<400> SEQUENCE: 61
cngctaccan tnnngnsccn natctaatnt tttcntnnng tnatttnnnt tangnntaga    60
```

```
<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: misc_feature
<222> LOCATION: (42)..(42)
<223> OTHER INFORMATION: May or may not be present
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: May or may not be present

<400> SEQUENCE: 62
anaattattn tgggngnggn nggggggtnt ttttntgggg gnatttggat gaggnngtgg    60
```

```
<210> SEQ ID NO 63
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (12)..(14)
<223> OTHER INFORMATION: a, c, t, g, unknown or other
<220> FEATURE:
<221> NAME/KEY: misc_feature
<222> LOCATION: (12)..(14)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (37)..(39)
<223> OTHER INFORMATION: a, c, t, g, unknown or other
<220> FEATURE:
<221> NAME/KEY: misc_feature
<222> LOCATION: (37)..(39)
<223> OTHER INFORMATION: May or may not be present
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: misc_feature
<222> LOCATION: (42)..(42)
<223> OTHER INFORMATION: May or may not be present
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: modified_base
<222> LOCATION: (47)..(49)
<223> OTHER INFORMATION: a, c, t, g, unknown or other
```

```
<220> FEATURE:
<221> NAME/KEY: misc_feature
<222> LOCATION: (47)..(49)
<223> OTHER INFORMATION: May or may not be present
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: misc_feature
<222> LOCATION: (53)..(53)
<223> OTHER INFORMATION: May or may not be present
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: May or may not be present

<400> SEQUENCE: 63
cngctaccan tnnngnccn nagctaatnt ttttctnnng tnanttnnnt gangnntata    60

<210> SEQ ID NO 64
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (12)..(14)
<223> OTHER INFORMATION: a, c, t, g, unknown or other
<220> FEATURE:
<221> NAME/KEY: misc_feature
<222> LOCATION: (12)..(14)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
```

```
<222> LOCATION: (35)..(35)
<223> OTHER INFORMATION: May or may not be present
<220> FEATURE:
<221> NAME/KEY: modified_base
<222> LOCATION: (37)..(39)
<223> OTHER INFORMATION: a, c, t, g, unknown or other
<220> FEATURE:
<221> NAME/KEY: misc_feature
<222> LOCATION: (37)..(39)
<223> OTHER INFORMATION: May or may not be present
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: misc_feature
<222> LOCATION: (47)..(49)
<223> OTHER INFORMATION: May or may not be present
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: misc_feature
<222> LOCATION: (53)..(53)
<223> OTHER INFORMATION: May or may not be present
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: May or may not be present

<400> SEQUENCE: 64
ggcgatngtn annncnnggn ntcgattaga aacanannnc actaagnnna ttnnnnatct    60

<210> SEQ ID NO 65
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (12)..(14)
<223> OTHER INFORMATION: a, c, t, g, unknown or other
<220> FEATURE:
<221> NAME/KEY: misc_feature
<222> LOCATION: (12)..(14)
<223> OTHER INFORMATION: May or may not be present
<220> FEATURE:
<221> NAME/KEY: modified_base
<222> LOCATION: (20)..(21)
<223> OTHER INFORMATION: a, c, t, g, unknown or other
```

```
<220> FEATURE:
<221> NAME/KEY: misc_feature
<222> LOCATION: (20)..(21)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present
<220> FEATURE:
<221> NAME/KEY: modified_base
<222> LOCATION: (37)..(39)
<223> OTHER INFORMATION: a, c, t, g, unknown or other
<220> FEATURE:
<221> NAME/KEY: misc_feature
<222> LOCATION: (37)..(39)
<223> OTHER INFORMATION: May or may not be present
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: misc_feature
<222> LOCATION: (42)..(42)
<223> OTHER INFORMATION: May or may not be present
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: misc_feature
<222> LOCATION: (47)..(49)
<223> OTHER INFORMATION: May or may not be present
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: misc_feature
<222> LOCATION: (53)..(53)
<223> OTHER INFORMATION: May or may not be present

<400> SEQUENCE: 65
gncgatggtn annnccgggn ntcgattana aaacnannnc antaaannna ttncttatct    60

<210> SEQ ID NO 66
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: May or may not be present
<220> FEATURE:
<221> NAME/KEY: modified_base
<222> LOCATION: (12)..(14)
<223> OTHER INFORMATION: a, c, t, g, unknown or other
<220> FEATURE:
<221> NAME/KEY: misc_feature
```

<222> LOCATION: (12)..(14)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: May or may not be present
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: misc_feature
<222> LOCATION: (42)..(42)
<223> OTHER INFORMATION: May or may not be present
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: misc_feature
<222> LOCATION: (47)..(49)
<223> OTHER INFORMATION: May or may not be present
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: misc_feature
<222> LOCATION: (53)..(53)
<223> OTHER INFORMATION: May or may not be present
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: May or may not be present

<400> SEQUENCE: 66
cngctaccat tnnnangccn nagctaatnt ttttntcnnt tnatttnnnt tangnntaga    60

-continued

```
<210> SEQ ID NO 67
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (12)..(14)
<223> OTHER INFORMATION: a, c, t, g, unknown or other
<220> FEATURE:
<221> NAME/KEY: misc_feature
<222> LOCATION: (12)..(14)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present
<220> FEATURE:
<221> NAME/KEY: modified_base
<222> LOCATION: (37)..(39)
<223> OTHER INFORMATION: a, c, t, g, unknown or other
<220> FEATURE:
<221> NAME/KEY: misc_feature
<222> LOCATION: (37)..(39)
<223> OTHER INFORMATION: May or may not be present
<220> FEATURE:
<221> NAME/KEY: modified_base
<222> LOCATION: (42)..(42)
```

<223> OTHER INFORMATION: a, c, t, g, unknown or other
<220> FEATURE:
<221> NAME/KEY: misc_feature
<222> LOCATION: (42)..(42)
<223> OTHER INFORMATION: May or may not be present
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: misc_feature
<222> LOCATION: (47)..(49)
<223> OTHER INFORMATION: May or may not be present
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: misc_feature
<222> LOCATION: (53)..(53)
<223> OTHER INFORMATION: May or may not be present
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: May or may not be present

<400> SEQUENCE: 67
gncgatagtn annncnnggn ntcaattana aaacnannnc antaaannna ntncnnatct    60

<210> SEQ ID NO 68
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: May or may not be present
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (12)..(14)
<223> OTHER INFORMATION: a, c, t, g, unknown or other
<220> FEATURE:
<221> NAME/KEY: misc_feature
<222> LOCATION: (12)..(14)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:

```
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present
<220> FEATURE:
<221> NAME/KEY: modified_base
<222> LOCATION: (37)..(39)
<223> OTHER INFORMATION: a, c, t, g, unknown or other
<220> FEATURE:
<221> NAME/KEY: misc_feature
<222> LOCATION: (37)..(39)
<223> OTHER INFORMATION: May or may not be present
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: misc_feature
<222> LOCATION: (42)..(42)
<223> OTHER INFORMATION: May or may not be present
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: misc_feature
<222> LOCATION: (47)..(49)
<223> OTHER INFORMATION: May or may not be present
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: misc_feature
<222> LOCATION: (53)..(53)
<223> OTHER INFORMATION: May or may not be present
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: May or may not be present

<400> SEQUENCE: 68
gncgatggtn annncnggga gtcgattnna aaacnannnc antaaannna ttncnnatct    60

<210> SEQ ID NO 69
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
```

```
<223> OTHER INFORMATION: May or may not be present
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: misc_feature
<222> LOCATION: (10)..(10)
<223> OTHER INFORMATION: May or may not be present
<220> FEATURE:
<221> NAME/KEY: modified_base
<222> LOCATION: (12)..(14)
<223> OTHER INFORMATION: a, c, t, g, unknown or other
<220> FEATURE:
<221> NAME/KEY: misc_feature
<222> LOCATION: (12)..(14)
<223> OTHER INFORMATION: May or may not be present
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: misc_feature
<222> LOCATION: (16)..(16)
<223> OTHER INFORMATION: May or may not be present
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: May or may not be present
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: May or may not be present
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: May or may not be present
<220> FEATURE:
<221> NAME/KEY: modified_base
<222> LOCATION: (37)..(39)
<223> OTHER INFORMATION: a, c, t, g, unknown or other
<220> FEATURE:
<221> NAME/KEY: misc_feature
<222> LOCATION: (37)..(39)
<223> OTHER INFORMATION: May or may not be present
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: misc_feature
<222> LOCATION: (42)..(42)
<223> OTHER INFORMATION: May or may not be present
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: misc_feature
<222> LOCATION: (47)..(49)
<223> OTHER INFORMATION: May or may not be present
<220> FEATURE:
<221> NAME/KEY: modified_base
```

<222> LOCATION: (53)..(53)
<223> OTHER INFORMATION: a, c, t, g, unknown or other
<220> FEATURE:
<221> NAME/KEY: misc_feature
<222> LOCATION: (53)..(53)
<223> OTHER INFORMATION: May or may not be present
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: May or may not be present

<400> SEQUENCE: 69
gncgatngtn annncngggn ntcgattana aacanannnc antaaannna ttncnnatct    60

<210> SEQ ID NO 70
<211> LENGTH: 34
<212> TYPE: DNA
<213> ORGANISM: Homo sapiens
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: misc_feature
<222> LOCATION: (6)..(8)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: misc_feature
<222> LOCATION: (16)..(18)
<223> OTHER INFORMATION: May or may not be present
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: misc_feature
<222> LOCATION: (22)..(22)
<223> OTHER INFORMATION: May or may not be present
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)

<223> OTHER INFORMATION: May or may not be present

<400> SEQUENCE: 70
tttntnnngt natttnnntc angnntagan ngac                34

<210> SEQ ID NO 71
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: misc_feature
<222> LOCATION: (6)..(8)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: misc_feature
<222> LOCATION: (16)..(18)
<223> OTHER INFORMATION: May or may not be present
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: misc_feature
<222> LOCATION: (22)..(22)
<223> OTHER INFORMATION: May or may not be present
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present

<400> SEQUENCE: 71
ttcntnnngt natttnnntt angnntagan ngac                34

<210> SEQ ID NO 72
<211> LENGTH: 34
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present

<400> SEQUENCE: 72
tttntggggg natttggatg aggnngtggn ngat                                 34

<210> SEQ ID NO 73
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: misc_feature
<222> LOCATION: (6)..(8)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: misc_feature
<222> LOCATION: (16)..(18)
<223> OTHER INFORMATION: May or may not be present
<220> FEATURE:
<221> NAME/KEY: modified_base

```
<222> LOCATION: (22)..(22)
<223> OTHER INFORMATION: a, c, t, g, unknown or other
<220> FEATURE:
<221> NAME/KEY: misc_feature
<222> LOCATION: (22)..(22)
<223> OTHER INFORMATION: May or may not be present
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present

<400> SEQUENCE: 73
tttctnnngt nanttnnntg angnntatan ngac                                 34

<210> SEQ ID NO 74
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: misc_feature
<222> LOCATION: (6)..(8)
<223> OTHER INFORMATION: May or may not be present
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: misc_feature
<222> LOCATION: (16)..(18)
<223> OTHER INFORMATION: May or may not be present
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: misc_feature
<222> LOCATION: (22)..(22)
<223> OTHER INFORMATION: May or may not be present
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present
```

```
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present

<400> SEQUENCE: 74
acanannnca ctaagnnnat tnnnnatctn nctg                               34

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: misc_feature
<222> LOCATION: (6)..(8)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: misc_feature
<222> LOCATION: (16)..(18)
<223> OTHER INFORMATION: May or may not be present
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: misc_feature
<222> LOCATION: (22)..(22)
<223> OTHER INFORMATION: May or may not be present

<400> SEQUENCE: 75
aacnannnca ntaaannnat tncttatctg gctg                               34

<210> SEQ ID NO 76
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
```

```
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: misc_feature
<222> LOCATION: (7)..(8)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: misc_feature
<222> LOCATION: (16)..(18)
<223> OTHER INFORMATION: May or may not be present
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: misc_feature
<222> LOCATION: (22)..(22)
<223> OTHER INFORMATION: May or may not be present
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present

<400> SEQUENCE: 76
tttntcnntt natttnnntt angnntagan ngac                         34

<210> SEQ ID NO 77
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: misc_feature
<222> LOCATION: (6)..(8)
```

```
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: misc_feature
<222> LOCATION: (16)..(18)
<223> OTHER INFORMATION: May or may not be present
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: misc_feature
<222> LOCATION: (22)..(22)
<223> OTHER INFORMATION: May or may not be present
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present

<400> SEQUENCE: 77
aacnannnca ntaaannnan tncnnatctn nctg                                34

<210> SEQ ID NO 78
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: misc_feature
<222> LOCATION: (6)..(8)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
```

```
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: misc_feature
<222> LOCATION: (16)..(18)
<223> OTHER INFORMATION: May or may not be present
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: misc_feature
<222> LOCATION: (22)..(22)
<223> OTHER INFORMATION: May or may not be present
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present

<400> SEQUENCE: 78
aacnannnca ntaaannnat tncnnatctn nctg                                34

<210> SEQ ID NO 79
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: May or may not be present
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: misc_feature
<222> LOCATION: (6)..(8)
<223> OTHER INFORMATION: May or may not be present
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: misc_feature
<222> LOCATION: (11)..(11)
<223> OTHER INFORMATION: May or may not be present
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: misc_feature
<222> LOCATION: (16)..(18)
```

```
<223> OTHER INFORMATION: May or may not be present
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: misc_feature
<222> LOCATION: (22)..(22)
<223> OTHER INFORMATION: May or may not be present
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: misc_feature
<222> LOCATION: (30)..(31)
<223> OTHER INFORMATION: May or may not be present

<400> SEQUENCE: 79
acanannnca ntaaannnat tncnnatctn nctg                                34

<210> SEQ ID NO 80
<211> LENGTH: 604
<212> TYPE: DNA
<213> ORGANISM: Homo sapiens

<400> SEQUENCE: 80
atctgctgct gctgctgctg ctgctgctgc tgctgctgct gctgctgctg ctgctgctgc    60
tgctgctgct gctgctgctg ctgctgctgc tgctgctgct gctgctgctg ctgctgctgc   120
tgctgctgct gctgctgctg ctgctgctgc tgctgctgct gctgctgctg ctgctgctgc   180
tgctgctgct gctgctgctg ctgctgctgc tgctgctgct gctgctgctg ctgctgctgc   240
tgctgctgct gctgctgctg ctgctgctgc tgctgctgct gctgctgctg ctgctgctgc   300
tgctgctgct gctgctgctg ctgctgctgc tgctgctgct gctgctgctg ctgctgctgc   360
tgctgctgct gctgctgctg ctgctgctgc tgctgctgct gctgctgctg ctgctgctgc   420
tgctgctgct gctgctgctg ctgctgctgc tgctgctgct gctgctgctg ctgctgctgc   480
tgctgctgct gctgctgctg ctgctgctgc tgctgctgct gctgctgctg ctgctgctgc   540
tgctgctgct gctgctgctg ctgctgctgc tgctgctgct gctgctgctg ctgctgctgc   600
tgag                                                                604

<210> SEQ ID NO 81
<211> LENGTH: 34
<212> TYPE: DNA
<213> ORGANISM: Homo sapiens

<400> SEQUENCE: 81
gcctgctgct gctgctgctg ctgctgctgc tgga                                34

<210> SEQ ID NO 82
<211> LENGTH: 213
<212> TYPE: DNA
<213> ORGANISM: Homo sapiens

<400> SEQUENCE: 82
gtctgctgct gctgctgctg ctgctgctgc tgctgctgct gctgctgctg ctgctgctgc    60
```

```
tgctgctgct gctgctgctg ctgctgctgc tgctgctgct gctgctgctg ctgctgctgc    120
tgctgctgct gctgctgctg ctgctgctgc tgctgctgct gctgctgctg ctgctgctgc    180
tgctgctgct gctgctgctg ctgctgctgc tga                                 213
```

<210> SEQ ID NO 83
<211> LENGTH: 19
<212> TYPE: DNA
<213> ORGANISM: Homo sapiens

<400> SEQUENCE: 83

```
atctgctgct gctgctgag                                                  19
```

<210> SEQ ID NO 84
<211> LENGTH: 22
<212> TYPE: DNA
<213> ORGANISM: Homo sapiens

<400> SEQUENCE: 84

```
atctgctgct gctgctgctg ga                                              22
```

<210> SEQ ID NO 85
<211> LENGTH: 12
<212> TYPE: DNA
<213> ORGANISM: Homo sapiens

<400> SEQUENCE: 85

```
ccccgccccg cg                                                         12
```

<210> SEQ ID NO 86
<211> LENGTH: 21
<212> TYPE: DNA
<213> ORGANISM: Homo sapiens

<400> SEQUENCE: 86

```
caaaaaaaaa aaaaaaaaa a                                                21
```

<210> SEQ ID NO 87
<211> LENGTH: 23
<212> TYPE: DNA
<213> ORGANISM: Homo sapiens

<400> SEQUENCE: 87

```
ctttttttttt tttttttttt ttt                                            23
```

<210> SEQ ID NO 88
<211> LENGTH: 13
<212> TYPE: DNA
<213> ORGANISM: Homo sapiens

<400> SEQUENCE: 88

```
ctgtgtgtgt gtg                                                        13
```

<210> SEQ ID NO 89
<211> LENGTH: 23
<212> TYPE: DNA
<213> ORGANISM: Homo sapiens

<400> SEQUENCE: 89

```
ctgtgtgtgt gtgtgtgtgt gtg                                             23
```

<210> SEQ ID NO 90

```
<211> LENGTH: 11
<212> TYPE: DNA
<213> ORGANISM: Homo sapiens

<400> SEQUENCE: 90
ctgtgtgtgt g                                                           11

<210> SEQ ID NO 91
<211> LENGTH: 13
<212> TYPE: DNA
<213> ORGANISM: Homo sapiens

<400> SEQUENCE: 91
gtaaataaat aaa                                                         13

<210> SEQ ID NO 92
<211> LENGTH: 10
<212> TYPE: DNA
<213> ORGANISM: Homo sapiens

<400> SEQUENCE: 92
aaataataat                                                             10

<210> SEQ ID NO 93
<211> LENGTH: 16
<212> TYPE: DNA
<213> ORGANISM: Homo sapiens

<400> SEQUENCE: 93
aaataataat aataat                                                      16
```